(12) United States Patent
Wei et al.

(10) Patent No.: US 10,155,954 B2
(45) Date of Patent: Dec. 18, 2018

(54) AGENTS FOR ENHANCEMENT OF PRODUCTION OF BIOFUEL PRECURSORS IN MICROALGAE

(71) Applicant: The Regents of the University of California, Oakland, CA (US)

(72) Inventors: Chia-Lin Wei, West Hartford, CT (US); Chew Yee Ngan, West Hartford, CT (US); Chee Hong Wong, West Hartford, CT (US); Cindy Choi, San Ramon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/243,896

(22) Filed: Aug. 22, 2016

(65) Prior Publication Data

US 2017/0016016 A1    Jan. 19, 2017

Related U.S. Application Data

(63) Continuation of application No. PCT/US2015/017586, filed on Feb. 25, 2015.

(60) Provisional application No. 62/051,265, filed on Sep. 16, 2014, provisional application No. 61/944,507, filed on Feb. 25, 2014.

(51) Int. Cl.
  *C12N 15/82* (2006.01)
  *C12N 1/12* (2006.01)
  *C12P 7/64* (2006.01)
  *C07K 14/405* (2006.01)

(52) U.S. Cl.
  CPC ........ *C12N 15/8247* (2013.01); *C07K 14/405* (2013.01); *C12P 7/64* (2013.01)

(58) Field of Classification Search
  None
  See application file for complete search history.

(56) References Cited

U.S. PATENT DOCUMENTS

2005/0288866 A1    12/2005    Sachdeva et al.
2012/0252080 A1    10/2012    Kristof et al.

OTHER PUBLICATIONS

Shen et al 2010 (Plant Physiology 153: p. 980-987).*
Wykoff et al 1999 (PNAS 96:26, p. 15336-15341).*
International Search Report and Written Opinion, PCT/US2015/017586, dated Aug. 4, 2015, 12 pages.
Rubio, et al., "A conserved MYB transcription factor involved in phosphate starvation signaling both in vascular plants and in unicellular algae," Genes & Development 15, 2122-2133 (2001).
Wykoff, et al., "Psr1, a nuclear localized protein that regulates phosphorus metabolism in Chlamydomonas," Proceedings of the National Academy of Sciences of the United States of America 96, 15336-15341 (1999).

* cited by examiner

*Primary Examiner* — Matthew R Keogh
(74) *Attorney, Agent, or Firm* — Kilpatrick Townsend & Stockton LLP

(57) ABSTRACT

We identified 17 transcription factor genes that regulate lipid production and activity in an organism. We subsequently detailed characterization of one of them (psr1). Constructs, methods and systems for enhancing or increasing lipid production in an organism are described.

4 Claims, 41 Drawing Sheets

Figure 1:
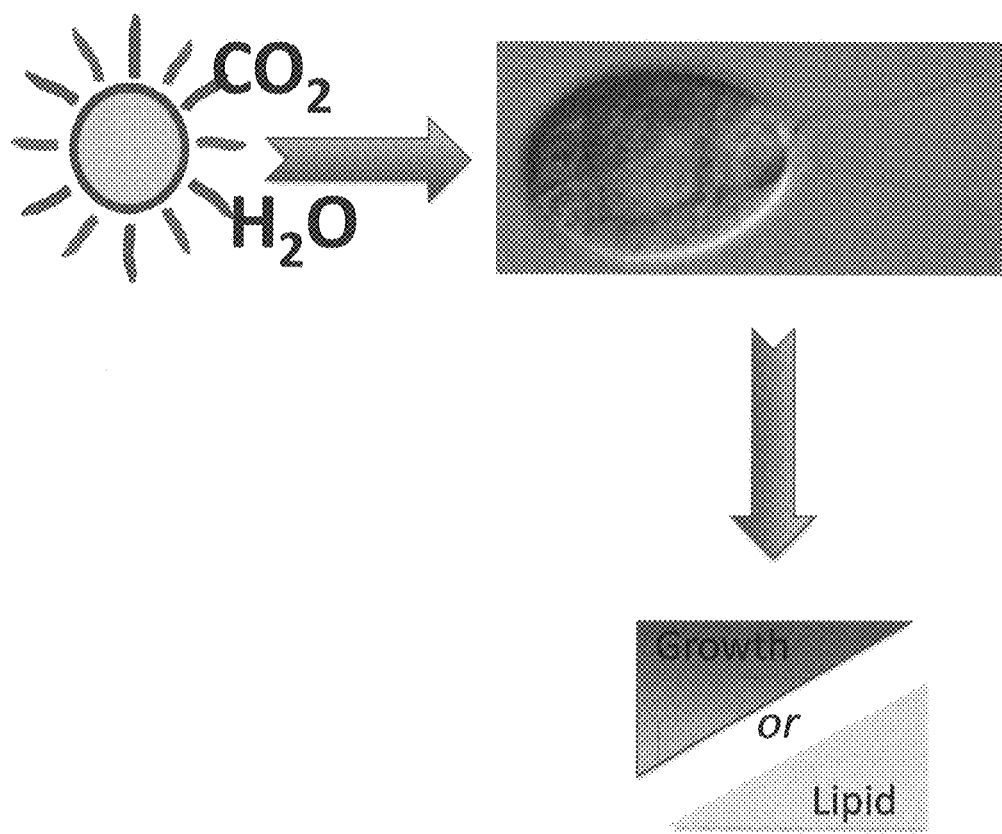

Specification includes a Sequence Listing.

Figure 5
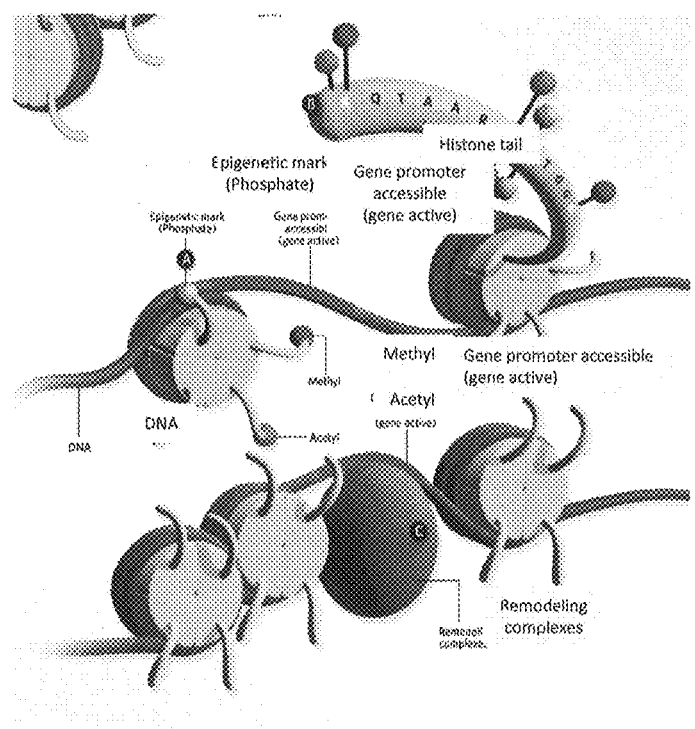
Histone modification
Small RNA
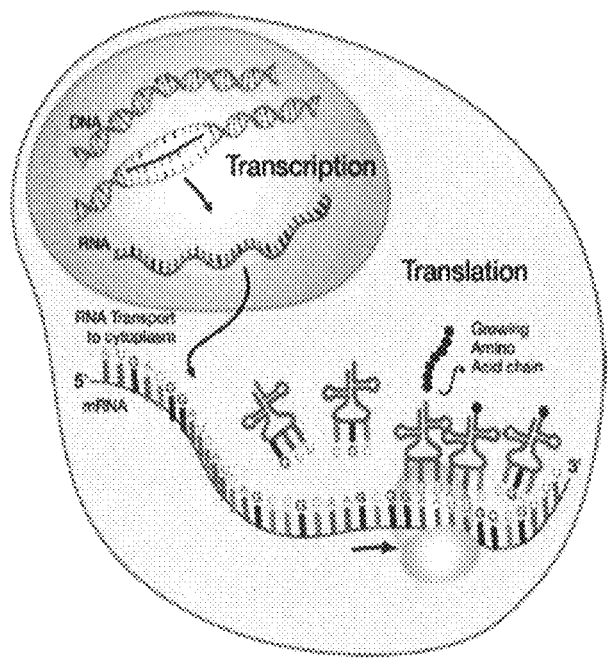

Figure 6
No methylation= active
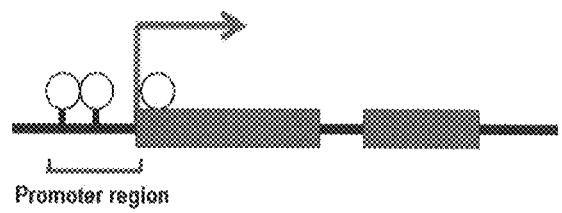
Promoter region
Methylation= inactive
DNA methylation
Ⓜ Methylated
◯ Unmethylated

Figure 11
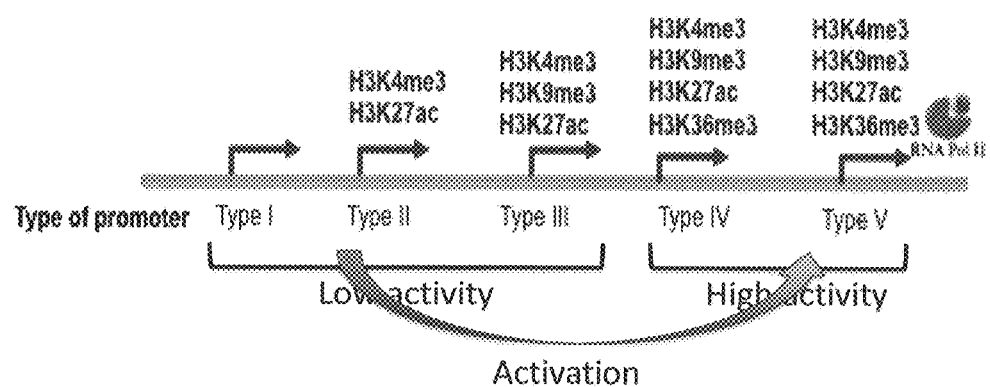
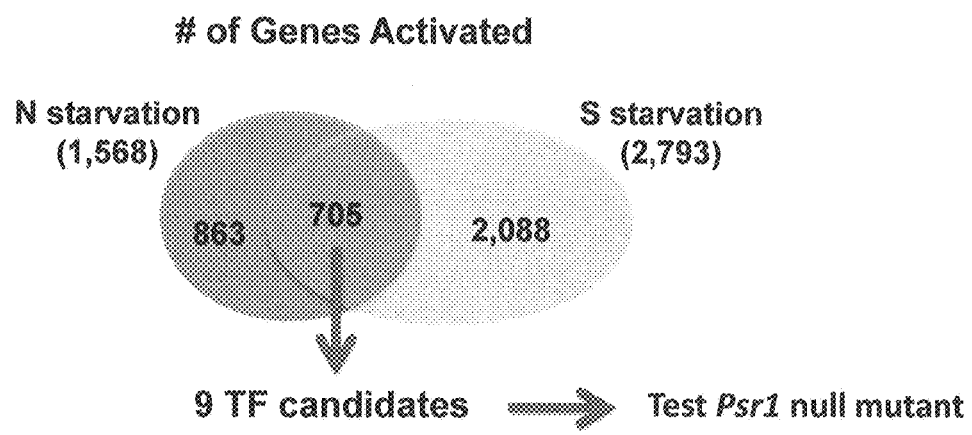

48 WT & 48 *Psr1* over-expressing clones 48 hr growth in rich medium (TAP)

Cell # & total Nile Red fluorescence

Figure 26
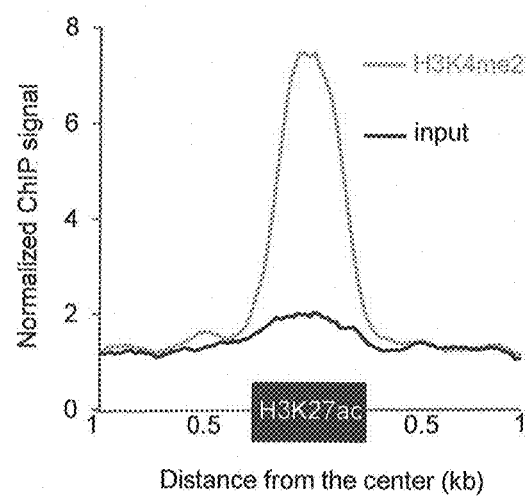
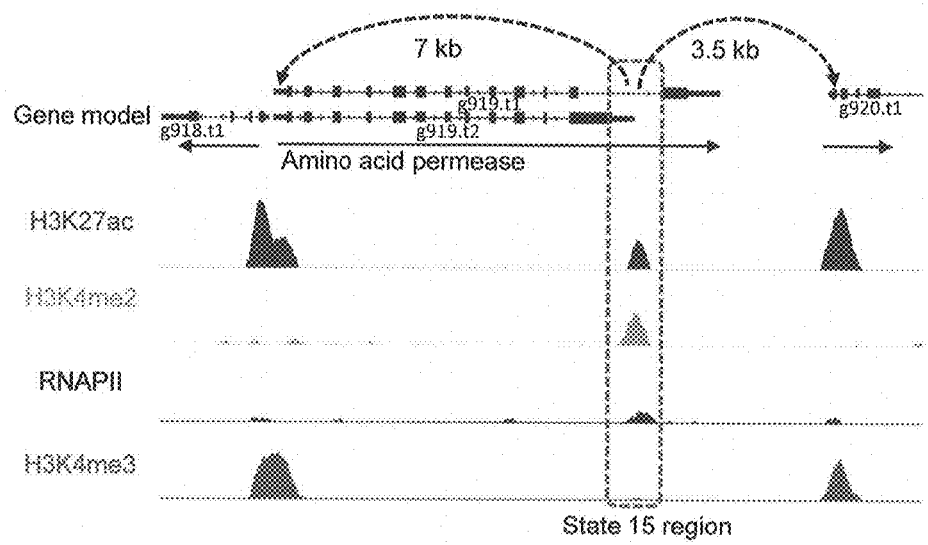

Figure 27
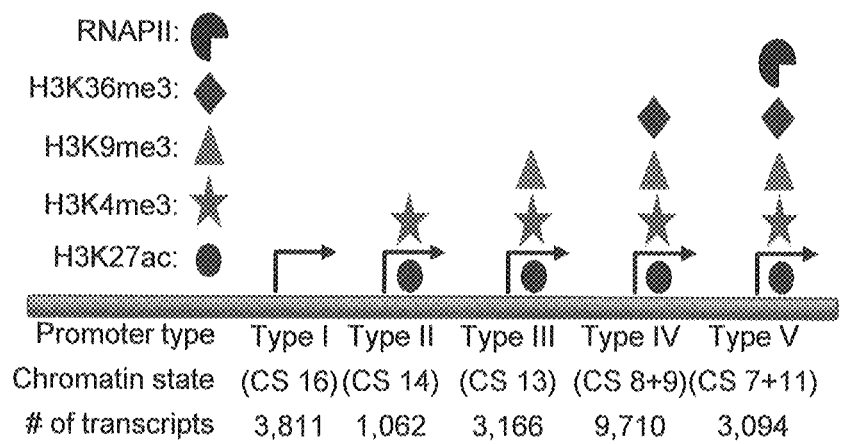
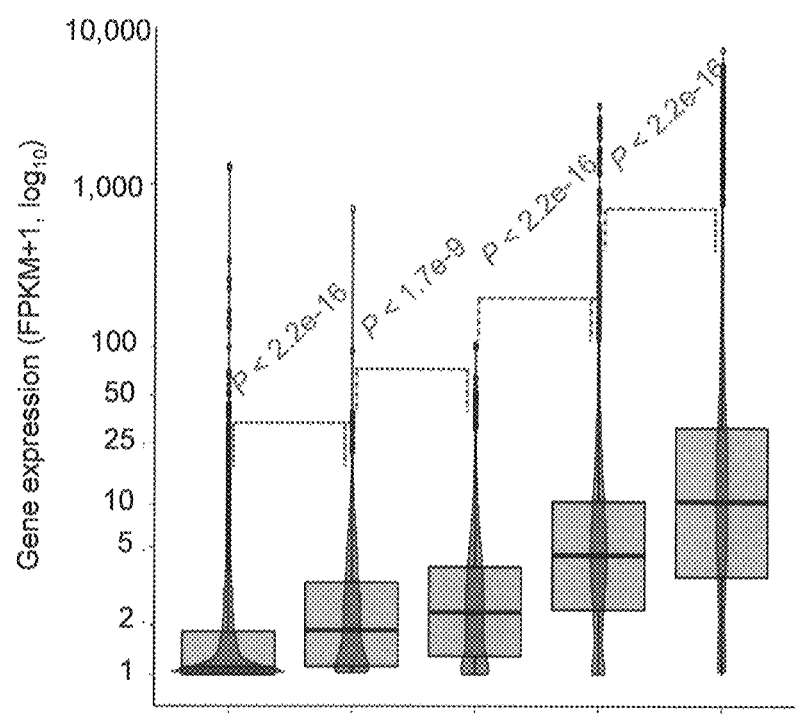

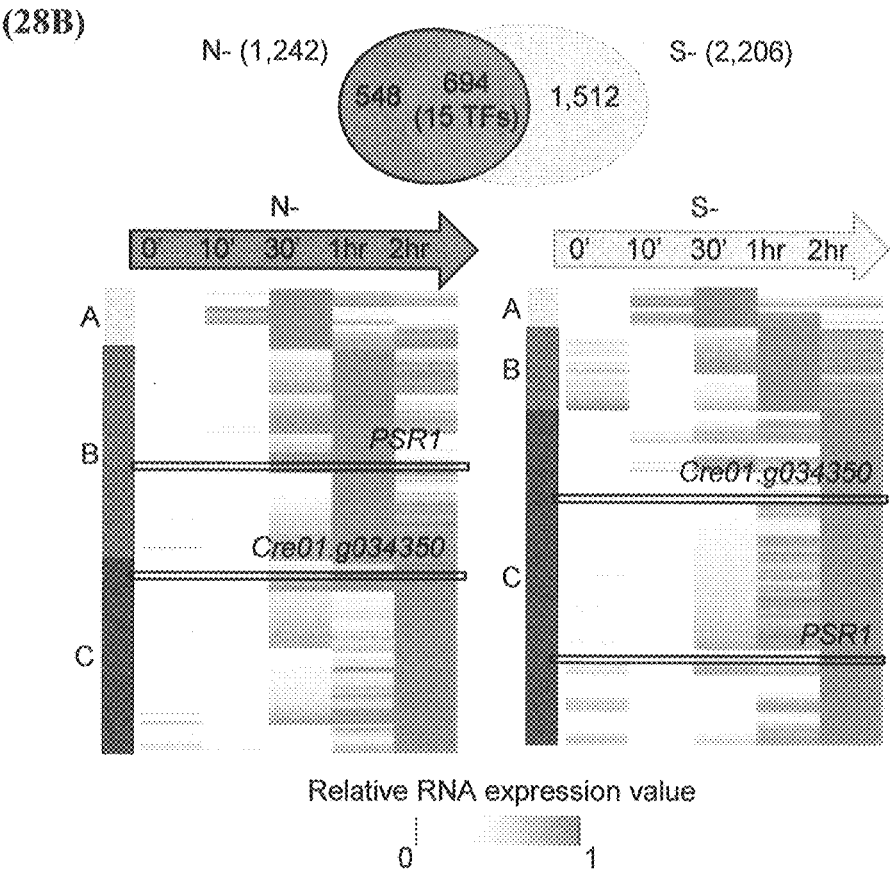
Figure 28A-B

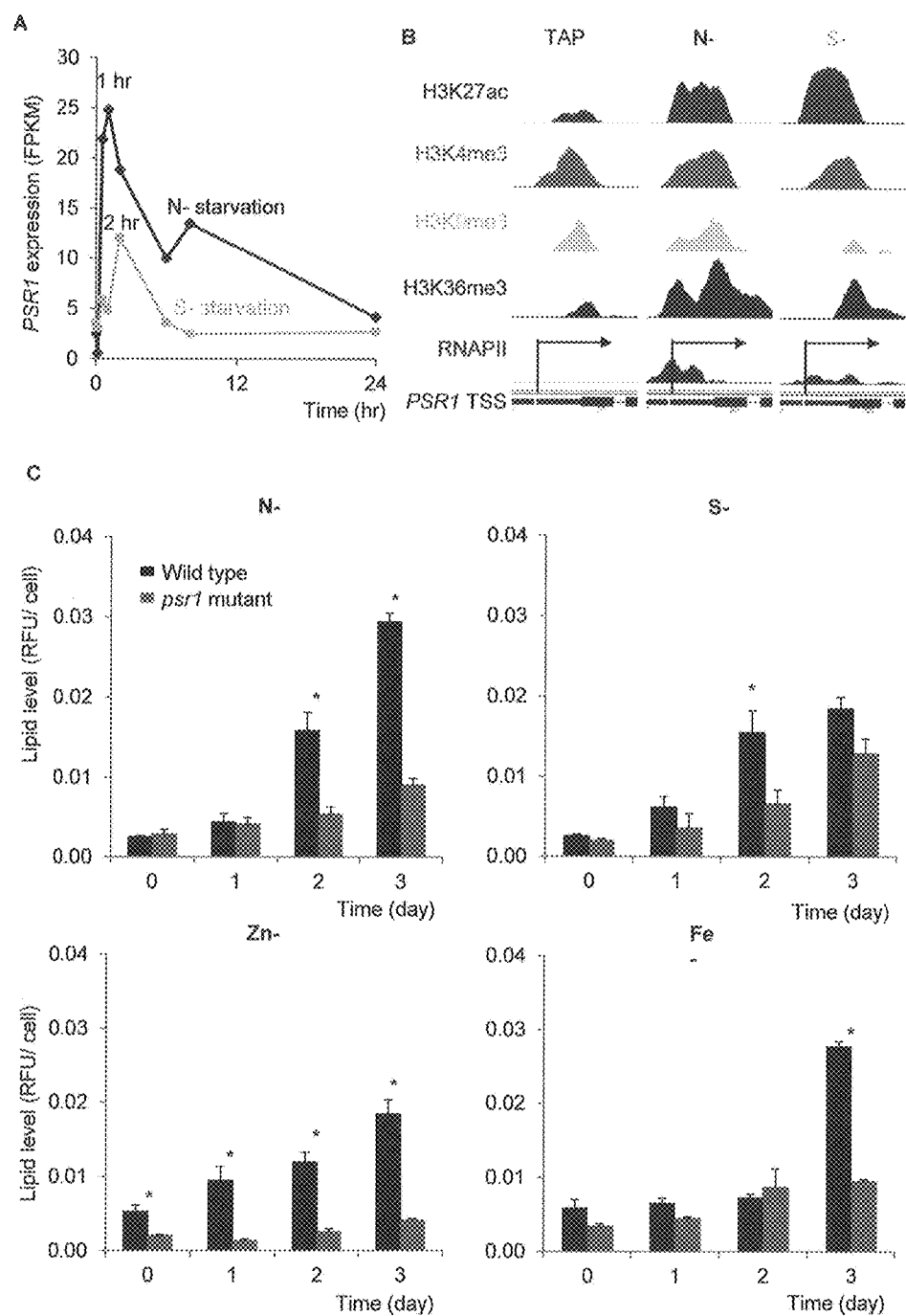

Figure 30A-B
(A)
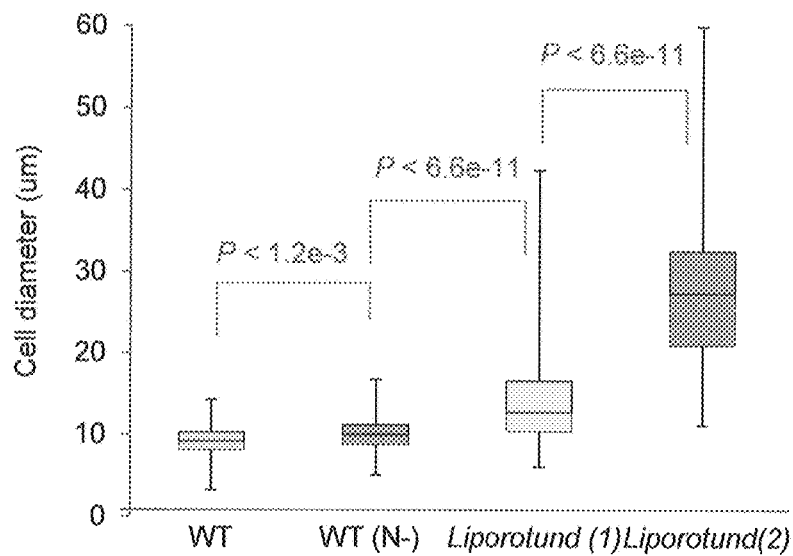
(B)
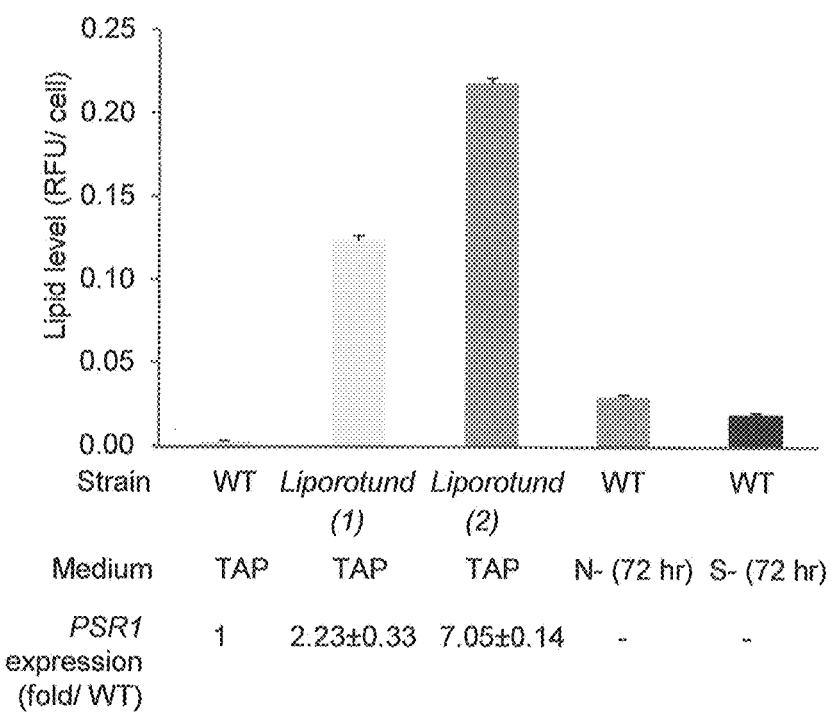

Figure 32A-C
(A)
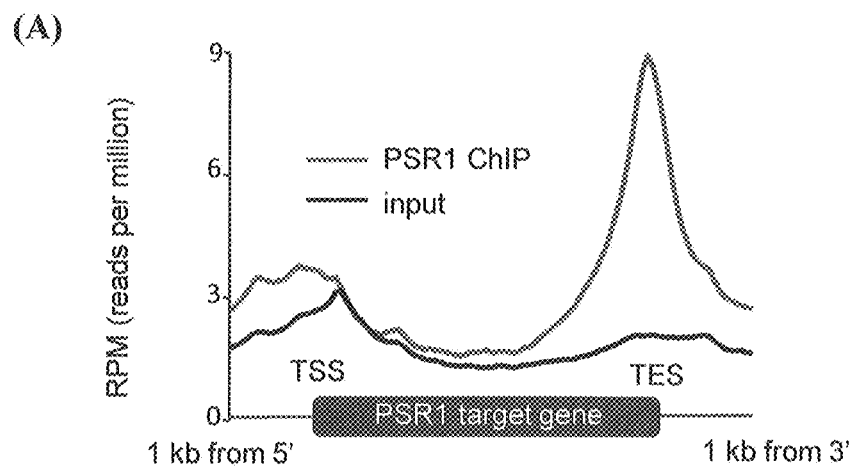
(B)
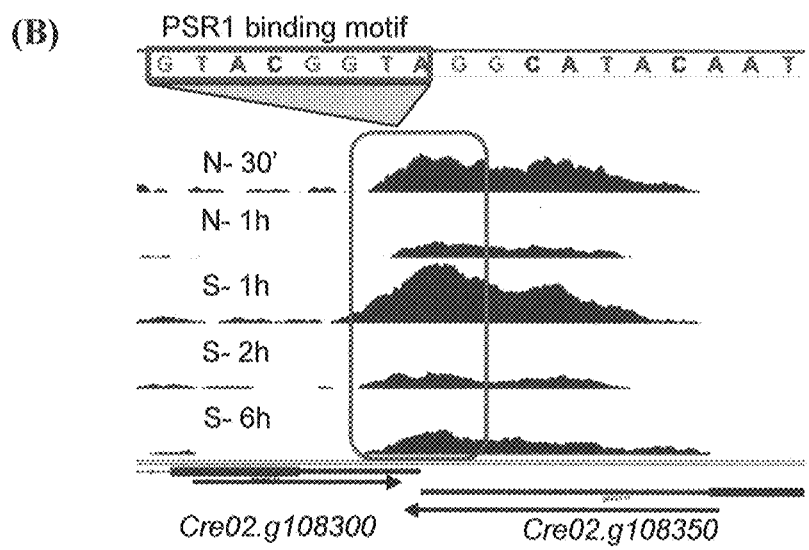
(C)
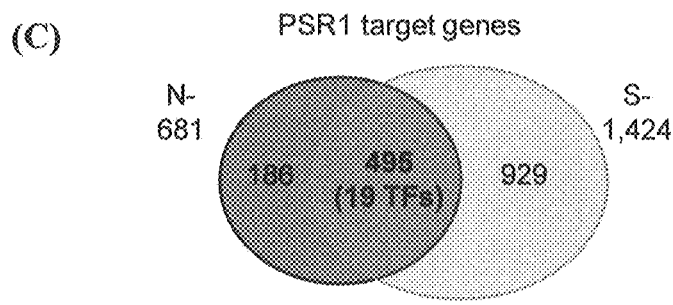

Figure 35A-B
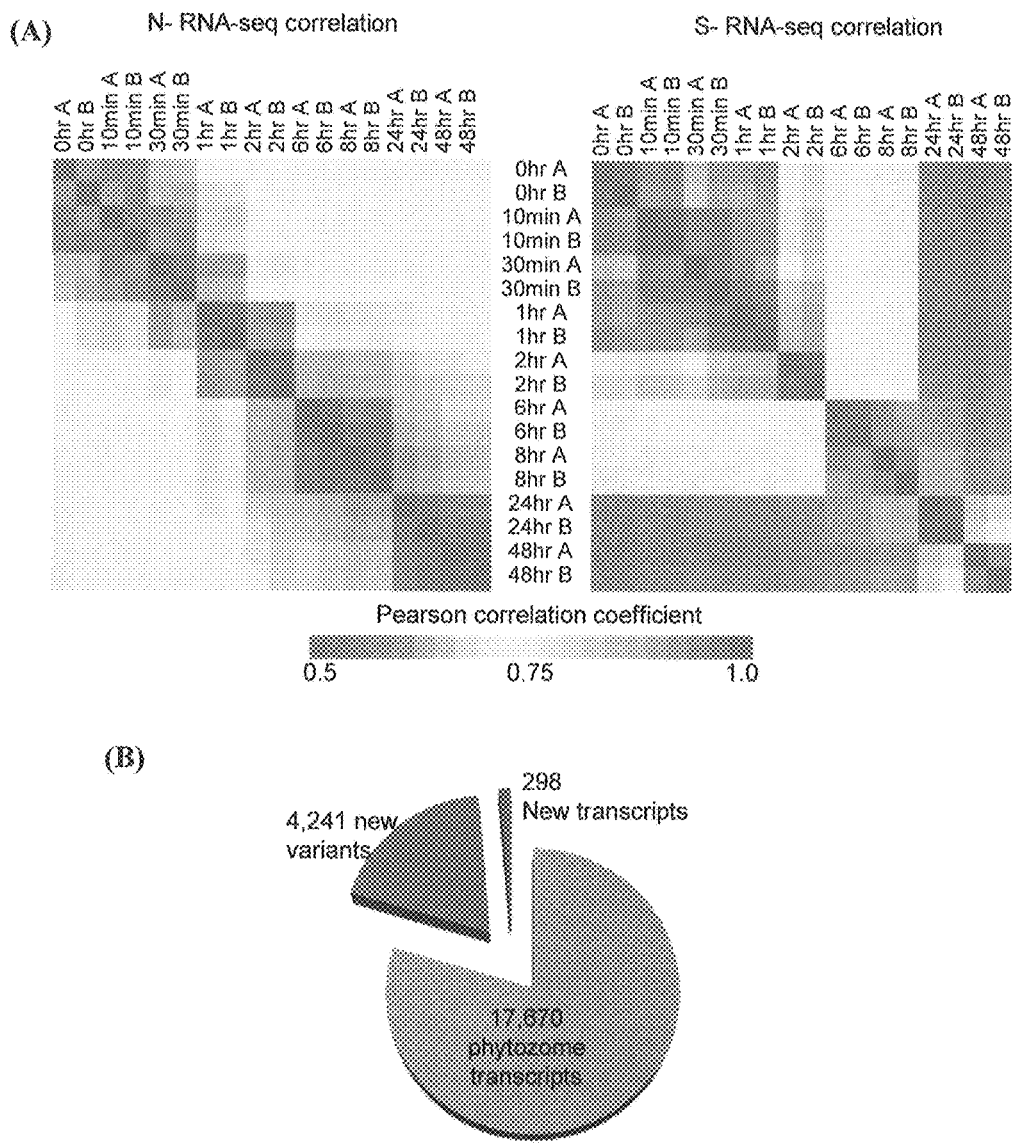

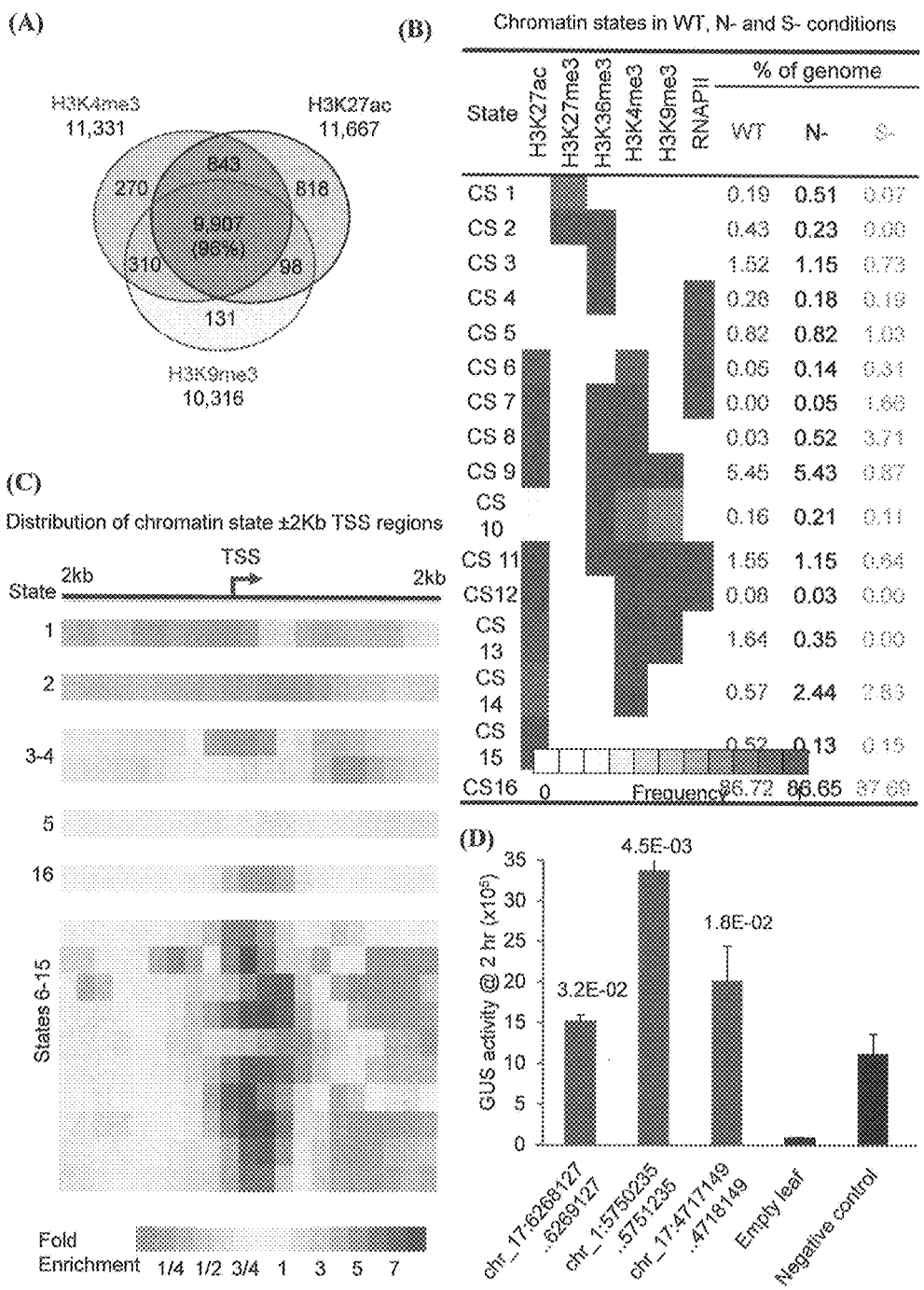
Figure 36A-D

Figure 37A-B
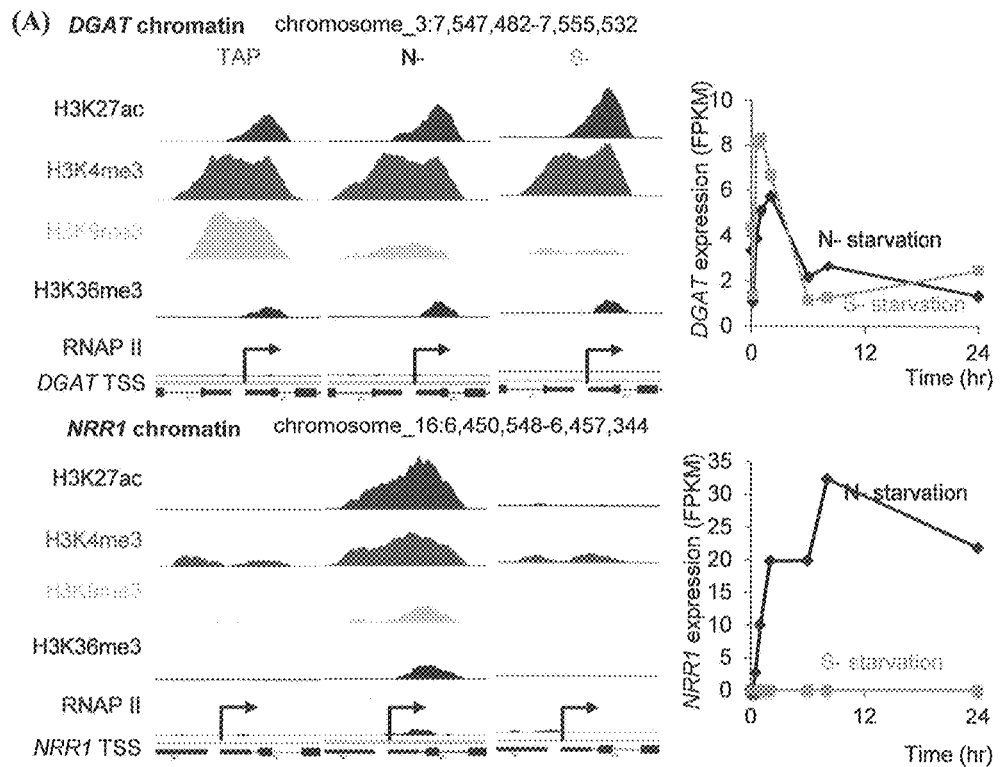
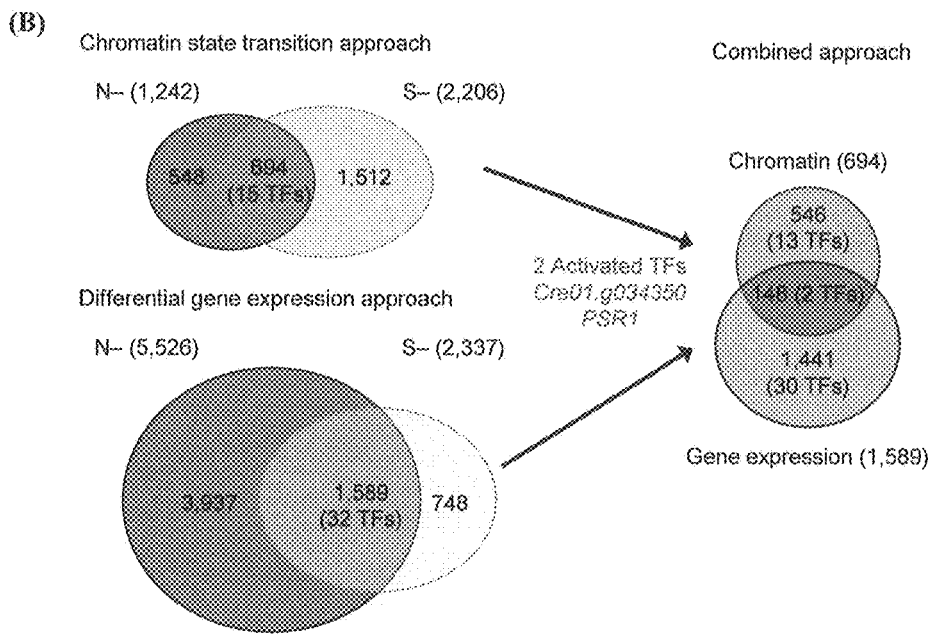

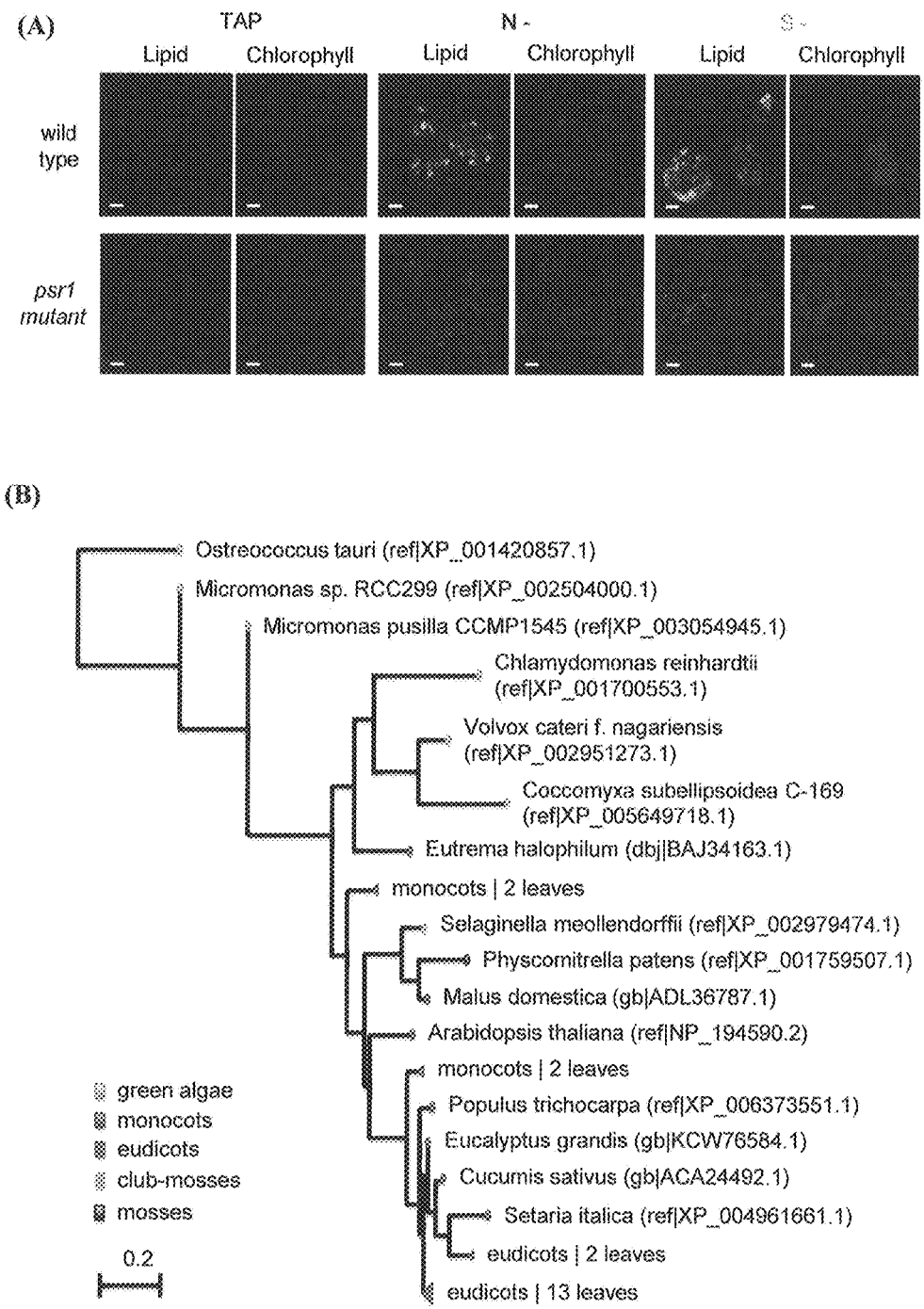

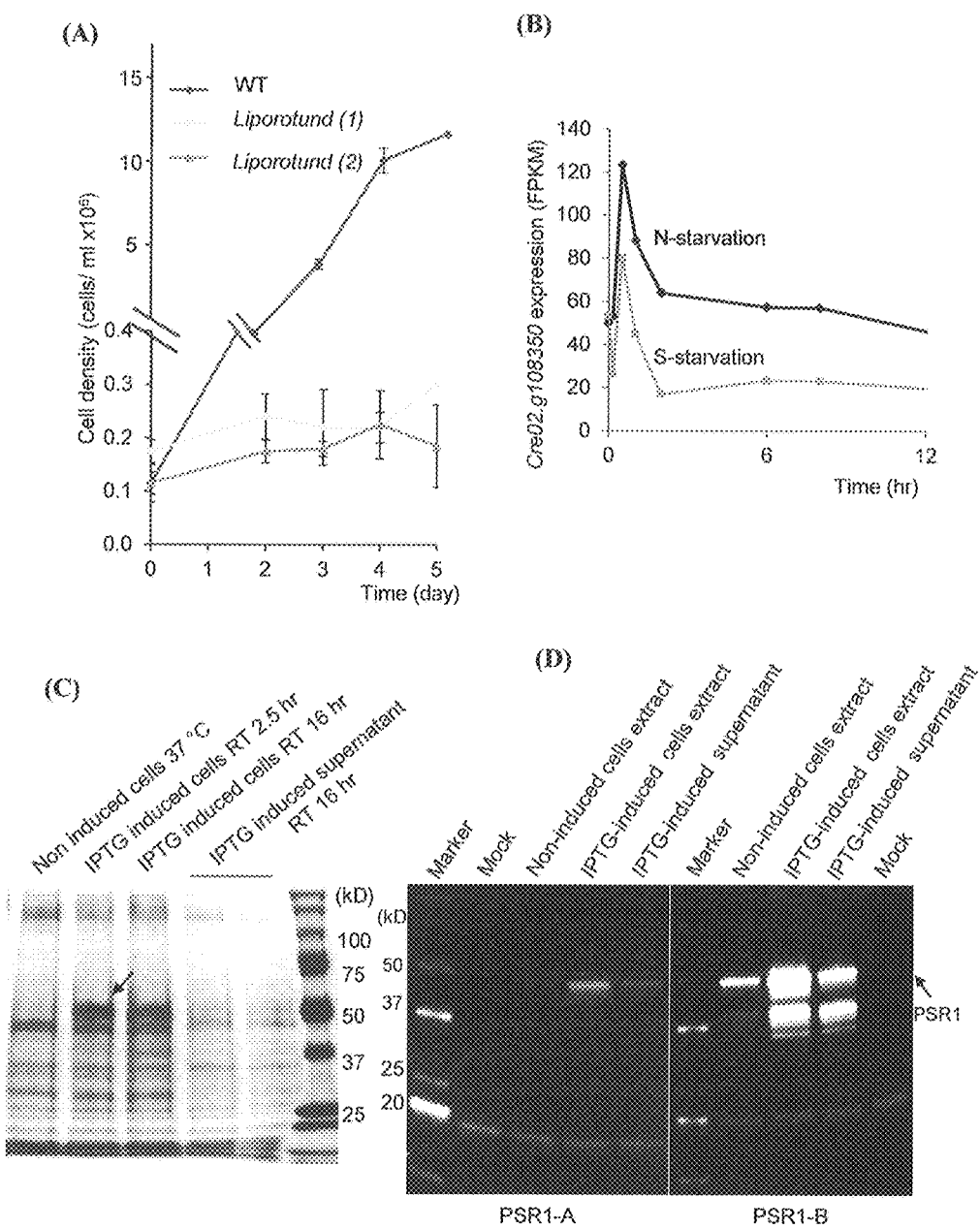
Figure 39A-D

Figure 40A-B

(A)

```
>sp|P68431|H31_HUMAN Histone H3.1 OS=Homo sapiens
GN=HIST1H3A PE=1 SV=2
>Creinhardtii|Cre06.g265000|Cre06.g265000.t1.2
(histone3, 32 copies in total)

Query coverage=98%, E-value=3e-92
Identities=127/134(95%), Positives=130/134(97%),
Gaps=1/134(0%)

01  MARTKQTARKSTGGKAPRKQLATKAARKSAPATGGVKKPHRYRPGTVALR
      |||||||||||||||||||||||||||| + |||||||||||||||||||
 01  MARTKQTARKSTGGKAPRKQLATKAARKT-PATGGVKKPHRYRPGTVALR

51  EIRRYQKSTELLIRKLPFQRLVREIAQDFKTDLRFQSSAVMALQEACEAY
      ||| +||||||||||||||||||||||||||||||||||| ||+|||| |||
 51  EIRKYQKSTELLIRKLPFQRLVREIAQDFKTDLRFQSQAVLALQEAAEAY

101  LVGLFEDTNLCAIHAKRVTIMPKDIQLARRIRGERA--------------
      |||||||||||||||||||||||||||||||||||
101  LVGLFEDTNLCAIHAKRVTIMPKDIQLARRIRGSTPANTYGLLDTAAAGD

150  --------------------------------------------------

150  LLFSVSPRSGSVVVDVSGGSMASRQLLAAGLPVSSMGLAVAC
```

(B)

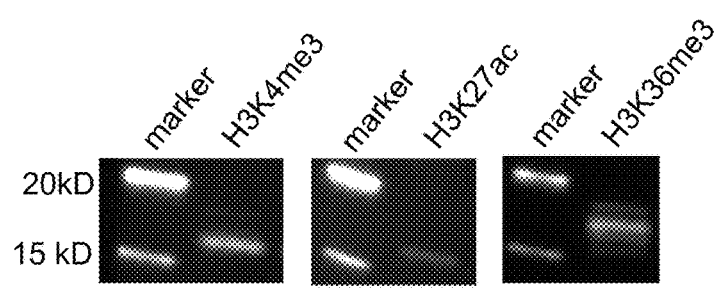

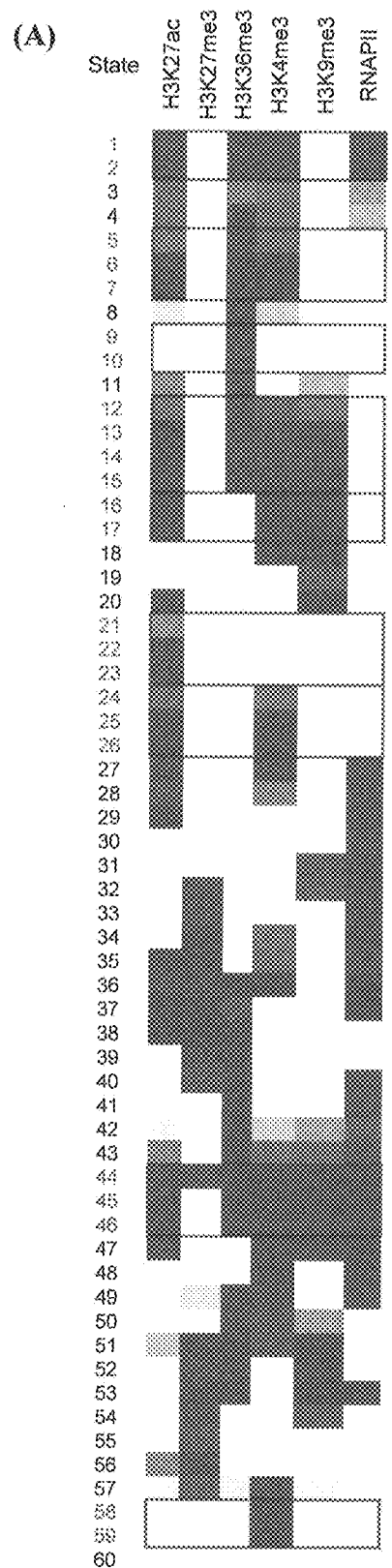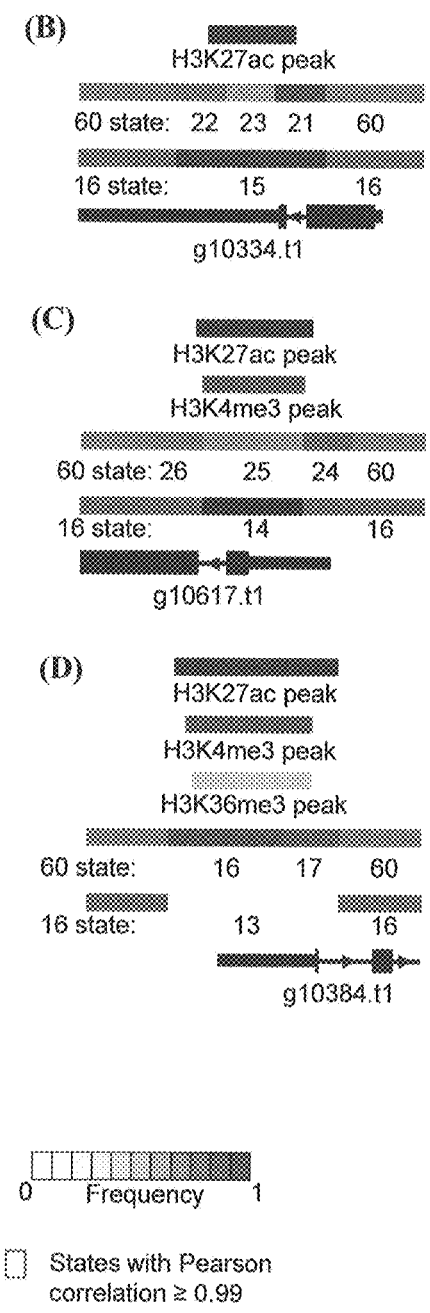
Figure 41A-D

US 10,155,954 B2

AGENTS FOR ENHANCEMENT OF PRODUCTION OF BIOFUEL PRECURSORS IN MICROALGAE

CROSS-REFERENCES TO RELATED APPLICATIONS

This application is a continuation of PCT application PCT/US15/17586, Feb. 25, 2015, which is a non-provisional of and claims the benefit of the filing date of U.S. Patent Application No. 61/944,507, filed on Feb. 25, 2014 and U.S. Patent Application No. 62/051,265, filed on Sep. 16, 2014. Each application is herein incorporated by reference in its entirety for all purposes.

STATEMENT OF GOVERNMENTAL SUPPORT

This invention was made with government support under Contract No. DE-AC02-05CH11231 awarded by the U.S. Department of Energy. The government has certain rights in the invention.

REFERENCE TO SEQUENCE LISTING AND TABLES

This application also incorporates by reference the attached sequence listing, written in file 077429_1021586_SEQ_LST_ST25.txt, created on Aug. 22, 2016; 451,085 bytes, machine format IBM-PC, MS-Windows operating system; and tables.

BACKGROUND OF THE INVENTION

Field of the Invention

The present invention relates to synthetic biology, especially using microalgae for the production of biofuels.

Related Art

Biodiesel is one of the most promising renewable transportation fuels that have achieved remarkable success worldwide. However, the current contribution of biodiesel to global transportation fuel consumption is only 0.14%. Oil-rich microalgae have been demonstrated to be a promising alternative source of lipids for biodiesel production. To enhance the economical cost-effectiveness and environmental sustainability, many strategies were proposed and extensive studies have been carried out to attempt lipid overproduction in microalgae. These approaches include, but not limit to, manipulating the nutritional or cultivation conditions and genetic engineering microalgae strain. overexpression key enzymes in the lipid precursor TAG biosynthetic pathways. Nevertheless, significant challenges remain as these approaches seem to be either harmful to cell growth or lack of success due to the emerging of "secondary bottlenecks"

Challenges for algal biofuels include that there is no "ideal" algal species identified. Lipid accumulation tightly coupled to nutrient stress. Lipid pathway gene over-expression is largely unsuccessful. Efficient fuel production will require pathway engineering and there is only a rudimentary understanding of metabolic regulation in algae. Thus, a systems-level understanding of metabolic regulation in microalgae is needed.

BRIEF DESCRIPTION OF THE SEQUENCES

The sequences described in the sequence listing provide the nucleotide and protein sequences of 17 transcription factors which can be used for enhancing or increasing lipid production or activity in an organism.

SEQ ID No:1 is chr_12:8383195 . . . 8384442 forward primer for enhancer assay from Table 7.
SEQ ID No:2 is chr_12:8383195 . . . 8384442 reverse primer for enhancer assay from Table 7.
SEQ ID No:3 is chr_17:6268127 . . . 6269127 forward primer for enhancer assay from Table 7.
SEQ ID No:4 is chr_17:6268127 . . . 6269127 reverse primer for enhancer assay from Table 7.
SEQ ID No:5 is chr_1:5750235 . . . 5751235 forward primer for enhancer assay from Table 7.
SEQ ID No:6 is chr_1:5750235 . . . 5751235 reverse primer for enhancer assay from Table 7.
SEQ ID No:7 is chr_5:1650592 . . . 1651592 forward primer for enhancer assay from Table 7.
SEQ ID No:8 is chr_5:1650592 . . . 1651592 reverse primer for enhancer assay from Table 7.
SEQ ID No:9 is chr_7:1252718 . . . 1253788 forward primer for enhancer assay from Table 7.
SEQ ID No:10 is chr_7:1252718 . . . 1253788 reverse primer for enhancer assay from Table 7.
SEQ ID No:11 is chr_16:1135475 . . . 1136475 forward primer for enhancer assay from Table 7.
SEQ ID No:12 is chr_16:1135475 . . . 1136475 reverse primer for enhancer assay from Table 7.
SEQ ID No:13 is chr_14:2768740 . . . 2769740 forward primer for enhancer assay from Table 7.
SEQ ID No:14 is chr_14:2768740 . . . 2769740 reverse primer for enhancer assay from Table 7.
SEQ ID No:15 is chr_4:2122753 . . . 2123753 forward primer for enhancer assay from Table 7.
SEQ ID No:16 is chr_4:2122753 . . . 2123753 reverse primer for enhancer assay from Table 7.
SEQ ID No:17 is chr_17:4717149 . . . 4718149 forward primer for enhancer assay from Table 7.
SEQ ID No:18 is chr_17:4717149 . . . 4718149 reverse primer for enhancer assay from Table 7.
SEQ ID No:19 is chr_7:2540672 . . . 2541672 forward primer for enhancer assay from Table 7.
SEQ ID No:20 is chr_7:2540672 . . . 2541672 reverse primer for enhancer assay from Table 7.
SEQ ID No:21 is chr_1:4459808 . . . 4460808 forward primer for enhancer assay from Table 7.
SEQ ID No:22 is chr_1:4459808 . . . 4460808 reverse primer for enhancer assay from Table 7.
SEQ ID No:23 is chr_3:1,064,061 . . . 1,065,052 forward primer for enhancer assay from Table 7.
SEQ ID No:24 is chr_3:1,064,061 . . . 1,065,052 reverse primer for enhancer assay from Table 7.
SEQ ID No:25 is chr_5:2426137 . . . 2427133 forward primer for enhancer assay from Table 7.
SEQ ID No:26 is chr_5:2426137 . . . 2427133 reverse primer for enhancer assay from Table 7.
SEQ ID No:27 is chr_2:1,048,210 . . . 1,049,203 forward primer for enhancer assay from Table 7.
SEQ ID No:28 is chr_2:1,048,210 . . . 1,049,203 reverse primer for enhancer assay from Table 7.
SEQ ID No:29 is human pair-wise alignment sequence of H3 protein sequences between *C. reinhardtii* and human from FIG. 40A.
SEQ ID No:30 is *C. reinhardtii* pair-wise alignment sequence of H3 protein sequences between *C. reinhardtii* and human from FIG. 40A.
SEQ ID No:31 is human pair-wise alignment sequence of H3 protein sequences between *C. reinhardtii* and human from FIG. 40A.

SEQ ID No:32 is *C. reinhardtii* pair-wise alignment sequence of H3 protein sequences between *C. reinhardtii* and human from FIG. 40A.

SEQ ID No:33 is human pair-wise alignment sequence of H3 protein sequences between *C. reinhardtii* and human from FIG. 40A.

SEQ ID No:34 is *C. reinhardtii* pair-wise alignment sequence of H3 protein sequences between *C. reinhardtii* and human from FIG. 40A.

SEQ ID No:35 is *C. reinhardtii* pair-wise alignment sequence of H3 protein sequences between *C. reinhardtii* and human from FIG. 40A.

SEQ ID No:36 is transcript sequence for activated transcription factor.

SEQ ID No:37 is coding sequence for activated transcription factor.

SEQ ID No:38 is protein sequence for activated transcription factor.

SEQ ID No:39 is transcript sequence for activated transcription factor.

SEQ ID No:40 is coding sequence for activated transcription factor.

SEQ ID No:41 is protein sequence for activated transcription factor.

SEQ ID No:42 is transcript sequence for activated transcription factor.

SEQ ID No:43 is coding sequence for activated transcription factor.

SEQ ID No:44 is protein sequence for activated transcription factor.

SEQ ID No:45 is transcript sequence for activated transcription factor.

SEQ ID No:46 is coding sequence for activated transcription factor.

SEQ ID No:47 is protein sequence for activated transcription factor.

SEQ ID No:48 is transcript sequence for activated transcription factor.

SEQ ID No:49 is coding sequence for activated transcription factor.

SEQ ID No:50 is protein sequence for activated transcription factor.

SEQ ID No:51 is transcript sequence for activated transcription factor.

SEQ ID No:52 is coding sequence for activated transcription factor.

SEQ ID No:53 is protein sequence for activated transcription factor.

SEQ ID No:54 is transcript sequence for activated transcription factor.

SEQ ID No:55 is coding sequence for activated transcription factor.

SEQ ID No:56 is protein sequence for activated transcription factor.

SEQ ID No:57 is transcript sequence for activated transcription factor.

SEQ ID No:58 is coding sequence for activated transcription factor.

SEQ ID No:59 is protein sequence for activated transcription factor.

SEQ ID No:60 is transcript sequence for activated transcription factor.

SEQ ID No:61 is coding sequence for activated transcription factor.

SEQ ID No:62 is protein sequence for activated transcription factor.

SEQ ID No:63 is transcript sequence for inactivated transcription factor.

SEQ ID No:64 is coding sequence for inactivated transcription factor.

SEQ ID No:65 is protein sequence for inactivated transcription factor.

SEQ ID No:66 is transcript sequence for inactivated transcription factor.

SEQ ID No:67 is coding sequence for inactivated transcription factor.

SEQ ID No:68 is protein sequence for inactivated transcription factor.

SEQ ID No:69 is transcript sequence for inactivated transcription factor.

SEQ ID No:70 is coding sequence for inactivated transcription factor.

SEQ ID No:71 is protein sequence for inactivated transcription factor.

SEQ ID No:72 is transcript sequence for inactivated transcription factor.

SEQ ID No:73 is coding sequence for inactivated transcription factor.

SEQ ID No:74 is protein sequence for inactivated transcription factor.

SEQ ID No:75 is transcript sequence for inactivated transcription factor.

SEQ ID No:76 is coding sequence for inactivated transcription factor.

SEQ ID No:77 is protein sequence for inactivated transcription factor.

SEQ ID No:78 is transcript sequence for inactivated transcription factor.

SEQ ID No:79 is coding sequence for inactivated transcription factor.

SEQ ID No:80 is protein sequence for inactivated transcription factor.

SEQ ID No:81 is transcript sequence for inactivated transcription factor.

SEQ ID No:82 is coding sequence for inactivated transcription factor.

SEQ ID No:83 is protein sequence for inactivated transcription factor.

SEQ ID No:84 is transcript sequence for inactivated transcription factor.

SEQ ID No:85 is coding sequence for inactivated transcription factor.

SEQ ID No:86 is protein sequence for inactivated transcription factor.

SEQ ID No:87 is a rabbit polyclonal antibody raised against PSR1 peptide.

SEQ ID No:88 is a rabbit polyclonal antibody raised against PSR1 peptide.

SEQ ID No:89 is forward primer for PCR amplification of *C. reinhardtii* PSR1 cDNA.

SEQ ID No:90 is reverse primer for PCR amplification of *C. reinhardtii* PSR1 cDNA.

SEQ ID No:91 is forward primer for amplification of psr1 open reading frame fragments.

SEQ ID No:92 is reverse primer for amplification of psr1 open reading frame fragments.

SEQ ID No:93 is forward primer for amplification of PSR1 cDNA.

SEQ ID No:94 is reverse primer for amplification of PSR1 cDNA.

SEQ ID No:95 is PSR1 forward primer.

SEQ ID No:96 is PSR1 reverse primer.

SEQ ID No:97 is CBLP forward primer.

SEQ ID No:98 is CBLP reverse primer.

SEQ ID No:99 is XP_001700553.1, phosphorus starvation response 1 protein, transcriptional regulator, *Chlamydomonas reinhardtii*.

SEQ ID No:100 is 6-base repeats.

SEQ ID No:101 is palindromic motif.

BRIEF DESCRIPTION OF THE DRAWINGS AND TABLES

FIG. 1: Biofuels from Microalgae: The Current Challenges. Challenges for algal biofuels include that there are no "ideal" algal species identified, lipid accumulation is tightly coupled to nutrient stress, lipid pathway gene over-expression is largely unsuccessful, efficient fuel production will require pathway engineering, and there is a rudimentary understanding of metabolic regulation in algae. A systems-level understanding of metabolic regulation in microalgae is needed.

Figure 2:
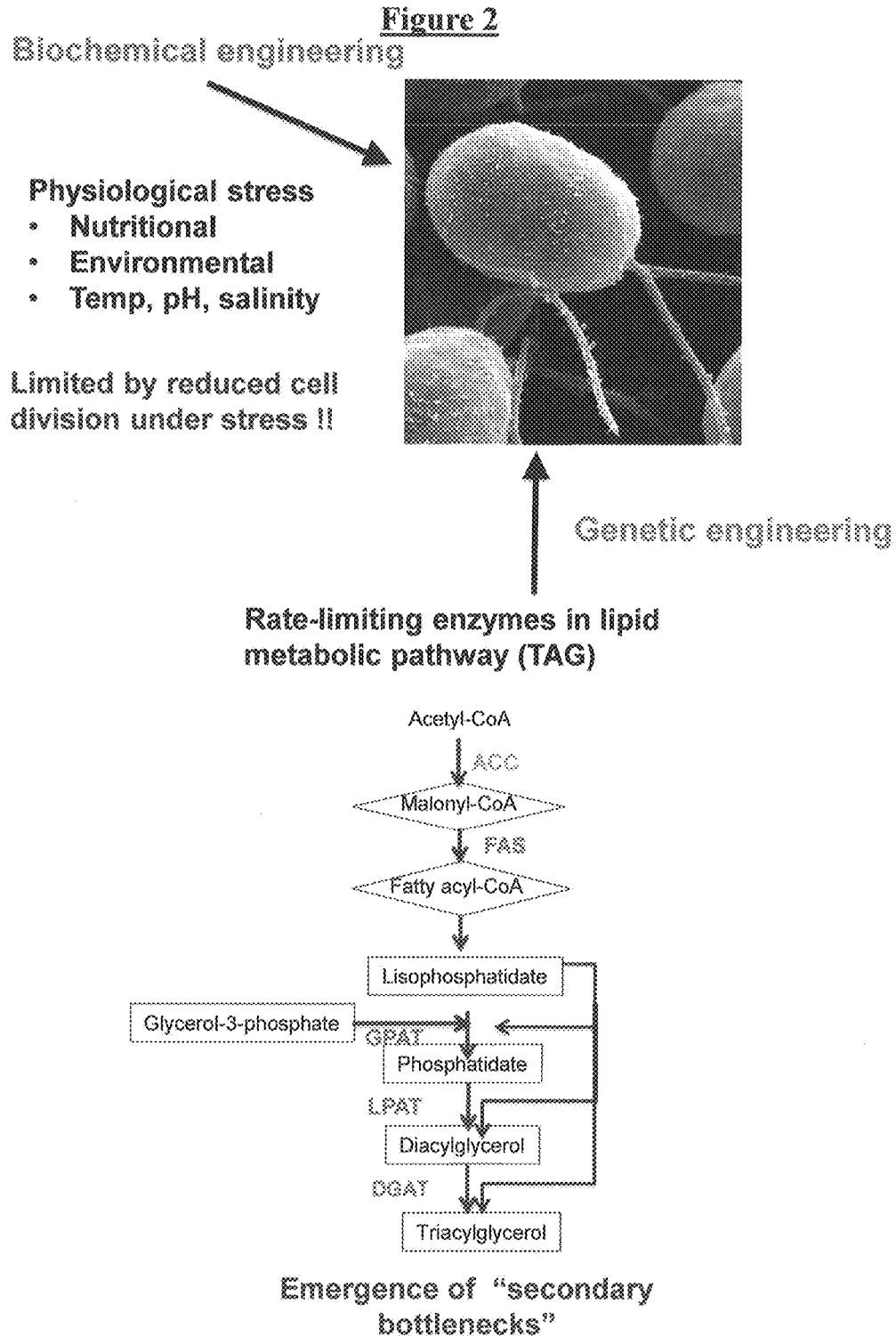

FIG. 2: Schematic describing lipid over-production strategies in microalgae.

Figure 3:
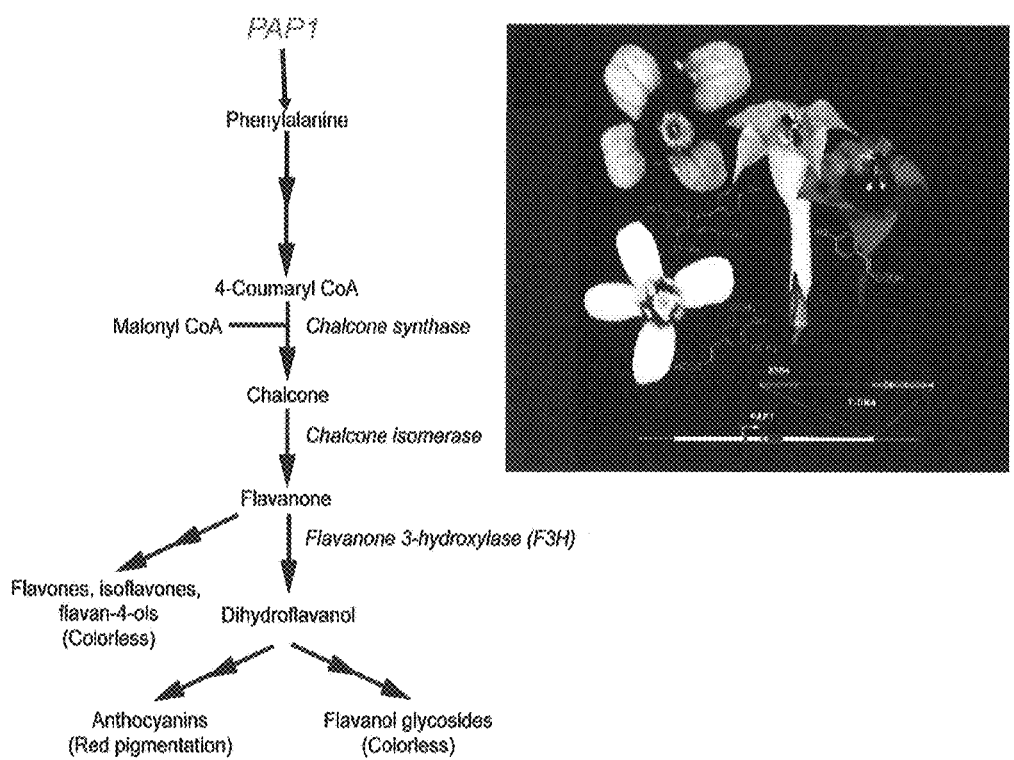

FIG. 3: Transcription Factor Engineering for PAP1 over-expression enhances pigmentation in *Arabidopsis*. Manipulate the transcriptional regulators that control TAG synthesis & storage.

Figure 4:
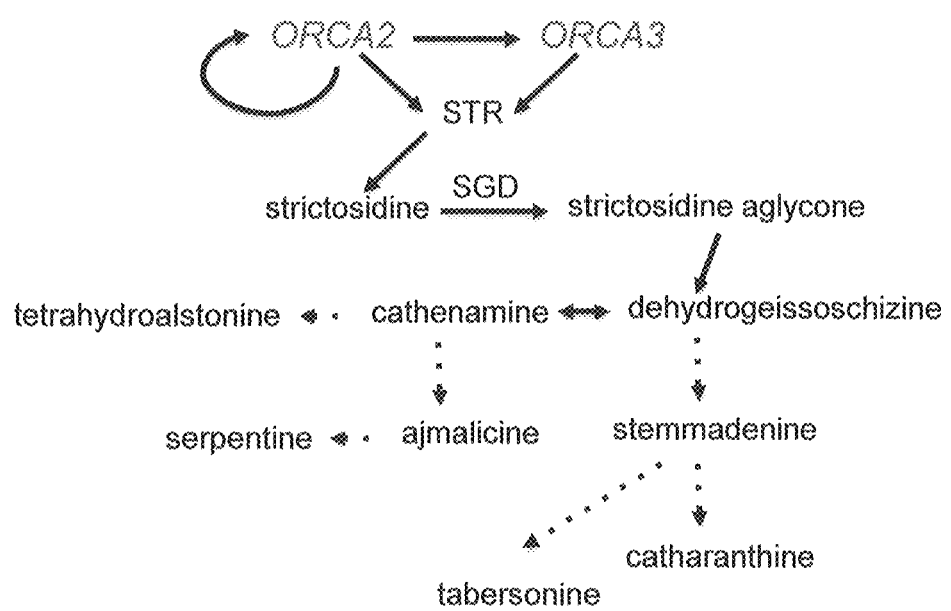

FIG. 4: Transcription Factor Engineering for ORCA3 over-expression enhances TIA biosynthesis in Tobacco. Manipulate the transcriptional regulators that control TAG synthesis & storage.

FIG. 5 illustrates Epigenome Analysis—chromatin state directly reflects transcriptional activity.

FIG. 6 illustrates Epigenome Analysis—chromatin state directly reflects transcriptional activity. Epigenetic analysis can identify master regulators of lipid accumulation. We hypothesized that TFs acting as master regulators for lipid biosynthetic pathways are induced by the *Chlamydomonas* stress response and that changes in chromatin state can predict TF regulators that standard transcript abundance studies have missed. Our approach was to measure genome-wide changes in chromatin state in *Chlamydomonas* subjected to lipid-inducing conditions, identify genes activated or repressed based on chromatin state & focus on transcription factors and test TF function by gene inactivation and over-expression.

Figure 7:
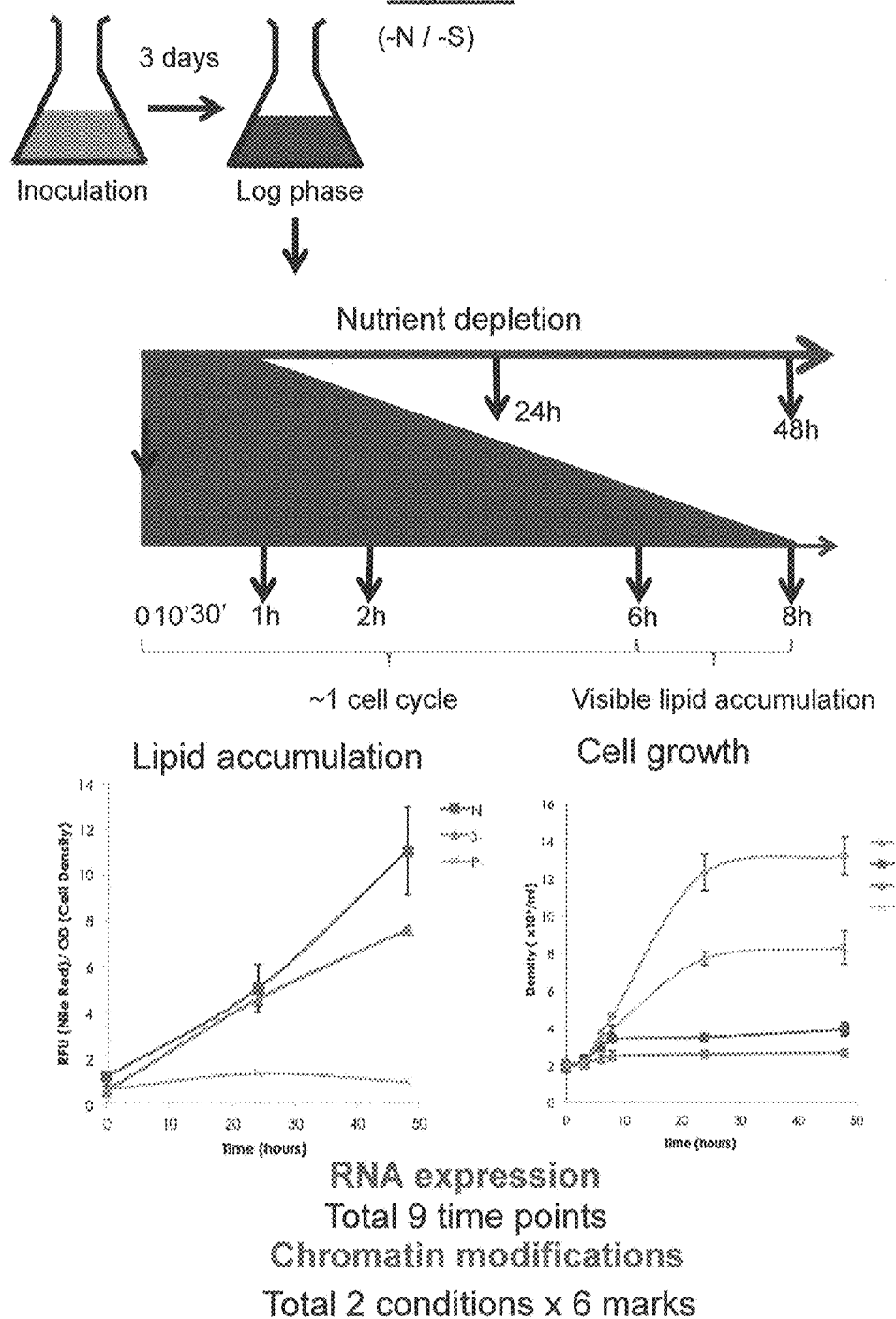

FIG. 7 shows preliminary experiments performed.

Figure 8:
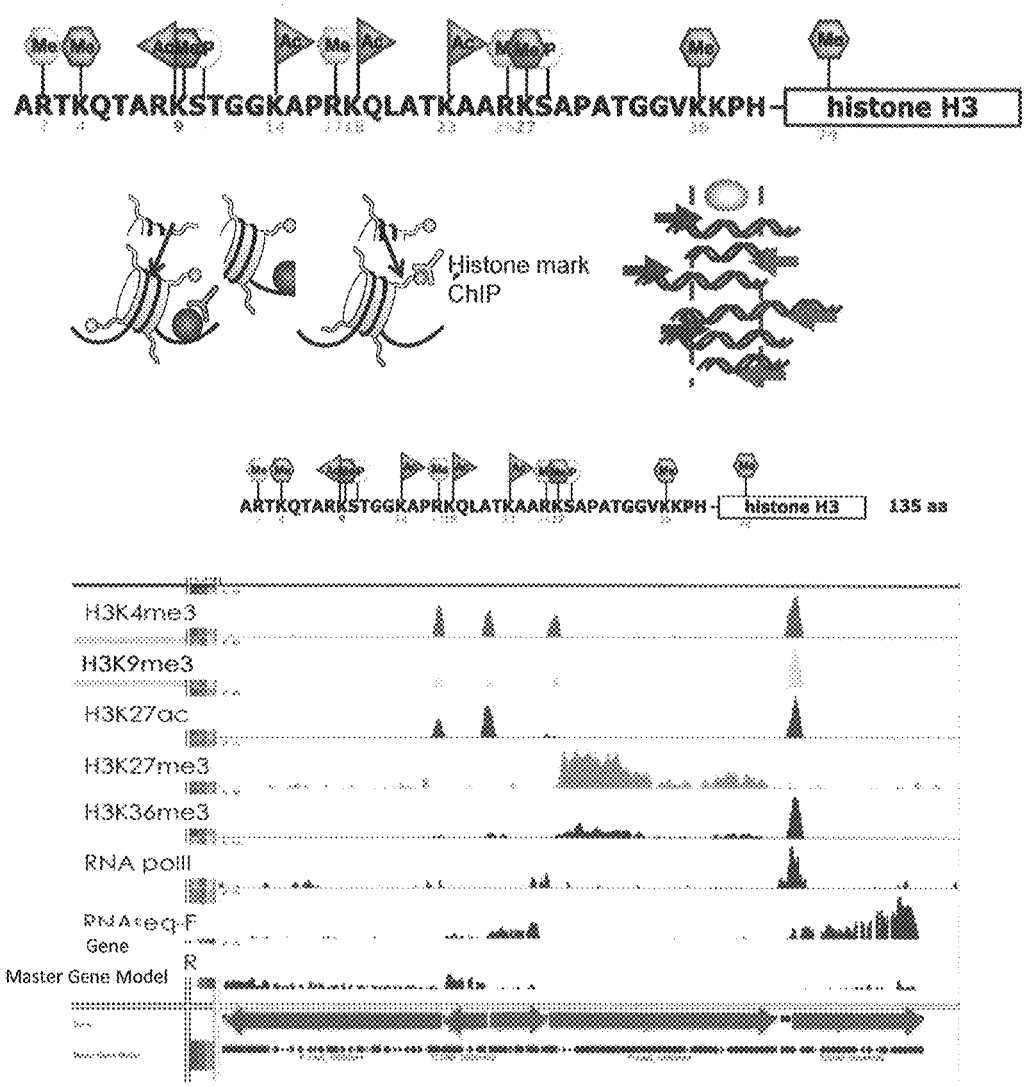
Figure 9:
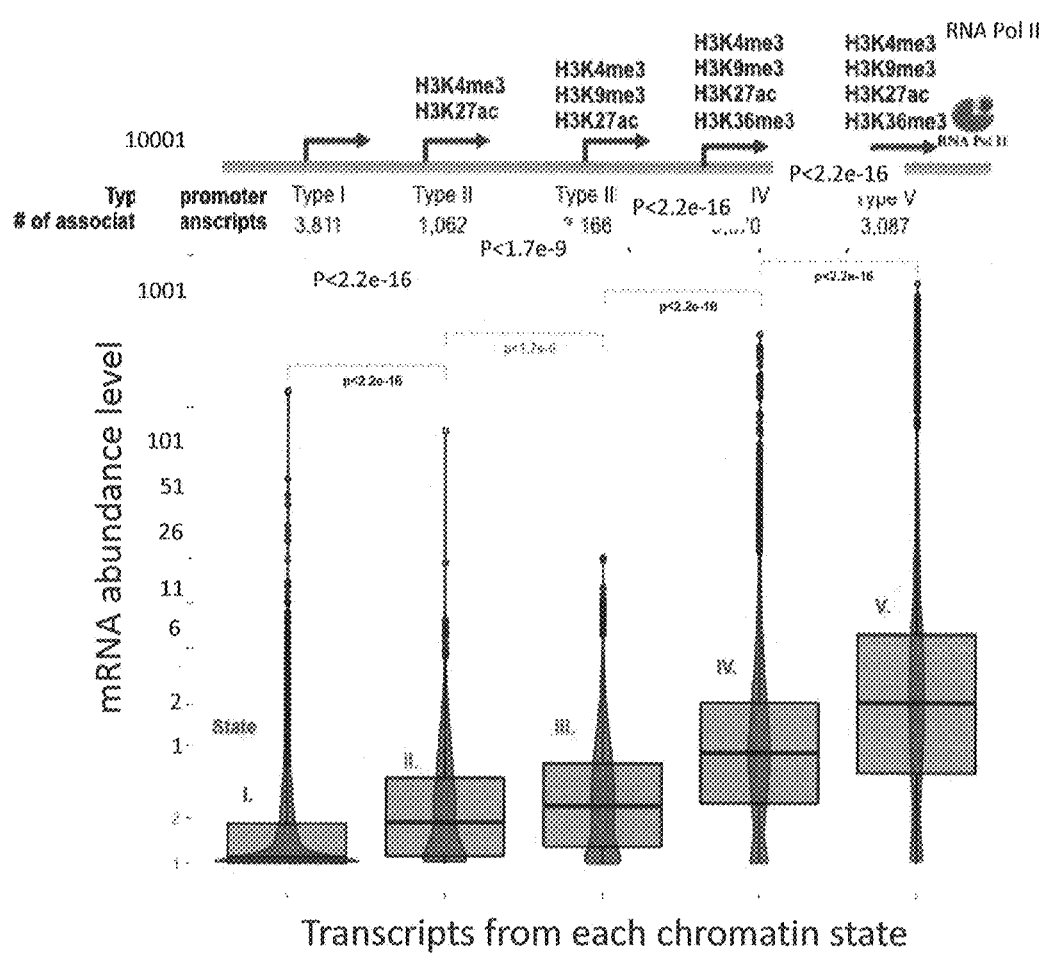

FIG. 8 CHIP-Seq mapping of chromatin modifications. A ChIP-Seq experiment start by fragmenting the sample, follow by enriching with antibody specific to the protein of interest. The DNA fragments bound by the targeted proteins is than released for sequencing. The reads from the sequenced are mapped and extended to construct a combined read density profile. We perform the experiment for 7 PTMs on histone H3 protein and the protein Pol II. This is how the data look like after processing FIG. 9 shows Chromatin state is highly correlated with transcript abundance in *Chlamydomonas*. Chromatin modifications occur in particular patterns and we are able to assign all the gene promoters in the Chlamy genome to one of 5 patterns differing by progressive addition of modifications. These patterns are highly associated with the abundance transcripts driven by these promoters, but note the very wide variation in abundance for each promoter type. The power of chromatin state analysis comes from being able to identify genes encoding relatively low abundance transcripts as transcriptionally activated. Then point to the bottom of range of type Iv and type V promoters.

Figure 10:
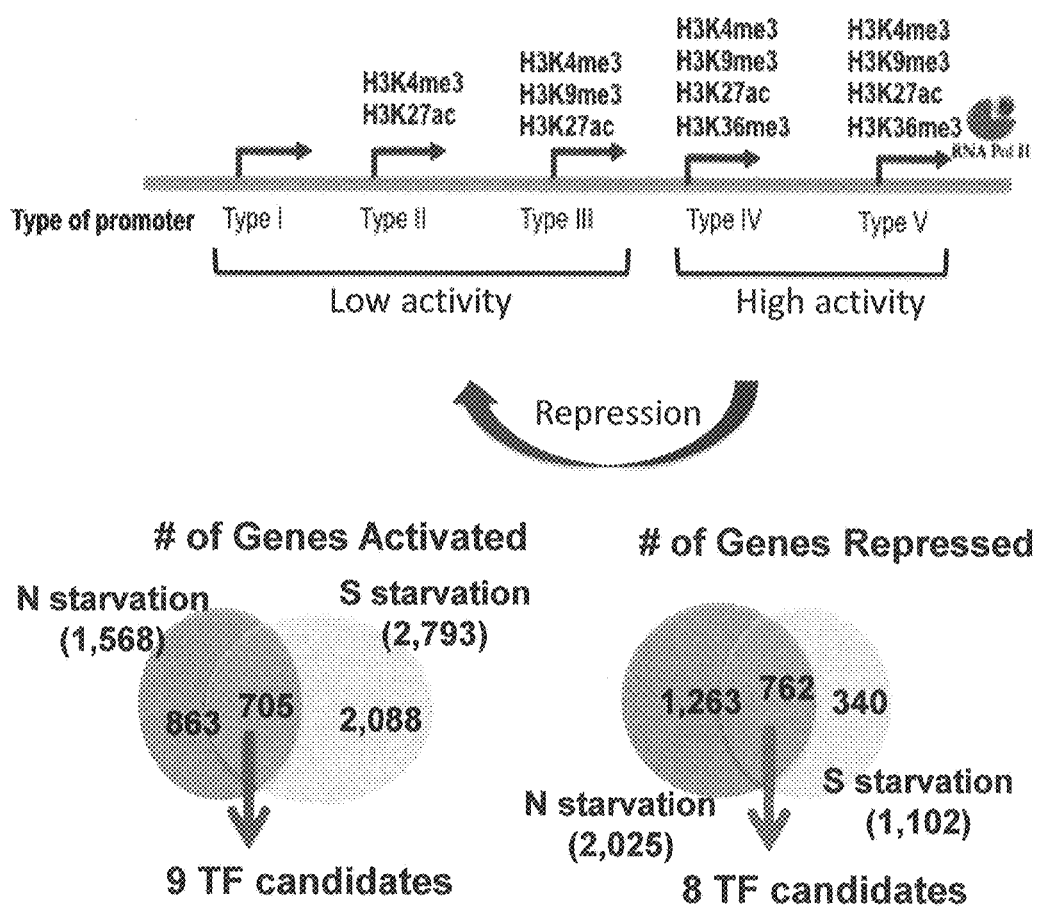

FIG. 10: Candidate regulators inferred from chromatin state transitions.

FIG. 11: Candidate regulators inferred from chromatin state transitions.

Figure 12:
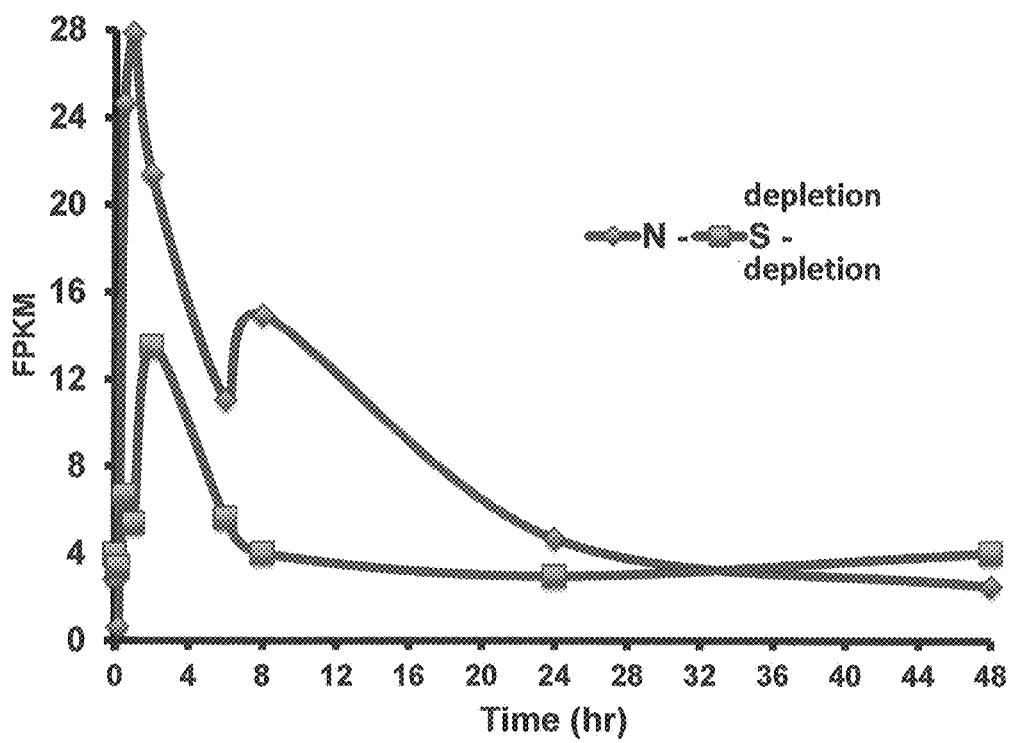

FIG. 12 shows Psr1 mRNA level during stress. Psr1 overlooked from expression data alone. Expression is transient and peak expression is low to modest. This demonstrates the power of epigenomic analysis.

Figure 13:
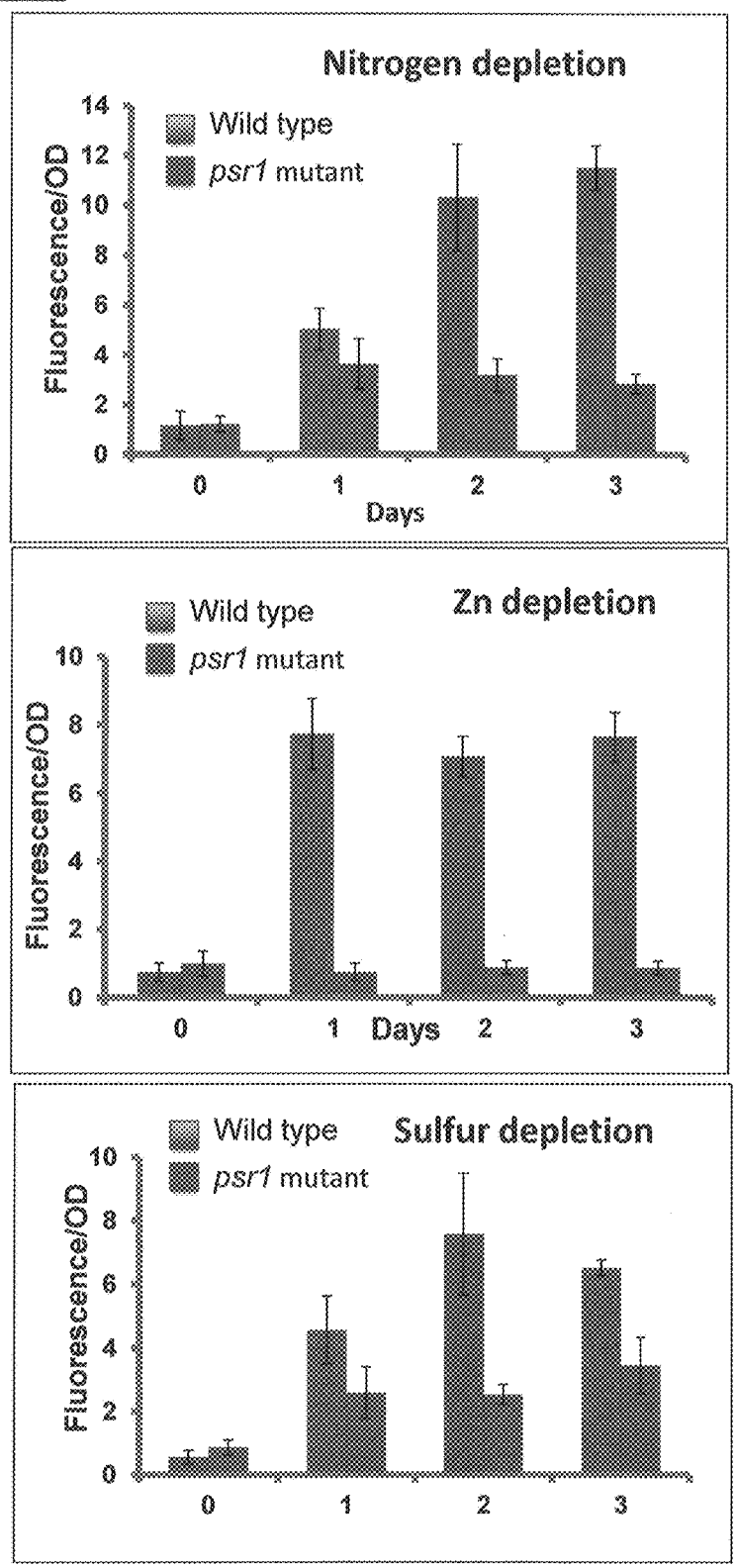

FIG. 13: PSR1 loss-of-function prevents storage lipid accumulation during nutrient stress. Psr1 mutant: 50-90% reductions in lipid accumulation during nutrient stress. 1st TF to be required for lipid storage in multiple conditions.

Figure 14:
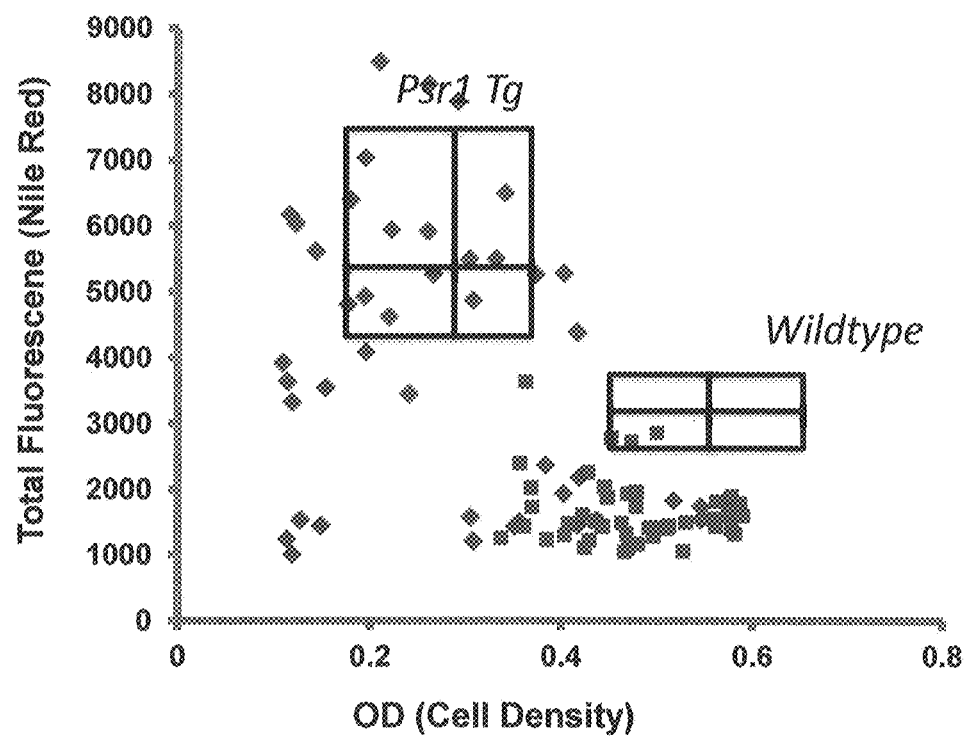

FIG. 14: Psr1 over-expression is sufficient to drive lipid accumulation. Up to 6× increase in total lipid & >12× increase in lipid/cell. Psr1 is necessary & sufficient for storage lipid accumulation. c/w role as a master regulator of lipid accumulation.

Figure 15:
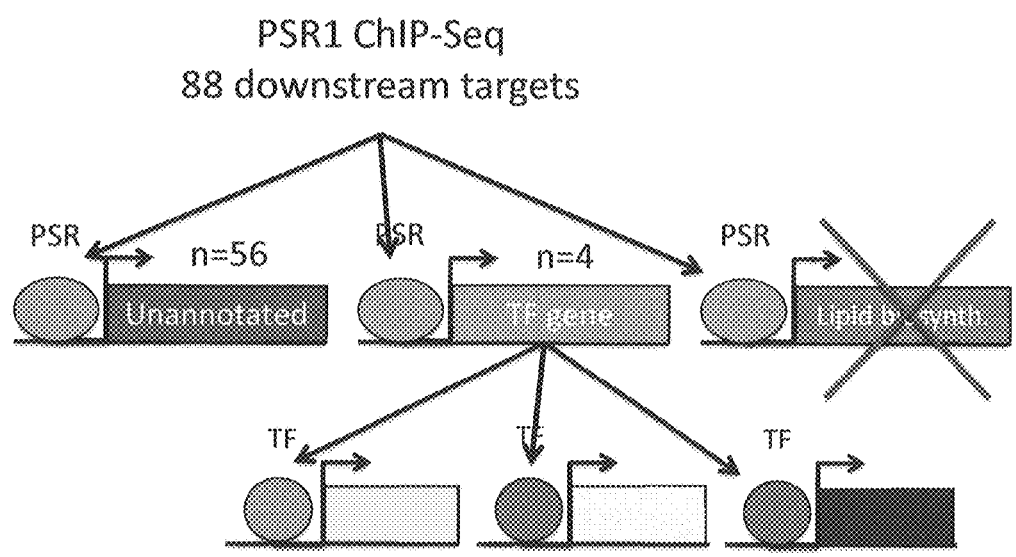

FIG. 15 shows a schematic of Psr1 downstream targets. This suggests Psr1 effects may be pleiotropic which is consistent with proximal regulator of stress response.

Figure 16:
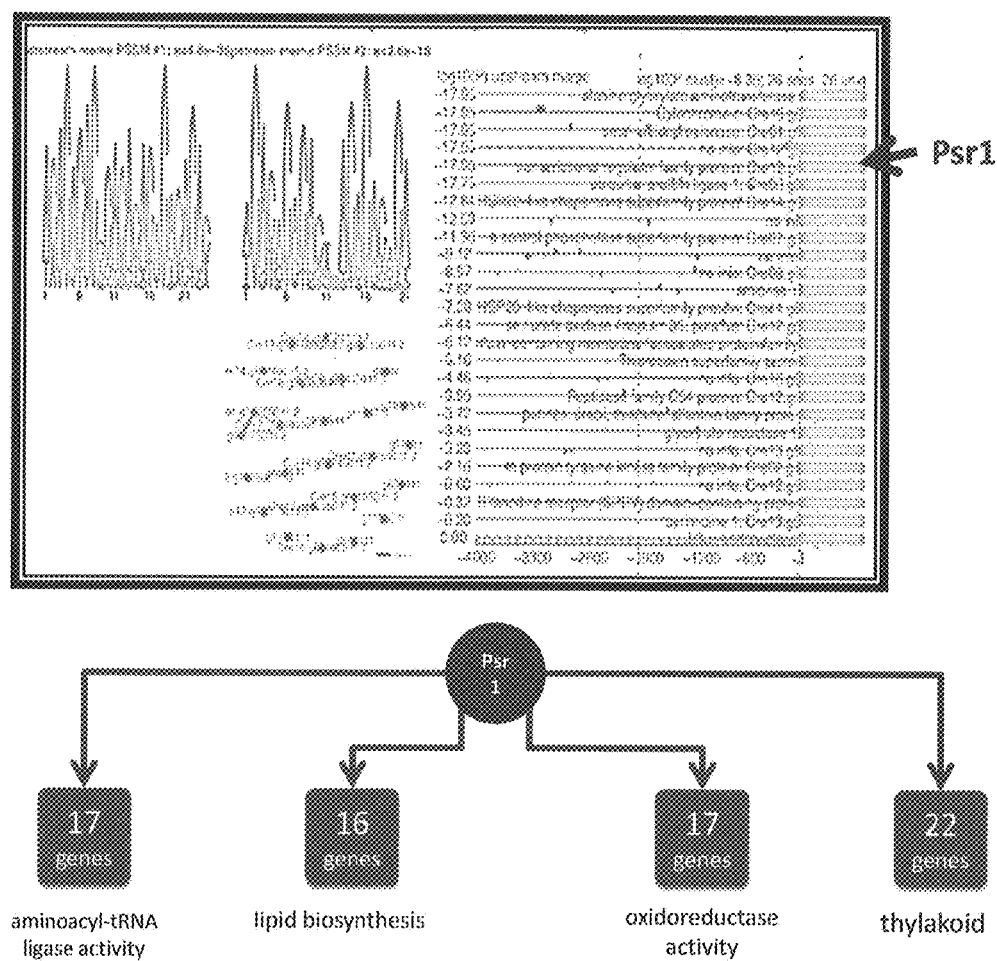

FIG. 16: Computational model of the Psr1 regulatory network.

Figure 17:
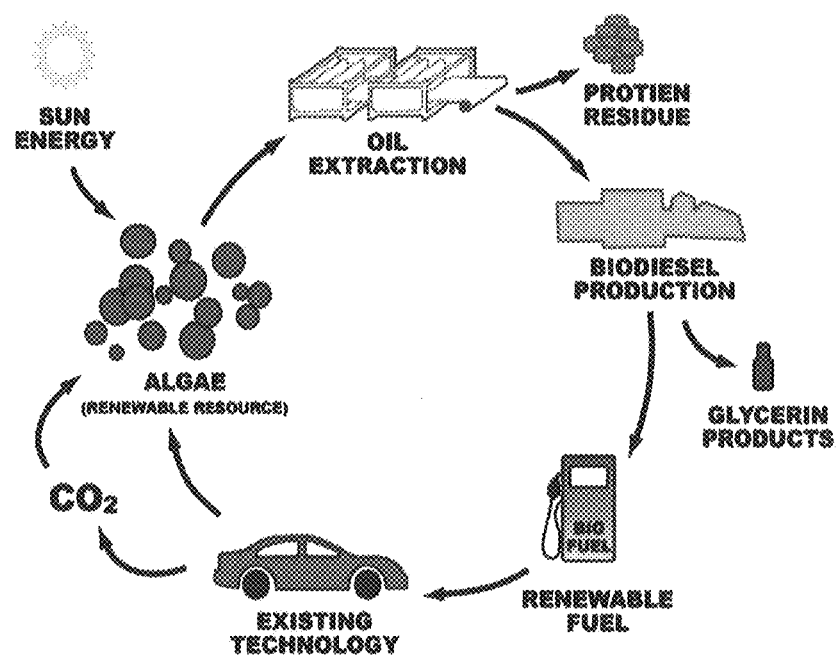

FIG. 17: Many aspects of lipid metabolism must be controlled to enable algal biofuels. Like our understanding of metabolic regulation in Chlamy, our understanding of the lipid biosynthetic pathways is also very limited. If we are ever to produce algal biofuels we need an understanding of the both to be able to do intelligent engineering. Among other things, we need a better understanding of lipid titer, lipid composition, lipid flux, higher value fuels and desire to switch between growth and target lipid production.

Figure 18:
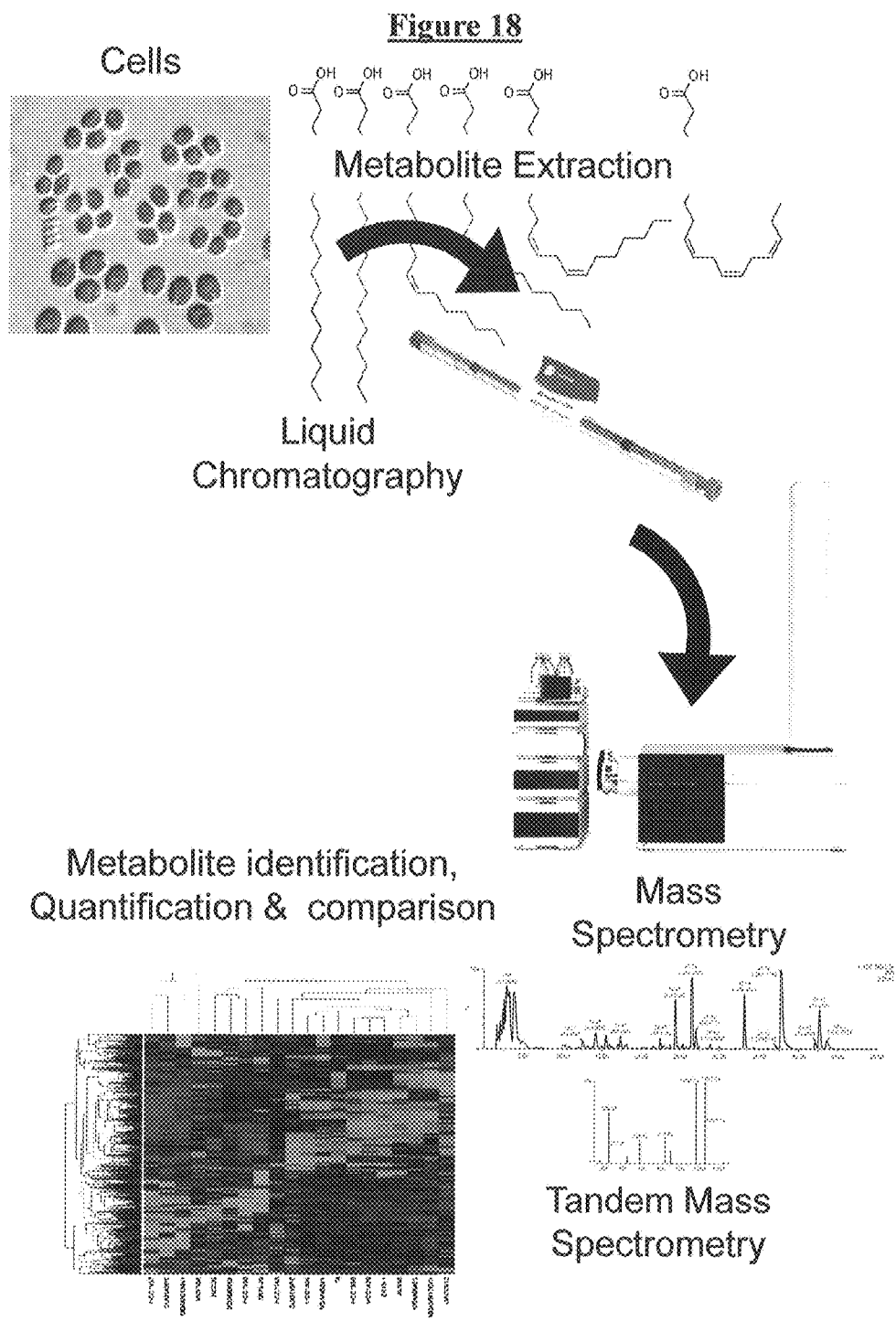

FIG. 18: Algal lipid and metabolite analysis using LC-MS/MS.

Figure 19:
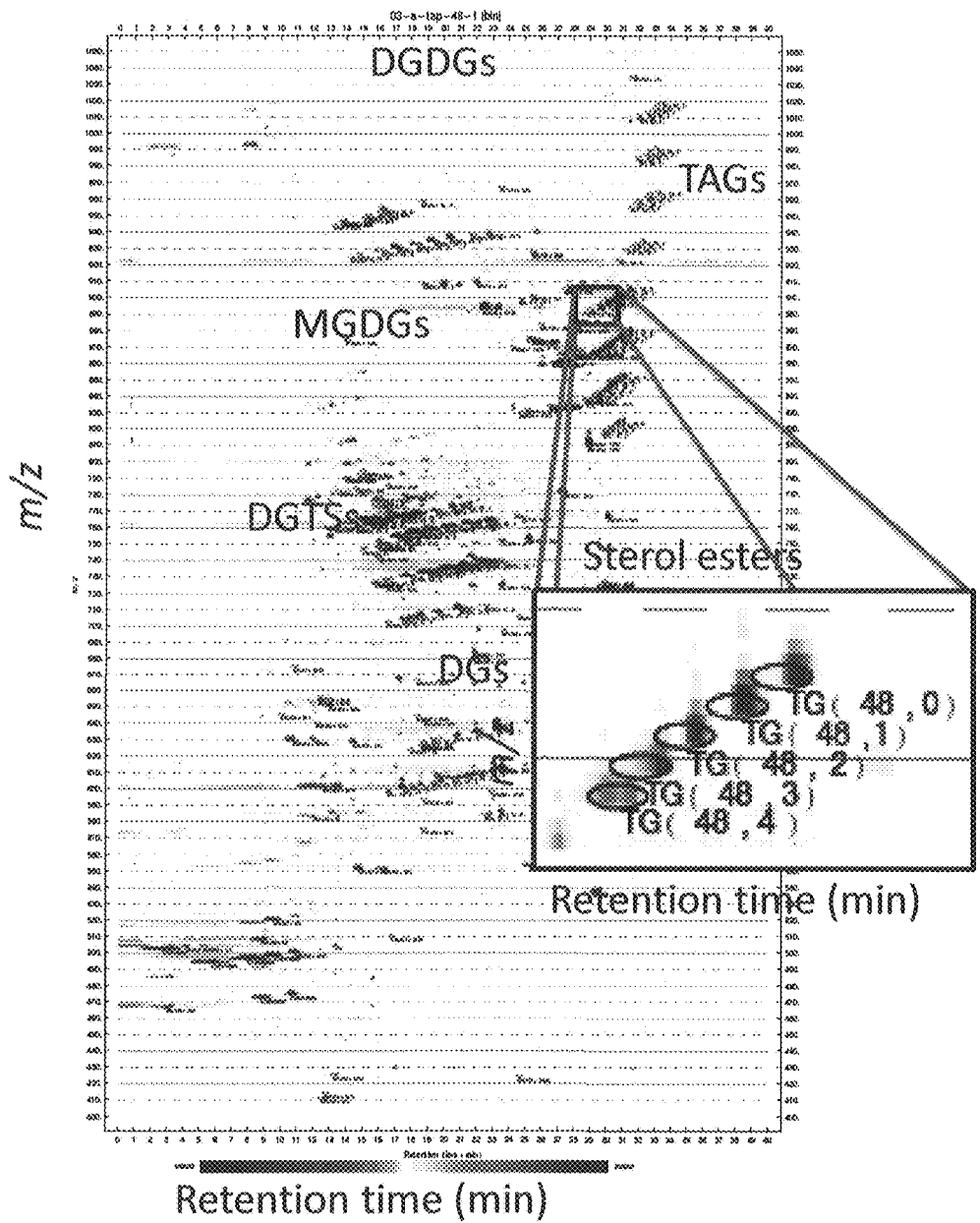

FIG. 19: Preliminary results: LC-MS/MS lipidomics method. WT Chlamy grown rich medium (TAP) produces a wide range of lipid classes. A surprisingly complex >200 lipids total detected. Once developed this can be performed quickly. LC-MS/MS methods will be used to measure lipid precursors including Acyl-ACPs. A database of the lipids and lipid precursors can be made available.

Figure 20:
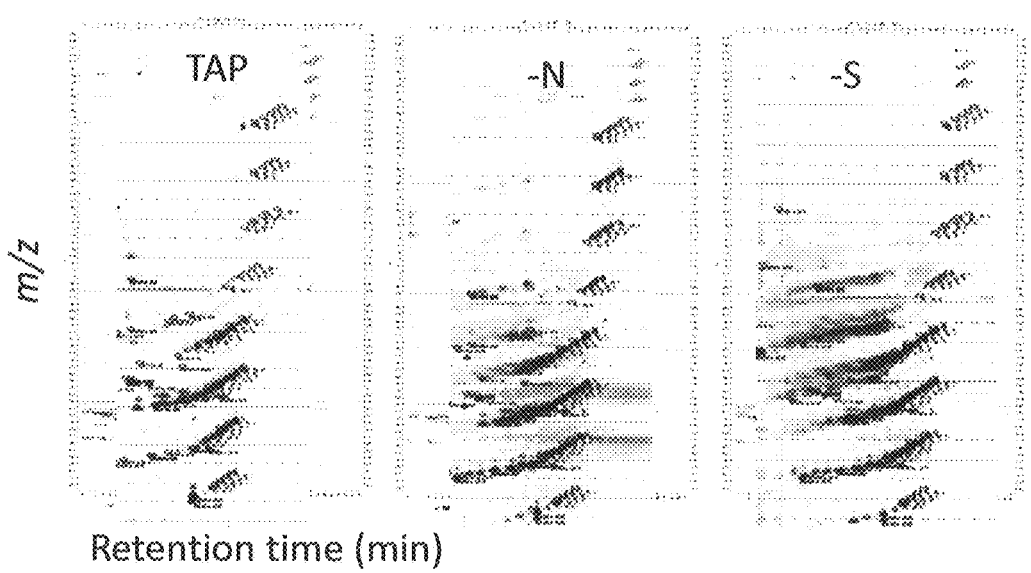

FIG. 20: Preliminary results: wide-spread changes in response to nutrient starvation. Performed 2 experiments characterizing —N and —S. Four replicates per condition in the two experiments (n=8 total). Data are highly reproducible. Observe the expected large-scale changes in lipid composition with nutrient starvation.

Figure 21:
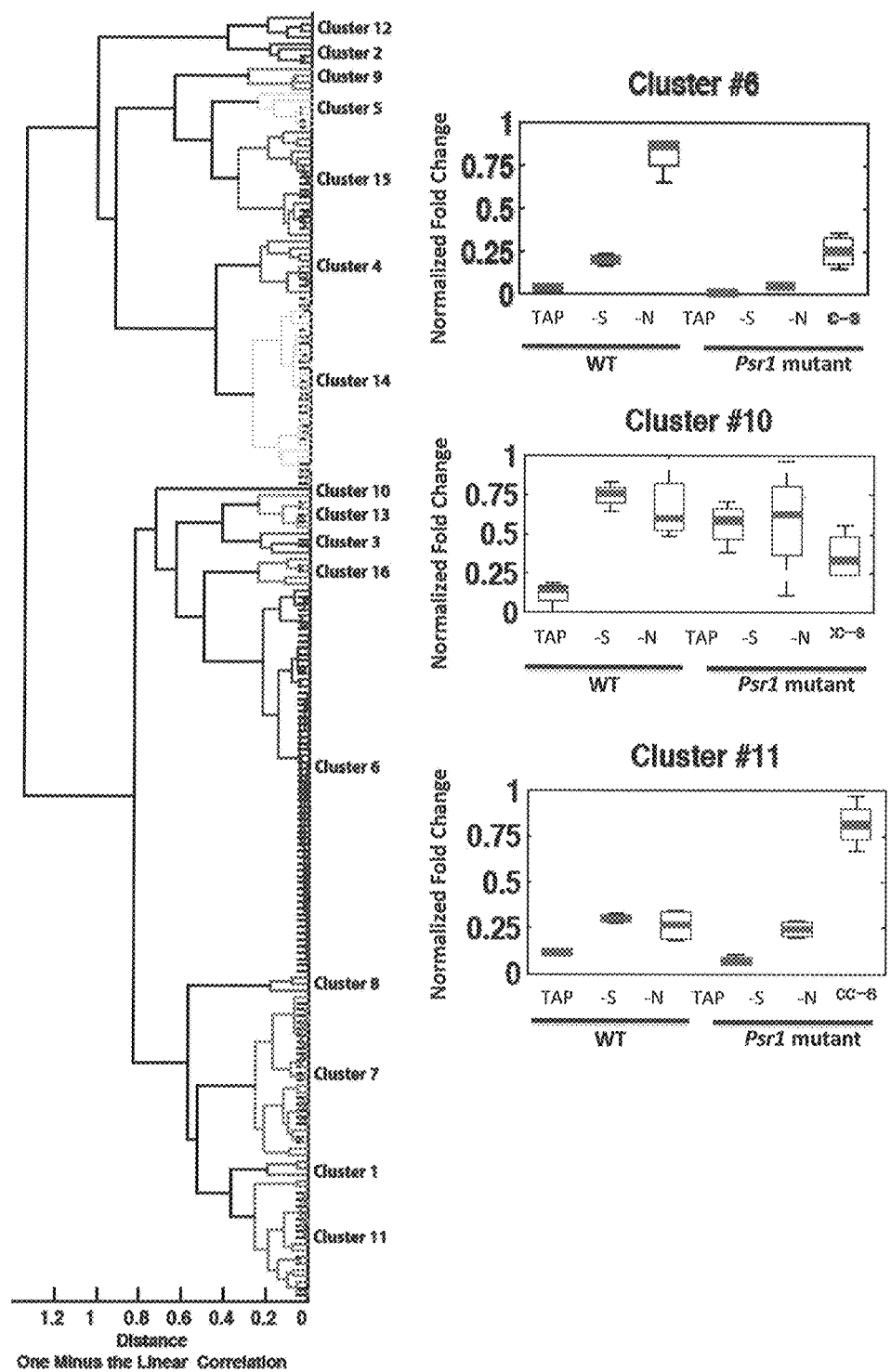

FIG. 21: Global changes in lipid production in Psr1 mutant vs WT. 162/202 lipids were altered in Psr1 mut vs WT. These results are highly reproducible. The largest cluster c/w Nile red staining. We suspected that derangement of lipid metabolism responsible for decreased growth. Specific engineering is required. Psr1 candidate gene summary: Psr1 is required for lipid storage under multiple stresses and is capable of driving lipid accumulation in non-stress conditions, powerful proof-of-concept for all 4 aims and the general concept of TF engineering, evaluation of Psr1 demonstrates effectiveness & synergy of consortium team, complex effects of Psr1 underscore why foundational understanding must precede engineering.

Figure 22:
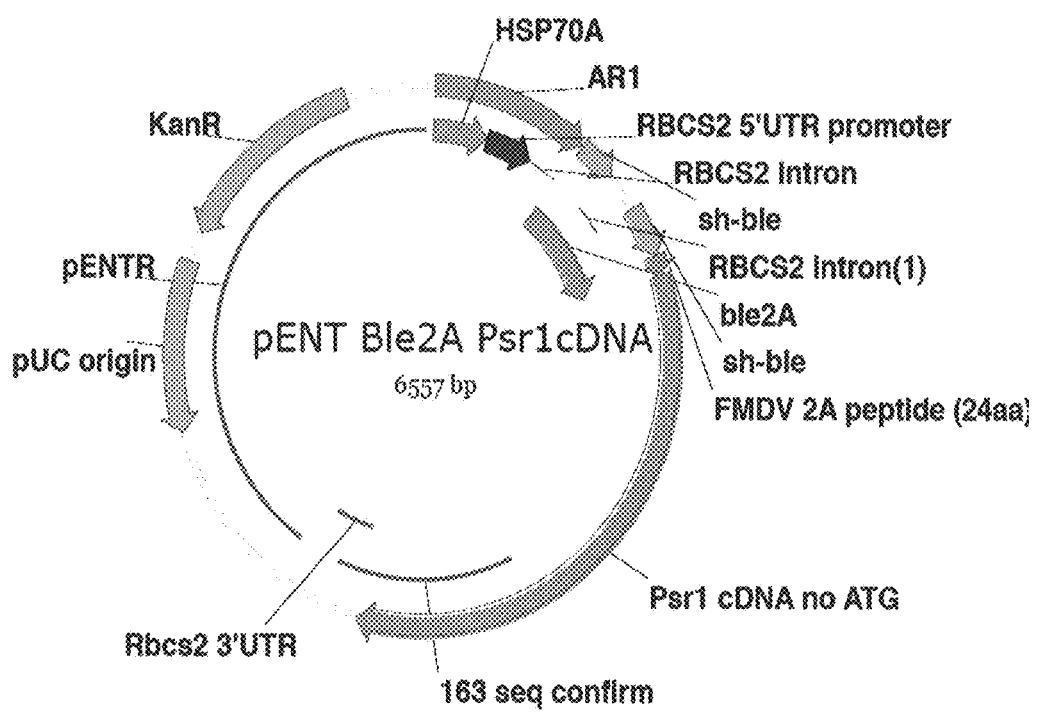

FIG. 22: Schematic of Psr1 cDNA construct and its components

FIG. 23A-B: An integrative epigenetic and transcriptomic strategy to identify lipid regulators in *C. reinhardtii*. (23A) *C. reinhardtii* cells in log phase were subjected to acute N- and S- depletion for 48 hr. Cell growth and lipid accumulation were measured to confirm the effect of nutrient starvation. RNA expression, histone modifications and RNAPII occupancy were profiled at designated time points. (23B) Genes whose TSSs display inactive (left) and active (right) chromatin state changes in response to starvations were selected to evaluate their temporal RNA expression patterns. Inactivated cre02.g110500 (chromosome_2: 5,751, 191-5,752,593) and activated LCR1 (chromosome_9:5,231, 514-5,245,409) expression are shown as examples.

FIG. 24A-D: Chromatin states analysis reveals unique signatures in C. reinhardtii. (24A) An overview of histone modification profile in C. reinhardtii. Pattern of five histone modifications and RNA polymerase II occupancy as well as RNA expression along genomic region chromosome_14:1, 935,619-1,962,314 is shown. Gene model is shown based on the assembled transcripts from this study. (24B) Enrichment of histone modification signals between ±2 Kb of TSS. (24C) Pairwise marks co-occurrence in C. reinhardtii. Overlap is defined as the ratio of co-occupied regions between the row and column marks over the number of row mark's regions. (24D) Predicted chromatin states defined by the combinatory histone modifications, potential functional features and conservation with other species are shown. The representative marks for individual states are highlighted in blue. The fraction of transcripts associated with major promoter states are listed. Similar patterns are also found in the N- and S- cells (FIG. S2B).

Figure 25:
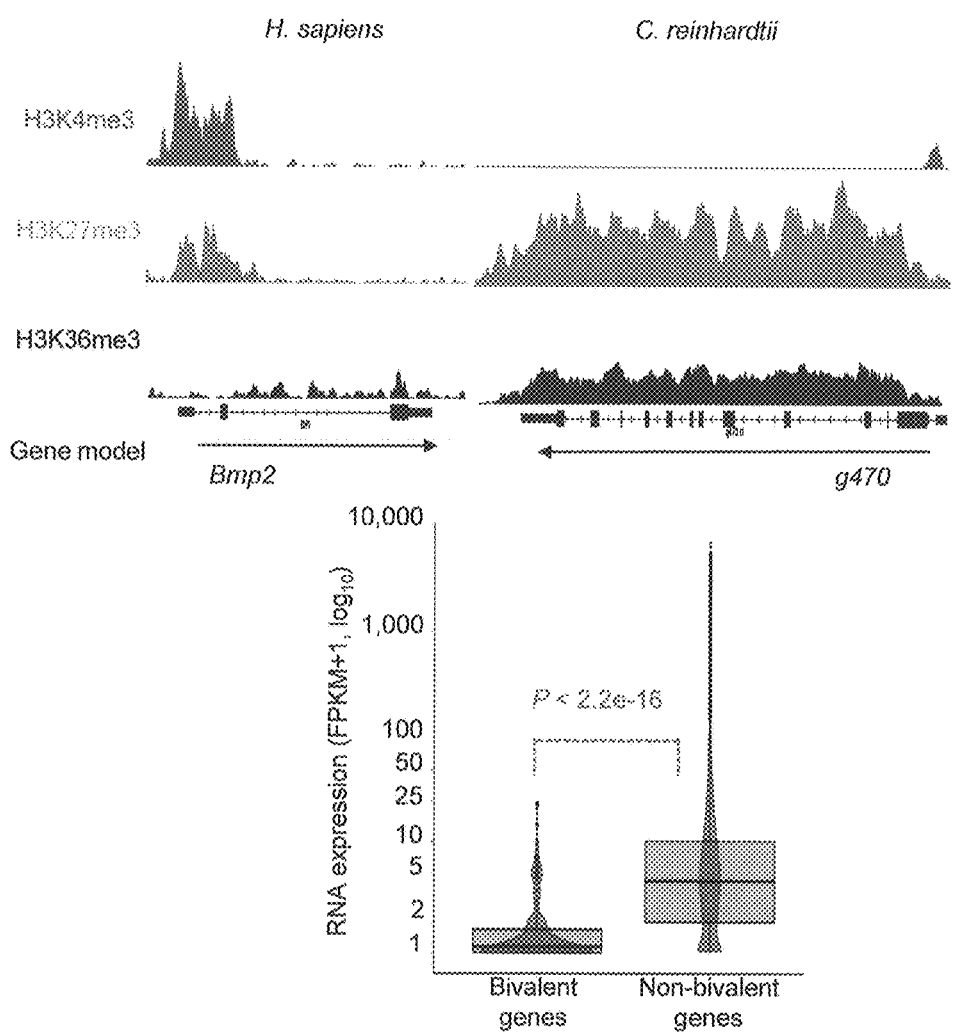

FIG. 25: Distinct chromatin features in C. reinhardtii compared to vertebrate. Chromatin state 2: Bivalent domain. Putative bivalent domain defined by chromatin state 2. Different modification patterns between C. reinhardtii and Homo sapiens (ENCODE data) are shown (Left). Bivalent state-associated transcripts are expressed at a significantly (Wilcoxon rank-sum test) lower level (Right).

FIG. 26: Distinct chromatin features in C. reinhardtii compared to vertebrate. Chromatin state 15: Putative enhancer. Putative enhancer state defined by chromatin state 15. H3K4me2 enrichment at distal H3K27ac marked regions (Left). An example of putative enhancer region (chr_1:5, 739,311-5,755,673) exhibiting enhancer activity (FIG. S2D) is shown (Right). H3K27ac peak is found in the 3' intron of the amino acid permease gene, 7 kb and 3.5 kb away from its neighboring promoters.

FIG. 27: Chromatin state changes predict regulators of lipid accumulation. Five promoter types are defined by progressive addition of histone modifications (top panel) and are highly correlated with expression levels (bottom panel).

FIG. 28A-B: Chromatin state changes predict regulators of lipid accumulation. (28A) Numbers of genes found in each promoter type during growth in TAP (column) and corresponding state at nutrient depletion (row). Numbers of genes with activated chromatin (Types I+II+III changing to IV or V, plus IV changing to V) are marked in red and green, for N- and S-starvation, respectively. (28B) Venn diagram displays the activated genes found in both N- and S-starvation. Clustering of normalized expression levels from the genes activated during N- (left) and S- (right) cells across different time points. Clusters A, B and C are defined by peak expression at 30 min, 1 hr and 2 hr, respectively. TF genes are highlighted.

FIG. 29A-C: Lack of lipid induction in psr1 mutant in response to nutrient deprivation. (29A) Temporal expression of PSR1 gene in N- (red) or S- (green) starved cells. (29B) Chromatin modifications changes at the PSR1 promoter regions following N- and S-starvation. (29C) Lipid accumulation in wild type and psr1 mutant cells in four nutrient starvation regimens. Nile red fluorescence (RFU) normalized per cell is shown during 3 days of nutrient starvation (n=3). Statistical significance by student t-test is indicated as *$P<0.05$. Depletion time course for trace metal depletion (Zn— and Fe—) was performed after a pre-inoculation of cells in depleted media (see details in Experimental Procedures).

FIG. 30A-B: Overexpression of PSR1 triggers lipid accumulation in C. reinhardtii. (30A) Cell size measurement of wild type cells in TAP, N- and two independent clones of liporotund. (30B) Comparison of lipid accumulation in wild type cells (in TAP and during nutrient starvation) and liporotund grown in TAP (n=3). The fold of PSR1 overexpression is shown below.

Figure 31:
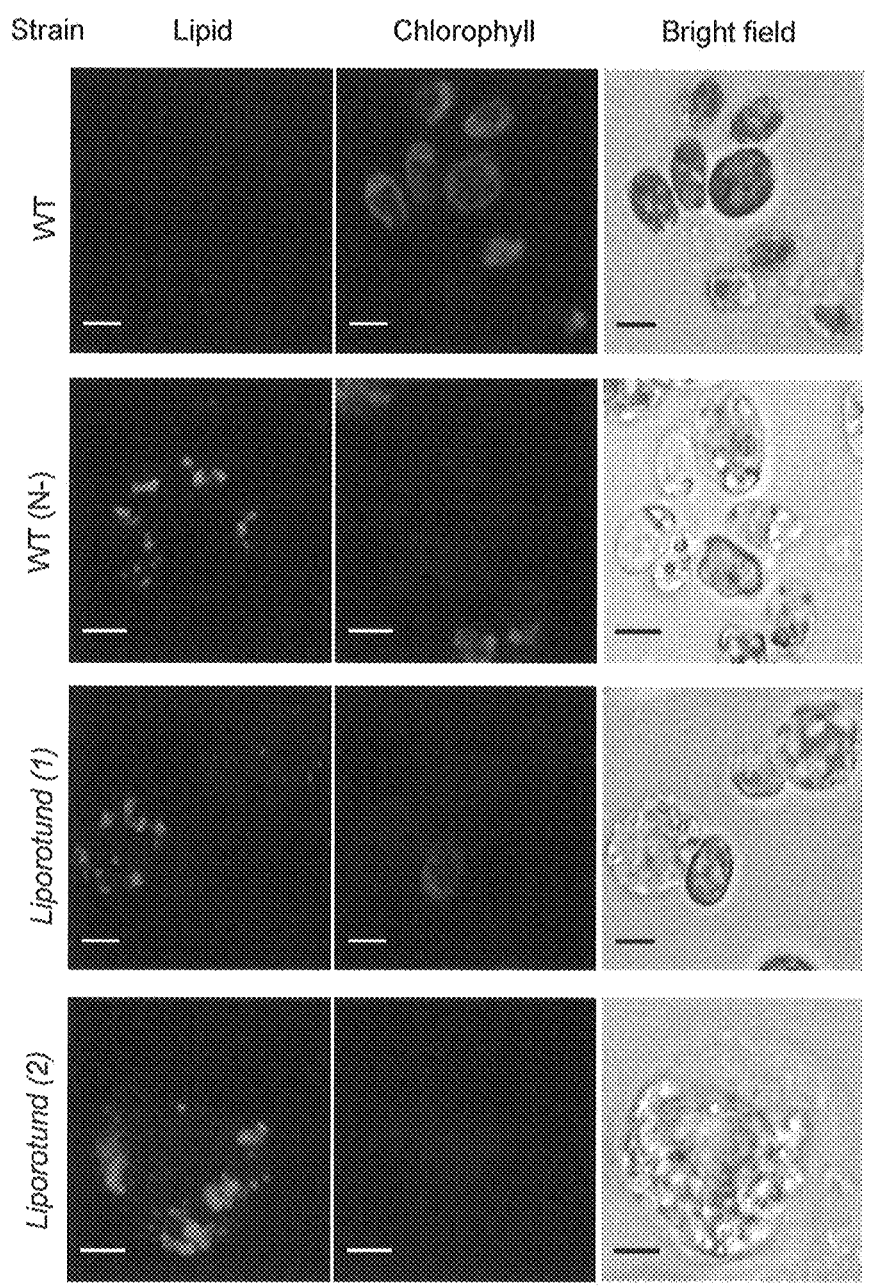

FIG. 31: Overexpression of PSR1 triggers lipid accumulation in C. reinhardtii. Images of LipidTOX Green-stained PSR1-overexpressing cells confirmed an increased number of lipid bodies. Chlorophyll autofluorescence and cell morphology images were taken with the same laser power to facilitate cross-comparison (scale bar: 5 um).

FIG. 32A-C: Characterization of PSR1 binding and target genes. (32A) PSR1 ChIP-seq signal intensity along the bound genes. (32B) PSR1 binding profiles across 2 time points in N- and 3 time points in S- cells at TF gene Cre02.g108350. The predicted binding motif is highlighted. (32C) Number of PSR1 target genes common and specific in N-, S- states.

Figure 33:
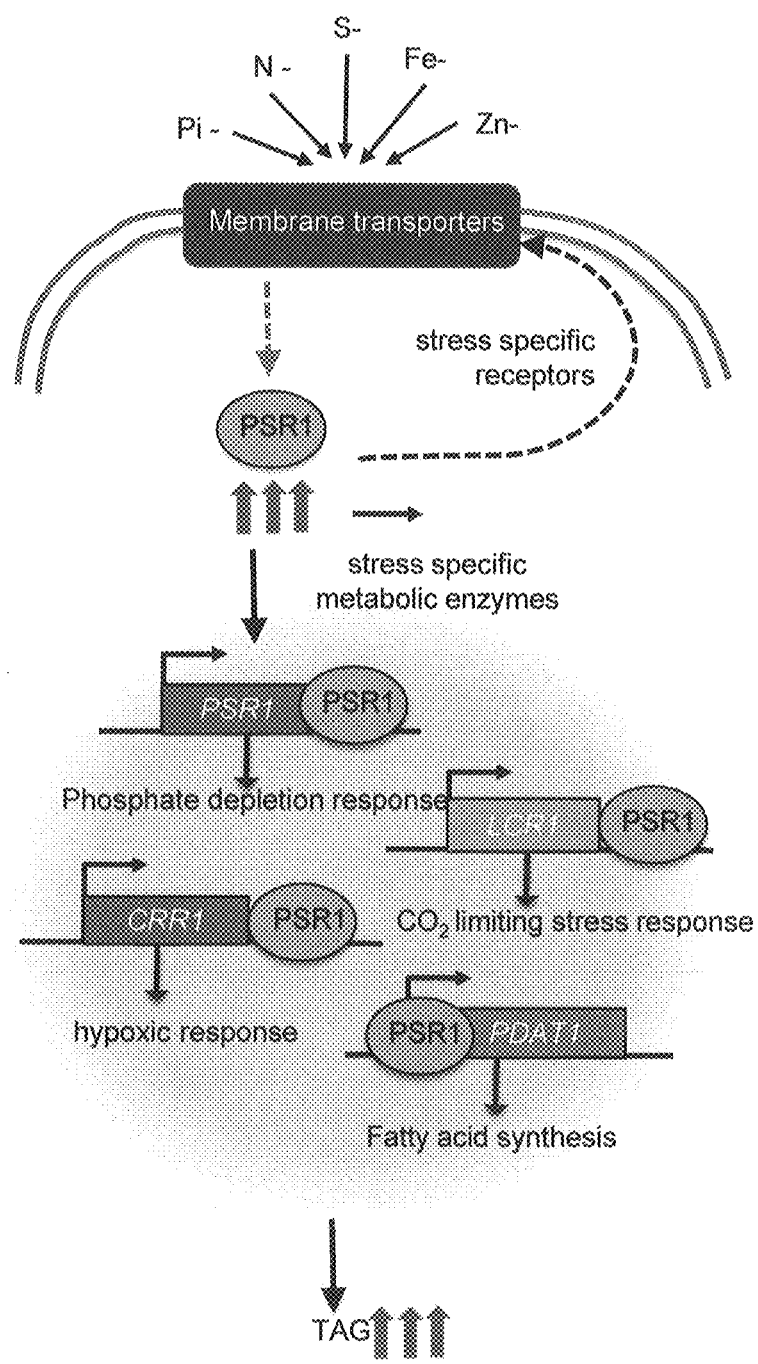

FIG. 33: Characterization of PSR1 binding and target genes. Proposed model of PSR1-mediated lipid regulation.

Figure 34:
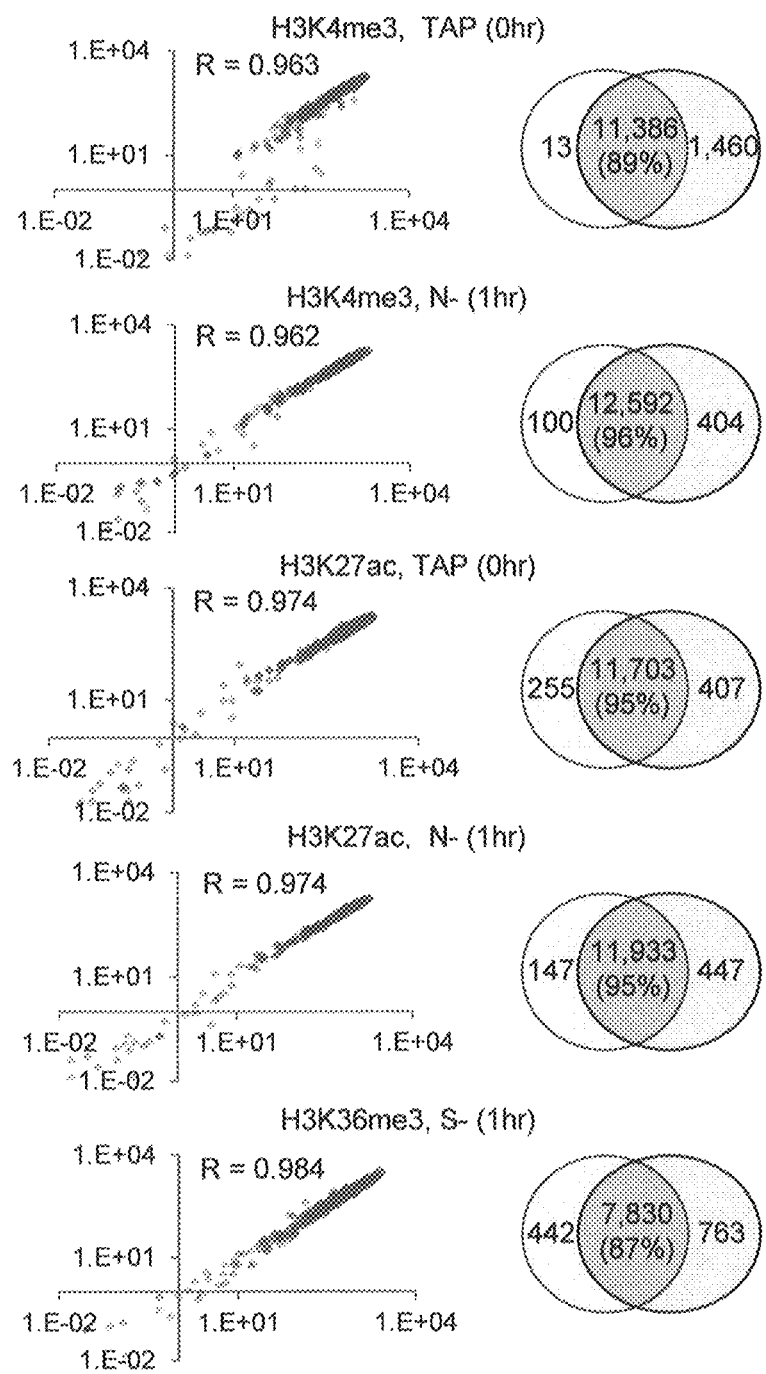

FIG. 34: Data reproducibility of ChIP-seq and RNA-seq analysis, related to FIG. 1. Two biological replicates (BR1 and BR2) were generated for 5 ChIP-seq experiments. Numbers of the mapped reads from each genomic bin (100 kb) were plotted in log scale between two replicates (X-axis: BR1; Y-axis: BR2). R values calculated by Pearson correlation coefficient at 1 kb genomic bin are shown. Venn diagrams display the high % of overlaps between peaks called for each replicate.

FIG. 35A-B: Data reproducibility of ChIP-seq and RNA-seq analysis, related to FIG. 1. (35A) Pair-wise comparison between 18 RNA-seq libraries of different time points from N- (left panel) and S- (right panel). Replicates for each data point were indicated as A and B. Pearson correlation coefficient (R) calculated from expression value (FPKM) of each transcripts model was shown in color scale. (35B) The classification of 22,209 assembled transcripts among the known, new variant and new transcripts is shown.

FIG. 36A-D: Chromatin features in C. reinhardtii, related to FIGS. 2 and 3. (36A) H3K9me3 co-occupies regions modified by the active H3K4me3 and H3K27ac marks in C. reinhardtii. (36B) Chromatin states defined by ChromHMM for cells cultured in WT (TAP), N- or S-depleted media. The major histone modifications found in each state are highlighted in blue. The % of occupied genome is listed. (36C) The enrichment of chromatin state at ±2 kb of transcription start site (TSS). The fold of enrichment of each state is shown in color scale. (36D) GUS activity driven by putative enhancer elements predicted by chromatin states. The genomic coordinates of the tested regions and one random negative control are shown in X-axis. GUS activity was measured at 2 hr post inoculation. P-values above indicate the significance of the enhanced activities by Mann-Whitney test (one-tailed).

FIG. 37A-B: Chromatin state accurately predicts transcription activity, related to FIG. 4. (37A) Chromatin profile changes found in the TSS of DGAT (upper panel) and NRR1 (lower panel) in N and S starvation. (37B) Candidate genes activated in both N and S starvation inferred by chromatin state transition (top left), RNA-seq approach (bottom left) and combined approach (right) are shown in the overlap in the Venn Diagrams.

FIG. 38A-B: PSR1 functions as a lipid trigger in *C. reinhardtii*, related to FIG. 5. (38A) Confocal microscopy and lipid specific staining (LipidTOX Green) and chlorophyll autofluorescence of wild type 4a+ cell (upper) and psr1 mutant (lower) cells. Samples were collected 48 h after depletion. Pictures were taken with the same laser power. Scale bar: 2 um. (38B) PSR1 conservation across multiple plant species in high-level taxonomy categories is shown in a tree view. *C. reinhardtii*'s PSR1 protein sequence's BLAST search returned 2404 hits across different plant and algae species (data not shown).

FIG. 39A-D: PSR1 overexpression and target genes, related to FIG. 6. (39A) Growth rate analysis of liporotund along 5 days culture in TAP media. (39B) PSR1 target gene expression profile of Cre02.g108350. (39C) A truncated form of *C. reinhardtii* PSR1 protein containing target epitopes was expressed in *E. coli*. 39(D) Two PSR1 antibodies (PSR1-A and PSR1-B) detect a ~47 kD protein of the *E. coli* protein extract.

FIG. 40A-B: Antibodies validation and states reduction approach, related to Experimental Procedures. (40A) Pairwise alignment of H3 protein sequences between *C. reinhardtii* and human. (40B) Western blot confirmed antibodies used for ChIP-seq analysis recognize a ~17 kDa protein in *C. reinhardtii*, an expected size for H3.

FIG. 41A-D: Antibodies validation and states reduction approach, related to Experimental Procedures. (41A) Additional states captures finer-grain chromatin distinction but introduces state redundancy for biological interpretation. Chromatin mark frequency for each chromatin state of the best HMM amongst 693 HMMs. The frequency is shown in color scale. The red box indicates states with Pearson correlation ≥0.99. (41B, 41C, 41D) Examples of state redundancy introduced by spatial consideration in the best HMM and their concise state representation in the final non-redundant 16-states HMM. Each panel shows the detected chromatin peak in a genome region (top), its genome segmentation by the best HMM (60 states) and the final non-redundant 16-state HMM (middle), and the gene model in the vicinity (bottom).

Table 1. ChIP-seq summary, related to FIG. 23.

Table 2. ChIP-seq summary, related to FIG. 23.

Table 3. RNA-seq data summary and processing, related to FIG. 23.

Table 4. Transcript models constructed from RNA-seq data, related to FIG. 23.

Table 5. Differential gene expression analysis, related to FIG. 23.

Table 6. PSR1 ChIP-seq summary, related to FIGS. 32 and 33.

Table 7. Primers sequences for enhancer assay.

Table 8. H4K3me3 time series ChIP-seq data summary.

SUMMARY OF THE INVENTION

Alga-derived lipids represent an attractive potential source of biofuels. However, lipid accumulation in algae is a stress response tightly coupled to growth arrest, thereby imposing a major limitation on productivity. To identify master regulators of lipid accumulation and decipher the regulation of lipid biosynthetic pathway, we performed an integrative chromatin signature and transcriptomic analysis in the alga *Chlamydomonas reinhardtii*. Genome-wide histone modification profiling revealed remarkable differences in functional chromatin states between algae and higher eukaryotes and uncovered regulatory components at the core of lipid accumulation pathways. We identified the transcription factor PSR1 as a pivotal master switch that triggers cytosolic lipid hyper-accumulation an order of magnitude higher than stress regimens have achieved. Dissection of the PSR1 target network corroborates its central role in coordinating multiple stress responses. The comprehensive maps of functional chromatin signatures in a major clade of eukaryotic life and the discovery of a central regulator of algal lipid metabolism will facilitate targeted engineering strategies in microalgae.

Briefly, we describe genome-wide functional chromatin profiling in a major clade of plant lineage. An integrative chromatin and trasncriptome analysis reveals core lipid regulators. PSR1 is a master lipid switch triggering hyper-lipid accumulation in microalgae. PSR1 target gene network coordinates multiple lipid-inducing stress responses

Description Of The Embodiments

Introduction

We have discovered and identified key transcription factors (TFs) that act as master regulators of biodiesel precursor pathways in microalgae. Such knowledge will enable one to genetically manipulate microalgae through transgenetic approaches to create lipid over-producing strains. Such capability and resulted strains can be used for the production of renewable biofuels. As described in the earlier section, this approach was not possible before because the lack knowledge on the specific regulators and our discovery enables such approach The challenges for identifying key transcriptional regulators include that the key transcription factors (TF) controlling lipid accumulation in microalgae are not known, the TF genes are not well annotated, TF expression may be transient and low level, there is a huge range of mRNA abundance in the cell and measured mRNA levels reflect balance of transcription and degradation rates.

Our discovery was made because we adopted a novel and integrated experimental platform to dissect the genetic regulatory pathways of TAG synthesis. The platform utilized a combinatory experimental interrogation on the genomic, transcriptomic and epigenetic dynamics in microalgae throughout lipid accumulation culture conditions. To do so, we have to develop several related technologies in microalgae and overcome a lot of technical issues during the method development (such as cell lysis for native chromatin isolation, chromatin immunoprecipitation and micro-algae specific antibody characterization).

Herein is described a general strategy for increasing lipid production in a heterologous host environment. Host species such as *Chlamydomonas* may be suitable hosts and used for industrial-scale production Definitions An "expression vector" or "expression cassette" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells including but not limited to, algae such as *Chlamydomonas*, cyanobacteria, or eukaryotic cells including but not limited to, yeast, insect, amphibian, or mammalian cells such as CHO, HeLa and the like, e.g., cultured cells, explants, and cells in vivo.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this invention are those genes encoded by the same genetic locus. Thus, any "transcription factor gene" as referred to herein is meant to include any polynucleotide that regulates a gene encoding a lipid protein or variants thereof.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 15 amino acids of each of the transcription factor genes), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs).

Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid can be used interchangeably with gene, cDNA, mRNA, oligonucleotide, and polynucleotide.

A "label" or "detectable label" is a composition detectable by spectroscopic, photochemical, biochemical, immunochemical, or chemical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., lipid proteins can be made detectable, e.g., by incorporating a radiolabel into the protein, and used to detect antibodies specifically reactive with the protein).

The present invention provides for the overexpression of regulatory proteins, specifically transcription factors (TFs) to up-regulate the activity of multiple enzymes in the TAG biosynthetic pathway of microalgae. Different from prior strategies, over-expression of transcription factors affects a large number of genes involving multiple pathways, resulting in an integrated regulation of these pathways simultaneously. Thus, such TF-engineered microalgal strains offer as an attractive mean for cost-effective TAG production. Towards this goal, we uncovered key TFs that can be used to use for generating transgenic lipid over-producing microalgae. Such microalgae can be used as green cell-factories to produce commercial biodiesel industry. Thus, our invention describes the use of these genes, their protein products and the transgenic strains as agents to produce biodiesel at economic scale.

In one embodiment, the present invention provides for a construct or an expression cassette comprising a polynucleotide encoding a transcription factor gene selected from the 17 transcription factors in the sequence listing for the expression in a host cell.

The expression cassette can be used to provide a cell comprising in its genome at least one stably incorporated expression cassette, where the expression cassette comprising a heterologous nucleotide sequence or a fragment thereof operably linked to a promoter that drives expression in the cell.

Also provided are methods for enhancing lipid production activity in an organism. In one method, comprising introducing into an organism at least one expression cassette operably linked to a promoter that drives expression in the organism, where the expression cassette comprising a transcription factor gene identified herein.

In one embodiment, lipid overexpression is described and methods for increasing overexpression using the Psr1 transcription factor.

In one embodiment, polynucleotides which regulate lipid expression, are cloned into an appropriate plasmid, inserted into an expression vector, and used to transform cells from any host organism. Suitable host organisms include, but are not limited to, bacteria such as *E. coli, B. subtilis, S. cerevisiae*, cyanobacteria, algae such as *Chlamydomonas*, plants such as *Nicotiana tabacum* and *Camelina sativa*, fungi, or other eukaryotic organisms.

In one embodiment, the polynucleotides are in an inducible expression system which maintains the expression of the inserted genes silent unless an inducer molecule (e.g., IPTG) is added to the medium containing the host cell. The expression vector or construct may be a vector for coexpression or in some embodiments, it may be a neutral site vector for insertion into a host genome such as *Chlamydomonas*. The construct may include either inducible transcription elements or may be constitutively expressed in the host organism.

Bacterial colonies are allowed to grow after gene expression has begun, or if required, after induction of gene expression. Thus, in some embodiments, expression vectors comprising a promoter operably linked to a heterologous nucleotide sequence or a fragment thereof, that regulates expression of a lipid protein are further provided. The expression vectors of the invention find use in generating transformed plants, plant cells, microorganisms, algae, fungi, and other eukaryotic organisms as is known in the art and described herein. The expression vector will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The vector may additionally contain at least one additional gene to be co-transformed into the organism. Alternatively, the additional gene(s) can be provided on multiple expression vectors or cassettes. Such an expression vectors is provided with a plurality of restriction sites and/or recombination sites for insertion of the polynucleotide that is a transcription factor gene or a regulatory factor of gene expression of lipids. The expression vector may additionally contain selectable marker genes.

In one embodiment, the expression vector will include in the 5'-3' direction of transcription, a transcriptional initiation region (i.e., a promoter), a cluster of bacterial compartment genes each preceded by a translational initiation site (RBS) specific to the organism and type of shell protein and followed by a translation termination signal (stop codon), and, optionally, a transcriptional termination region functional in the host organism. The regulatory regions (i.e., promoters, transcriptional regulatory regions, ribosomal binding sites and translational termination regions) and/or any targeting sequences may be native/analogous to the host cell or to each other. Alternatively, the regulatory regions and/or the targeting regions may be heterologous to the host cell or to each other. As used herein, "heterologous" in reference to a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In other embodiments, the transcription genes described herein can be incorporated into multiple expression vectors and/or under multiple promoter control.

Where appropriate, the polynucleotides may be optimized for increased expression in the transformed organism. For example, the polynucleotides can be synthesized using preferred codons for improved lipid expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) 1 Cell *Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). The above list of selectable marker genes is not meant to be limiting. Any selectable marker gene can be used in the present invention.

In various embodiments, it is beneficial to express the gene from an inducible promoter, particularly from an inducible promoter in order to induce lipid production or overexpression.

In some embodiments, the expression vector comprising multiple copies of the lipid genes and transcription regulatory factors.

In some embodiments, an engineered or non-natural strain whose genome comprises one of the 17 transcription genes, wherein the strain is capable of increased production or overexpression of lipids.

In some embodiments, an engineered or non-natural strain whose genome comprises at least one of the 9 activated transcription genes, wherein the strain is capable of increased production or expression of lipids.

In some embodiments, an engineered or non-natural strain whose genome comprises at least one of the 8 inactivated transcription genes, wherein the strain is capable of increased production or expression of lipids.

In some embodiments, an engineered or non-natural strain whose genome comprises at least one of the 8 inactivated transcription genes and at least one of the 9 activated transcriptions genes, wherein the strain is capable of increase production or expression of lipids.

In some embodiments, an engineered or non-natural strain whose genome comprises overexpression of at least one of the 9 activated transcription genes, wherein the strain is capable of increased production or expression of lipids.

In some embodiments, an engineered or non-natural strain whose genome comprises disruption of at least one of the 8 inactivated transcription genes, wherein the strain is capable of increased production or expression of lipids. Methods of gene disruption include, without limitation, mutation, down-regulation, insertional inactivation of a gene, use of nucleases or recombinases, homologous recombination, and/or siRNA (Guo, Chang-An, O'Neill, Lucas M, and Ntambi, James M (October 2014) Gene Inactivation Strategies: An Update. In: eLS. John Wiley & Sons Ltd, Chichester; Bischof, J. et al., Recombinases and their use in gene activation, gene inactivation, and transgenesis, Methods Mol Biol. 2008; 420:175-95).

In some embodiments, an engineered or non-natural strain whose genome comprises overexpression of at least one of the 9 activated transcription genes and disruption of at least one of the 8 inactivated transcription genes, wherein the strain is capable of increased production or expression of lipids.

EXAMPLE 1

Lineage-Specific Chromatin Signatures Reveal a Master Lipid Switch in Microalgae Algae naturally accumulate energy-dense oils that can be converted into transportation fuels, potentially rendering them an attractive system for large-scale biofuel production (Wijffels and Barbosa, 2010). Algae-derived biofuels offer the promise of high areal productivity, minimal competition with food crops, utilization of a wide variety of water sources, and $CO_2$ capture from stationary emission sources (U.S. DOE 2010. National Algal Biofuels Technology Roadmap. DOE EERE Website for algal-biofuels; Merchant et al., 2012). However, high-yield lipid accumulation in algae is a stress response inducible through conditions like nutrient deprivation, which limits overall yield and thus commercial viability (Chisti, 2013). Extensive research efforts have been aimed at improving algal lipid productivity, but these approaches including metabolic engineering (Blatti et al., 2013), mutant screening (Cagnon et al., 2013) and growth manipulation (Csavina et al., 2011) have yet to substantially boost intracellular lipid levels (Courchesne et al., 2009).

The microalga *Chlamydomonas reinhardtii* is one of the model organisms for studying algal growth and lipid metabolism. This species accumulates substantial amounts of triacylglycerol (TAG) during nutrient stress and is amenable to well-established classical genetic methods (Chisti, 2007). A high quality and functionally annotated genome sequence is available in public repositories (Merchant et al., 2007) and large collections of mutant strains have been produced (http://chlamycollection.org). Despite growing amounts of transcriptome and proteome data (Boyle et al., 2012; Castruita et al., 2011), the molecular mechanisms that govern algal lipid production have remained elusive. In particular, it is unclear how various responses to distinct environmental stressors converge into the transcriptional control of a single common TAG biosynthesis pathway.

In higher plants, many stress-elicited responses are controlled at the level of epigenetic (Tanurdzic et al., 2008; Zhong et al., 2013) and transcriptional regulation (Boyle et al., 2012; Hemschemeier et al., 2013), particularly through the activation of master transcription factors (TFs) (Borevitz et al., 2000; Nuruzzaman et al., 2013). Because of substantial variation in transcript stability and degradation rates, transcript levels are an imperfect proxy for the transcriptional status of individual genes. This problem is likely exacerbated by the transient expression and potentially low abundance of stress-responding TF transcripts, rendering their identification through transcription profiling alone difficult. Due to these challenges, only a single algal TF, NRR1, has been functionally implicated in lipid accumulation albeit with moderate effects on lipid accumulation only during nitrogen (N-) starvation and none during other nutrient stresses (Boyle et al., 2012). In contrast to transcriptome profiling, distinct patterns of histone modifications can reveal active or repressed chromatin states (Kouzarides, 2007) and provide information about the transcriptional activity of the associated genes (Li et al., 2008; Wang et al., 2009a). For instance, alterations in histone modifications have been used to identify central regulatory genes in the *Arabidopsis* leaf senescence process (Ay et al., 2009). We thus hypothesized that a combination of chromatin state and transcriptome changes induced by lipid-inducing starvation conditions in *C. reinhardtii* may provide a sensitive and specific readout for detecting key switches controlling the lipid accumulation process.

In this study, we constructed genome-wide maps of chromatin states and their dynamics in *C. reinhardtii*. Compared with patterns found in metazoans (Celniker et al., 2009; Consortium et al., 2012) and land plants (Ben et al., 2011; Roudier et al., 2011), functional chromatin signatures in microalgae are a combination of both conserved and lineage-specific histone codes. We exploited chromatin signature changes to infer master regulators of lipid accumulation and applied targeted genetic perturbation to confirm one of these TF genes, PSR1, as a core switch activating lipid accumulation. Mapping the in vivo PSR1 target genes reveals intricate connectivity between different stress responses and provides insights into the regulation of TAG biosynthetic pathway as well as strategies for their targeted genetic engineering.

Results

Mapping Epigenomic Changes in Response to Lipid-Inducing Conditions.

Figure 23:
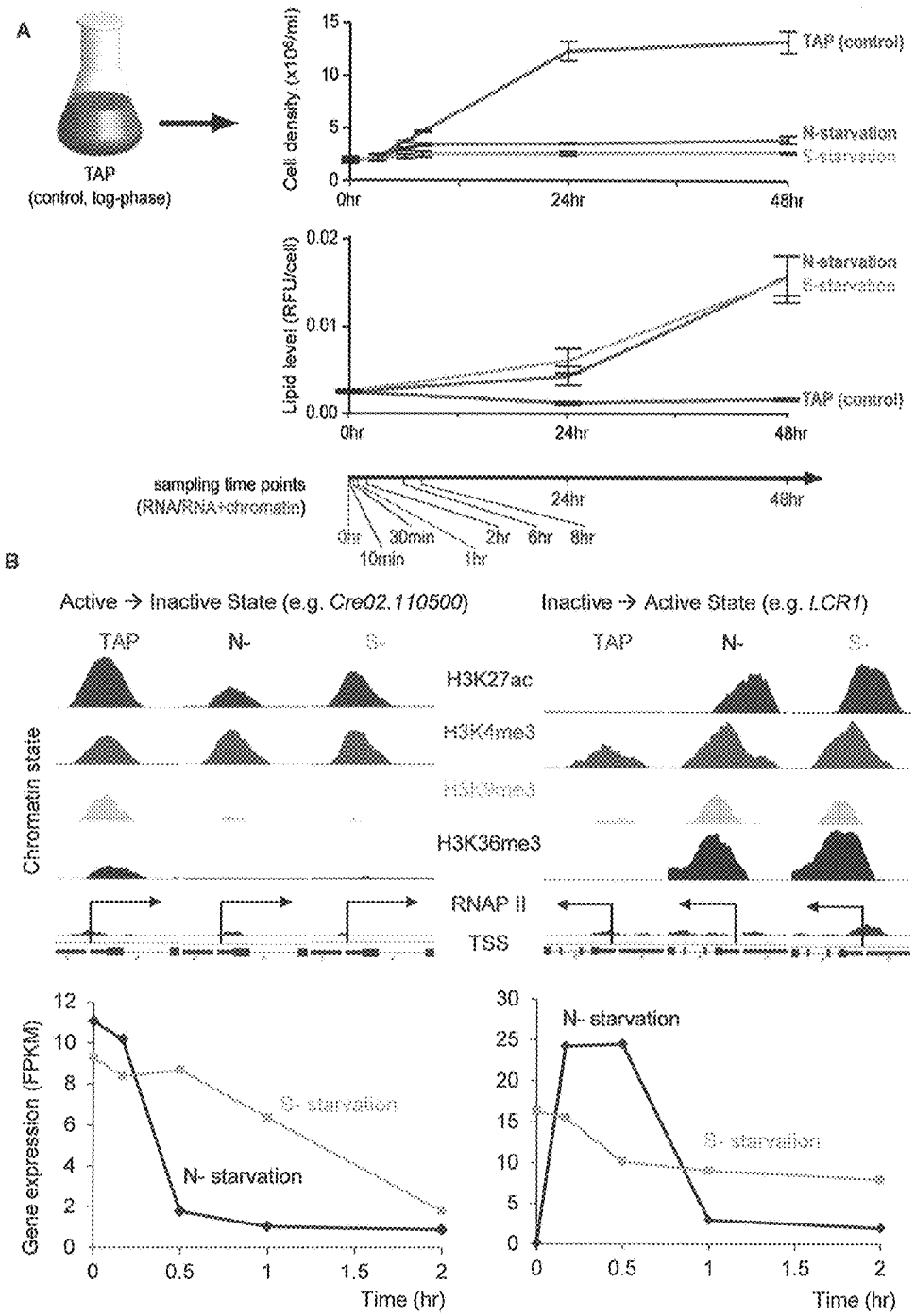

To characterize chromatin states in *C. reinhardtii* and profile their changes in response to stress-induced lipid accumulation, we cultured *C. reinhardtii* cells under two different acute nutrient depletion schemes known to induce TAG accumulation, nitrogen (N-) and sulfur (S-) starvation (Boyle et al., 2012). A slow rate of cell growth and high lipid levels confirmed that the expected stress responses were achieved (FIG. 23). We used chromatin immuno-precipitation followed by sequencing (ChIP-seq) to profile the genome-wide distribution of RNA polymerase II (RNAPII), as well as five distinct post-translational modifications of histone H3 including trimethylation of lysine residues 4 (H3K4me3), 9 (H3K9me3), 27 (H3K27me3), 36 (H3K36me3) and lysine 27 acetylation (H3K27ac) in control cells, cultured in Tris-acetate-phosphate (TAP) media and 1 hr post-starvation under both N- and S- conditions (FIG. 23). ChIP-seq reads were mapped to the *C. reinhardtii* reference genome and used to determine modified regions with high reproducibility across biological replicates (overall reproducibility Pearson correlation, R>0.96 in all cases, FIG. 34, Tables 1-5).

To monitor the transcriptional responses associated with chromatin changes at high temporal resolution, we also performed deep RNA-seq analysis throughout the course of nutrient depletion up to 48 hr post-starvation when lipid accumulation is pronounced. Comprehensive expression changes in both early (0-8 hr, within one cell cycle) and late (24-48 hr) phases were captured (FIG. 23). Similar to the epigenomic data, high correlations between biological replicates were observed (Pearson correlation ≥0.99, FIG. 35A). To ensure that all transcripts specifically expressed in response to N- and S- starvation were included in our analysis, we performed a reference-guided transcript assembly from these deep RNA-seq data sets, which revealed 4,241 new alternative splice variants and 298 previously unannotated transcripts (FIG. S1C). Across all 22,209 transcripts assembled, approximately half are differentially expressed (>2 fold, P<0.01) in at least one time point along the course of N- or S-starvation (Tables 1-5), suggesting extensive transcriptional changes associated with nutrient starvation and lipid induction.

Plant- and Alga-Specific Histone Signatures.

Figure 24:
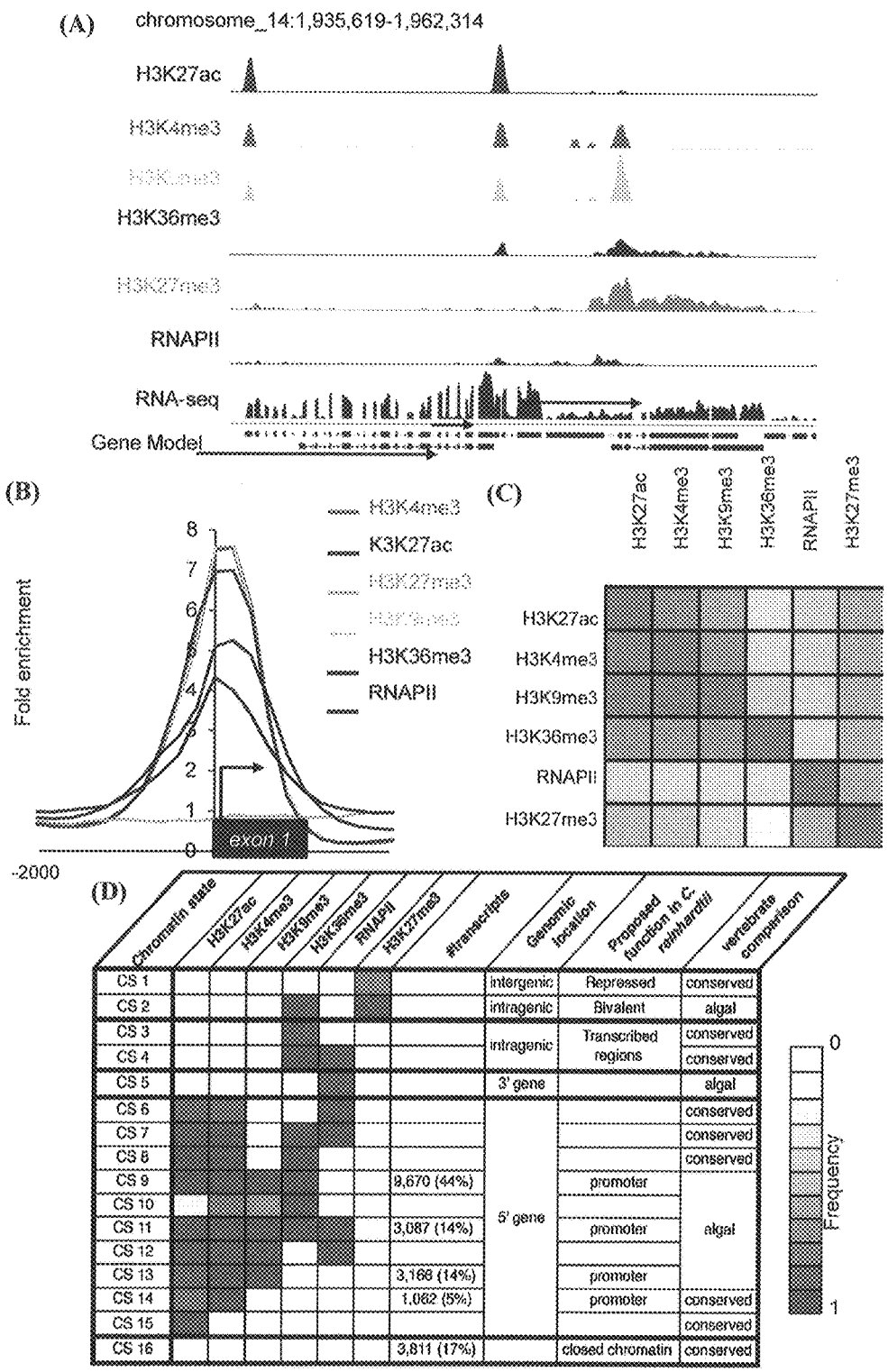

Similar to metazoans, histone modifications in *C. reinhardtii* largely exhibit punctuated patterns across the *C. reinhardtii* genome (FIG. 24A) and are primarily clustered within 1 kb of the transcription start sites (TSSs) of annotated genes (FIG. 24B). Examination of individual histone marks revealed similarities, but also marked differences compared to the well-characterized histone code of animals. Overall, H3K4me3, H3K27ac, H3K9me3 and H3K36me3 (to a lesser degree) are co-localized (FIG. 24C). In vertebrates, H3K9me3 is associated with repressed heterochromatin (Peters et al., 2002), but in *C. reinhardtii*, this mark nearly universally (96% of H3K9me3 regions) co-localizes with active marks H3K4me3 or H3K27ac (FIG. 36A). While a general activity-associated and promoter-centric distribution of H3K9me3 was observed in *Arabidopsis* (Roudier et al., 2011), the co-occurrence of H3K9me3 with active marks and mutual exclusion with repressive mark H3K27me3 observed in *C. reinhardtii* may be restricted to algae or could represent a previously unappreciated general plant-specific histone signature. A second mark divergent from vertebrates is H3K36me3, which spans broad regions along actively transcribed genes in vertebrates (Guenther et al., 2007), but is largely confined between active promoters (90%; 7,978 out of 8,873 regions) in *C. reinhardtii* (FIG. 24B). Hence, while the general existence of these histone modifications is highly conserved, their functions appear to have diverged across the different eukaryotic clades.

Because the individual histone patterns were found unique in *C. reinhardtii*, we adopted an unsupervised approach to systematically analyze combinatorial patterns from these histone modifications and RNAPII occupancy through the established ChromHMM (Ernst and Kellis, 2012), which led to the identification of 16 distinct chromatin states (CS). Most of the genomic regions (87%) are devoid of any modification (CS 16). The remaining 15 states contain one or more marks in different combinations and associated with different genomic locations (FIG. 24D, FIG. 36B). CS 1-5 account for 3% of the genome, are mainly defined by H3K27me3, H3K36me3 and RNAPII and distributed among non-promoter regions, while CS 6-15 occupy 10% of the genome, are mainly defined by H3K27ac, H3K4me3 and H3K9me3 and found around promoter regions (FIG. 36C).

Two states, CS 2 and CS 15, are of particular interest in comparison to known animal and plant chromatin signatures (FIG. 25, middle panel). CS 2 represents bivalent domains showing an active mark (H3K36me3) in combination with a repressive mark (H3K27me3). Bivalent domains, initially uncovered in animal cells as the regions co-modified by H3K4me3 and H3K27me3, pervasively associate with developmental regulator genes in early developmental cells (Bernstein et al., 2006) (FIG. 25, left panel). Similar "K4/K27me3" bivalent status was also detected in *Arabidopsis*, including the flowering locus C (Luo et al., 2012). In support of a bivalent status, *C. reinhardtii* transcripts associated with K36/K27me3 are expressed at substantially lower levels than those with non-bivalent marks (P<2.2e-16, FIG. 25) and significantly enriched for genes encoding metabolic enzymes and protein kinase activities (P=1.8e-03 & 6.8e-03). In contrast, CS 15 is defined through H3K27ac single modification and, based on what has been observed in metazoan genomes, this signature is overall a characteristic of distal transcriptional enhancers (Creyghton et al., 2010). As expected, a significant portion of these regions is outside ±1 kb of the known TSS. To evaluate this functional feature, we profiled the known enhancer mark H3K4me2 in log-phase *C. reinhardtii* cells and found that CS 15 is enriched for H3K4me2 modification (FIG. 26). Experimental validation of individual sequences identified by this signature confirmed their enhancer activity in 3 out of 11 cases tested (one-tailed Mann-Whitney test with P<0.05) by placing them upstream of reporter GUS gene in a heterologous Tobacco enhancer reporter assay, despite it is distally related to algae (FIG. 36D). One such region is shown in FIG. 26 where a H3K27ac peak is found in the 3' of amino acid permease gene; 7 kb and 3.5 kb away from its neighboring promoters. These data indicate the presence of potential distant-acting regulatory elements similar to those extensively characterized in vertebrate genomes (Shlyueva et al., 2014) in algae and possibly other plants.

Promoter histone modification patterns reflect genes transcriptional status. Among all 16 different chromatin states defined, five types of histone modification patterns were associated with nearly all (20,843; 94%) transcript promoters in *C. reinhardtii* (FIG. 27). These five types differ mainly by progressive addition of modifications ranging from Type I promoter depleted of any mark to Type V promoter with all four active marks (H3K4me3, H3K27ac, H3K9me3 and H3K36me3) and the presence of RNAPII. Transcript abundance levels are highly correlated with the chromatin state of their respective promoters. Each consecutive class is associated with a significant increase in expression (FIG. 27, lower panel) (P<1.7e-9 in all cases, Wilcoxon rank sum test). Quantitative increases are most pronounced in Type IV vs. I-III (8.6-fold, P<2.2e-16) and V vs. IV (2.4-fold, P<2.2e-16), characterized by the addition of H3K36me3 and RNAPII, respectively. For all following analyses, Types IV and V were considered transcriptionally active in *C. reinhardtii* cells. Despite these overall highly significant correlations, within each promoter class a wide range of transcript levels was observed. This variation may result from a combination of inherently different transcription rates from individual promoters ("weak" vs. "strong" promoters) as well as from differences in post-transcriptional RNA stability, highlighting the limitations of transcriptome data alone for inferring the transcriptional status of individual genes. Taken together, histone modification landscape of model algae *C. reinhardtii* reveals chromatin signatures signifying functional elements both homologous to and distinct from those characterized for vertebrates and land plants. *C. reinhardtii* also exhibits unique histone modification states, particularly centered on promoters, suggesting that these promoter chromatin state assignments may provide a substrate for sensitive and accurate identification of regulatory genes like TFs responding changes in lipid metabolism.

Chromatin changes reveal candidate genes transcriptionally regulated in N- and S- conditions. To infer regulatory gene candidates involved in lipid accumulation, we evaluated genes whose promoters exhibit chromatin state changes during both N- and S- starvations. We focused on promoters transitioning from Types I-III (no/low transcriptional activity) in control medium to Types IV (high) or V (very high transcription activity), i.e., promoters with substantial activation in response to nutrient depletion (FIG. 28A). Among 1,242 and 2,206 promoters transitioning to an active chromatin state under either of the starvation regimens, 694 genes are common to both conditions, including 15 annotated TFs (FIG. 28B). As expected, several genes known to be involved in TAG accumulation and stress responses are found among the 694 candidate genes. For example, the promoter of gene encoding DGAT (diacylglycerol acyltransferase), a critical enzyme converting DAG (diacylglycerol) to TAG (triacylglycerol) in the TAG biosynthesis pathway (Merchant et al., 2012) transitions from Type III to Type IV in both N- and S-, which is accompanied by substantially increased DGAT transcripts in starved cells (FIG. S3A). In contrast, NRR1 (nitrogen response regulator 1), a plant-specific TF gene involved in nitrogen assimilation and TAG accumulation (Boyle et al., 2012), is not found among the 694 candidates genes because its promoter switches from Type I to Type IV following N-starvation, but remains Type II under S-starvation. This is mirrored by a >25-fold increase in transcript level under N- but not S-starvation (FIG. 37A) (Boyle et al., 2012). To further prioritize this candidate list, we incorporated the RNA expression data of the 694 candidate genes. Because master regulatory genes are expected to function in early stages of the starvation, we focused on a subset of 397 genes that are differentially expressed between 0 and 2 hr under N- and S- starvation (>2-fold, P<0.01). These 397 genes were subjected to cluster analysis and grouped by the time point of highest expression for activated transcripts (see Experimental Procedures). Normalized expression values of the genes from the major clusters were displayed in heat maps and confirmed that those with activated promoter types tend to be up-regulated along the course of both starvation treatments (FIG. 28B, Table 7). We observed 3 broad categories of up-regulated expression patterns: clusters of genes with peak expression at 30 min (cluster A), 1 hr (cluster B) or 2 hr (cluster C) after the onset of nutrient starvation. Two of the 15 TF genes behave similarly within 2 hr in the courses of both N- and S- conditions whereas the remaining 13 TFs were either up-regulated after 2 hr or exhibited discordant expression patterns between the courses of N- and S- starvation. Compared to this integrative approach combining chromatin states with expression data, as many as 1,589 (32 TFs) candidate genes were up-regulated between 0 and 2 hr under both N- and S- starvations if only differential expression analysis is used (FIG. 37B). These results highlight how the intersection of orthogonal transcriptomic and epigenomic data sets enabled the stratification of genes into distinct clusters to retrieve a small number of high-confidence candidates.

PSR1 is a master regulator of lipid accumulation. Between the two highest-priority candidate TFs (PSR1 and Cre01.g034350), PSR1 (phosphorus-stress response 1) was the first TF up-regulated at 1 hr under N-starvation (10-fold), with a delayed and less pronounced increase in expression (3-fold) under S-starvation at 2 hr (FIG. 30A). Such expression pattern differences between N- and S-depletion correlate with differences in lipid accumulation, which is higher under N- than S-starvation (FIG. 1). The PSR1 promoter acquires a substantial amount of H3K36me3 and RNAPII binding in nutrient-deficient medium (FIG. 30B).

PSR1 is a member of the MYB-CC (MYB/coiled-coil domain) TF family and was first described as a component of the phosphate starvation response pathway, but initial studies did not suggest a link to lipid accumulation and its genomic targets are unknown (Wykoff et al., 1999). To confirm that PSR1 is a key regulator of lipid accumulation, we examined lipid levels during stress response in a psr1 loss-of-function mutant containing a nonsense mutation (see Extended Experimental Procedures) and the psr1 mRNA is undetectable (Wykoff et al., 1999). Throughout the 3-day starvation period, the psr1 mutant exhibited a 50-90% reduction in lipid accumulation compared to wild type under multiple, well characterized lipid induction regimens (nitrogen, sulfur, zinc, and iron starvation) (FIGS. 34 and 35). Differences in lipid content were also confirmed by a separate lipid staining (LipidTOX Green). In N- than S- starvation, wild type cells displayed intense green staining while the psr1 mutant showed only red chlorophyll autofluorescence (FIG. 38A). These results indicate that in the absence of PSR1, C. reinhardtii shows defects in normal lipid accumulation in response to a range of nutrient stress, raising the possibility that PSR1 may be a key switch of lipid accumulation in C. reinhardtii.

To examine if PSR1 alone is sufficient to drive lipid accumulation in the absence of nutrient depletion, we evaluated the consequences of its overexpression by nuclear transformation of a constitutively expressed PSR1 transgene into C. reinhardtii cells. Psr1 cDNA was transcriptionally fused to bleomycin (zeocin-resistance) gene sh-ble linked by a self-cleavage peptide 2A from foot-and-mouth-disease-virus (FMDV) under the control of constitutive hsp70/rbcs2 promoter (Rasala et al., 2012). The 2A peptide mediates a self-cleavage reaction to process the fusion protein into two discrete and functional proteins: bleomycin and PSR1. Therefore, the presence zeocin resistant clones indicate overexpression of PSR1 protein. PSR1-overexpressing cells show major morphological differences from wild-type cells grown in control (TAP) medium or under N-starvation. PSR1-overexpressing cells lose their flagella, display an over two-fold increase in diameter, suggesting an ~8-fold increase in cell size (FIG. 6A), and they have a round shape, termed here "liporotund" as it appears to be associated with excessive formation of lipid bodies in the cytoplasm. When the quantity of accumulated lipids was compared between two independent PSR1-overexpressing clones, the level of lipid was positively correlated with the amount of PSR1 overexpression determined by quantitative RT-PCR (FIG. 30B). These clonal PSR1-overexpressing, lipid hyper-accumulating "liporotund" cells have substantially higher (70×) levels of intracellular lipid than wild-type cells when grown in TAP medium and 10× higher lipid levels than wild-type cells grown under nutritional starvation regimens (Mann-Whitney P<1.65e-11) (FIG. 30B). This level is also considerably higher than in transgenic strains overexpressing key enzymes of lipid metabolic pathways (Courchesne et al., 2009), cells blocked in starch biosynthesis (Wang et al., 2009b) or lipid hyper-accumulating cells isolated through random mutagenesis screens (Xie et al., 2014). Microscopy of LipidTOX-stained PSR1-overexpressing cells confirmed an increased number of lipid bodies (FIGS. 34 and 35), which correlates with normalized fluorescence measured by Nile red staining. Similar to the effects of nutrient starvation regimens, increases in lipid content were accompanied by decreases in chlorophyll staining and overall growth delays (FIG. 39A), suggesting that PSR1 alone can convey the common lipid accumulating response from different stress regimens. These results demonstrate that PSR1 is both necessary and sufficient for storage lipid accumulation and confirm its role as a master regulator that uncouples the induction of lipid biosynthesis from specific stress responses.

Deciphering PSR1 target gene circuitry reveals cross-talk between stress responses. Given the properties of structurally related TFs (Prouse and Campbell, 2012), it is expected that PSR1 regulates lipid accumulation by direct binding to specific nucleotide motifs in regulatory sequences near its target genes, thereby altering their transcription. To characterize PSR1 DNA-binding characteristics and determine its genome-wide regulatory targets, we raised polyclonal antibodies against PSR1 peptides and used ChIP-seq to determine the in vivo binding sites of PSR1 at selected time points following nutrient starvation when PSR1 expressions were significantly elevated (30 min and 1 hr in N-; 1 hr, 2 hr and 6 hr in S-) (Table 6). In total, there were 631 and 1,404 PSR1 binding sites found under N- and S-starvation, respectively, with 391 sites shared across conditions. In contrast to the majority of known TFs, PSR1 binding is most frequently observed at the 3' ends of the genes (transcription end site, TES) (FIG. 32A). Among a total 1,644 PSR1-bound regions, 1,234 (75%) are within 1 kb of TES, whereas only 629 (38%) are within 1 kb of TSS, and 101 (6%) in intergenic regions. Besides preferential binding at the 3' ends of genes, PSR1-DNA interactions also appear to be sequence-specific. Using a de novo motif prediction algorithm (Bailey and Elkan, 1994), we found a novel partially palindromic motif ([G/A]TAC[G/A/C]GTA (SEQ ID No:102)) highly enriched (MEME motif E=9.1e-97 based on genomic background) within the binding regions in N- and S- cells. As an illustrative example, FIG. 7B shows PSR1 binding at the 3' TES of Myb family TF gene Cre02.g108350 through the consensus motif within 1 hr after N- and S-depletion. These results are consistent with the temporal dynamics of Cre02.g108350 up-regulation (FIG. 39B). Taken together, these results suggest that PSR1 regulates its target genes via sequence-specific binding to sites preferentially located at the 3' ends of the genes.

The majority (74%) of PSR1-bound genes showed differential expression in response to N- and S- conditions and was inferred as PSR1 target genes. Overall, 495, 186 and 929 PSR1 targets are defined in N-/S- common, N- specific and S- specific conditions, respectively (FIG. 7C; Table 6). Among the N-/S- common PSR1 targets, both transcription regulators (Fisher's Exact Test, P=2.1e-6) and lipid metabolic enzymes (P=2.7e-5) are over-represented, demonstrating that PSR1 acts both upstream and as a direct regulator of lipid metabolism. For example, PDAT1, a gene encoding phospholipid:diacylglycerol acyltransferase is found as a N-/S-common PSR1 target. In *Arabidopsis*, overexpression of PDAT1 enhances fatty acid synthesis and diverting fatty acids from membrane lipids to triacylglycerol. In *C. reinhardtii*, pdat1 mutant accumulates 25% less TAG compared with the parent strain (Boyle et al., 2012; Fan et al., 2013). Besides known key lipid metabolic enzyme, the N-/S-common PSR1 targets also contain an over-representative transcription factors (19 TFs, Fisher's Exact Test p-value=2.047e-6) that could directly or indirectly regulate lipid metabolism; implicating that PSR1 acts upstream of the direct regulators of lipid metabolism. TF genes bound by PSR1 include previously known stress-specific regulators, like Copper response regulator1 (CRR1) (Sommer et al., 2010), Low-$CO_2$ response regulator1 (LCR1) (Ohnishi et al., 2010) and PSR1 itself (Table 6), revealing the potential genetic basis for the integration of different regulatory circuits controlling stress responses (Vischi Winck et al., 2013). Among condition-specific PSR1 target genes, cellular metabolic (P<9e-3) and transporter activities (P<2e-2) are enriched. These genes include ammonium transporter AMT4 in N- cells as well as sulfate anion transporters SUL2 and SLP3 in S- cells. Beyond these enriched functional categories, more than half of the PSR1 targets have no functional annotation, providing a rich collection of direct PSR1 downstream candidate genes for further functional exploration of lipid metabolism.

In summary, these converging lines of evidence support a model (FIG. 37) in which PSR1 is a key switch in the transcriptional regulatory network of lipid biosynthesis and has pleiotropic effects on overall cellular stress response including affecting the expression of membrane transporters.

Discussion

Microalgal are considered one of the most promising sources for biofuels (Wijffels and Barbosa, 2010). As such, a detailed characterization of chromatin landscape and transcription regulation, particularly pertinent to stress response and lipid biosynthesis in model algae can offer keys to understand, and eventually manipulate growth and lipid production. By linking epigenomic dynamics and gene expression profiling, we demonstrate an effective approach of using chromatin state changes to reveal potential regulatory components triggering lipid accumulation in *C. reinhardtii*. Furthermore, our study also provides major advancements in understanding the genetic basis for communication between various stress responses and deciphering the target gene pathway inducing lipid accumulation.

Although histone modifications are largely conserved among eukaryotes, differences have been observed between plants and animals in their genomic distribution and biological function. The global chromatin modification maps from the model alga *C. reinhardtii* reveal unique, as well as common epigenetic features between green algae, land plants, and metazoans. Specifically, the classification of genes with different transcription activities through progressive addition of histone modifications at their TSS may be unique to algae. Since algae often have a compact genome with relatively little intergenic space, it is plausible to assume that the chromatin states at promoters reflect most of the transcriptional activities. Hence, the promoter-associated chromatin states can be used as a readout to infer their corresponding transcription activity. We demonstrated that chromatin analysis, coupled with RNA analysis, enables the detection of some known genes involved in TAG biosynthesis, but also the discovery of new candidates that function as master regulators. This strategy could be applied in other plant species to study environmentally elicited metabolic responses. Beyond the unique promoter chromatin states, complex epigenetic features including bivalent domains and enhancer elements that have so far only been observed in vertebrates (Bernstein et al., 2006) and/or land plants (Luo et al., 2012) are also present in *C. reinhardtii*. However, different sets of histone modification are associated with these features, raising the possibility that these functions may have evolved independently in algae.

*C. reinhardtii* has been adopted as a genetically accessible model for characterization of the genetic regulatory process of lipid metabolism in order to guide genetic engineering in other algal species with higher native lipid yield. The level of lipid accumulation achieved in the present study through a single targeted genetic manipulation, overexpression of the master regulator PSR1, results in higher yields than previous strategies including deficiencies in starch biosynthesis (Li et al., 2010), nitrogen starvation or lipid hyper-accumulating mutant screening (Xie et al., 2014). Although not considered as the production strain, PSR1-overexpressing *C. reinhardtii* can serve as a model for engineering of algal lipid production strains as well as for the identification of additional factors that contribute to lipid hyperaccumulation.

PSR1 is the first TF with genome-wide target genes mapped in *C. reinhardtii*. Intriguingly, PSR1 binds to the 3' regions of its target genes. While regulatory elements harbored at the 3' ends of genes in principle exist (Bigler and Eisenman, 1995; Chen et al., 1998), they appear to be uncommon across eukaryotes and could suggest a mechanism like enhancer:promoter chromatin looping events known in metazoans (Zhang et al., 2013). Currently, it is not clear whether transcription regulation through 3' binding is a common property in microalgae, which may be resolved when more TFs and their target gene interactions are characterized.

PSR1 is highly conserved among a wide range of photosynthetic organisms ranging from marine algae to land plants (FIG. S4B). Beyond sequence conservation, at least some aspects of PSR1 function are also conserved. The *Arabidopsis* homolog PHR1 is involved in the phosphate starvation response (Rubio et al., 2001). This high degree of conservation is consistent with its role in the regulation of fundamental metabolic responses. Thus, we expect that PSR1 and its homologs have similar activities in lipid regulation in other microalgae species, particularly in production strains including *Botryococcus* and *Nannochloropsis* (Li et al., 2014; Vieler et al., 2012). Alignment of transcriptome data suggests that PSR1 homologs are present in *Botryococcus braunii*, *Nannochloropsis gaditana* and *Dunaliella tertiolecta*. We expect the approaches demonstrated and the knowledge learned in the present study of *C. reinhardtii* to be applicable to other algal species and bioenergy crops, enabling the characterization of additional environment elicited metabolic responses and their targeted engineering.

Experimental Procedures

Cell growth and starvation treatment. *C. reinhardtii* wild type strain 4a+ and psr1 mutant strain cc-4267 were cultured using Tris-acetate-phosphate (TAP) medium. N-free (TAP-N), $SO_4^{2-}$-free (TAP-S), Zn-free and Fe-free media were prepared as described (Boyle et al., 2012; Kropat et al., 2011). For N- and S- starvation conditions, cells were grown to mid-log phase, washed twice with depleted media and re-suspended in TAP-N or TAP-*S media* to a density of $2 \times 10^6$ cells/ml. For Zn— and Fe— starvation conditions, cells were grown to mid-log phase in Zn— or Fe-free media and then re-inoculate at $2 \times 10^6$ cells/ml as day 0 for the depletion assays. Cells were counted using the Countess® (Invitrogen) and optical density (OD) at 750 nm at time points indicated.

Lipid analysis. Two types of dyes; Nile Red (Chen et al., 2009) and LipidTOX Green (Invitrogen) were used to analyze the level of neutral lipid in *C. reinhardtii* cells. Cells were stained with a final concentration of 0.5 ug/ml Nile Red. Wavelength of 530 nm was used for excitation and 570 nm for emission. Fluorescence intensity was normalized with cell count or cell density measured at $OD_{750}$. Data was expressed as mean values from 3 biological replicates with standard deviation. For staining intracellular lipid, cells were fixed at 1% formaldehyde and stained with LipidTOX Green for 30 min in the dark. Images were captured by Zeiss LSM710 Confocal Laser Scanning Microscopes using Zen software.

Chromatin immunoprecipitation sequencing (ChIP-Seq). ChIP-seq was performed as previously described (Chen et al., 2008). Briefly, cross-linked cells were lysed with Lysis Buffer (50 mM Tris-HCl pH8, 5 mM EDTA, 1% SDS) and chromatin was then sheared. 5-50 ug of chromatin was used in each immuno-precipitation. Antibodies for histone modifications including H3K4me2 (ab11946), H3K4me3 (ab8580), H3K9me3 (ab8898), H3K27ac (ab4729), H3K27me3 (ab6002) and H3K36me3 (ab9050) were obtained from Abcam and antibody for RNAPII (clone 8WG16) was obtained from Covance (#MMS-126R). For PSR1 ChIP, two rabbit polyclonal antibodies were raised against PSR1 peptide sequences aa54-69 (peptide A: C-QQQGLALGGYGLTQQP (SEQ ID No:87)) and aa465-48 (peptide B: C-LQHQPQLLQPQGSLPA (SEQ ID No:88)) and affinity purified. Chromatin was first pre-cleared and then mixed with beads pre-bound with antibody. Beads were washed and eluted at 37° C. The eluate was then de-crosslinked and DNA was purified by phenol/chloroform extraction, followed by ethanol precipitation. 5-10 ng of purified DNA was used in ChIP-seq library preparation using Truseq DNA Sample Preparation Kit (Illumina) and sequenced on Illumina Mi seq.

Strand-specific RNA-seq analysis. Cells were first lysed and total RNA extracted using Trizol and cleaned up using RNeasy column (Qiagen). PolyA+ RNA was isolated and then fragmented using RNA Fragmentation Reagents (Ambion). Strand-specific RNA-seq library (Parkhomchuk et al., 2009) was constructed using Illumina DNA Sample Preparation Kit (Illumina) or the Kapa Library Amplification Kit (Kapa Biosystems) with 10 cycles PCR amplification. Sequencing was done on the Illumina Hiseq platform of $2 \times 100$ bp or $2 \times 150$ bp.

PSR1 overexpression. PSR1 cDNA was PCR amplified and fused to bleomycin (zeocin-resistance) gene sh-ble linked by a self-cleavage peptide 2A from foot-and-mouth-disease-virus (FMDV) in a expression vector, Bpms4841, a gift from Dr. Rasala, as ble-2A-PSR1 under the control of constitutive hsp70A/rbcs2 promoter (Rasala et al., 2012) and transformed into *C. reinhardtii* cells by electroporation. The zeocin-positive clones were further analyzed for expression of PSR1 and lipid production. For cell size determination, multiple photos were captured using microscope Axio Observer.D1 (Carl Zeiss) at 320× magnification. The longest diameter was determined for each cell by two operators independently using AxioVision rel.4.8 software (Carl Zeiss). A minimum of 200 cells was counted for each condition. Analysis of Variance (ANOVA) was performed which rejected the null hypothesis that the mean diameters were equal between all 4 groups. Tukey's HSD (honest significant difference) test was then performed to find mean diameters that were significantly different from each other. The adjusted P-values were reported.

Informatics Analysis.

Characterization of chromatin state and transcript assignment. ChromHMM v1.0.6 (Ernst and Kellis, 2010) was used to perform unsupervised segmentation of the genome into a certain number of states based on the combination of chromatin modifications. We reduced the number of states by merging the redundant states indicated by correlation ≥0.99. Enrichment analysis of chromatin states was performed with ChromHMM. Based on ChromHMM signal enrichment profile around TSS (FIG. 36A), the chromatin state found between 400 bp upstream to 1000 bp downstream of the TSS was defined as the state for each individual transcript. If multiple chromatin states were found in the TSS region, the state with the most different chromatin modifications was chosen. Transcripts were classified into five types as follow: Type I (state 16), Type II (state 14), Type III (state 13), Type IV (state 8+9) and Type V (state 7+11).

RNA-seq analysis. High quality reads for each of the RNA-seq libraries were mapped to the *C. reinhardtii* genome (Phytozome v5.3.1) using TopHat v2.0.8 (Kim et al., 2013) with Bowtie v2.1.0 (Langmead and Salzberg, 2012). TopHat's parameters were adjusted for the genome characteristics with sensitive and fusion mapping enabled. Next, Cufflinks (modified to work on compact genomes) was used to reconstruct the transcripts guided with the Phytozome v5.3.1 reference transcriptome. Multi-mapped reads were addressed. The remaining transcript assemblies from different time points were merged into a unified set of gene models. Sequential steps of filtering criteria were applied to remove "noise" transcripts. The filtered transcripts were then compared with the reference transcriptome. Differentially expressed transcripts were defined based on the comparison of expression values for each transcript between individual time points and at time 0. The transcripts with significant absolute expression fold change >2, $P<0.01$ were selected as differentially expressed. Transcripts expression profile clustering was performed for each condition separately.

Accession numbers.

All data described in this study will be deposited in the GEO database. The chromatin patterns and assembled transcripts can be visualized and downloaded from the JGI comparative plant genomics portal Phytozome (DOE JGI website).

Chromatin Immunoprecipitation (ChIP) Analysis: Antibody Characterization. Epitopes recognized by antibodies against these seven proteins (H3K4me2, H3K36me3, H3K4me3, H3K27ac, H3K27me3, H3K9me3 and RNAPII) are conserved among *S. cerevisae*, *C. reinhardtii* and human. These histone modifications were selected based on studies done in metazoans. Genomic regions associated with these histone modifications are known to represent functional chromatin states. Specifically, H3K4me3 and H3K36me3 mark active promoters and transcribed regions, respectively. H3K27ac is enriched at distal enhancer elements while H3K27me3 and H3K9me3 represent transcription repressive regions and heterochromatin.

Antibodies against modified histones were designed based on human histone H3 protein. *C. reinhardtii* H3 peptide sequences are highly conserved with 95% identical (Figure S6A). We further confirmed that the target epitopes for H3K4me3 and H3K9m3 match exactly to sequences found in *C. reinhardtii* while H3K27ac/me3 and H3K36me3 showed 95% of identity (data not shown). Western blot results from selected antibodies confirmed their specificity to *C. reinhardtii* histone H3 at the expected size of 17 kDa (FIG. S6B). For RNAPII, antibody 8WG16 recognizes consensus peptide YSPTSP (Patturajan et al., 1998) present in the carboxy-terminal domain (CTD) repeats in *C. reinhardtii* RNAPII. For PSR1 antibodies, in order to determine the specificity of the two PSR1 rabbit polyclonal antibodies, we performed western blot analysis against the recombinant PSR1 protein generated in *E. coli*. The induced expression of the truncated recombinant PSR1 protein was confirmed by SDS-PAGE followed by Coomassie Brilliant Blue staining (FIG. 41A). As expected, both batches of the polyclonal antibodies reacted with N-terminal 6×His-tagged PSR1 fusion protein and displayed a MW of 47 kDa protein on Western blot analysis (FIG. 41B).

Western Blot. Whole cell protein lysate was prepared using CelLytic M (Sigma-Aldrich) and nuclear lysate was prepared using CelLytic NuCLEAR Extraction kit (Sigma-Aldrich). Protein containing-lysate was mixed with Laemmli sample loading buffer (BioRad) containing 2-mercaptoethanol and denatured for 10 min at 98° C. The samples were then ran on a Mini PROTEAN® TGX™ Gel (BioRad). Proteins were electrically transferred onto a PVDF membrane using the Transblot® Turbo™ transfer system (Bio-Rad). The membrane was blocked with 5% nonfat milk in TTBS (TBS+0.05% Tween 20) at room temperature for an hour followed by a 1 hr incubation with a primary antibody and another hour of incubation with StrepTactin-HRP conjugated secondary antibody (BioRad) at 4° C. Signal was detected and imaged using the Immun-Star™ WesternC™ Chemiluminescence Kit and ChemiDoc™ (Biorad).

Generation of recombinant PSR1 protein. *C. reinhardtii* PSR1 cDNA was PCR amplified using the forward primer 5'-GGAATTCCATATGCTGTCGCAGCATCAAGAC-3' (SEQ ID No:89) and reverse primer 5'-ACAGGATCCT-CAATGGGCTTCAGAGGAACC-3' (SEQ ID No:90) including a forward NdeI and reverse BamHI restriction sites, respectively. NdeI-BamHI fragment containing PSR1 coding region from aa38 to aa488, including two target peptide sequences used in raising antibodies, was subcloned into the pET28 (a+) vector (Novagen). The production of 6×His-tagged recombinant PSR1 proteins was induced with 2 mM IPTG and expressed in *E. coli* BL21 (DE3) (Novagen).

Enhancer assay: Target region selection. Of 1339 regions defined in CS 15 (H3K27ac only), we identified 369 potential distal-acting enhancer elements located more than 1 kb upstream or downstream of any known TSS. In order to further dissect the function of these potential enhancers, we applied further filtering criteria to select high confident candidates for screening. We eliminated regions that overlapped with H3K4me3 signals in any of the conditions (TAP, N- or S-depleted) as these regions could be potential novel TSS. We identified 93 candidate enhancers and validated 11 regions randomly selected with the GUS reporter assay. We also included 3 randomly selected regions from CS 16 as negative controls. P-values were calculated against the average of 3 negative controls.

Tobacco GUS (β-glucuronidase) Reporter Asssay. GUS-reporter construct driven by a CaMV 35S minimal promoter (−46/+8) was a gift from Dr. John Harada from UC, Davis. The reporter cassette was cloned into pEG301 (Earley et al., 2006) via a Gateway LR reaction (Invitrogen). Putative target enhancer regions of approximately 1 kb in length based on the selection criteria described above were amplified from genomic DNA using KAPA HiFi HotStart DNA Polymerase (Kapa Biosystems, Inc). Genomic location of regions of interest and primers used are listed in Table 7. Fragments were inserted via EcoRI restriction site using Quick Ligase (NEB). Selected clones were transformed into *Agrobacterium tumefaciens* strain GV3101. Transformants were selected on LB agar containing 50 ug/ml gentamycin and 30 ug/ml kanamycin. Agro strains were resuspended in 1 ml induction medium (10 mM $MgCl_2$, 10 mM MES pH5.6, 150 uM acetosyringeone) and incubated for 2 hr at 28° C. The cultures were then diluted to an OD of 0.5 and injected into *Nicotiana benthamiana* leaves (3 replicates per construct). Plants were placed under constant light (~70 uE) for 48 hr. 0.5 $cm^2$ leaf discs were powdered (6.5 m/s for 60 sec) using the cryo rotor of a Fastprep-24 (MP Bio) and resuspended in 150 ul of lysis buffer (50 mM sodium phosphate buffer pH 7.0, 10 mM EDTA, 0.1% Triton X-100, and 10 mM β-mercaptoethanol). Debris was pelleted and 100 ul of supernatant was collected. 100 ul of 1 mM 4-methylumbelliferyl-β-D-glucuronide (MUG) in lysis buffer was added to each well and the plate was placed at 37° C. Fluorescence was read at various time points with a FluoroMax-4 spectrofluormeter (Horiba Scientific) using an excitation of 365 nm and emission of 455 nm.

PSR1 functional analysis: Characterization of psr1 loss-of-function mutant. We obtained psr1 knockout strain cc-4267 from *Chlamydomonas* Resource Center (chlamycollection.org website). cc-4267 was isolated through UV mutagenesis and screened by failing to activate high-affinity Pi uptake during P starvation with poor growth (growth arrest) and down-regulation of photosynthesis (Shimogawara et al., 1999; Wykoff et al., 1999). In order to identify the exact mutation(s) resided in the psr1 open reading frame in cc-4267, psr1 open reading frame fragments were amplified from both WT 4A+ and mutant cc-4267 genomic DNA using forward primer TGGAGAGCAACCCGGGC-CCCCTCGAGGACAAAGCTGAACGCGCTGCT GGTG-GCCCTAACG (SEQ ID No:91) and reverse primer GAGTGGGTCGACGTCGGAGAGGTACCCTATG-GCTCCACTCGCTGCCGCTTTGCGCGATC (SEQ ID No:92), The fragment is cloned into pENTR vector via KpnI and XhoI using In-Fusion system (Clontech) and subjected to sequencing analysis. A single nucleotide cytosine deletion on exon 1 at amino acid 153 was detected from 3 independent clones. This deletion causes a frame-shift and a stop codon in exon 2.

PSR1 overexpression. First strand cDNA was synthesized using Superscript III First-Strand Synthesis SuperMix (Invitrogen) with $dT_{20}$ oligo followed by PCR to amplify PSR1 cDNA with forward primer: GACAAAGCTGAACGCGCT-GCTGGT (SEQ ID No:93) and reverse primer: CTATG-GCTCCACTCGCTGCCGCTTT (SEQ ID No:94). Fragment containing hsp70/rbcs2 promoter, Ble2A and PSR1 cDNA was then built into pENTR backbone vector via NotI restriction site, creating pENT_Ble2A PSR1 using In-Fusion system (Clontech). *C. reinhardtii* cells grown to mid log phase were resuspended in TAP medium containing 40 mM sucrose to a density of $2 \times 10^8$ cells/ml. About 1 ug of vector, linearized by AsiSI site, was electroporated with Gene Pulser II (BioRad) at 2000 V/cm with 50 uF capacitance. The transformants were incubated overnight in the dark in TAP media with 40 mM sucrose before spread on 1.5% TAP agar containing 5 ug/ml of zeocin. Upon nuclear transformation of PSR1 transgene, PSR1 were transcriptionally fused with the selection marker through 2A peptide, and the 2A peptide mediates a self-cleavage reaction to process the fusion protein into two discrete and functional proteins: bleomycin and PSR1. Therefore, the presence of zeocin resistance indicates the expression of PSR1 protein.

A total of 264 zeocin-positive clones were selected through multiple transformations. These transformant clones were screened for lipid accumulation using Nile Red assay. A cutoff of OD reading (OD750<0.01 after normalization with blank) was applied to filter off clones that did not grow. PSR1 transformants showed a wide range of lipid accumulation and higher levels of lipid detected in the transformants were significant when compared to log phase grown wild type control cells cultured in TAP media. We further examined a few selected clones with high lipid accumulation. RT-PCR results showed 3 out of 6 clones have more than 2-fold PSR1 expression. Two of these clones, termed liporotund (1) and (2) were further characterized.

Reverse transcription-PCR (RT-PCR). Two μg of total RNA was primed with Oligo $(dT)_{12-18}$ (Invitrogen) and reverse transcribed using the Superscript® First-Strand Synthesis System for RT-PCR kit (Life Technologies). The first strand cDNA was used for qPCR using the LightCycler®480 (Roche), KAPA SYBR® FAST qPCR Kit (Kapa Biosystems). PSR1 forward primer: ATGGGCAGTACT-TCATGC (SEQ ID No:95), reverse primer TGAC-GAAGCGGTTGTG (SEQ ID No:96). CBLP was used as a housekeeping control (Sommer et al., 2010); forward primer: GCCACACCGAGTGGGTGTCGTGCG (SEQ ID No:97) and reverse primer: CCTTGCCGCCCGAGGCG-CACAGCG (SEQ ID No:98).

Informatics analysis: ChIP-seq analysis. ChIP was performed to enrich DNA fragments associated with specific modified histones and RNAPII followed by sequencing analysis. 2.5-7 million raw reads were generated from each ChIP experiments and were mapped to *C. reinhardtii* genome (v5.3.1) by BWA v0.6.2 (Li and Durbin, 2009) with default parameters. Enriched regions in the non-redundant mapped reads were identified by MACS2 v2.0.10 (Zhang et al., 2008) (effective genome size=107270392, FDR<5%) (Tables 1 and 2). Normalized ChIP-Seq signal correlation (Pearson's coefficient) between two biological replicates was computed genome-wide over 1 kb bins. The P-value for the number of overlapped peaks between two replicates was computed using the hypergeometric model. The 5 pairwise comparisons of the biological replicates peak list for H3K4me3 and H3K27ac (at 0 and 1 hr after N- condition) and H3K36me3 (at 1 hr after S- condition) demonstrated both high Pearson correlation (R>0.96) in normalized ChIP-seq signal and high proportion (87-96%) of common peaks (P-value of zero) (FIG. 34).

Determination of time point to capture maximal chromatin changes. H3K4me3 ChIP-Seq peaks were called as above for the 9 time points across starvation time courses (Table 8). Averagely, 11,837 peaks were called for each of the 9 time points. For time points with replicates (0 hr, 1 hr), peaks present in only one of the replicates were excluded. The peaks called from 9 time points were merged to produce a common unified list of peaks and pair-wise comparison between the 0 hr and each of the remaining 8 time points' peaks were computed. The number of peaks called increased from 0 to 1 hr but remained mostly above the average after 1 hr. The 12,543 peaks called at 1 hr time point covered 97.5% of the 12,868 union peaks from all 9 time points and contained the highest number (1,272) of unique peaks compared to the rest of the starvation conditions. Thus, we conclude that 1 hr time point captures the maximal chromatin changes.

Characterization of chromatin state. ChromHMM v1.0.6 (Ernst and Kellis, 2010) was used to perform unsupervised segmentation of the genome into a certain number of states based on the combination of chromatin modifications. First, the genome was divided into 200 bp bins. For each data set (5 histone modifications and RNAPII in each of the 3 conditions), ChromHMM marked a bin as "1" if it overlapped with the MACS identified enriched regions. Next, ChromHMM learned 10 randomly initialized HMMs and 1 HMM initialized by information initialization strategy for each number of states, from 2 to 64. The Bayesian Information Criterion (BIC) scores of each model were computed as in (Ernst and Kellis, 2010). The model with the best BIC score (, the 60-states HMM initialized by ChromHMM information initialization strategy, (FIG. S6C)) among the 693 models was selected. While additional states enable increasingly finer-grain distinction, we sought after a smaller number of states that allow for appropriate biological interpretations of the chromatin marks. Pearson correlation was computed for all-to-all chromatin states based on their input marks' emission probabilities. There were 15 redundant states reflected by Pearson correlation ≥0.99, indicating that a 45-states HMM could be sufficient by merging them. The additional states captured the spatial distinction besides the presence of chromatin marks (FIG. 41A). For instance, ChromHMM represented the H3K27ac peak that spanned three 200 bp bins by the two flanking bins (State 21 and 22) and the sandwiched bin (State 23). This spatial distinction became more pronounced for wider peaks where the number of sandwiched bins increased (FIG. 41B). Conversely, two states may be sufficient to represent the peak (FIG. 41C). Although the spatial distinctions were meticulously represented by the additional states, they were mostly the consequence of transiting from one chromatin combination to another where the boundary bins shared almost the exact characteristics of the sandwiched bin (FIG. 41D). Thus, they were considered 'biologically' redundant. We then picked the best scored 45-states HMM amongst the eleven 45-states HMMs and repeated the redundancy check. Progressively, we selected HMMs with 45-, 37-, 30-, 26-, 23-, 21-, 18-, and finally 16-states where no two states have high similarity in their emission probabilities. We then ran additional 489 randomly initialized HMMs for the smallest number of states determined (16-states) and picked the best from among these 500 models. This 16-state HMM has a BIC score −937,141 and remained the best model among the total of five hundreds 16-states HMMs learned.

ChromHMM was used to perform enrichment analysis of chromatin states in the neighborhood of an anchor point and overlap with specific genomics features. Features from the transcripts assembled by RNA-Seq analysis (see RNA-Seq analysis below) were prepared in. bed format accordingly.

RNA-seq analysis. Strand-specific paired-end RNA-seq data was generated for each time point; 9 time points for each of the N- and S- conditions, 2 biological replicates each. From a total of 36 libraries, an average of 44 million mappable paired reads were generated for each sample (Table 3). Trimmed reads with average quality ≥20, ≤3 Ns, and ≥32 bases and not associated with artifacts were kept. These high quality reads for each of the 36 libraries were mapped to the C. reinhardtii genome (Phytozome v5.3.1) using TopHat v2.0.8 (Kim et al., 2013) with Bowtie v2.1.0 (Langmead and Salzberg, 2012). TopHat's parameters were adjusted for the genome characteristics with sensitive and fusion mapping enabled. Specifically, valid intron length was 20 bp to 25 kbp and minimum distance between intra-chromosomal fusions was 1 Mbp. The library type "fr-firststrand" stated and read alignments with >3 mismatches were discarded. To assess the quality between replicates, Pearson correlation between each pair of the 18 libraries for each condition was computed based on the expression values of Phytozome transcripts models generated by Cufflinks v2.1.1 (Trapnell et al., 2013). The biological replicates for each time point showed high correlation (≥0.988, Pearson, FIG. S1B). Next, Cufflinks (modified to work on compact genomes) was used to reconstruct the transcripts guided with the Phytozome v5.3.1 reference transcriptome. Multi-mapped read correction was turned on and transcript composed of >50% multi-mapped reads or <25 reads were discarded. The remaining transcript assemblies from different time points were merged into a unified set of gene models, which was then compared to the annotated transcriptome. In total, 66,561 transcripts were assembled (Table 4). Potential noise was filtered from these predicted transcripts. Sequential steps of filtering criteria were applied as follows; 1). FPKM >0 for both replicates at least at one time point; 2) length of CDS>=50 amino acid; candidate coding regions were predicted based on transcript sequences using TransDecoder script v2013-02-25 from the Trinity package (Grabherr et al., 2011), 3) Remove "noise" transcripts of CuffDiff classes 'E', 'O' and 'P' and single exon transcripts of CuffDiff classes '.', 'C' and 'I'. The three-step filtering generated 22,209 high confident transcript models, which were then compared with the reference transcriptome using CuffCompare. 90% of the 19,526 Phytozome annotated transcripts (v5.3.1), 4,241 new variants and 298 new transcripts were found (FIG. 35B, Table 4). 277 and 250 transcripts were assigned to putative TFs and TRs, respectively (Table 4).

Expression was defined by the expression value (FPKM) combining both replicates calculated by statistical model used in CuffDiff with geometric library normalization and per-condition cross-replicate dispersion estimation. Differentially expressed transcripts were defined based on the comparison of expression values for each transcript between individual time points and at time 0. The transcripts with significant absolute expression fold change >2, P<0.01 were selected as differentially expressed. In total, 12,144 and 12,242 transcripts were differentially expressed in N- and S-, respectively; among them, roughly half were up-regulated and half were down-regulated (Table 5). Transcripts expression profile clustering was performed using ClassDiscovery (Coombes, 2013) for each condition separately. Transcript expression profile was first log 10-transformed with a pseudo count 1 before the Min-Max normalization. Complete linkage clustering with Spearman correlation distance threshold ≤0.05 defined clusters of transcripts with similar expression patterns. Clusters were grouped by the time point of highest expression for activated transcripts.

GO Analysis. C. reinhardtii GO annotations were downloaded from Phytozome and set up for GOstats (Falcon and Gentleman, 2007). Conditional GO terms over-representation was tested with P<0.05.

Classification of C. reinhardtii expressed transcripts as TF and transcription regulator (TR). An earlier attempt to generate a high quality set of TF annotated gene list from C. reinhardtii Phytozome genes Cre 3.0 defined 378 TF genes (Perez-Rodriguez et al., 2010). Since then, the number of annotated genes in C. reinhardtii has greatly expanded and, with higher quality of genome sequence and better annotation tools, their predicted protein domains were also changed. Therefore, we decided to generate an improved and updated TF gene list. PFAM (Punta et al., 2012) annotations of the C. reinhardtii proteome (v5.3.1) were downloaded from Phytozome. Based on the presence of required and the absence of forbidden domain(s) as defined in PlnTFDB classification rules (Perez-Rodriguez et al., 2010), we classified the proteins and their corresponding transcripts in C. reinhardtii into their respective TF or TR family. We found that 7 of the PFAM domain ids used in PlnTFDB have been superseded. In total, we defined 547 TF transcripts expressed from 499 genomic coding loci. Among them, 518 transcripts (277 TFs and 250 TRs) are expressed in our experimental conditions and 344 and 318 are differentially expressed in N- and S- conditions, respectively. They serve as the basis for discovering TFs in this study.

PSR1 ChIP-seq analysis. ChIP was performed to enrich DNA fragments associated with PSR1 followed by sequencing analysis. Two sets of ChIP experiments were performed at selected time points, based on expression data, following nutrient starvation (30 min, 1 hr in N- and 1 hr, 2 hr, 6 hr in S-) targeting peptide A and peptide B separately (Table 6). The time points were selected based on the times when high levels of Psr1 transcript were detected. Paired-end reads generated from each ChIP experiments were treated as 2 sets of single-end read and processed as stated above (see ChIP-seq analysis). Common enriched regions identified by both Read/1 and Read/2 in each experiment were retained. These regions from all 10 experiments were merged to produce the final putative binding regions.

PSR1 conservation. *C. reinhardtii* PSR1 protein sequence (XP_001700553.1 (SEQ ID No:99)) was searched against non-redundant protein sequences database using NCBI's BLAST (http://blast.ncbi.nlm.nih.gov/) (Altschul et al., 1997; Altschul et al., 2005) with BLOSUM45 scoring matrix and 5000 maximum target sequences. A Grishin General distance (Grishin, 1995) tree was built using BLAST tree view based on BLAST pairwise alignment results by Neighbor joining method (Saitou and Nei, 1987).

PSR1 binding motif analysis. Merged peaks containing high proportion of 6-base repeats (e.g. (CCCTAA)n (SEQ ID No:100)) were removed. MEME (Bailey and Elkan, 1994) version 4.9.1 was run with the parameters "-mod anr -bfile Chlre5_CnM.bfile -maxsites 1000 -dna -revcomp -evt 0.01 -nmotifs 30 -minw 8 -maxw 9" on the remaining merged peaks. MEME identified multiple motifs enriched within the binding peaks with high significance (E<1e-7). Manual curation was performed to remove motifs containing high proportion of repeat sequences, which resulted in two motifs (a 8-base motif and a 9-base motif). TOMTOM (Gupta et al., 2007) determined that both remaining motifs to be highly similar (E=8.0e-7). The palindromic motif [AG]TACCGTA (SEQ ID No:101) (E=9.4e-102) with smaller E-value was chosen as the representative. There were 312 motif sites found in the 1625 merged peaks and 158 motif sites were found amongst the 376 common merged peaks between N- and S-depletion conditions.

REFERENCES

1. Ay, N., Irmler, K., Fischer, A., Uhlemann, R., Reuter, G., and Humbeck, K. (2009). Epigenetic programming via histone methylation at WRKY53 controls leaf senescence in *Arabidopsis thaliana*. The Plant journal: for cell and molecular biology 58, 333-346.
2. Bailey, T. L., and Elkan, C. (1994). Fitting a mixture model by expectation maximization to discover motifs in biopolymers. Proceedings/International Conference on Intelligent Systems for Molecular Biology; ISMB International Conference on Intelligent Systems for Molecular Biology 2, 28-36.
3. Bernstein, B. E., Mikkelsen, T. S., Xie, X., Kamal, M., Huebert, D. J., Cuff, J., Fry, B., Meissner, A., Wernig, M., Plath, K., et al. (2006). A bivalent chromatin structure marks key developmental genes in embryonic stem cells. Cell 125, 315-326.
4. Berr, A., Shafiq, S., and Shen, W. H. (2011). Histone modifications in transcriptional activation during plant development. Biochimica et biophysica acta 1809, 567-576.
5. Bigler, J., and Eisenman, R. N. (1995). Novel location and function of a thyroid hormone response element. The EMBO journal 14, 5710-5723.
6. Blatti, J. L., Michaud, J., and Burkart, M. D. (2013). Engineering fatty acid biosynthesis in microalgae for sustainable biodiesel. Current opinion in chemical biology 17, 496-505.
7. Borevitz, J. O., Xia, Y., Blount, J., Dixon, R. A., and Lamb, C. (2000). Activation tagging identifies a conserved MYB regulator of phenylpropanoid biosynthesis. The Plant cell 12, 2383-2394.
8. Boyle, N. R., Page, M. D., Liu, B., Blaby, I. K., Casero, D., Kropat, J., Cokus, S. J., Hong-Hermesdorf, A., Shaw, J., Karpowicz, S. J., et al. (2012). Three acyltransferases and nitrogen-responsive regulator are implicated in nitrogen starvation-induced triacylglycerol accumulation in *Chlamydomonas*. The Journal of biological chemistry 287, 15811-15825.
9. Cagnon, C., Mirabella, B., Nguyen, H. M., Beyly-Adriano, A., Bouvet, S., Cuine, S., Beisson, F., Peltier, G., and Li-Beisson, Y. (2013). Development of a forward genetic screen to isolate oil mutants in the green microalga *Chlamydomonas reinhardtii*. Biotechnology for biofuels 6, 178.
10. Castruita, M., Casero, D., Karpowicz, S. J., Kropat, J., Vieler, A., Hsieh, S. I., Yan, W., Cokus, S., Loo, J. A., Benning, C., et al. (2011). Systems biology approach in *Chlamydomonas* reveals connections between copper nutrition and multiple metabolic steps. The Plant cell 23, 1273-1292.
11. Celniker, S. E., Dillon, L. A., Gerstein, M. B., Gunsalus, K. C., Henikoff, S., Karpen, G. H., Kellis, M., Lai, E. C., Lieb, J. D., MacAlpine, D. M., et al. (2009). Unlocking the secrets of the genome. Nature 459, 927-930.
12. Chen, R., Silver, D. L., and de Bruijn, F. J. (1998). Nodule parenchyma-specific expression of the *sesbania rostrata* early nodulin gene SrEnod2 is mediated by its 3' untranslated region. The Plant cell 10, 1585-1602.
13. Chen, W., Zhang, C., Song, L., Sommerfeld, M., and Hu, Q. (2009). A high throughput Nile red method for quantitative measurement of neutral lipids in microalgae. J Microbiol Methods 77, 41-47.
14. Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.
15. Chisti, Y. (2007). Biodiesel from microalgae. Biotechnology advances 25, 294-306.
16. Chisti, Y. (2013). Constraints to commercialization of algal fuels. Journal of biotechnology 167, 201-214.
17. Consortium, E. P., Bernstein, B. E., Birney, E., Dunham, I., Green, E. D., Gunter, C., and Snyder, M. (2012). An integrated encyclopedia of DNA elements in the human genome. Nature 489, 57-74.
18. Courchesne, N. M., Parisien, A., Wang, B., and Lan, C. Q. (2009). Enhancement of lipid production using biochemical, genetic and transcription factor engineering approaches. Journal of biotechnology 141, 31-41.
19. Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. Proceedings of the National Academy of Sciences of the United States of America 107, 21931-21936.
20. Csavina, J. L., Stuart, B. J., Riefler, R. G., and Vis, M. L. (2011). Growth optimization of algae for biodiesel production. Journal of applied microbiology 111, 312-318.
21. Ernst, J., and Kellis, M. (2010). Discovery and characterization of chromatin states for systematic annotation of the human genome. Nature biotechnology 28, 817-825.

22. Ernst, J., and Kellis, M. (2012). ChromHMM: automating chromatin-state discovery and characterization. Nature methods 9, 215-216.
23. Fan, J., Yan, C., Zhang, X., and Xu, C. (2013). Dual role for phospholipid:diacylglycerol acyltransferase: enhancing fatty acid synthesis and diverting fatty acids from membrane lipids to triacylglycerol in *Arabidopsis* leaves. The Plant cell 25, 3506-3518.
24. Guenther, M. G., Levine, S. S., Boyer, L. A., Jaenisch, R., and Young, R. A. (2007). A chromatin landmark and transcription initiation at most promoters in human cells. Cell 130, 77-88.
25. Hemschemeier, A., Casero, D., Liu, B., Benning, C., Pellegrini, M., Happe, T., and Merchant, S. S. (2013). Copper response regulator1-dependent and -independent responses of the *Chlamydomonas reinhardtii* transcriptome to dark anoxia. The Plant cell 25, 3186-3211.
26. Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome biology 14, R36.
27. Kouzarides, T. (2007). Chromatin modifications and their function. Cell 128, 693-705.
28. Kropat, J., Hong-Hermesdorf, A., Casero, D., Ent, P., Castruita, M., Pellegrini, M., Merchant, S. S., and Malasarn, D. (2011). A revised mineral nutrient supplement increases biomass and growth rate in *Chlamydomonas reinhardtii*. The Plant journal: for cell and molecular biology 66, 770-780.
29. Langmead, B., and Salzberg, S. L. (2012). Fast gapped-read alignment with Bowtie 2. Nature methods 9, 357-359.
30. Li, J., Han, D., Wang, D., Ning, K., Jia, J., Wei, L., Jing, X., Huang, S., Chen, J., Li, Y., et al. (2014). Choreography of Transcriptomes and Lipidomes of *Nannochloropsis* Reveals the Mechanisms of Oil Synthesis in Microalgae. The Plant cell.
31. Li, X., Wang, X., He, K., Ma, Y., Su, N., He, H., Stolc, V., Tongprasit, W., Jin, W., Jiang, J., et al. (2008). High-resolution mapping of epigenetic modifications of the rice genome uncovers interplay between DNA methylation, histone methylation, and gene expression. The Plant cell 20, 259-276.
32. Li, Y., Han, D., Hu, G., Dauvillee, D., Sommerfeld, M., Ball, S., and Hu, Q. (2010). *Chlamydomonas* starchless mutant defective in ADP-glucose pyrophosphorylase hyper-accumulates triacylglycerol. Metabolic engineering 12, 387-391.
33. Luo, C., Sidote, D. J., Zhang, Y., Kerstetter, R. A., Michael, T. P., and Lam, E. (2012). Integrative analysis of chromatin states in *Arabidopsis* identified potential regulatory mechanisms for natural antisense transcript production. The Plant journal: for cell and molecular biology.
34. Merchant, S. S., Kropat, J., Liu, B., Shaw, J., and Warakanont, J. (2012). TAG, you're it! *Chlamydomonas* as a reference organism for understanding algal triacylglycerol accumulation. Current opinion in biotechnology 23, 352-363.
35. Merchant, S. S., Prochnik, S. E., Vallon, O., Harris, E. H., Karpowicz, S. J., Witman, G. B., Terry, A., Salamov, A., Fritz-Laylin, L. K., Marechal-Drouard, L., et al. (2007). The *Chlamydomonas* genome reveals the evolution of key animal and plant functions. Science 318, 245-250.
36. Nuruzzaman, M., Sharoni, A. M., and Kikuchi, S. (2013). Roles of NAC transcription factors in the regulation of biotic and abiotic stress responses in plants. Frontiers in microbiology 4, 248.
37. Ohnishi, N., Mukherjee, B., Tsujikawa, T., Yanase, M., Nakano, H., Moroney, J. V., and Fukuzawa, H. (2010). Expression of a low $CO(2)$-inducible protein, LCI1, increases inorganic carbon uptake in the green alga *Chlamydomonas reinhardtii*. The Plant cell 22, 3105-3117.
38. Parkhomchuk, D., Borodina, T., Amstislayskiy, V., Banaru, M., Hallen, L., Krobitsch, S., Lehrach, H., and Soldatov, A. (2009). Transcriptome analysis by strand-specific sequencing of complementary DNA. Nucleic acids research 37, e123.
39. Peters, A. H., Mermoud, J. E., O'Carroll, D., Pagani, M., Schweizer, D., Brockdorff, N., and Jenuwein, T. (2002). Histone H3 lysine 9 methylation is an epigenetic imprint of facultative heterochromatin. Nature genetics 30, 77-80.
40. Prouse, M. B., and Campbell, M. M. (2012). The interaction between MYB proteins and their target DNA binding sites. Biochimica et biophysica acta 1819, 67-77.
41. Rasala, B. A., Lee, P. A., Shen, Z., Briggs, S. P., Mendez, M., and Mayfield, S. P. (2012). Robust expression and secretion of Xylanase1 in *Chlamydomonas reinhardtii* by fusion to a selection gene and processing with the FMDV 2A peptide. PloS one 7, e43349.
42. Roudier, F., Ahmed, I., Berard, C., Sarazin, A., Mary-Huard, T., Cortijo, S., Bouyer, D., Caillieux, E., Duvernois-Berthet, E., Al-Shikhley, L., et al. (2011). Integrative epigenomic mapping defines four main chromatin states in *Arabidopsis*. The EMBO journal 30, 1928-1938.
43. Rubio, V., Linhares, F., Solano, R., Martin, A. C., Iglesias, J., Leyva, A., and Paz-Ares, J. (2001). A conserved MYB transcription factor involved in phosphate starvation signaling both in vascular plants and in unicellular algae. Genes & development 15, 2122-2133.
44. Shlyueva, D., Stampfel, G., and Stark, A. (2014). Transcriptional enhancers: from properties to genome-wide predictions. Nature reviews Genetics 15, 272-286.
45. Sommer, F., Kropat, J., Malasarn, D., Grossoehme, N. E., Chen, X., Giedroc, D. P., and Merchant, S. S. (2010). The CRR1 nutritional copper sensor in *Chlamydomonas* contains two distinct metal-responsive domains. The Plant cell 22, 4098-4113.
46. Tanurdzic, M., Vaughn, M. W., Jiang, H., Lee, T. J., Slotkin, R. K., Sosinski, B., Thompson, W. F., Doerge, R. W., and Martienssen, R. A. (2008). Epigenomic consequences of immortalized plant cell suspension culture. PLoS biology 6, 2880-2895.
47. Vieler, A., Wu, G., Tsai, C. H., Bullard, B., Cornish, A. J., Harvey, C., Reca, I. B., Thornburg, C., Achawanantakun, R., Buehl, C. J., et al. (2012). Genome, functional gene annotation, and nuclear transformation of the heterokont oleaginous alga *Nannochloropsis* oceanica CCMP1779. PLoS genetics 8, e1003064.
48. Vischi Winck, F., Arvidsson, S., Riano-Pachon, D. M., Hempel, S., Koseska, A., Nikoloski, Z., Urbina Gomez, D. A., Rupprecht, J., and Mueller-Roeber, B. (2013). Genome-wide identification of regulatory elements and reconstruction of gene regulatory networks of the green alga *Chlamydomonas reinhardtii* under carbon deprivation. PloS one 8, e79909.
49. Wang, X., Elling, A. A., Li, X., Li, N., Peng, Z., He, G., Sun, H., Qi, Y., Liu, X. S., and Deng, X. W. (2009a). Genome-wide and organ-specific landscapes of epigenetic modifications and their relationships to mRNA and small RNA transcriptomes in maize. The Plant cell 21, 1053-1069.

50. Wang, Z. T., Ullrich, N., Joo, S., Waffenschmidt, S., and Goodenough, U. (2009b). Algal lipid bodies: stress induction, purification, and biochemical characterization in wild-type and starchless *Chlamydomonas reinhardtii*. Eukaryotic cell 8, 1856-1868.
51. Wijffels, R. H., and Barbosa, M. J. (2010). An outlook on microalgal biofuels. Science 329, 796-799.
52. Wykoff, D. D., Grossman, A. R., Weeks, D. P., Usuda, H., and Shimogawara, K. (1999). Psr1, a nuclear localized protein that regulates phosphorus metabolism in *Chlamydomonas*. Proceedings of the National Academy of Sciences of the United States of America 96, 15336-15341.
53. Xie, B., Stessman, D., Hart, J. H., Dong, H., Wang, Y., Wright, D. A., Nikolau, B. J., Spalding, M. H., and Halverson, L. J. (2014). High-throughput fluorescence-activated cell sorting for lipid hyperaccumulating *Chlamydomonas reinhardtii* mutants. Plant biotechnology journal.
54. Zhang, Y., Wong, C. H., Birnbaum, R. Y., Li, G., Favaro, R., Ngan, C. Y., Lim, J., Tai, E., Poh, H. M., Wong, E., et al. (2013). Chromatin connectivity maps reveal dynamic promoter-enhancer long-range associations. Nature 504, 306-310.
55. Zhong, S., Fei, Z., Chen, Y. R., Zheng, Y., Huang, M., Vrebalov, J., McQuinn, R., Gapper, N., Liu, B., Xiang, J., et al. (2013). Single-base resolution methylomes of tomato fruit development reveal epigenome modifications associated with ripening. Nature biotechnology 31, 154-159.

SUPPLEMENTAL REFERENCES

56. Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic acids research 25, 3389-3402.
57. Altschul, S. F., Wootton, J. C., Gertz, E. M., Agarwala, R., Morgulis, A., Schaffer, A. A., and Yu, Y. K. (2005). Protein database searches using compositionally adjusted substitution matrices. The FEBS journal 272, 5101-5109.
58. Coombes, K. R. (2013). ClassDiscovery: Classes and methods for "class discovery" with microarrays or proteomics.
59. Earley, K. W., Haag, J. R., Pontes, O., Opper, K., Juehne, T., Song, K., and Pikaard, C. S. (2006). Gateway-compatible vectors for plant functional genomics and proteomics. The Plant journal: for cell and molecular biology 45, 616-629.
60. Falcon, S., and Gentleman, R. (2007). Using GOstats to test gene lists for GO term association. Bioinformatics 23, 257-258.
61. Grabherr, M. G., Haas, B. J., Yassour, M., Levin, J. Z., Thompson, D. A., Amit, I., Adiconis, X., Fan, L., Raychowdhury, R., Zeng, Q., et al. (2011). Full-length transcriptome assembly from RNA-Seq data without a reference genome. Nature biotechnology 29, 644-652.
62. Grishin, N. V. (1995). Estimation of the number of amino acid substitutions per site when the substitution rate varies among sites. Journal of molecular evolution 41, 675-679.
63. Gupta, S., Stamatoyannopoulos, J. A., Bailey, T. L., and Noble, W. S. (2007). Quantifying similarity between motifs. Genome biology 8, R24.
64. Li, H., and Durbin, R. (2009). Fast and accurate short read alignment with Burrows-Wheeler transform. Bioinformatics 25, 1754-1760.
65. Patturajan, M., Schulte, R. J., Sefton, B. M., Berezney, R., Vincent, M., Bensaude, O., Warren, S. L., and Corden, J. L. (1998). Growth-related changes in phosphorylation of yeast RNA polymerase II. The Journal of biological chemistry 273, 4689-4694.
66. Perez-Rodriguez, P., Riano-Pachon, D. M., Correa, L. G., Rensing, S. A., Kersten, B., and Mueller-Roeber, B. (2010). PlnTFDB: updated content and new features of the plant transcription factor database. Nucleic acids research 38, D822-827.
67. Punta, M., Coggill, P. C., Eberhardt, R. Y., Mistry, J., Tate, J., Boursnell, C., Pang, N., Forslund, K., Ceric, G., Clements, J., et al. (2012). The Pfam protein families database. Nucleic acids research 40, D290-301.
68. Saitou, N., and Nei, M. (1987). The neighbor-joining method: a new method for reconstructing phylogenetic trees. Molecular biology and evolution 4, 406-425.
69. Shimogawara, K., Wykoff, D. D., Usuda, H., and Grossman, A. R. (1999). *Chlamydomonas reinhardtii* mutants abnormal in their responses to phosphorus deprivation. Plant physiology 120, 685-694.
70. Sommer, F., Kropat, J., Malasarn, D., Grossoehme, N. E., Chen, X., Giedroc, D. P., and Merchant, S. S. (2010). The CRR1 nutritional copper sensor in *Chlamydomonas* contains two distinct metal-responsive domains. The Plant cell 22, 4098-4113.
71. Trapnell, C., Hendrickson, D. G., Sauvageau, M., Goff, L., Rinn, J. L., and Pachter, L. (2013). Differential analysis of gene regulation at transcript resolution with RNA-seq. Nature biotechnology 31, 46-53.
72. Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

The figures, sequences and examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 1

| | | | Baseline (0hr) | | | | |
|---|---|---|---|---|---|---|---|
| Marks | Replicate | Type | # of reads | Mappable reads | Mapped (%) | # of dedupl-unique reads | Dedupl-unique % | #MACS2 peaks* |
| H3K4me2 | | IP | 8,921,796 | 8,720,202 | 97.7% | 7,029,002 | 80.6% | 6,032 |
| | | Input | 7,597,576 | 7,342,003 | 96.6% | 3,596,656 | 49.0% | |
| H3K4me3 | R1 | IP | 6,991,217 | 6,660,886 | 95.3% | 5,146,811 | 77.3% | 11,487 |
| | | Input | 6,743,218 | 6,382,897 | 94.7% | 4,040,258 | 63.3% | |
| | R2 | IP | 5,015,597 | 4,930,521 | 98.3% | 3,780,635 | 76.7% | 12,857 |
| | | Input | 3,973,127 | 3,843,943 | 96.7% | 2,327,899 | 60.6% | |

TABLE 1-continued

Baseline (0hr)

| Marks | Replicate | Type | # of reads | Mappable reads | Mapped (%) | # of dedupl-unique reads | Dedupl-unique % | #MACS2 peaks* |
|---|---|---|---|---|---|---|---|---|
| H3K27ac | R1 | IP | 4,112,025 | 3,739,326 | 90.9% | 2,924,426 | 78.2% | 11,992 |
|  |  | Input | 5,394,178 | 4,713,175 | 87.4% | 3,158,292 | 67.0% |  |
|  | R2 | IP | 6,335,579 | 6,209,650 | 98.0% | 4,389,420 | 70.7% | 12,175 |
|  |  | Input | 3,973,127 | 3,843,943 | 96.7% | 2,327,899 | 60.6% |  |
| H3K9me3 |  | IP | 5,174,636 | 4,816,363 | 93.1% | 3,214,285 | 66.7% | 10,575 |
|  |  | Input | 3,797,702 | 3,608,874 | 95.0% | 2,558,492 | 70.9% |  |
| H3K27me3 |  | IP | 2,541,255 | 2,337,799 | 92.0% | 1,744,210 | 74.6% | 484 |
|  |  | Input | 4,099,370 | 3,896,239 | 95.0% | 2,529,618 | 64.9% |  |
| H3K36me3 | R1 | IP | 4,339,861 | 4,253,142 | 98.0% | 3,371,955 | 79.3% | 8,873 |
|  |  | Input | 4,070,390 | 3,929,062 | 96.5% | 2,681,361 | 68.2% |  |
|  | R2 | IP | n.a | n.a | n.a | n.a | n.a | n.a |
|  |  | Input | n.a | n.a | n.a | n.a | n.a |  |
| RNAPII |  | IP | 3,791,640 | 89.2% | 89.2% | 2,077,194 | 61.4% | 3,143 |
|  |  | Input | 2,475,900 | 93.4% | 93.4% | 1,550,148 | 67.0% |  |

TABLE 2

| # of reads | Mappable reads | Mapped (%) | # of dedupl-unique reads | Dedupl-unique % | #MACS2 peaks* | # of reads | Mappable reads | Mapped (%) | # of dedupl-unique reads | Dedupl-unique % | #MACS2 peaks* |
|---|---|---|---|---|---|---|---|---|---|---|---|
| Nitrogen Depreviation (1 hr) | | | | | | Sulphur Depreviation (1 hr) | | | | | |
| n.a | n.a | n.a | n.a | n.a | n.a | n.a | n.a | n.a | n.a | n.a | n.a |
| n.a | n.a | n.a | n.a | n.a | n.a | n.a | n.a | n.a | n.a | n.a | n.a |
| 3,977,733 | 3,859,385 | 97.0% | 3,074,149 | 79.7% | 12,821 | 6,860,877 | 6,569,112 | 95.7% | 4,651,112 | 70.8% | 12,868 |
| 3,719,293 | 3,544,825 | 95.3% | 2,216,073 | 62.5% |  | 6,382,232 | 6,139,895 | 96.2% | 3,638,293 | 59.3% |  |
| 5,733,447 | 5,587,201 | 97.4% | 4,149,765 | 74.3% | 13,048 | n.a | n.a | n.a | n.a | n.a | n.a |
| 3,954,921 | 3,819,769 | 96.6% | 2,672,471 | 70.0% |  | n.a | n.a | n.a | n.a | n.a |  |
| 4,060,312 | 3,917,846 | 96.5% | 3,028,160 | 77.3% | 12,244 | 7,591,542 | 7,277,309 | 95.9% | 4,914,747 | 67.5% | 12,623 |
| 3,719,293 | 3,544,825 | 95.3% | 2,216,073 | 62.5% |  | 6,131,473 | 5,855,234 | 95.5% | 2,868,969 | 49.0% |  |
| 4,852,751 | 4,747,843 | 97.8% | 3,555,971 | 74.9% | 12,412 | n.a | n.a | n.a | n.a | n.a | n.a |
| 3,954,921 | 3,819,769 | 96.6% | 2,672,471 | 70.0% |  | n.a | n.a | n.a | n.a | n.a |  |
| 4,091,263 | 3,888,102 | 95.0% | 2,851,236 | 73.3% | 8,120 | 8,704,508 | 7,936,605 | 91.2% | 3,107,982 | 39.2% | 2,293 |
| 4,369,910 | 4,209,239 | 96.3% | 2,942,246 | 69.9% |  | 7,722,693 | 7,383,081 | 95.6% | 3,787,568 | 51.3% |  |
| 5,786,549 | 5,034,533 | 87.0% | 3,321,965 | 66.0% | 521 | 4,983,273 | 4,253,982 | 85.4% | 1,057,077 | 24.8% | 510 |
| 3,867,019 | 3,668,587 | 94.9% | 2,411,860 | 65.7% |  | 6,541,621 | 6,247,061 | 95.5% | 3,509,535 | 56.2% |  |
| 4,710,003 | 4,577,918 | 97.2% | 3,554,242 | 77.6% | 9,188 | 8,481,474 | 8,125,826 | 95.8% | 4,456,946 | 54.8% | 8,528 |
| 4,369,910 | 4,209,239 | 96.3% | 2,942,246 | 69.9% |  | 7,722,693 | 7,383,081 | 95.6% | 3,787,568 | 51.3% |  |
| n.a | n.a | n.a | n.a | n.a | n.a | 7,940,234 | 6,232,638 | 78.5% | 4,358,067 | 69.9% | 8,647 |
| n.a | n.a | n.a | n.a | n.a |  | 7,755,521 | 7,492,746 | 96.6% | 3,867,641 | 51.6% |  |
| 3,877,267 | 3,538,792 | 91.3% | 2,119,854 | 59.9% | 3,138 | 6,729,049 | 6,330,305 | 94.1% | 1,945,188 | 30.7% | 4,385 |
| 3,649,425 | 3,492,461 | 95.7% | 2,221,803 | 63.6% |  | 6,382,232 | 6,139,895 | 96.2% | 3,638,293 | 59.3% |  |

TABLE 3

| Treatment | Time Point | Replicate | Raw Pairs | Trimed Pairs | Mapped and Properly paired | % of raw data |
|---|---|---|---|---|---|---|
| Baseline | 0 hr | A | 71,422,643 | 64,747,175 | 47,024,606 | 66% |
| Baseline | 0 hr | B | 110,470,791 | 100,922,597 | 75,531,765 | 68% |
| N- | 10' | A | 61,464,593 | 53,177,133 | 37,727,829 | 61% |
| N- | 10' | B | 49,909,719 | 46,685,339 | 32,188,759 | 64% |
| N- | 30' | A | 75,769,515 | 67,777,184 | 50,055,526 | 66% |
| N- | 30' | B | 97,014,730 | 92,635,222 | 57,015,580 | 59% |
| N- | 1 hr | A | 64,554,510 | 59,103,917 | 41,486,758 | 64% |
| N- | 1 hr | B | 167,115,974 | 149,991,988 | 109,796,223 | 66% |
| N- | 2 hr | A | 78,005,952 | 63,606,449 | 46,538,643 | 60% |
| N- | 2 hr | B | 81,926,123 | 74,193,002 | 53,657,960 | 65% |
| N- | 6 hr | A | 69,255,663 | 63,306,952 | 46,908,149 | 68% |
| N- | 6 hr | B | 81,034,852 | 74,198,626 | 55,391,284 | 68% |
| N- | 8 hr | A | 47,825,305 | 45,149,030 | 33,339,635 | 70% |
| N- | 8 hr | B | 50,370,863 | 48,030,881 | 34,701,013 | 69% |
| N- | 24 hr | A | 62,005,731 | 57,492,037 | 40,931,543 | 66% |
| N- | 24 hr | B | 54,600,205 | 48,711,746 | 33,704,301 | 62% |
| N- | 48 hr | A | 52,092,730 | 48,630,104 | 34,093,344 | 65% |
| N- | 48 hr | B | 46,821,585 | 43,359,198 | 31,827,819 | 68% |
| Baseline | 0 hr | A | 51,484,492 | 49,836,381 | 41,734,327 | 81% |
| Baseline | 0 hr | B | 66,475,777 | 63,977,422 | 52,441,434 | 79% |
| S- | 10' | A | 65,883,075 | 63,261,591 | 52,045,540 | 79% |

TABLE 3-continued

| Treatment | Time Point | Replicate | Raw Pairs | Trimed Pairs | Mapped and Properly paired | % of raw data |
|---|---|---|---|---|---|---|
| S- | 10' | B | 51,722,869 | 49,157,939 | 40,923,320 | 79% |
| S- | 30' | A | 29,074,565 | 25,247,048 | 20,782,696 | 71% |
| S- | 30' | B | 50,965,858 | 48,907,146 | 40,567,280 | 80% |
| S- | 1 hr | A | 40,992,077 | 38,830,624 | 32,334,403 | 79% |
| S- | 1 hr | B | 54,304,828 | 52,632,770 | 44,342,126 | 82% |
| S- | 2 hr | A | 65,124,047 | 62,126,856 | 48,635,207 | 75% |
| S- | 2 hr | B | 41,780,378 | 39,974,674 | 31,898,329 | 76% |
| S- | 6 hr | A | 45,698,133 | 44,101,007 | 35,598,874 | 78% |
| S- | 6 hr | B | 50,023,019 | 48,175,137 | 38,122,275 | 76% |
| S- | 8 hr | A | 50,546,965 | 48,474,179 | 39,276,801 | 78% |
| S- | 8 hr | B | 71,838,370 | 67,634,921 | 51,761,322 | 72% |
| S- | 24 hr | A | 47,824,291 | 45,437,606 | 35,856,850 | 75% |
| S- | 24 hr | B | 62,820,960 | 60,205,464 | 46,077,329 | 73% |
| S- | 48 hr | A | 50,169,761 | 47,968,838 | 37,328,836 | 74% |
| S- | 48 hr | B | 52,360,125 | 50,226,696 | 39,089,036 | 75% |
| Total | | | 2,270,751,074 | 2,107,974,879 | 1,590,736,722 | |
| Average | | | | | 44,187,131 | |

TABLE 4

| Filtering step/break down | Total | Phytozome annotations v5.3.1 (19,526 transcripts) |
|---|---|---|
| Merged; unfiltered | 66,561 | 19,140 (98%) |
| FPKM > 0 for both BR1/BR2 in ≥ one time point | 24,499 | 18,161 (93%) |
| CDS length ≥ 50 a.a. | 23,169 | 17,670 (90%) |
| Post-filtering on obvious noise by CuffDiff classes | 22,209* | 17,670 (90%) |
| non-reference transcripts | 298 | |
| w/histone mark support~ | 228 (77%) | |
| transcript variants | 4,241 | |
| Transcription factor (TF) | 277 | |
| Transcription regulator (TR) | 250 | |
| TF & TR | 518 | |

*used in assiging ChromoHMM state and differential expression analysis

TABLE 5

| | N starvation | | S starvation | |
|---|---|---|---|---|
| DE | up-regulated | down-regulated | up-regulated | down-regulated |
| o vs 10' | 933 (51) | 1,273 (46)* | 701 (14) | 1,285 (42) |
| 0 vs 30' | 3,002 (128)* | 2,403 (64) | 633 (20) | 1,065 (28) |
| 0 vs 60' | 3,555 (121)* | 2,044 (55) | 723 (23) | 804 (16) |
| 0 vs 2 hr | 4,437 (150)* | 1,721 (41) | 1,658 (42)* | 1,350 (32) |
| 0 vs 6 hr | 2,633 (83)* | 2,084 (49) | 2,629 (56) | 2,603 (56) |
| 0 vs 8 hr | 3,231 (97)* | 2,216 (45) | 2,744 (75) | 2,842 (64) |
| 0 vs 24 hr | 3,339 (103) | 2,351 (45) | 3,458 (92) | 4,484 (125) |
| 0 vs 48 hr | 3,391 (99) | 2,087 (46) | 4,149 (99) | 2,589 (82) |
| Total | 12,144 (344) | | 12,242 (318) | |
| Union | 7,871 (256) | 6,265 (149) | 6,931 (166) | 7,387 (197) |

Cuffdiff, fold change >2, p < 0.01
(tf/tr): number of tf/tr in the categories
*containing Psr1

TABLE 6

| Protein | Condition | Replicate | Read | Type | # of reads | Mappable reads | Mapped (%) | # of dedupl-unique reads | Dedupl-unique % | #MACS2 peaks* |
|---|---|---|---|---|---|---|---|---|---|---|
| Peptide A PSR1 ChIP-Seq | | | | | | | | | | |
| PSR1 | N- 30 min | BR1 | R/1 | IP | 4,536,359 | 2,936,198 | 64.70% | 1,555,304 | 52.97% | 428 |
| | | BR1 | | Input | 9,419,422 | 8,707,412 | 92.40% | 4,886,365 | 56.12% | |
| PSR1 | N- 30 min | BR1 | R/2 | IP | 4,536,359 | 2,847,120 | 62.80% | 1,509,646 | 53.02% | 396 |
| | | BR1 | | Input | 9,419,422 | 8,368,085 | 88.80% | 4,680,375 | 55.93% | |
| PSR1 | N- 1 hr | BR1 | R/1 | IP | 10,443,930 | 8,631,817 | 82.60% | 4,792,817 | 55.53% | 215 |
| | | BR1 | | Input | 7,966,639 | 7,318,997 | 91.90% | 4,457,715 | 60.91% | |
| PSR1 | N- 1 hr | BR1 | R/2 | IP | 10,443,930 | 8,322,723 | 79.70% | 4,591,363 | 55.17% | 228 |
| | | BR1 | | Input | 7,966,639 | 7,068,458 | 88.70% | 4,288,024 | 60.66% | |
| PSR1 | S- 1 hr | BR1 | R/1 | IP | 5,352,712 | 3,302,972 | 61.70% | 2,069,291 | 62.65% | 645 |
| | | BR1 | | Input | 8,780,319 | 8,088,585 | 92.10% | 4,400,801 | 54.41% | |
| PSR1 | S- 1 hr | BR1 | R/2 | IP | 5,352,712 | 3,062,119 | 57.20% | 1,917,072 | 62.61% | 598 |
| | | BR1 | | Input | 8,780,319 | 7,876,621 | 89.70% | 4,274,408 | 54.27% | |
| PSR1 | S- 2 hr | BR1 | R/1 | IP | 9,100,455 | 6,942,267 | 76.30% | 3,845,762 | 55.40% | 446 |
| | | BR1 | | Input | 11,085,316 | 10,259,042 | 92.50% | 5,774,503 | 56.29% | |
| PSR1 | S- 2 hr | BR1 | R/2 | IP | 9,100,455 | 6,631,646 | 72.90% | 3,669,039 | 55.33% | 438 |
| | | BR1 | | Input | 11,085,316 | 9,832,631 | 88.70% | 5,518,151 | 56.12% | |
| PSR1 | S- 6 hr | BR1 | R/1 | IP | 6,198,290 | 4,269,698 | 68.90% | 2,164,926 | 50.70% | 942 |
| | | BR1 | | Input | 8,018,891 | 7,408,931 | 92.40% | 4,641,986 | 62.65% | |
| PSR1 | S- 6 hr | BR1 | R/2 | IP | 6,198,290 | 4,086,743 | 65.90% | 2,081,045 | 50.92% | 942 |
| | | BR1 | | Input | 8,018,891 | 7,140,684 | 89.00% | 4,483,476 | 62.79% | |

TABLE 6-continued

| Protein | Condition | Replicate | Read | Type | # of reads | Mappable reads | Mapped (%) | # of dedupl-unique reads | Dedupl-unique % | #MACS2 peaks* |
|---|---|---|---|---|---|---|---|---|---|---|
| | | | | | Peptide B PSR1 ChIP-Seq | | | | | |
| PSR1 | N- 30 min | BR1 | R/1 | IP | 9,469,335 | 6,684,315 | 70.60% | 1,287,315 | 19.26% | 130 |
| | | BR1 | | Input | 9,204,146 | 8,475,911 | 92.10% | 1,030,460 | 12.16% | |
| PSR1 | N- 30 min | BR1 | R/2 | IP | 9,469,335 | 6,315,377 | 66.70% | 1,198,478 | 18.98% | 126 |
| | | BR1 | | Input | 9,204,146 | 8,229,829 | 89.40% | 997,558 | 12.12% | |
| PSR1 | N- 1 hr | BR1 | R/1 | IP | 6,423,040 | 4,193,106 | 65.30% | 703,310 | 16.77% | 89 |
| | | BR1 | | Input | 5,363,016 | 4,911,810 | 91.60% | 413,718 | 8.42% | |
| PSR1 | N- 1 hr | BR1 | R/2 | IP | 6,423,040 | 3,982,173 | 62.00% | 652,427 | 16.38% | 88 |
| | | BR1 | | Input | 5,363,016 | 4,760,002 | 88.80% | 389,638 | 8.19% | |
| PSR1 | S- 1 hr | BR1 | R/1 | IP | 8,171,440 | 5,370,526 | 65.70% | 1,091,117 | 20.32% | 189 |
| | | BR1 | | Input | 9,602,576 | 8,715,534 | 90.80% | 908,160 | 10.42% | |
| PSR1 | S- 1 hr | BR1 | R/2 | IP | 8,171,440 | 5,188,059 | 63.50% | 1,042,721 | 20.10% | 208 |
| | | BR1 | | Input | 9,602,576 | 8,474,546 | 88.30% | 879,836 | 10.38% | |
| PSR1 | S- 2 hr | BR1 | R/1 | IP | 4,358,803 | 2,776,962 | 63.70% | 433,081 | 15.60% | 144 |
| | | BR1 | | Input | 7,755,490 | 7,108,259 | 91.70% | 1,259,262 | 17.72% | |
| PSR1 | S- 2 hr | BR1 | R/2 | IP | 4,358,803 | 2,634,276 | 60.40% | 400,977 | 15.22% | 186 |
| | | BR1 | | Input | 7,755,490 | 6,896,065 | 88.90% | 1,206,055 | 17.49% | |
| PSR1 | S- 6 hr | BR1 | R/1 | IP | 7,422,062 | 6,255,330 | 84.30% | 887,828 | 14.19% | 292 |
| | | BR1 | | Input | 7,718,460 | 6,556,885 | 85.00% | 2,077,202 | 31.68% | |
| PSR1 | S- 6 hr | BR1 | R/2 | IP | 7,422,062 | 6,071,733 | 81.80% | 856,263 | 14.10% | 262 |
| | | BR1 | | Input | 7,718,460 | 6,312,432 | 81.80% | 1,989,159 | 31.51% | |

*Peaks are called with FDR < 0.05

TABLE 7

| # | Genomic location | Forward primer | Reverse primer | Region span (bp) |
|---|---|---|---|---|
| 1 | chr_12:8383195..8384442 | ACGAGTCCACTAGGTCAAGTCA (SEQ ID No: 1) | GTAGGAGGGACACCTGGCA (SEQ ID No: 2) | 1226 |
| 2 | chr_17:6268127..6269127 | GGGCTGCAAGAAACACACC (SEQ ID No: 3) | GCTCGAAGCTGCGTGATATT (SEQ ID No: 4) | 900 |
| 3 | chr_1:5750235..5751235 | ATTTGGGGATGGCGGCATTTCC (SEQ ID No: 5) | GAGTGAGCGGAGTGTGTACGATA (SEQ ID No: 6) | 873 |
| 4 | chr_5:1650592..1651592 | CGGGCTATGGGTTATGTTCTT (SEQ ID No: 7) | CTGTCGCTGTTTGCTCCTG (SEQ ID No: 8) | 961 |
| 5 | chr_7:1252718..1253788 | GATGTCGTGCACGGTTGTG (SEQ ID No: 9) | CGGATGGTGAAGCATCATATAG (SEQ ID No: 10) | 971 |
| 6 | chr_16:1135475..1136475 | GAGCACGCACATTGCATCA (SEQ ID No: 11) | AGAGCCTTCGAGGACTTCAC (SEQ ID No: 12) | 974 |
| 7 | chr_14:2768740..2769740 | GTTCTAGCCGCACGAACAG (SEQ ID No: 13) | TTTGGGATTTCGGCCACTT (SEQ ID No: 14) | 924 |
| 8 | chr_4:2122753..2123753 | GCGGCCTGTAGTACTGTAATC (SEQ ID No: 15) | GATCGCGGTTCCCTGAATC (SEQ ID No: 16) | 965 |
| 9 | chr_17:4717149..4718149 | AAGCATGTATCATAGGAATCTTGGG (SEQ ID No: 17) | CAAGGGCGAACTTGAACTTACT (SEQ ID No: 18) | 964 |
| 10 | chr_7:2540672..2541672 | CGGGTAGGAGGGTAGGAAAT (SEQ ID No: 19) | GACTGGCGTGGTTTCCC (SEQ ID No: 20) | 978 |
| 11 | chr_1:4459808..4460808 | GTCACACATGCGAATGTAACAG (SEQ ID No: 21) | GTTGGACGTGTTTGATGCTG (SEQ ID No: 22) | 990 |
| Neg ctrl | chr_3:1,064,061..1,065,052 | TGTTTACGTGCGAAAACCTG (SEQ ID No: 23) | AGCGTACGGTGAGAGGTACG (SEQ ID No: 24) | 992 |
| Neg ctrl | chr_5:2426137..2427133 | CCTGGTCCGAAAGACCATC (SEQ ID No: 25) | GACCTGCACGAAATTCAAGG (SEQ ID No: 26) | 996 |
| Neg ctrl | chr_2:1,048,210..1,049,203 | AAATGCAACGGCTAGGTCTG (SEQ ID No: 27) | TTTGCACGCTTGCATAAGTC (SEQ ID No: 28) | 994 |

TABLE 8

| | | | | Nitrogen Depletion Time Series | | | | | |
|---|---|---|---|---|---|---|---|---|---|
| Time | Marks | Replicate | Type | # of reads | Mappable reads | Mapped (%) | # of dedupl-unique reads | Dedupl-unique % | #MACS2 peaks* |
| 0 hr | H3K4me3 | R1 | IP | 6,991,217 | 6,660,886 | 95.30% | 5,146,811 | 77.27% | 11,487 |
| | | | Input | 6,743,218 | 6,382,897 | 94.70% | 4,040,258 | 63.30% | |
| 0 hr | H3K4me3 | R2 | IP | 5,015,597 | 4,930,521 | 98.30% | 3,780,635 | 76.68% | 12,857 |
| | | | Input | 3,973,127 | 3,843,943 | 96.70% | 2,327,899 | 60.56% | |
| 10 min | H3K4me3 | R1 | IP | 6,402,847 | 6,207,514 | 96.90% | 4,370,387 | 70.40% | 11,659 |
| | | | Input | 6,871,315 | 6,616,833 | 96.30% | 2,414,104 | 36.48% | |
| 30 min | H3K4me3 | R1 | IP | 6,771,909 | 6,552,696 | 96.80% | 4,609,518 | 70.35% | 11,856 |
| | | | Input | 7,145,723 | 6,833,261 | 95.60% | 2,831,179 | 41.43% | |
| 1 hr | H3K4me3 | R1 | IP | 3,977,733 | 3,859,385 | 97.00% | 3,074,099 | 79.65% | 12,821 |
| | | | Input | 3,719,293 | 3,544,825 | 95.30% | 2,216,073 | 62.52% | |
| 1 hr | H3K4me3 | R2 | IP | 5,733,447 | 5,587,201 | 97.40% | 4,149,765 | 74.27% | 13,048 |
| | | | Input | 3,954,921 | 3,819,769 | 96.60% | 2,672,471 | 69.96% | |
| 2 hr | H3K4me3 | R1 | IP | 8,556,234 | 8,376,084 | 97.90% | 5,598,650 | 66.84% | 11,971 |
| | | | Input | 7,990,163 | 7,691,362 | 96.30% | 2,765,931 | 35.96% | |
| 6 hr | H3K4me3 | R1 | IP | 8,852,681 | 8,680,042 | 98.00% | 5,684,969 | 65.49% | 12,142 |
| | | | Input | 6,696,078 | 6,465,297 | 96.60% | 3,188,760 | 49.32% | |
| 8 hr | H3K4me3 | R1 | IP | 6,323,140 | 6,198,760 | 98.00% | 4,388,501 | 70.80% | 12,076 |
| | | | Input | 8,392,944 | 8,026,621 | 95.60% | 3,826,305 | 47.67% | |
| 24 hr | H3K4me3 | R1 | IP | 7,649,839 | 7,488,617 | 97.90% | 5,165,870 | 68.98% | 12,053 |
| | | | Input | 8,029,758 | 7,687,005 | 95.70% | 4,466,748 | 58.11% | |
| 48 hr | H3K4me3 | R1 | IP | 6,769,530 | 6,605,952 | 97.60% | 4,899,245 | 74.16% | 11,948 |
| | | | Input | 8,191,636 | 7,914,010 | 96.60% | 4,965,240 | 62.74% | |

| time point | #peaks | % peaks | unique to 0 hr | unique to time point | common set(0 hr, point) | union | #peaks not capture |
|---|---|---|---|---|---|---|---|
| 0 hr | 11,310 | 87.89% | n.a. | n.a. | n.a. | n.a. | n.a. |
| 10 min | 11,504 | 89.40% | 262 | 456 | 11,048 | 11,766 | 1,102 |
| 30 min | 11,700 | 90.92% | 201 | 591 | 11,109 | 11,901 | 967 |
| 1 hr | 12,543 | 97.47% | 39 | 1,272 | 11,271 | 12,582 | 286 |
| 2 hr | 11,817 | 91.83% | 164 | 671 | 11,146 | 11,981 | 887 |
| 6 hr | 11,985 | 93.14% | 117 | 792 | 11,193 | 12,102 | 766 |
| 8 hr | 11,919 | 92.63% | 170 | 779 | 11,140 | 12,089 | 779 |
| 24 hr | 11,929 | 92.70% | 154 | 773 | 11,156 | 12,083 | 785 |
| 48 hr | 11,822 | 91.87% | 219 | 731 | 11,091 | 12,041 | 827 |
| Union | 12,868 | | | | | | |
| Average | 11,837 | | | | | | |

*Peaks are called with FDR < 0.05

---

What is claimed is:

1. A method for increasing lipid production in a host organism, said method comprising introducing into an organism an expression vector comprising a heterologous nucleotide sequence comprising (a) an operably linked promoter that drives expression in the organism; and (b) a lipid regulatory transcription factor gene that encodes a polypeptide comprising amino acid sequence SEQ ID NO:47; culturing the organism under conditions in which the heterologous nucleotide is expressed; and selecting an organism that produces increased amounts of lipid compared to wildtype.

2. The method of claim 1, wherein the host organism is cyanobacteria, plants, or algae.

3. The method of claim 2, wherein the host organism is microalgae.

4. The method of claim 3, wherein the microalgae into which the expression vector is introduced comprises a wildtype Psr1 gene.

* * * * *

SEQUENCE LISTING

<160> NUMBER OF SEQ ID NOS: 104

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
acgagtccac taggtcaagt ca                                              22

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gtaggaggga cacctggca                                                  19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gggctgcaag aaacacacc                                              19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gctcgaagct gcgtgatatt                                             20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
atttggggat ggcggcattt cc                                          22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gagtgagcgg agtgtgtacg ata                                         23

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cgggctatgg gttatgttct t                                           21

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctgtcgctgt ttgctcctg                                              19

<210> SEQ ID NO 9
<211> LENGTH: 19
<212> TYPE: DNA
<213> ORGANISM: Artificial Sequence
<220> FEATURE:
<223> OTHER INFORMATION: Primer

```
<400> SEQUENCE: 9
gatgtcgtgc acggttgtg                                              19

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
cggatggtgg aagcatcata tag                                         23

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
gagcacgcac attgcatca                                              19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
agagccttcg aggacttcac                                             20

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gttctagccg cacgaacag                                              19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
tttgggattt cggccactt                                              19

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gcggcctgta gtactgtaat c                                           21

<210> SEQ ID NO 16
<211> LENGTH: 19
```

```
<212> TYPE: DNA
<213> ORGANISM: Artificial Sequence
<220> FEATURE:
<223> OTHER INFORMATION: Primer

<400> SEQUENCE: 16
gatcgcggtt ccctgaatc                                                19

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
aagcatgtat cataggaatc ttggg                                         25

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
caagggcgaa cttgaactta ct                                            22

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cgggtaggag ggtaggaaat                                               20

<210> SEQ ID NO 20
<211> LENGTH: 17
<212> TYPE: DNA
<213> ORGANISM: Artificial Sequence
<220> FEATURE:
<223> OTHER INFORMATION: Primer

<400> SEQUENCE: 20
gactggcgtg gtttccc                                                  17

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gtcacacatg cgaatgtaac ag                                            22

<210> SEQ ID NO 22
<211> LENGTH: 20
<212> TYPE: DNA
<213> ORGANISM: Chlamydomonas reinhardtii

<400> SEQUENCE: 22
gttggacgtg tttgatgctg                                               20
```

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tgtttacgtg cgaaaacctg                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agcgtacggt gagaggtacg                                               20

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
cctggtccga aagaccatc                                                19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gacctgcacg aaattcaagg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aaatgcaacg gctaggtctg                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tttgcacgct tgcataagtc                                               20

<210> SEQ ID NO 29
<211> LENGTH: 50
<212> TYPE: PRT
<213> ORGANISM: Homo sapiens

<400> SEQUENCE: 29

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg
    50

<210> SEQ ID NO 30
<211> LENGTH: 49
<212> TYPE: PRT
<213> ORGANISM: Chlamydomonas reinhardtii

<400> SEQUENCE: 30

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Thr Pro Ala Thr
                20                  25                  30

Gly Gly Val Lys Lys Pro His Arg Tyr Arg Pro Gly Thr Val Ala Leu
            35                  40                  45

Arg

<210> SEQ ID NO 31
<211> LENGTH: 50
<212> TYPE: PRT
<213> ORGANISM: Homo sapiens

<400> SEQUENCE: 31

Glu Ile Arg Arg Tyr Gln Lys Ser Thr Glu Leu Leu Ile Arg Lys Leu
1               5                   10                  15

Pro Phe Gln Arg Leu Val Arg Glu Ile Ala Gln Asp Phe Lys Thr Asp
                20                  25                  30

Leu Arg Phe Gln Ser Ser Ala Val Met Ala Leu Gln Glu Ala Cys Glu
            35                  40                  45

Ala Tyr
    50

<210> SEQ ID NO 32
<211> LENGTH: 50
<212> TYPE: PRT
<213> ORGANISM: Chlamydomonas reinhardtii

<400> SEQUENCE: 32

Glu Ile Arg Lys Tyr Gln Lys Ser Thr Glu Leu Leu Ile Arg Lys Leu
1               5                   10                  15

Pro Phe Gln Arg Leu Val Arg Glu Ile Ala Gln Asp Phe Lys Thr Asp
                20                  25                  30

Leu Arg Phe Gln Ser Gln Ala Val Leu Ala Leu Gln Glu Ala Ala Glu
            35                  40                  45

Ala Tyr
    50

<210> SEQ ID NO 33
<211> LENGTH: 36
<212> TYPE: PRT
<213> ORGANISM: Homo sapiens

<400> SEQUENCE: 33

Leu Val Gly Leu Phe Glu Asp Thr Asn Leu Cys Ala Ile His Ala Lys
1               5                   10                  15

Arg Val Thr Ile Met Pro Lys Asp Ile Gln Leu Ala Arg Arg Ile Arg
                20                  25                  30

Gly Glu Arg Ala
            35

<210> SEQ ID NO 34
<211> LENGTH: 50
<212> TYPE: PRT
<213> ORGANISM: Chlamydomonas reinhardtii

<400> SEQUENCE: 34

Leu Val Gly Leu Phe Glu Asp Thr Asn Leu Cys Ala Ile His Ala Lys
1               5                   10                  15

Arg Val Thr Ile Met Pro Lys Asp Ile Gln Leu Ala Arg Arg Ile Arg
                20                  25                  30

Gly Ser Thr Pro Ala Asn Thr Tyr Gly Leu Leu Asp Thr Ala Ala Ala
            35                  40                  45

Gly Asp
    50

<210> SEQ ID NO 35
<211> LENGTH: 43
<212> TYPE: PRT
<213> ORGANISM: Chlamydomonas reinhardtii

<400> SEQUENCE: 35

Leu Leu Phe Ser Val Ser Pro Arg Ser Gly Ser Val Val Val Val Asp
1               5                   10                  15

Val Ser Gly Gly Ser Met Ala Ser Arg Gln Leu Leu Ala Ala Gly Leu
                20                  25                  30

Pro Val Ser Ser Met Gly Leu Ala Val Ala Cys
            35                  40

<210> SEQ ID NO 36
<211> LENGTH: 8119
<212> TYPE: DNA
<213> ORGANISM: Chlamydomonas reinhardtii

<400> SEQUENCE: 36
aagcattgtg agtttgaacg cgtttgccgt caccatggcg ggcgacacgc tctgcaggc      60 cgttttccgc gtaagcccaa gggaagtaga tactattgag tagttgtcaa cacttgctta    120
ctatcagcga cttgtcggtg taggcgtagg cgatagctgg cgacgcgagg agttttggag    180
gccagggtta aaggagccaa cgccgtggta tcacgaggta gccgggccag tgccttgtac    240
aagccgggcg cccgcatgtt gacagcaact aggcgttaag aatggaagac gaggttgaag    300
gagcggtggg ggcgcctgcg ggcggggag gcgggcgcgg ccagacccg cacctgctgc      360 ctccgcccgc accccttcaa cttcccatct caatcgagct gctgccgccg ccgccgcccc    420
tccagctacc cccaacatg gatccagtgc atagccctga tgcagcagcg ccggggtgg      480 ggtcggcagc ggaggccctg tcaccgtggc tgttgctgac gcagcaccaa tcgcaacacc    540
cgccacggcg gcccggctcg agcggtgggg gtgcgctgcg ccccccagac atgggctgc     600 ccggcgcggg gagcagcggc ggcgtgctcg gcggtggcgg cggcagcaac agcaccggaa    660
cagctctgcc cgactcgctg ctgctgtcgc ccgagacgtc gtccctgcgg tcacgcctgt    720

```
tgggccacct gtcttccgac tcaccgcagt tagggctgtc ggctcaggcc agcctgcaac    780
aggcgctgct acagctcggc agcgtgggcg gagcgtcggc ctggagcgag gcacacggca    840
gcggcgctgg cgttggcagt agccacagca acagccagct ggtgccgatg ggggcggcgg    900
gggagttgct gagcatcagc cgaagcagct tgggcgggcc gggaagcgtc agtcagaacg    960
tgttctcaca aggcctccgg agccctgatc acccgagttc ggccgcactg actgcgccct   1020
ggctcgccga cttgcagtcg ccacggccag cgcaacatca gcaacaacgc cagcaggaac   1080
aggagcaggc tggcggcagc agcgcaggcg ccagcagttt ggatgcgccg cagcaagcgt   1140
taacgggcag tctaggcatc ggccccactg caagtccagg gaccggaggc ggcggaccgc   1200
agggtggggg cggcgcggcg gccggcagcg tgcccggggg cagggcgcac ggcagtggcc   1260
ccacgtaccc ttcgctggcg gaggcgctgg cactggctca agccacgcta agggctgagc   1320
gcggcagcca cggaggaggc aacggcagtt caggtggcgg gagcgcaggc ggcaggggcc   1380
agcagcagcc ttcacgcagg cggagcggca actccgatgc cgcggcggcg ctgaccgccc   1440
tgcccgcgcc gcacaactca cgcggcgcg acggtggcag tggcggcggc ggcggcggcg   1500
```

```
cggacctggt tgcgaggtg ctggggctgt tccacccgcg gcgctacgtg gagggcaggg    3180
actgtgtgga gtacccgccg cactcgggca ccttcgtgtc gcgcagccac tttgaaaagg    3240
tgggcggcgc ggtgacggcc aagtggtacc gctccatccg ggtcctgccg cagatggagc    3300
acctcgggga ttggctggag gcgcacgggc tgcaggtctt caagggcacg ggccgcaagc    3360
gcggcggccg ctatggcggc ggcggtagcg gtgatgtgct agccatgctg gctttaggag    3420
ccgccgcagg gggcggcgcc ggcagcactg gcaccggcac ggaagctaca gccgagtccg    3480
agggccccga catggggggcg gcagtagcag ccacaggcgc aggcatgggg ttgggcgccc    3540
ttgcagccat gccgtactcc agccgaggag cagcggcagc ggccttggct cgggccaagc    3600
ctgttgacgg ggacacagcc gccgccgtcg ccgccctggc cgcgctgtcc gccgccgccg    3660 cggaagggggc ggcggccccg ccggcctcct ccgctgcggc agaggcagcg gcggcatcca    3720
ggtgggccgt tgcgccgctg gcggacaggc agtggcacgc tcagcacgcg accccgctgt    3780
cgatgctcca ccccagcgcc catgcggctg cctttgcaca tgcagctggc ccggcagcag    3840
cagcaggggc tgcttctctg cctgcagcgc gaggtgtggc tgcagcctcc ggtcccgccg    3900
gctcgcggcc gcccacgccc gcgtcccctc acgcccggca ggacccgccc gtgctgttgc    3960
atgccccgga gccgctgcct ctgccagaac ccgaggccgg gttggggcac gagtatgctg    4020
acgagcaacc cgagcagccg cggcagccat acgcggcggt gccgcacccc tcctacgcag    4080 ctgtgcccctt cccatacccg cacccgcacc cacacccctc ctaccccgtac ggtgcctacc    4140 cgtacccgta cccccacgcg ggcgcccgta ggcacagtgt gtggcctccc gcgctgcccc    4200
cgccgccgca aggccacgca ctgggatggc cgccgcacct gccgccgccc tacgccgcac    4260
gagccccagg cctgtacgcg ccctatcccc tgcatgggca cccgcagcat ccgcacccgt    4320
accctcagcg tctggcgcgc ccggggggtgc acctgcggcc acgccatca atgctggccg    4380 ctgggtaccc cggtgcaagc agcgacggct cggagggggcc cgaaggcggc agcggcgacg    4440
aagcagcgac ggcggcgctg gcagcagcgg ctgcgcacgg cagcgacgat gcggctgcag    4500
cggcagaggc gacgtcatcg cacgcgcagc actgggccac agcggcacgc ggcgcgctgc    4560
aaggcaccag gagccgcagc ttcggcgcct cctcgaccgc cgccgccgcc gctgcggccg    4620
tgcggcggga gcactggcgg tcggctgggg gtggtactca gcactggggc agtagcagcg    4680
gcggtgcagg tggcggctac agccacggac aggccgggct gctgctgccc gccgcgtcct    4740
ggccgggtcc gtcgcctctg ggaggaggtc agcgggggca gcacggcgca ccgcctcgcg    4800
tgagtgcccc cgcggccacg ggttccggga gcgagcgtgg gtacgagctg gaggcgcggc    4860
aggccgccgt ggcggccacg gcggctgcgg cggctgcgga ctggctcgat accgagcaca    4920
tgccagagct gcagcagcag cagcagcagc agcagcagca gcagcagcag ccctgctgg    4980 cgcttcccgc accgcccatg acggcggccg cagggccctc gccgccccac gggctgctac    5040
ggggcgcgct ggaggcggct gcggcggccg ccgccagctc tgccgcgcac ggcggcggcc    5100
ggcagggagc caagggcagt gcgacgaggg gtacggcaga gggtgccggc ggcgctcctg    5160
ctgcctcacc agcgcagccc cgcgtaagcg aaagctgtgc caccagtggc ggcagcgatg    5220
tcagctatgc ctcggctgga gccgccgctg ccgctggcgc ggcggcaggc gcggcagcag    5280
gcgcagcggc aggcgcggca ccgcagccg ctgcagcggc agcggcgcat gcgggagggc    5340
aacaggcatc cggctgggcg ggcggagccg cgctcccacc gctgccgcac gcgcacccgc    5400
acgcgcacct ccacccaaat ctcccccggg gtctgcccgg catgcacccg tcgtcgtacg    5460
```

```
gtgcaggaac acgcccgtac ggctatgccc tgccgccgcc gcacccgcac ccgcaagcgc    5520
acccgtaccc gcacgtgcac gcgcacatgt acccgcgtgc accgtgggcc ggcagctggg    5580
cgcagcgccc gccaccgtac ggtacggcac ccccatacgg ctacgcgccg ccgccgccgc    5640
cgtcgtacgg ggcgtggccg ccgccgacag ctgtactgcc gccgtatgtg gctgctgctc    5700
ggcctcccgg ccccgccggg gtgctgccgc cgccaccgca tctccgaggt cccgctgtag    5760
cggctgcggt tgcggctgcg gctgcggcgg ctgctggcgg cgcggctcat cacgaggagc    5820
tgccgacccg ggccagcggt gagcggctgt ctgcaggagg ctcgcctcat cactaccagc    5880
cgcaccagta ccaccagcag caccagcagc agcagaggct gcggcgcacg ggtagttcgg    5940
agagggcacc ttcgtcaggc ccacaccgcc agcagcacga gcaacaagga caggagctcc    6000
cgcagcaagg ccagcaggac caacagcaac aacagcagcg caggcgcacc gcggcggctg    6060
tggctgcggc gttggcggcg gcgctggtgg ctgctgttga tccgggcgcg gcggggggagc    6120 cgcccaccca ccgcagcggg ggcggcccta ccggagcagc agcagcagcc gagggagggc    6180
ctggcattgc gggggggccc tcgacaagcg ctggggccag ggccccgatc ccctcgtcaa    6240
ccccagcaca tcagaaccac ccgcaccacc agcacgcctc gcgcgcgtcg catggcatcg    6300
gggtgtcgca tcccggccag gctgtgacgt cccaaagccc agccgccgcc acgccgccac    6360
gtcgcagtca cgggatctcg actgaggcgc tgatgcctgc agcggcggcg aacctcctgc    6420
gcagtggcgg cggcggcggc gggcagctgg cgggcgtggg ggacggcggc gcgcttccga    6480
ctgcctttgg tgcgcagctg cagtggccgc cgccgggcct ggagccggga tcgcgtggtg    6540
ctgctgcagg ggcggcggcg gggcaacaca cggctacgcc gtttgcatgg gcggcagctg    6600
cgacggcgcc gggtgtgcag gtgcggccgc tggtgccgcg tgctggcagc aagcggcgtg    6660
cggagggcgc ggaggatggg gaggaggggc agcaataggc aggcacaggg gagcaaagca    6720
gtgcgtgtgg ggtgaagttg caagggcgct ggtcacggag cgcatacaat gtggtaccag    6780
tagctagctt tgacgtgaag gtttggtgtt aaggtacaat tgttgcgtcg gaacgaattg    6840
gtgcaggacg ttcgagttgc agtggtatca aagcaagtgt gtgcggctga ggtgttggca    6900
ggccctagtt gcaggcgtga cacggcgtgt gtgggcgggg ggtttggggc tctcaatcga    6960
tggttgtgga tggatgggtg tacgtgatat ggacgttgag cttatttcc attgaccgct    7020 cgctgctgtg ccaatcaata catgagctga tttccgtaat tgtgtgtcgc gagcagcagc    7080
aggcaggcga agacatgccg ggtccgcata cggcccacca ttgctggctt aacatttttt    7140
gaggggtagc tatagacgcg tcgcattcgt tgttatacgg caggactgct tatgtctcgt    7200
gtgtttgcta ggcgttgatg taggtctcga taccacacac gttctaccca cacaccatgc    7260
tcgaggtggc atttccacgt gctcgttctc gtacagactt ttcgcctcac agcttttttt    7320
atcagcgtgc gcaccagcgt catactcctg cttccaatcg ctgtatctgt tctgctcgcg    7380
agccattctg cccgcgaccg tagtagctgg ggctgtcgtg tgttttacaa ctcccagctg    7440
tgtgggaaga ataaccttgg catcaagcgc aggcacgacg ttttcgcgct aggcgcggtc    7500
aaaagggaaa ggttgcttct gcgacatgca acctgtccag tgcggtcctg tcggccctca    7560
atgccaagtc gtggatgcat ctgtgttatg ttgcgtttgt gttgttgcaa atgtttgtca    7620
tttacgtggg ggggggcgac aggttacgcc aacctcctcc ggtacacggc gcaggagctg    7680
caactccttc gggggcccac gcatgacggg ccaggcgtca ttcttgaaga ctgcatgggg    7740
cggtattgca tggcgcttca tacctttacg cgtgtctaca taattaggga agaaagctcg    7800
cggtctaatg agcgtattgg ctgtgaatta agctgcggcg tctcggctgc ttgcgctgga    7860
```

| | | |
|---|---|---|
| tggctggcag cttggctggc aggagttttc aggtgtggct aagatgtggg tacagagcac | | 7920 |
| aaggggctgg tgaggttacg catacgtgat acgtacacca gtcatgagtc atacatcgtt | | 7980 |
| atgcagtaaa tggtcgcggt tattgcgtgc acggtacaca agaccacgag gtcacgattg | | 8040 |
| cgttgtaagg tacatgacta catgaggcag tggtagattg gttagaggct gtgacgtcag | | 8100 |
| actgtaatga ttggcccgt | | 8119 |

<210> SEQ ID NO 37
<211> LENGTH: 6417
<212> TYPE: DNA
<213> ORGANISM: Chlamydomonas reinhardtii

<400> SEQUENCE: 37

| | | |
|---|---|---|
| atggaagacg aggttgaagg agcggtgggg gcgcctgcgg gcggggggagg cgggcgcggg | | 60 |
| ccagacccgc acctgctgcc tccgcccgca ccccttcaac ttcccatctc aatcgagctg | | 120 |
| ctgccgccgc cgccgcccct ccagctaccc cccaacatgg atccagtgca tagccctgat | | 180 |
| gcagcagcgc cggggggtggg gtcggcagcg gaggccctgt caccgtggct gttgctgacg | | 240 |
| cagcaccaat cgcaacaccc gccacggcgg cccggctcga gcggtggggg tgcgctgcgc | | 300 |
| cccccagaca tggggctgcc cggcgcgggg agcagcggcg gcgtgctcgg cggtggcggc | | 360 |
| ggcagcaaca gcaccggaac agctctgccc gactcgctgc tgctgtcgcc cgagacgtcg | | 420 |
| tccctgcggt cacgcctgtt gggccacctg tcttccgact caccgcagtt agggctgtcg | | 480 |
| gctcaggcca gcctgcaaca ggcgctgcta cagctcggca gcgtgggcgg agcgtcggcc | | 540 |
| tggagcgagg cacacggcag cggcgctggc gttggcagta gccacagcaa cagccagctg | | 600 |
| gtgccgatgg gggcggcggg ggagttgctg agcatcagcc gaagcagctt gggcgggccg | | 660 |
| ggaagcgtca gtcagaacgt gttctcacaa ggcctccgga gccctgatca cccgagttcg | | 720 |
| gccgcactga ctgcgccctg gctcgccgac ttgcagtcgc cacggccagc gcaacatcag | | 780 |
| caacaacgcc agcaggaaca ggagcaggct ggcggcagca gcgcaggcgc cagcagtttg | | 840 |
| gatgcgccgc agcaagcgtt aacgggcagt ctaggcatcg gccccactgc aagtccaggg | | 900 |
| accggaggcg gcgaccgca gggtgggggc ggcgcggcgg ccggcagcgt gcccgggggc | | 960 |
| agggcgcacg gcagtggccc cacgtaccct tcgctggcgg aggcgctggc actggctcaa | | 1020 |
| gccacgctaa gggctgagcg cggcagccac ggaggaggca acggcagttc aggtggcggg | | 1080 |
| agcgcaggcg gcaggggcca gcagcagcct tcacgcaggc ggagcggcaa ctccgatgcc | | 1140 |
| gcggcggcgc tgaccgccct gcccgcgccg cacaactcac gcggcggcga cggtggcagt | | 1200 |
| ggcggcggcg gcggcggcgg ggacacgcac tcgcacccgc aggcacacaa ctcggctttc | | 1260 |
| cgcccctaca cagtcgtggt gactagcggg cagctgcgcg cgtcggatgc cgtgcttcgg | | 1320 |
| gctgcggacg ttgcgggtgc cgctgcaggc ggcggcggtg gcggcggcgg cacgctcagc | | 1380 |
| ggaggcgctg gttcacacgt cgcccacacg cactctccag cacggacgcc ggagcggctg | | 1440 |
| ccgaggtcgg gcgacagcgg tcggggcgcg caggcagcgg atcgcatggc tggcctgacg | | 1500 |
| gcggcggccg cggcggtgct tggcagcgcc tccagcggcc cgggcccgt gacgactgga | | 1560 |
| ctcacgcaca gcgggcggtc aacgccgccg gggcacgcca cgccgcccgg ccaagtgacc | | 1620 |
| cgccagggc agaccacgcc ggagcgcctg cggggcgccg ctggtgctgc gggcgccgcg | | 1680 |
| ggggcggcg gtgggaggc ttggtcagcg gctggtgcgg cggcgctcac tctacagcac | | 1740 |
| ttggcagcta gtgactcggg tgcgctgcat ccgcggcccc ggcaggcttt ggagccggga | | 1800 |

```
cagcagcagc agcagcagca gcagcagcag gtggcgcccc agttgtcgac accgtttgcc    1860
gggagggcgc aggctgaatt actgcagacg ctcgggcagc agcagcagca cgcagcgaag    1920
catcgtgcac cggagcgcgg gcagtcaacg ccagagcggg ggccagcgtc tcaggatgcg    1980
gacactgctg gcaagttcgc tgctgcagag gccgcaggac cgtccagcac acccacgtac    2040
gcagccgcag cacgagtgac acacgcgatg cctgcacccc agccgacacc agcgtacgcc    2100
cctggacctt ctcgaccggc gatggctcat cccggcgcag cttcggccca gctccggcac    2160
acgcctcaat ggcccactgg cgacgccgcc atgcgtgctt tccatgatgt gccgcgtggt    2220 gcggggcgg atggcgccgt caaggctgac gccgtggccg gctccacggc agctggaggc    2280
gcaggcagca gcgggcttgt aggcgcagca gtcccgctga caacgcacga gcatgggccc    2340
ggtccccgcc cgcccctctt acgagcacag gcgtccaaat cgctgttctc gcagcagcag    2400
cagcagcagc agcagcagca gcaggcacaa ggggctgcac cggcgaccgg cactttgccc    2460
gatctggaca cggggccaat gcacgagtca gcgggtgaag acgcagagga ggggccggat    2520
gcatatcccg acgtgcatgc gccgcccggt caggcgcggc gccctccgca gctgcggccg    2580
ccgcccgcgg accctcagca gcagcagcag cagcagcagc tgccagagcc catcttcgtc    2640
acggtggcgg cgtcggcctc caagcggccg cgcaacgacc ggcccgggac ctccggcgcc    2700
gaaggcgccg ccgcaggcgg cggagccgca gccgctgcgg cggagccgca cacggccgcg    2760
ggtggcggcg gcggcggcac agactcctcg ccgttacgtc gtacggtggt gttgggcagc    2820
ttcacgttgc agctgcggtc ggacctggtt tgcgaggtgc tggggctgtt ccacccgcgg    2880
cgctacgtgg agggcaggga ctgtgtggag tacccgccgc actcgggcac cttcgtgtcg    2940
cgcagccact ttgaaaaggt gggcggcgcg gtgacggcca agtggtaccg ctccatccgg    3000
gtcctgccgc agatggagca cctcggggat tggctggagg cgcacgggct gcaggtcttc    3060
aagggcacgg gccgcaagcg cggcggccgc tatggcggcg gcggtagcgg tgatgtgcta    3120
gccatgctgg cttttaggagc cgccgcagcg ggcggcgccg gcagcactgg caccggcacg    3180
gaagctacag ccgagtccga gggccccgac atggggggcgg cagtagcagc cacaggcgca    3240
ggcatggggt tgggcgccct tgcagccatg ccgtactcca gccgaggagc agcggcagcg    3300
gccttggctc gggccaagcc tgttgacggg gacacagccg ccgccgtcgc cgccctggcc    3360
gcgctgtccg ccgccgccgc ggaaggggcg cggccccgc cggcctcctc cgctgcggca    3420
gaggcagcgg cggcatccag gtgggccgtt cgccgctgg cggacaggca gtggcacgct    3480
cagcacgcga ccccgctgtc gatgctccac cccagcgccc atgcggctgc ctttgcacat    3540
gcagctggcc cggcagcagc agcaggggct gcttctctgc ctgcagcgcg aggtgtggct    3600
gcagcctccg gtcccgccgg ctcgcggccg cccacgcccg cgtcccctca cgcccggcag    3660
gacccgcccg tgctgttgca tgccccggag ccgctgcctc tgccagaacc cgaggccggg    3720
ttggggcacg agtatgctga cgagcaaccc gagcagccgc ggcagccata cgcggcggtg    3780
ccgcacccct cctacgcagc tgtgcccttc ccatacccgc accgcacccc acaccctcc    3840 tacccgtacg gtgcctaccc gtacccgtac ccccacgcgg gcgcccgtag gcacagtgtg    3900
tggcctcccg cgctgcccc gccgccgcaa ggccacgcac tgggatggcc gccgcacctg    3960
ccgccgccct acgccgcacg agcccaggc ctgtacgcgc cctatcccct gcatgggcac    4020
ccgcagcatc cgcacccgta ccctcagcgt ctggcgcgcc cggggtgca cctgcggcca    4080 cgcctatcaa tgctggccgc tgggtacccc ggtgcaagca gcgacggctc ggaggggccc    4140
gaaggcggca gcggcgacga agcagcgacg gcggcgctgg cagcagcggc tgcgcacggc    4200
```

```
agcgacgatg cggctgcagc ggcagaggcg acgtcatcgc acgcgcagca ctgggccaca    4260
gcggcacgcg gcgcgctgca aggcaccagg agccgcagct tcggcgcctc ctcgaccgcc    4320
gccgccgccg ctgcggccgt ggcggcggag cactggcggt cggctggggg tggtactcag    4380
cactggggca gtagcagcgg cggtgcaggt ggcggctaca gccacggaca ggccgggctg    4440
ctgctgcccg ccgcgtcctg gccgggtccg tcgcctctgg gaggaggtca gcggggggcag   4500 cacggcgcac cgcctcgcgt gagtgccccc gcggccacgg gttccgggag cgagcgtggg    4560
tacgagctgg aggcgcggca ggccgccgtg gcggccacgg cggctgcggc ggctgcggac    4620
tggctcgata ccgagcacat gccagagctg cagcagcagc agcagcagca gcagcagcag    4680
cagcagcagc ccctgctggc gcttcccgca ccgcccatga cggcggccgc agggccctcg    4740
ccgccccacg ggctgctacg gggcgcgctg gaggcggctg cggcggccgc cgccagctct    4800
gccgcgcacg gcggcggccg gcagggagcc aagggcagtg cgacgagggg tacggcagag    4860
ggtgccggcg gcgctcctgc tgcctcacca gcgcagcccc gcgtaagcga aagctgtgcc    4920
accagtggcg gcagcgatgt cagctatgcc tcggctggag ccgccgctgc cgctggcgcg    4980
gcggcaggcg cggcagcagg cgcagcggca ggcgcggcag ccgcagccgc tgcagcggca    5040
gcggcgcatg cgggagggca acaggcatcc ggctgggcgg gcggagccgc gctcccaccg    5100
ctgccgcacg cgcaccccgca cgcgcacctc cacccaaatc tcccccccggg tctgcccggc   5160 atgcacccgt cgtcgtacgg tgcaggaaca cgcccgtacg gctatgccct gccgccgccg    5220
cacccgcacc cgcaagcgca cccgtacccg cacgtgcacg cgcacatgta cccgcgtgca    5280
ccgtgggccg gcagctgggc gcagcgcccg ccaccgtacg gtacggcacc cccatacggc    5340
tacgcgccgc cgccgccgcc gtcgtacggg gcgtggccgc cgccgacagc tgtactgccg    5400
ccgtatgtgg ctgctgctcg gcctcccggc cccgccgggg tgctgccgcc gccaccgcat    5460
ctccgaggtc ccgctgtagc ggctgcggct gcggctgcgg ctgcggcggc tgctggcggc    5520
gcggctcatc acgaggagct gccgacccgg gccagcggtg agcggctgtc tgcaggaggc    5580
tcgcctcatc actaccagcc gcaccagtac caccagcagc accagcagca gcagaggctg    5640
cggcgcacgg gtagttcgga gagggcacct tcgtcaggcc acaccgcca gcagcacgag    5700 caacaaggac aggagctccc gcagcaaggc cagcaggacc aacagcaaca acagcagcgc    5760
aggcgcaccg cggcggctgt ggctgcgcg ttggcggcgg cgctggtggc tgctgttgat     5820
ccgggcgcgg cggggagcc gcccaccac cgcagcgggg cggccctac cggagcagca      5880 gcagcagccg agggagggcc tggcattgcg gggggggccct cgacaagcgc tggggccagg    5940
gccccgatcc cctcgtcaac cccagcacat cagaaccacc cgcaccacca gcacgcctcg    6000
cgcgcgtcgc atggcatcgg ggtgtcgcat cccggccagg ctgtgacgtc ccaaagccca    6060
gccgccgcca cgccgccacg tcgcagtcac gggatctcga ctgaggcgct gatgcctgca    6120
gcggcggcga acctcctgcg cagtggcgg ggcggcggcg gcagctggc gggcgtgggg      6180 gacggcggcg cgcttccgac tgcctttggt gcgcagctgc agtggccgcc gccgggcctg    6240
gagccgggat cgcgtggtgc tgctgcaggg gcggcggcgg ggcaacacac ggctacgccg    6300
tttgcatggg cggcagctgc gacggcgccg ggtgtgcagg tgcggccgct ggtgccgcgt    6360
gctggcagca agcggcgtgc ggagggcgcg gaggatgggg aggagggca gcaatag         6417
```

<210> SEQ ID NO 38
<211> LENGTH: 2138
<212> TYPE: PRT

<213> ORGANISM: Chlamydomonas reinhardtii

<400> SEQUENCE: 38

```
Met Glu Asp Glu Val Glu Gly Ala Val Gly Ala Pro Ala Gly Gly Gly
1               5                   10                  15

Gly Gly Arg Gly Pro Asp Pro His Leu Leu Pro Pro Ala Pro Leu
            20                  25                  30

Gln Leu Pro Ile Ser Ile Glu Leu Leu Pro Pro Pro Pro Leu Gln
        35                  40                  45

Leu Pro Pro Asn Met Asp Pro Val His Ser Pro Asp Ala Ala Pro
    50                  55                  60

Gly Val Gly Ser Ala Ala Glu Ala Leu Ser Pro Trp Leu Leu Leu Thr
65                  70                  75                  80

Gln His Gln Ser Gln His Pro Pro Arg Arg Pro Gly Ser Ser Gly Gly
                85                  90                  95

Gly Ala Leu Arg Pro Pro Asp Met Gly Leu Pro Gly Ala Gly Ser Ser
            100                 105                 110

Gly Gly Val Leu Gly Gly Gly Gly Ser Asn Ser Thr Gly Thr Ala
        115                 120                 125

Leu Pro Asp Ser Leu Leu Leu Ser Pro Glu Thr Ser Ser Leu Arg Ser
    130                 135                 140

Arg Leu Leu Gly His Leu Ser Ser Asp Ser Pro Gln Leu Gly Leu Ser
145                 150                 155                 160

Ala Gln Ala Ser Leu Gln Gln Ala Leu Leu Gln Leu Gly Ser Val Gly
                165                 170                 175

Gly Ala Ser Ala Trp Ser Glu Ala His Gly Ser Gly Ala Gly Val Gly
            180                 185                 190

Ser Ser His Ser Asn Ser Gln Leu Val Pro Met Gly Ala Ala Gly Glu
        195                 200                 205

Leu Leu Ser Ile Ser Arg Ser Ser Leu Gly Gly Pro Gly Ser Val Ser
    210                 215                 220

Gln Asn Val Phe Ser Gln Gly Leu Arg Ser Pro Asp His Pro Ser Ser
225                 230                 235                 240

Ala Ala Leu Thr Ala Pro Trp Leu Ala Asp Leu Gln Ser Pro Arg Pro
                245                 250                 255

Ala Gln His Gln Gln Arg Gln Gln Glu Gln Glu Gln Ala Gly Gly
            260                 265                 270

Ser Ser Ala Gly Ala Ser Ser Leu Asp Ala Pro Gln Gln Ala Leu Thr
        275                 280                 285

Gly Ser Leu Gly Ile Gly Pro Thr Ala Ser Pro Gly Thr Gly Gly Gly
    290                 295                 300

Gly Pro Gln Gly Gly Gly Ala Ala Ala Gly Ser Val Pro Gly Gly
305                 310                 315                 320

Arg Ala His Gly Ser Gly Pro Thr Tyr Pro Ser Leu Ala Glu Ala Leu
                325                 330                 335

Ala Leu Ala Gln Ala Thr Leu Arg Ala Glu Arg Gly Ser His Gly Gly
            340                 345                 350

Gly Asn Gly Ser Ser Gly Gly Gly Ser Ala Gly Gly Arg Gly Gln Gln
        355                 360                 365

Gln Pro Ser Arg Arg Arg Ser Gly Asn Ser Asp Ala Ala Ala Leu
    370                 375                 380

Thr Ala Leu Pro Ala Pro His Asn Ser Arg Gly Gly Asp Gly Gly Ser
385                 390                 395                 400
```

Gly Gly Gly Gly Gly Gly Asp Thr His Ser His Pro Gln Ala His
            405                 410                 415

Asn Ser Ala Phe Arg Pro Tyr Thr Val Val Thr Ser Gly Gln Leu
        420                 425                 430

Arg Ala Ser Asp Ala Val Leu Arg Ala Ala Asp Val Ala Gly Ala Ala
        435                 440                 445

Ala Gly Gly Gly Gly Gly Gly Gly Thr Leu Ser Gly Gly Ala Gly
    450                 455                 460

Ser His Val Ala His Thr His Ser Pro Ala Arg Thr Pro Glu Arg Leu
465                 470                 475                 480

Pro Arg Ser Gly Asp Ser Gly Arg Gly Ala Gln Ala Ala Asp Arg Met
            485                 490                 495

Ala Gly Leu Thr Ala Ala Ala Ala Val Leu Gly Ser Ala Ser Ser
            500                 505                 510

Gly Pro Gly Pro Val Thr Thr Gly Leu Thr His Ser Gly Arg Ser Thr
            515                 520                 525

Pro Pro Gly His Ala Thr Pro Pro Gly Gln Val Thr Pro Pro Gly Gln
        530                 535                 540

Thr Thr Pro Glu Arg Leu Arg Gly Ala Ala Gly Ala Ala Gly Ala Ala
545                 550                 555                 560

Gly Gly Gly Gly Gly Glu Ala Trp Ser Ala Ala Gly Ala Ala Ala Leu
            565                 570                 575

Thr Leu Gln His Leu Ala Ala Ser Asp Ser Gly Ala Leu His Pro Arg
            580                 585                 590

Pro Arg Gln Ala Leu Glu Pro Gly Gln Gln Gln Gln Gln Gln Gln Gln
        595                 600                 605

Gln Gln Val Ala Pro Gln Leu Ser Thr Pro Phe Ala Gly Arg Ala Gln
    610                 615                 620

Ala Glu Leu Leu Gln Thr Leu Gly Gln Gln Gln His Ala Ala Lys
625                 630                 635                 640

His Arg Ala Pro Glu Arg Gly Gln Ser Thr Pro Glu Arg Gly Pro Ala
            645                 650                 655

Ser Gln Asp Ala Asp Thr Ala Gly Lys Phe Ala Ala Ala Glu Ala Ala
        660                 665                 670

Gly Pro Ser Ser Thr Pro Thr Tyr Ala Ala Ala Ala Arg Val Thr His
        675                 680                 685

Ala Met Pro Ala Pro Gln Pro Thr Pro Ala Tyr Ala Pro Gly Pro Ser
        690                 695                 700

Arg Pro Ala Met Ala His Pro Gly Ala Ala Ser Ala Gln Leu Arg His
705                 710                 715                 720

Thr Pro Gln Trp Pro Thr Gly Asp Ala Ala Met Arg Ala Phe His Asp
            725                 730                 735

Val Pro Arg Gly Ala Gly Ala Asp Gly Ala Val Lys Ala Asp Ala Val
            740                 745                 750

Ala Gly Ser Thr Ala Ala Gly Gly Ala Gly Ser Ser Gly Leu Val Gly
        755                 760                 765

Ala Ala Val Pro Leu Thr Thr His Glu His Gly Pro Gly Pro Arg Pro
    770                 775                 780

Pro Leu Leu Arg Ala Gln Ala Ser Lys Ser Leu Phe Ser Gln Gln Gln
785                 790                 795                 800

Gln Gln Gln Gln Gln Gln Gln Ala Gln Gly Ala Ala Pro Ala Thr
        805                 810                 815

Gly Thr Leu Pro Asp Leu Asp Thr Gly Pro Met His Glu Ser Ala Gly

```
                    820             825             830
Glu Asp Ala Glu Glu Gly Pro Asp Ala Tyr Pro Asp Val His Ala Pro
                835             840             845
Pro Gly Gln Ala Arg Arg Pro Pro Gln Leu Arg Pro Pro Pro Ala Asp
            850             855             860
Pro Gln Gln Gln Gln Gln Gln Gln Leu Pro Glu Pro Ile Phe Val
865             870             875             880
Thr Val Ala Ala Ser Ala Ser Lys Arg Pro Arg Asn Asp Arg Pro Gly
                885             890             895
Thr Ser Gly Ala Glu Gly Ala Ala Gly Gly Ala Ala Ala
            900             905             910
Ala Ala Glu Pro His Thr Ala Ala Gly Gly Gly Gly Thr Asp
            915             920             925
Ser Ser Pro Leu Arg Arg Thr Val Val Leu Gly Ser Phe Thr Leu Gln
        930             935             940
Leu Arg Ser Asp Leu Val Cys Glu Val Leu Gly Leu Phe His Pro Arg
945             950             955             960
Arg Tyr Val Glu Gly Arg Asp Cys Val Glu Tyr Pro Pro His Ser Gly
            965             970             975
Thr Phe Val Ser Arg Ser His Phe Glu Lys Val Gly Ala Val Thr
            980             985             990
Ala Lys Trp Tyr Arg Ser Ile Arg Val Leu Pro Gln Met Glu His Leu
            995            1000            1005
Gly Asp Trp Leu Glu Ala His Gly Leu Gln Val Phe Lys Gly Thr
        1010            1015            1020
Gly Arg Lys Arg Gly Gly Arg Tyr Gly Gly Gly Ser Gly Asp
        1025            1030            1035
Val Leu Ala Met Leu Ala Leu Gly Ala Ala Ala Ala Gly Gly Ala
        1040            1045            1050
Gly Ser Thr Gly Thr Gly Thr Glu Ala Thr Ala Glu Ser Glu Gly
        1055            1060            1065
Pro Asp Met Gly Ala Ala Val Ala Ala Thr Gly Ala Gly Met Gly
        1070            1075            1080
Leu Gly Ala Leu Ala Ala Met Pro Tyr Ser Ser Arg Gly Ala Ala
        1085            1090            1095
Ala Ala Ala Leu Ala Arg Ala Lys Pro Val Asp Gly Asp Thr Ala
        1100            1105            1110
Ala Ala Val Ala Ala Leu Ala Ala Leu Ser Ala Ala Ala Ala Glu
        1115            1120            1125
Gly Ala Ala Ala Pro Pro Ala Ser Ser Ala Ala Ala Glu Ala Ala
        1130            1135            1140
Ala Ala Ser Arg Trp Ala Val Ala Pro Leu Ala Asp Arg Gln Trp
        1145            1150            1155
His Ala Gln His Ala Thr Pro Leu Ser Met Leu His Pro Ser Ala
        1160            1165            1170
His Ala Ala Ala Phe Ala His Ala Ala Gly Pro Ala Ala Ala Ala
        1175            1180            1185
Gly Ala Ala Ser Leu Pro Ala Ala Arg Gly Val Ala Ala Ala Ser
        1190            1195            1200
Gly Pro Ala Gly Ser Arg Pro Pro Thr Pro Ala Ser Pro His Ala
        1205            1210            1215
Arg Gln Asp Pro Pro Val Leu Leu His Ala Pro Glu Pro Leu Pro
        1220            1225            1230
```

```
Leu Pro Glu Pro Glu Ala Gly Leu Gly His Glu Tyr Ala Asp Glu
    1235            1240                1245

Gln Pro Glu Gln Pro Arg Gln Pro Tyr Ala Ala Val Pro His Pro
    1250            1255                1260

Ser Tyr Ala Ala Val Pro Phe Pro Tyr Pro His Pro His
    1265            1270                1275

Pro Ser Tyr Pro Tyr Gly Ala Tyr Pro Tyr Pro Tyr Pro His Ala
    1280            1285                1290

Gly Ala Arg Arg His Ser Val Trp Pro Ala Leu Pro Pro Pro
    1295            1300                1305

Pro Gln Gly His Ala Leu Gly Trp Pro Pro His Leu Pro Pro Pro
    1310            1315                1320

Tyr Ala Ala Arg Ala Pro Gly Leu Tyr Ala Pro Tyr Pro Leu His
    1325            1330                1335

Gly His Pro Gln His Pro His Pro Tyr Pro Gln Arg Leu Ala Arg
    1340            1345                1350

Pro Gly Val His Leu Arg Pro Arg Leu Ser Met Leu Ala Ala Gly
    1355            1360                1365

Tyr Pro Gly Ala Ser Ser Asp Gly Ser Glu Gly Pro Glu Gly Gly
    1370            1375                1380

Ser Gly Asp Glu Ala Ala Thr Ala Ala Leu Ala Ala Ala Ala Ala
    1385            1390                1395

His Gly Ser Asp Asp Ala Ala Ala Ala Glu Ala Thr Ser Ser
    1400            1405                1410

His Ala Gln His Trp Ala Thr Ala Ala Arg Gly Ala Leu Gln Gly
    1415            1420                1425

Thr Arg Ser Arg Ser Phe Gly Ala Ser Ser Thr Ala Ala Ala Ala
    1430            1435                1440

Ala Ala Ala Val Ala Ala Glu His Trp Arg Ser Ala Gly Gly Gly
    1445            1450                1455

Thr Gln His Trp Gly Ser Ser Ser Gly Gly Ala Gly Gly Gly Tyr
    1460            1465                1470

Ser His Gly Gln Ala Gly Leu Leu Leu Pro Ala Ala Ser Trp Pro
    1475            1480                1485

Gly Pro Ser Pro Leu Gly Gly Gly Gln Arg Gly Gln His Gly Ala
    1490            1495                1500

Pro Pro Arg Val Ser Ala Pro Ala Ala Thr Gly Ser Gly Ser Glu
    1505            1510                1515

Arg Gly Tyr Glu Leu Glu Ala Arg Gln Ala Ala Val Ala Ala Thr
    1520            1525                1530

Ala Ala Ala Ala Ala Ala Asp Trp Leu Asp Thr Glu His Met Pro
    1535            1540                1545

Glu Leu Gln Gln Gln Gln Gln Gln Gln Gln Gln Gln Gln Gln Gln
    1550            1555                1560

Pro Leu Leu Ala Leu Pro Ala Pro Pro Met Thr Ala Ala Ala Gly
    1565            1570                1575

Pro Ser Pro Pro His Gly Leu Leu Arg Gly Ala Leu Glu Ala Ala
    1580            1585                1590

Ala Ala Ala Ala Ala Ser Ser Ala Ala His Gly Gly Gly Arg Gln
    1595            1600                1605

Gly Ala Lys Gly Ser Ala Thr Arg Gly Thr Ala Glu Gly Ala Gly
    1610            1615                1620
```

```
Gly Ala Pro Ala Ala Ser Pro Ala Gln Pro Arg Val Ser Glu Ser
    1625                1630                1635

Cys Ala Thr Ser Gly Gly Ser Asp Val Ser Tyr Ala Ser Ala Gly
    1640                1645                1650

Ala Ala Ala Ala Ala Gly Ala Ala Ala Gly Ala Ala Ala Gly Ala
    1655                1660                1665

Ala Ala Gly Ala Ala Ala Ala Ala Ala Ala Ala Ala Ala Ala His
    1670                1675                1680

Ala Gly Gly Gln Gln Ala Ser Gly Trp Ala Gly Gly Ala Ala Leu
    1685                1690                1695

Pro Pro Leu Pro His Ala His Pro His Ala His Leu His Pro Asn
    1700                1705                1710

Leu Pro Pro Gly Leu Pro Gly Met His Pro Ser Ser Tyr Gly Ala
    1715                1720                1725

Gly Thr Arg Pro Tyr Gly Tyr Ala Leu Pro Pro Pro His Pro His
    1730                1735                1740

Pro Gln Ala His Pro Tyr Pro His Val His Ala His Met Tyr Pro
    1745                1750                1755

Arg Ala Pro Trp Ala Gly Ser Trp Ala Gln Arg Pro Pro Pro Tyr
    1760                1765                1770

Gly Thr Ala Pro Pro Tyr Gly Tyr Ala Pro Pro Pro Pro Pro Ser
    1775                1780                1785

Tyr Gly Ala Trp Pro Pro Pro Thr Ala Val Leu Pro Pro Tyr Val
    1790                1795                1800

Ala Ala Ala Arg Pro Pro Gly Pro Ala Gly Val Leu Pro Pro Pro
    1805                1810                1815

Pro His Leu Arg Gly Pro Ala Val Ala Ala Ala Ala Ala Ala Ala
    1820                1825                1830

Ala Ala Ala Ala Ala Gly Gly Ala Ala His His Glu Glu Leu Pro
    1835                1840                1845

Thr Arg Ala Ser Gly Glu Arg Leu Ser Ala Gly Gly Ser Pro His
    1850                1855                1860

His Tyr Gln Pro His Gln Tyr His Gln Gln His Gln Gln Gln Gln
    1865                1870                1875

Arg Leu Arg Arg Thr Gly Ser Ser Glu Arg Ala Pro Ser Ser Gly
    1880                1885                1890

Pro His Arg Gln Gln His Glu Gln Gln Gly Gln Glu Leu Pro Gln
    1895                1900                1905

Gln Gly Gln Gln Asp Gln Gln Gln Gln Gln Arg Arg Arg Thr
    1910                1915                1920

Ala Ala Ala Val Ala Ala Ala Leu Ala Ala Ala Leu Val Ala Ala
    1925                1930                1935

Val Asp Pro Gly Ala Ala Gly Glu Pro Pro Thr His Arg Ser Gly
    1940                1945                1950

Gly Gly Pro Thr Gly Ala Ala Ala Ala Ala Glu Gly Gly Pro Gly
    1955                1960                1965

Ile Ala Gly Gly Pro Ser Thr Ser Ala Gly Ala Arg Ala Pro Ile
    1970                1975                1980

Pro Ser Ser Thr Pro Ala His Gln Asn His Pro His Gln His
    1985                1990                1995

Ala Ser Arg Ala Ser His Gly Ile Gly Val Ser His Pro Gly Gln
    2000                2005                2010

Ala Val Thr Ser Gln Ser Pro Ala Ala Ala Thr Pro Pro Arg Arg
```

| | | | | | | | | | | |
|---|---|---|---|---|---|---|---|---|---|---|
| | | 2015 | | | 2020 | | | 2025 | | |
| Ser | His | Gly | Ile | Ser | Thr | Glu | Ala | Leu | Met | Pro | Ala | Ala | Ala | Ala |
| | | 2030 | | | 2035 | | | 2040 | | |

Ser His Gly Ile Ser Thr Glu Ala Leu Met Pro Ala Ala Ala Ala
          2030            2035            2040

Asn Leu Leu Arg Ser Gly Gly Gly Gly Gly Gln Leu Ala Gly
          2045            2050            2055

Val Gly Asp Gly Gly Ala Leu Pro Thr Ala Phe Gly Ala Gln Leu
          2060            2065            2070

Gln Trp Pro Pro Pro Gly Leu Glu Pro Gly Ser Arg Gly Ala Ala
          2075            2080            2085

Ala Gly Ala Ala Ala Gly Gln His Thr Ala Thr Pro Phe Ala Trp
          2090            2095            2100

Ala Ala Ala Ala Thr Ala Pro Gly Val Gln Val Arg Pro Leu Val
          2105            2110            2115

Pro Arg Ala Gly Ser Lys Arg Arg Ala Glu Gly Ala Glu Asp Gly
          2120            2125            2130

Glu Glu Gly Gln Gln
    2135

<210> SEQ ID NO 39
<211> LENGTH: 5955
<212> TYPE: DNA
<213> ORGANISM: Chlamydomonas reinhardtii

<400> SEQUENCE: 39

```
cacaggcagc actgtagctc gcgcaacctt gctaagcaaa acaaagcgcc gtcgtgcatg      60
caacataaaa accgtttagt tgtatcatgt cgtccttgga atgagcaaag tttcaaggat     120
tctgcatagg aagagggaca cagcgcgtgc ggagcgggcg cgcgatgtgc tcgcggccaa     180
gcgggctgcc tccaaacgcg aacggcgtca gcttaggcga gccaaagctt ccagaagaaa     240
gaagaaagga ggtgctgagg cagccgccgg gccggcggac ccgccgcgca acaccgatgc     300
tgagtcgccc agcgtgcggc cgtcgcccgc cctgccggtt cacgcaggcg agccaagtgg     360
ccgtccggca gcgcgcgagg gcagccgcaa tacggcgctg ggtcactgtg tcgacagcgc     420
tccggcacac ccttaccggc agccagcacc tatctgcggc aagcgcaaac agcggagcac     480
cccgctggca cgggccttac ggctggtaca ggcggggggca ccgggcttgc agactggcgt     540
ggaccttgtt gcgggcgtga gagggcgaa ggaagcgcag caggcgcggc gcccagcgcc     600
cccagttgcc aaagtgcggc tgctgtcctt gcctctggag ccgaaggtgg acggtcaggt     660
tgggggggtgc tcacctggcc aggacacgca gccagcaccc agcagtcaag agggcgggcc     720
agcggtgata gtcagaccgg acgtggcggt gctcggccag gaccggggcc tgggggttgc     780
ggaggcagca ggaacttccg ctgccgctgc cgccgctgca gtgagccagc gggatcgcgg     840
cgcaggccgg cagcctggcc aggagccggc tgaatcacgg acaccagcc tcagcagtga     900
gttgcagcca caaccacaga tgcagacgca gcgccacgag caagggcagc aagggttgca     960
cgaaagcccg ccgtgtgaga gtgaggcagc ggtgtgtgcc agggaggcag ctgtggccgc    1020
agcgaggcta gcagccatta atgcggccgc tgccctgccc ccggacagcc cgtatgttcg    1080
ggcggtgatg aaacgtgca gcgggcaagc gactgggggt caggcgggac agaatcagct    1140
gtcggcacac ggcctgctgc agcccccagca tgagcagcag caacggcggc ggcggagggg    1200
cctgggggcg gtggacagcg agtacgtggc gtgcgccaag cacgccgctg cagccgcggc    1260
acacctagcg gccctggagg ctgcggctgc actgccagcc gacagtccgt acctgaaggc    1320
ggccgtcgag gtgggtcgtg gcgccggggtt cgggtggccg gatgagcggg acagcgacgt    1380
```

```
atgggcgcag cagcgcgcac tgctgcagca gcagacggcg cggctgcagc gggcgctggg      1440
ggctgcactg tgcgggcgag gaggggcagc caggtacacc cccgctgggc cagtaccaga      1500
agggcacggc gccggagctt gcagtagcgg cgccgcggcg tcactggagt tccgtgtggg      1560
atcttcgccc gggcacgctg aggcggcgag cggggcgcgc ggtgccgtgc tagcagcaga      1620
agcagcaaca gcagaagcag aagcagcagg tggcattctc gtgcctgccg tggtggcagg      1680
tggcggacct gcgggtagcg gccgcggcgg cggcacagat gaagtccgtg cgcatcacgg      1740
cagcgccgtt accacgatca ccccgggttg cagcgtgtgc agccgcatgc aagccagcag      1800
aaacggagtg caagcggctg acgccccagc cggtacgggt gttggcggcg cggctgaggc      1860
tcctgaggat gcagctgcag tgcctggagc agcgggccag ggtgcgcgtg tcagcgagtg      1920
ggtcggttcg ttactgctgc agagccctca agcggaatcc gcacctcctg ttttccagaa      1980
gtcgaagcca ggcgctgagg ccagcggccc tgcagcggag ggccgggacc ccagccccca      2040
agttcctgca gcaattgggt gtggagctag cagcaccact catgggagcg caccaccag       2100 cagtggcaat ggggcgacca ccggcagcag caacagcggc gatgacagcg gtgggagcac      2160
cagtagcggc gggagcttaa cgggcgctgc cgatagcagc catagcggtg gctccggcgg      2220
cgatagagtt cggagcttaa gcggcgccag acgcagcttg catggtatta cagacagcag      2280
cagaagcacc agcagtggcg gcagtgacca gagcacgagc aaggacgtta acgatgccgt      2340
gaccagcagc ggcggcggcg ggcttggcgc aggcggctgc ggtggtgggg cggggattgt      2400
cgcaggcgat gagccctcca cagcagtccc cgaaagcctt cacaggccgg cgtcagagcg      2460
cagccctgga cggtgcgagc tcactgcagc cgcaggcgg ggcgccgagg cgggcagcgc       2520
agaggcgggc ggaagggcag tagtccctgc gcgcgagtcg cagtcgtggg ctcaacaact      2580
actgccggag cacttgccgc agtgggaaga cgaggtgccg agcgacggca gcagttgcag      2640
cgacactgac agctccgagt ttgaagaggg agactgggag gacgacgatt ggcctggggg      2700
cgcagccgag gctaaagatg gcagccggga caagtcacag cactcagcgg acaagcccgg      2760
cgcctccgac gtcacggacc acatgatggc agccgtgctg tcgcaggctg cgcccgagca      2820
cagcgctggt gtcaaacgtg ctggcggcga ggcagcgatc ctctacgccg atggcagtga      2880
cagccacggt gggcctgacg cttcgttga caacgattca gcggcgtggg aggcagcact       2940
ggaggctggc gctggcccac atgaaagcca ggcggaggcc ccgcagcagc tggcggcggc      3000
cgtgacagtt tcgactctgg cgcttcttgg gcatggcaca ggtccggtgc agcaatcgcg      3060
gagacgcctg ccggcgtcag gaagcgggcc agcagggcat gacacagcag gattaggtgc      3120
tggcgcggtg gccctcgcag aaccccagtt gcagctgccg gagcagtttg atgttaatct      3180
gctggcgccg ccagtgctag tgccggccgg cacgaagctg caagccctgc cgccatggtc      3240
tgtagggtcg cccgtcacca gcccgggtt gacgcaggca gggcctggcc ccagtgcggc       3300
tgcaggcccc agggtggcgc aggtcgtgtc ggcagcccc tacacggacg cctatgagct       3360
gccggacgat ggcggccacc cgcacctggg cggaggcgcc gccccgcagc ccagcagtcg      3420
cgaggacggc gggggtgtgg ctgccggggt cggtgcacac gcgggctgca acgcacagcg      3480
gggcatgaca gcagcagtaa ttggtcctgg tggtactcgg gttggtgctg cctcgcctcc      3540
gcttgtgctt tcagcctcag gctccggggg agggctggcg actccaggtc ggcggcgcgg      3600
ccgtctggtg atgctgcacg gtgccggggc ggcggcatgt ggtacgccca tcgcagcc       3660 ccgtgccggc agggcggcga gcaatacagc aaccgctggg ggtgcgggcc ccagcgcagt      3720
```

| | |
|---|---|
| tgcagcggct gggccgggaa tgggcgacct cggccaccag ggcagccac tgccggccga | 3780 |
| gcccctgga gcagctacgc gaccggttgg cagggcaggg cgcgcgccac cgcttagccc | 3840 |
| tctgcgccgc agcagtcgcg tgcctggcgg acagcagcag cagcagcagc agcagcagca | 3900 |
| gcagcagcat gcagctggca tggcggccca gggccagggg cccgcggagc cttcggcaaa | 3960 |
| tggtggagca ggcaggagta gagcgtcggc aggcggtggc atgtcgccca gccgtagggc | 4020 |
| ggctgtgcgg cttcagcgac agccggtggt cccatcaccg aggctcgtgg aggattcaag | 4080 |
| gctgcatcgc tccggccagc agcaggcggt ggttggagta ggcacagcgg ggggaagccg | 4140 |
| cgtgggtgat cgcgcacggg gtggttcggg tgcagggttg tcggcagctg caacaggagt | 4200 |
| gatcaaggcc gccactgcct caccctcgcg cggccgcacc cgcagcaagc cacctgaacg | 4260 |
| ggcgtcgata gccgggcgag ggcgcggcgg cgtgggcgg cgggcgactg cgcgctctca | 4320 |
| ccggcagtcg gaaagcgacc aggaggagac agcagatgcg gtgcgcccgt ctgacccgga | 4380 |
| ggaggataag gagaaggagg gcggtgggca gcagactcgc ggcgcccctg ccaggcgccg | 4440 |
| agccccgcgc acacccagtg aagtgctcaa ccggctgcag gtgtcggacc tgcggccggt | 4500 |
| gctgcacctg cccctcgttg aggcggcacg gcagctgggg ctacaccgca ctagcttcat | 4560 |
| gacgcgctgc cgccaactgg ggatcgcgag atggccggcc aagcagctgc gcatgctgga | 4620 |
| cttgatggag gagcagctgc aggagctgga ggcgtgcggc gtcgcaaacc actacacggc | 4680 |
| caagaagtgc cttgaagaag ctccgggctg gctggcccag gtggccgctg cgcgctcggc | 4740 |
| gctgctggag aacccgtgcg gcttcaccat gccgcagccg ctggagctgc tgcgccagcg | 4800 |
| ccacgtgaag gtggcgtggg cgcaccgcca aaagtacaag gcggcactgg gcgaggaggg | 4860 |
| ggaggagggc gaggagggcg atgacctgga ctcgcaggcg cagatgtcac agtagtgtgc | 4920 |
| ggcgggctgc ggctgaggga gtgcggagac ctgagggcgt cagctgttgc tgcacatgcg | 4980 |
| gtgttggcga gccgtatccg cggcgtagca gcgcgtggag cagtgaagga ctgggcgggg | 5040 |
| agtgcagtgt ggcgcaaggg agcacgcagt atgtagaatt ttgcgatggc aggaaggcga | 5100 |
| tggcaggggc aacacatgcc agagcttcga cgtaaacacg gttgtcagtg cgccgtgcaa | 5160 |
| gtgggcaata caggatgatg cgaacgagct cagaactagc cgggactatc acatggttgc | 5220 |
| acctgtcctt gccgtcctcg cctgctaggt cgcatgtgat ttcactgatt tgtgttactg | 5280 |
| cattcccctt tgatccacca gctgcgggtt gagttcaggt gtcttgcgta tgtcggctgg | 5340 |
| cgagggcgtg ggcgggtcgt tgacggtgaa ctccaccaac accaggtcgg ggcgggcggc | 5400 |
| aggtgctggg ccagggctcc gaaatcagaa gatgtaaagg ccgcggtgca tgtagctagt | 5460 |
| gaacgatacc ggactcacct cgcgatgggt aatgggtaac gtcgcttgac gccttgaccg | 5520 |
| catacggtac cgtgcccgca cacgtgtggg aggggaactc ctaaccagcc tcaaatctta | 5580 |
| aggcatcttg cctgcactgg ccctgcataa cttgcagagt accagcggca tggaaaatct | 5640 |
| gcggggacaa aaaatgaaag ccagatggat gcagggtttg gtttgggccg ttggggtgtg | 5700 |
| tgcggccggg catgcgcagg caacgcaact tagcatagcc ttctgtgatg cggacttgcc | 5760 |
| aagggctgcg gacttgacat cagcgtggcc gagctcattt ctggccgttg atgctgaagg | 5820 |
| gctgggcttg cacacgtcgt gctggcagta ctcgccccct atgacagact gtgcaaacca | 5880 |
| ggggtagggc ttcccctggt gttttacgcg gcagttcaag ggctttcctg tttctagctc | 5940 |
| tcttacttac ttagg | 5955 |

<210> SEQ ID NO 40
<211> LENGTH: 4815

```
<212> TYPE: DNA
<213> ORGANISM: Chlamydomonas reinhardtii

<400> SEQUENCE: 40
atgagcaaag tttcaaggat tctgcatagg aagagggaca cagcgcgtgc ggagcgggcg      60
cgcgatgtgc tcgcgccaa gcgggctgcc tccaaacgcg aacggcgtca gcttaggcga     120
gccaaagctt ccagaagaaa gaagaaagga ggtgctgagg cagccgccgg ccggcggac     180
ccgccgcgca acaccgatgc tgagtcgccc agcgtgcggc cgtcgcccgc cctgccggtt     240
cacgcaggcg agccaagtgg ccgtccggca gcgcgcgagg gcagccgcaa tacggcgctg     300
ggtcactgtg tcgacagcgc tccggcacac ccttaccggc agccagcacc tatctgcggc     360
aagcgcaaac agcggagcac cccgctggca cgggccttac ggctggtaca ggcgggggca     420
ccgggcttgc agactggcgt ggaccttgtt gcgggcgtga gaggggcgaa ggaagcgcag     480
caggcgcggc gcccagcgcc cccagttgcc aaagtgcggc tgctgtcctt gcctctggag     540
ccgaaggtgg acggtcaggt tgggggggtgc tcacctggcc aggacacgca gccagcaccc     600
agcagtcaag agggcgggcc agcggtgata gtcagaccgg acgtggcggt gctcggccag     660
gaccggggcc tggggggttgc ggaggcagca ggaacttccg ctgccgctgc cgccgctgca     720
gtgagccagc gggatcgcgg cgcaggccgg cagcctggcc aggagccggc tgaatcacgg     780
gacaccagcc tcagcagtga gttgcagcca caaccacaga tgcagacgca gcgccacgag     840
caagggcagc aagggttgca cgaaagcccg ccgtgtgaga gtgaggcagc ggtgtgtgcc     900
agggaggcag ctgtggccgc agcgaggcta gcagccatta atgcgccgc tgccctgccc     960
ccggacagcc cgtatgttcg ggcggtgatg gaaacgtgca gcgggcaagc gactgggggt    1020
caggcgggac agaatcagct gtcggcacac ggcctgctgc agccccagca tgagcagcag    1080
caacggcggc ggcggaggggg cctgggggcg gtggacagcg agtacgtggc gtgcgccaag    1140
cacgccgctg cagccgcggc acacctagcg gccctggagg ctgcggctgc actgccagcc    1200
gacagtccgt acctgaaggc ggccgtcgag gtgggtcgtg gcgccgggtt cgggtggccg    1260
gatgagcggg acagcgacgt atgggcgcag cagcgcgcac tgctgcagca gcagacggcg    1320
cggctgcagc gggcgctggg ggctgcactg tgcgggcgag gaggggcagc caggtacacc    1380
cccgctgggc cagtaccaga agggcacggg gccggagctt gcagtagcgg cgccgcggcg    1440
tcactggagt ccgtgtgggt atcttcgccc gggcacgctg aggcggcgag cggggcgcgc    1500
ggtgccgtgc tagcagcaga agcagcaaca gcagaagcag aagcagcagg tggcattctc    1560
gtgcctgccg tggtggcagg tggcggacct gcgggtagcg gccgcggcgg cggcacagat    1620
gaagtccgtg cgcatcacgg cagcgccgtt accacgatca ccccgggttg cagcgtgtgc    1680
agccgcatgc aagccagcag aaacggagtg caagcggctg acgccccagc cggtacgggt    1740
gttggcggcg cggctgaggc tcctgaggat gcagctgcag tgcctggagc agcgggccag    1800
ggtgcgcgtg tcagcgagtg ggtcggttcg ttactgctgc agagccctca gcggaatcc     1860
gcacctcctg tttccagaa gtcgaagcca ggcgctgagg ccagcggccc tgcagcggag    1920
ggccgggacc ccagccccca agttcctgca gcaattgggt gtggagctag cagcaccact    1980
catgggagcg gcaccaccag cagtggcaat ggggcgacca ccggcagcag caacagcggc    2040
gatgacagcg gtgggagcac cagtagcggc gggagcttaa cgggcgctgc cgatagcagc    2100
catagcggtg gctccggcgg cgatagagtt cggagcttaa gcggcgccag acgcagcttg    2160
catggtatta cagacagcag cagaagcacc agcagtggcg gcagtgacca gagcacgagc    2220
```

```
aaggacgtta acgatgccgt gaccagcagc ggcggcggcg ggcttggcgc aggcggctgc    2280
ggtggtgggg cggggattgt cgcaggcgat gagccctcca cagcagtccc cgaaagcctt    2340
cacaggccgg cgtcagagcg cagccctgga cggtgcgagc tcactgcagc cgcaggcggc    2400
ggcgccgagg cgggcagcgc agaggcgggc ggaagggcag tagtccctgc gcgcgagtcg    2460
cagtcgtggg ctcaacaact actgccggag cacttgccgc agtgggaaga cgaggtgccg    2520
agcgacggca gcagttgcag cgacactgac agctccgagt ttgaagaggg agactgggag    2580
gacgacgatt ggcctggggg cgcagccgag gctaaagatg gcagccggga caagtcacag    2640
cactcagcgg acaagcccgg cgcctccgac gtcacggacc acatgatggc agccgtgctg    2700
tcgcaggctg cgcccgagca cagcgctggt gtcaaacgtg ctggcggcga ggcagcgatc    2760
ctctacgccg atggcagtga cagccacggt gggcctgacg cttttcgttga caacgattca    2820 gcggcgtggg aggcagcact ggaggctggc gctggcccac atgaaagcca ggcggaggcc    2880
ccgcagcagc tggcggcggc cgtgacagtt tcgactctgg cgcttcttgg gcatggcaca    2940
ggtccggtgc agcaatcgcg gagacggctg ccggcgtcag gaagcgggcc agcagggcat    3000
gacacagcag gattaggtgc tggcgcggtg gccctcgcag aaccccagtt gcagctgccg    3060
gagcagtttg atgttaatct gctggcgccg ccagtgctag tgccggccgg cacgaagctg    3120
caagccctgc cgccatggtc tgtagggtcg cccgtcacca gccccgggtt gacgcaggca    3180
gggcctggcc ccagtgcggc tgcaggcccc agggtggcgc aggtcgtgtc gggcagcccc    3240
tacacggacg cctatgagct gccggacgat ggcggccacc cgcacctggg cggaggcgcc    3300
gccccgcagc ccagcagtcg cgaggacggc ggggtgtgg ctgccggggt cggtgcacac    3360
gcgggctgca acgcacagcg gggcatgaca gcagcagtaa ttggtcctgg tggtactcgg    3420
gttggtgctg cctcgcctcc gcttgtgctt tcagcctcag gctccggggg agggctggcg    3480
actccaggtc ggcggcgcgg ccgtctggtg atgctgcacg gtgccggggc ggcggcatgt    3540
ggtacgccca catcgcagcc ccgtgccggc agggcggcga gcaatacagc aaccgctggg    3600
ggtgcgggcc ccagcgcagt tgcagcggct gggccgggaa tgggcgacct cggccaccag    3660
gggcagccac tgccggccga gccccctgga gcagctacgc gaccggttgg cagggcaggg    3720
cgcgcgccac cgcttagccc tctgcgccgc agcagtcgcg tgcctggcgg acagcagcag    3780
cagcagcagc agcagcagca gcagcagcat gcagctggca tggcggccca gggccagggg    3840
cccgcggagc cttcggcaaa tggtggagca ggcaggagta gagcgtcggc aggcggtggc    3900
atgtcgccca gccgtagggc ggctgtgcgg cttcagcgac agccggtggt cccatcaccg    3960
aggctcgtgg aggattcaag gctgcatcgc tccggccagc agcaggcggt ggttggagta    4020
ggcacagcgg ggggaagccg cgtgggtgat cgcgcacggg gtggttcggg tgcagggttg    4080
tcggcagctg caacaggagt gatcaaggcc gccactgcct caccctcgcg cggccgcacc    4140
cgcagcaagc cacctgaacg ggcgtcgata gccgggcgag ggcgcggcgg cgtgggcggg    4200
cgggcgactg cgcgctctca ccggcagtcg gaaagcgacc aggaggagac agcagatgcg    4260
gtgcgcccgt ctgacccgga ggaggataag gagaaggagg gcggtgggca gcagactcgc    4320
ggcgcccctg ccaggcgccg agcccgcgc acacccagtg aagtgctcaa ccggctgcag    4380
gtgtcggacc tgcggccggt gctgcacctg cccctcgttg aggcggcacg gcagctgggg    4440
ctacaccgca ctagcttcat gacgcgctgc cgccaactgg ggatcgcgag atggccggcc    4500
aagcagctgc gcatgctgga cttgatggag gagcagctgc aggagctgga ggcgtgcggc    4560
gtcgcaaacc actacacggc caagaagtgc cttgaagaag ctccgggctg gctggcccag    4620
```

```
gtggccgctg cgcgctcggc gctgctggag aacccgtgcg gcttcaccat gccgcagccg    4680
ctggagctgc tgcgccagcg ccacgtgaag gtggcgtggg cgcaccgcca aaagtacaag    4740
gcggcactgg gcgaggaggg ggaggagggc gaggagggcg atgacctgga ctcgcaggcg    4800
cagatgtcac agtag                                                    4815
```

```
<210> SEQ ID NO 41
<211> LENGTH: 1604
<212> TYPE: PRT
<213> ORGANISM: Chlamydomonas reinhardtii

<400> SEQUENCE: 41
```

| Met | Ser | Lys | Val | Ser | Arg | Ile | Leu | His | Arg | Lys | Arg | Asp | Thr | Ala | Arg |
|---|---|---|---|---|---|---|---|---|---|---|---|---|---|---|---|
| 1 | | | | 5 | | | | | 10 | | | | | 15 | |

| Ala | Glu | Arg | Ala | Arg | Asp | Val | Leu | Ala | Ala | Lys | Arg | Ala | Ala | Ser | Lys |
|---|---|---|---|---|---|---|---|---|---|---|---|---|---|---|---|
| | | | 20 | | | | | 25 | | | | | 30 | | |

| Arg | Glu | Arg | Arg | Gln | Leu | Arg | Arg | Ala | Lys | Ala | Ser | Arg | Arg | Lys | Lys |
|---|---|---|---|---|---|---|---|---|---|---|---|---|---|---|---|
| | | 35 | | | | | 40 | | | | | 45 | | | |

| Lys | Gly | Gly | Ala | Glu | Ala | Ala | Gly | Pro | Ala | Asp | Pro | Pro | Arg | Asn |
|---|---|---|---|---|---|---|---|---|---|---|---|---|---|---|
| | 50 | | | | | 55 | | | | | 60 | | | |

| Thr | Asp | Ala | Glu | Ser | Pro | Ser | Val | Arg | Pro | Pro | Ala | Leu | Pro | Val |
|---|---|---|---|---|---|---|---|---|---|---|---|---|---|---|
| 65 | | | | | 70 | | | | | 75 | | | | 80 |

| His | Ala | Gly | Glu | Pro | Ser | Gly | Arg | Pro | Ala | Ala | Arg | Glu | Gly | Ser | Arg |
|---|---|---|---|---|---|---|---|---|---|---|---|---|---|---|---|
| | | | | 85 | | | | | 90 | | | | | 95 | |

| Asn | Thr | Ala | Leu | Gly | His | Cys | Val | Asp | Ser | Ala | Pro | Ala | His | Pro | Tyr |
|---|---|---|---|---|---|---|---|---|---|---|---|---|---|---|---|
| | | | 100 | | | | | 105 | | | | | 110 | | |

| Arg | Gln | Pro | Ala | Pro | Ile | Cys | Gly | Lys | Arg | Lys | Gln | Arg | Ser | Thr | Pro |
|---|---|---|---|---|---|---|---|---|---|---|---|---|---|---|---|
| | | 115 | | | | | 120 | | | | | 125 | | | |

| Leu | Ala | Arg | Ala | Leu | Arg | Leu | Val | Gln | Ala | Gly | Ala | Pro | Gly | Leu | Gln |
|---|---|---|---|---|---|---|---|---|---|---|---|---|---|---|---|
| | 130 | | | | | 135 | | | | | 140 | | | | |

| Thr | Gly | Val | Asp | Leu | Val | Ala | Gly | Val | Arg | Gly | Ala | Lys | Glu | Ala | Gln |
|---|---|---|---|---|---|---|---|---|---|---|---|---|---|---|---|
| 145 | | | | | 150 | | | | | 155 | | | | | 160 |

| Gln | Ala | Arg | Arg | Pro | Ala | Pro | Pro | Val | Ala | Lys | Val | Arg | Leu | Leu | Ser |
|---|---|---|---|---|---|---|---|---|---|---|---|---|---|---|---|
| | | | | 165 | | | | | 170 | | | | | 175 | |

| Leu | Pro | Leu | Glu | Pro | Lys | Val | Asp | Gly | Gln | Val | Gly | Gly | Cys | Ser | Pro |
|---|---|---|---|---|---|---|---|---|---|---|---|---|---|---|---|
| | | | 180 | | | | | 185 | | | | | 190 | | |

| Gly | Gln | Asp | Thr | Gln | Pro | Ala | Pro | Ser | Ser | Gln | Glu | Gly | Gly | Pro | Ala |
|---|---|---|---|---|---|---|---|---|---|---|---|---|---|---|---|
| | | 195 | | | | | 200 | | | | | 205 | | | |

| Val | Ile | Val | Arg | Pro | Asp | Val | Ala | Val | Leu | Gly | Gln | Asp | Arg | Gly | Leu |
|---|---|---|---|---|---|---|---|---|---|---|---|---|---|---|---|
| | 210 | | | | | 215 | | | | | 220 | | | | |

| Gly | Val | Ala | Glu | Ala | Ala | Gly | Thr | Ser | Ala | Ala | Ala | Ala | Ala | Ala | Ala |
|---|---|---|---|---|---|---|---|---|---|---|---|---|---|---|---|
| 225 | | | | | 230 | | | | | 235 | | | | | 240 |

| Val | Ser | Gln | Arg | Asp | Arg | Gly | Ala | Gly | Arg | Gln | Pro | Gly | Gln | Glu | Pro |
|---|---|---|---|---|---|---|---|---|---|---|---|---|---|---|---|
| | | | | 245 | | | | | 250 | | | | | 255 | |

| Ala | Glu | Ser | Arg | Asp | Thr | Ser | Leu | Ser | Ser | Glu | Leu | Gln | Pro | Gln | Pro |
|---|---|---|---|---|---|---|---|---|---|---|---|---|---|---|---|
| | | | 260 | | | | | 265 | | | | | 270 | | |

| Gln | Met | Gln | Thr | Gln | Arg | His | Glu | Gln | Gly | Gln | Gln | Gly | Leu | His | Glu |
|---|---|---|---|---|---|---|---|---|---|---|---|---|---|---|---|
| | | 275 | | | | | 280 | | | | | 285 | | | |

| Ser | Pro | Pro | Cys | Glu | Ser | Glu | Ala | Ala | Val | Cys | Ala | Arg | Glu | Ala | Ala |
|---|---|---|---|---|---|---|---|---|---|---|---|---|---|---|---|
| | 290 | | | | | 295 | | | | | 300 | | | | |

| Val | Ala | Ala | Ala | Arg | Leu | Ala | Ala | Ile | Asn | Ala | Ala | Ala | Ala | Leu | Pro |
|---|---|---|---|---|---|---|---|---|---|---|---|---|---|---|---|
| 305 | | | | | 310 | | | | | 315 | | | | | 320 |

| Pro | Asp | Ser | Pro | Tyr | Val | Arg | Ala | Val | Met | Glu | Thr | Cys | Ser | Gly | Gln |
|---|---|---|---|---|---|---|---|---|---|---|---|---|---|---|---|
| | | | | 325 | | | | | 330 | | | | | 335 | |

```
Ala Thr Gly Gly Gln Ala Gly Gln Asn Gln Leu Ser Ala His Gly Leu
            340                 345                 350

Leu Gln Pro Gln His Glu Gln Gln Arg Arg Arg Arg Gly Leu
        355                 360                 365

Gly Ala Val Asp Ser Glu Tyr Val Ala Cys Ala Lys His Ala Ala Ala
        370                 375                 380

Ala Ala Ala His Leu Ala Ala Leu Glu Ala Ala Ala Leu Pro Ala
385                 390                 395                 400

Asp Ser Pro Tyr Leu Lys Ala Ala Val Glu Val Gly Arg Gly Ala Gly
                405                 410                 415

Phe Gly Trp Pro Asp Glu Arg Asp Ser Asp Val Trp Ala Gln Gln Arg
            420                 425                 430

Ala Leu Leu Gln Gln Gln Thr Ala Arg Leu Gln Arg Ala Leu Gly Ala
        435                 440                 445

Ala Leu Cys Gly Arg Gly Gly Ala Ala Arg Tyr Thr Pro Ala Gly Pro
    450                 455                 460

Val Pro Glu Gly His Gly Ala Gly Ala Cys Ser Ser Gly Ala Ala Ala
465                 470                 475                 480

Ser Leu Glu Phe Arg Val Gly Ser Ser Pro Gly His Ala Glu Ala Ala
                485                 490                 495

Ser Gly Ala Arg Gly Ala Val Leu Ala Ala Glu Ala Ala Thr Ala Glu
        500                 505                 510

Ala Glu Ala Ala Gly Gly Ile Leu Val Pro Ala Val Ala Gly Gly
        515                 520                 525

Gly Pro Ala Gly Ser Gly Arg Gly Gly Gly Thr Asp Glu Val Arg Ala
    530                 535                 540

His His Gly Ser Ala Val Thr Thr Ile Thr Pro Gly Cys Ser Val Cys
545                 550                 555                 560

Ser Arg Met Gln Ala Ser Arg Asn Gly Val Gln Ala Ala Asp Ala Pro
                565                 570                 575

Ala Gly Thr Gly Val Gly Gly Ala Ala Glu Ala Pro Glu Asp Ala Ala
        580                 585                 590

Ala Val Pro Gly Ala Ala Gly Gln Gly Ala Arg Val Ser Glu Trp Val
        595                 600                 605

Gly Ser Leu Leu Leu Gln Ser Pro Gln Ala Glu Ser Ala Pro Pro Val
    610                 615                 620

Phe Gln Lys Ser Lys Pro Gly Ala Glu Ala Ser Gly Pro Ala Ala Glu
625                 630                 635                 640

Gly Arg Asp Pro Ser Pro Gln Val Pro Ala Ile Gly Cys Gly Ala
                645                 650                 655

Ser Ser Thr Thr His Gly Ser Gly Thr Thr Ser Ser Gly Asn Gly Ala
            660                 665                 670

Thr Thr Gly Ser Ser Asn Ser Gly Asp Asp Ser Gly Gly Ser Thr Ser
        675                 680                 685

Ser Gly Gly Ser Leu Thr Gly Ala Ala Asp Ser Ser His Ser Gly Gly
    690                 695                 700

Ser Gly Gly Asp Arg Val Arg Ser Leu Ser Gly Ala Arg Arg Ser Leu
705                 710                 715                 720

His Gly Ile Thr Asp Ser Ser Arg Ser Thr Ser Ser Gly Gly Ser Asp
                725                 730                 735

Gln Ser Thr Ser Lys Asp Val Asn Asp Ala Val Thr Ser Ser Gly Gly
        740                 745                 750
```

-continued

Gly Gly Leu Gly Ala Gly Gly Cys Gly Gly Ala Gly Ile Val Ala
        755                 760                 765

Gly Asp Glu Pro Ser Thr Ala Val Pro Glu Ser Leu His Arg Pro Ala
    770                 775                 780

Ser Glu Arg Ser Pro Gly Arg Cys Glu Leu Thr Ala Ala Ala Gly Gly
785                 790                 795                 800

Gly Ala Glu Ala Gly Ser Ala Glu Ala Gly Gly Arg Ala Val Val Pro
            805                 810                 815

Ala Arg Glu Ser Gln Ser Trp Ala Gln Gln Leu Leu Pro Glu His Leu
        820                 825                 830

Pro Gln Trp Glu Asp Glu Val Pro Ser Asp Gly Ser Ser Cys Ser Asp
    835                 840                 845

Thr Asp Ser Ser Glu Phe Glu Glu Gly Asp Trp Glu Asp Asp Asp Trp
850                 855                 860

Pro Gly Gly Ala Ala Glu Ala Lys Asp Gly Ser Arg Asp Lys Ser Gln
865                 870                 875                 880

His Ser Ala Asp Lys Pro Gly Ala Ser Asp Val Thr Asp His Met Met
            885                 890                 895

Ala Ala Val Leu Ser Gln Ala Ala Pro Glu His Ser Ala Gly Val Lys
        900                 905                 910

Arg Ala Gly Gly Glu Ala Ala Ile Leu Tyr Ala Asp Gly Ser Asp Ser
    915                 920                 925

His Gly Gly Pro Asp Ala Phe Val Asp Asn Asp Ser Ala Ala Trp Glu
930                 935                 940

Ala Ala Leu Glu Ala Gly Ala Gly Pro His Glu Ser Gln Ala Glu Ala
945                 950                 955                 960

Pro Gln Gln Leu Ala Ala Ala Val Thr Val Ser Thr Leu Ala Leu Leu
            965                 970                 975

Gly His Gly Thr Gly Pro Val Gln Gln Ser Arg Arg Arg Leu Pro Ala
        980                 985                 990

Ser Gly Ser Gly Pro Ala Gly His Asp Thr Ala Gly Leu Gly Ala Gly
    995                 1000                1005

Ala Val Ala Leu Ala Glu Pro Gln Leu Gln Leu Pro Glu Gln Phe
    1010                1015                1020

Asp Val Asn Leu Leu Ala Pro Pro Val Leu Val Pro Ala Gly Thr
    1025                1030                1035

Lys Leu Gln Ala Leu Pro Pro Trp Ser Val Gly Ser Pro Val Thr
    1040                1045                1050

Ser Pro Gly Leu Thr Gln Ala Gly Pro Gly Pro Ser Ala Ala Ala
    1055                1060                1065

Gly Pro Arg Val Ala Gln Val Val Ser Gly Ser Pro Tyr Thr Asp
    1070                1075                1080

Ala Tyr Glu Leu Pro Asp Asp Gly Gly His Pro His Leu Gly Gly
    1085                1090                1095

Gly Ala Ala Pro Gln Pro Ser Ser Arg Glu Asp Gly Gly Gly Val
    1100                1105                1110

Ala Ala Gly Val Gly Ala His Ala Gly Cys Asn Ala Gln Arg Gly
    1115                1120                1125

Met Thr Ala Ala Val Ile Gly Pro Gly Gly Thr Arg Val Gly Ala
    1130                1135                1140

Ala Ser Pro Pro Leu Val Leu Ser Ala Ser Gly Ser Gly Gly Gly
    1145                1150                1155

Leu Ala Thr Pro Gly Arg Arg Arg Gly Arg Leu Val Met Leu His

```
            1160                1165                1170

Gly Ala Gly Ala Ala Ala Cys Gly Thr Pro Thr Ser Gln Pro Arg
        1175                1180                1185

Ala Gly Arg Ala Ala Ser Asn Thr Ala Thr Ala Gly Gly Ala Gly
        1190                1195                1200

Pro Ser Ala Val Ala Ala Ala Gly Pro Gly Met Gly Asp Leu Gly
        1205                1210                1215

His Gln Gly Gln Pro Leu Pro Ala Glu Pro Pro Gly Ala Ala Thr
        1220                1225                1230

Arg Pro Val Gly Arg Ala Gly Arg Ala Pro Pro Leu Ser Pro Leu
        1235                1240                1245

Arg Arg Ser Ser Arg Val Pro Gly Gly Gln Gln Gln Gln Gln Gln
        1250                1255                1260

Gln Gln Gln Gln Gln Gln His Ala Ala Gly Met Ala Ala Gln Gly
        1265                1270                1275

Gln Gly Pro Ala Glu Pro Ser Ala Asn Gly Gly Ala Gly Arg Ser
        1280                1285                1290

Arg Ala Ser Ala Gly Gly Gly Met Ser Pro Ser Arg Arg Ala Ala
        1295                1300                1305

Val Arg Leu Gln Arg Gln Pro Val Val Pro Ser Pro Arg Leu Val
        1310                1315                1320

Glu Asp Ser Arg Leu His Arg Ser Gly Gln Gln Gln Ala Val Val
        1325                1330                1335

Gly Val Gly Thr Ala Gly Gly Ser Arg Val Gly Asp Arg Ala Arg
        1340                1345                1350

Gly Gly Ser Gly Ala Gly Leu Ser Ala Ala Ala Thr Gly Val Ile
        1355                1360                1365

Lys Ala Ala Thr Ala Ser Pro Ser Arg Gly Arg Thr Arg Ser Lys
        1370                1375                1380

Pro Pro Glu Arg Ala Ser Ile Ala Gly Arg Gly Arg Gly Gly Arg
        1385                1390                1395

Gly Arg Arg Ala Thr Ala Arg Ser His Arg Gln Ser Glu Ser Asp
        1400                1405                1410

Gln Glu Glu Thr Ala Asp Ala Val Arg Pro Ser Asp Pro Glu Glu
        1415                1420                1425

Asp Lys Glu Lys Glu Gly Gly Gly Gln Gln Thr Arg Gly Ala Pro
        1430                1435                1440

Ala Arg Arg Arg Ala Pro Arg Thr Pro Ser Glu Val Leu Asn Arg
        1445                1450                1455

Leu Gln Val Ser Asp Leu Arg Pro Val Leu His Leu Pro Leu Val
        1460                1465                1470

Glu Ala Ala Arg Gln Leu Gly Leu His Arg Thr Ser Phe Met Thr
        1475                1480                1485

Arg Cys Arg Gln Leu Gly Ile Ala Arg Trp Pro Ala Lys Gln Leu
        1490                1495                1500

Arg Met Leu Asp Leu Met Glu Glu Gln Leu Gln Glu Leu Glu Ala
        1505                1510                1515

Cys Gly Val Ala Asn His Tyr Thr Ala Lys Lys Cys Leu Glu Glu
        1520                1525                1530

Ala Pro Gly Trp Leu Ala Gln Val Ala Ala Ala Arg Ser Ala Leu
        1535                1540                1545

Leu Glu Asn Pro Cys Gly Phe Thr Met Pro Gln Pro Leu Glu Leu
        1550                1555                1560
```

| Leu | Arg | Gln | Arg | His | Val | Lys | Val | Ala | Trp | Ala | His | Arg | Gln | Lys |
|---|---|---|---|---|---|---|---|---|---|---|---|---|---|---|
| 1565 | | | | 1570 | | | | | 1575 | | | | | |

| Tyr | Lys | Ala | Ala | Leu | Gly | Glu | Glu | Gly | Glu | Gly | Glu | Glu | Gly |
|---|---|---|---|---|---|---|---|---|---|---|---|---|---|
| 1580 | | | | | 1585 | | | | | 1590 | | | |

| Asp | Asp | Leu | Asp | Ser | Gln | Ala | Gln | Met | Ser | Gln |
|---|---|---|---|---|---|---|---|---|---|---|
| 1595 | | | | | 1600 | | | | | |

<210> SEQ ID NO 42
<211> LENGTH: 3367
<212> TYPE: DNA
<213> ORGANISM: Chlamydomonas reinhardtii

<400> SEQUENCE: 42

```
gcagctgtaa atcatttgca ccagcataca ccaaaatcta ttcgccttga aaccaacgga      60
ccccttcgat ctctctctgg ccactccaag ctttggtcgt tctgttttct gaccttgaga     120
agcgctgccc tctctacatt gagctagtgt aagggccatt gaacgactgc attttcctgc     180
aagccatata ccgctaggac gcccagtcgc agccgctgga gcaatgacgg agaccgacca     240
ccgccgaagc cgtccggact ggtctcgcgc acagtccctt cgtctaattc agctccacgt     300
caagctgggt aacagttgga ccgagatcgc taagcagctg cccggccgca ctcagaatga     360
ctgcaagaat ttcttcttcg gagccctgcg cgcaaagcgc ggctaccgtg acaacctggt     420
ctacgcctac gcgcgcgcgt tgccgcccgc ctccgcctct gcttgcgggt cgtgggagca     480
ggacaagcgc ggccccgacg ccctcacccg tgccgccgcc tacaaggcag ccatgcaaca     540
agtggcggcg caagaagtgg ccgagcagat ggagaagcag cagcgtagcc agcagcaaga     600
gggagaggac ggcggctgcg gctcgggtgc cgctggtgct actgccgagg acggcgggga     660
gccgggtgct gtagccgctg ccagccgccg cagtagcagt gtgtcagtgg gcgctgacgg     720
cgcggcgccc acggctcagg gcgacggcat ggacacgcaa gaggacgccg cgtccgcgcc     780
tgcctgcccc gcctcggctg ccgcgagccc ggttggtcct ggtgacgtca gcgtccgccg     840
gctctcatcc actggtgata ccgtcgtcac tgatgccgcc ggcaccagga ctgttgttgc     900
cgctggtgtt gttgctggcg gttggcgctc cgttgccgcc gcggcgtcaa tgccggccca     960
ccctgccgcc gtggtgtcga tgccgccggt ggtgcccgcc tctgttgtgg cggcggccag    1020
cggcgtgctt ggcgccgccg cggtgcccgc tgctggtgcc cctggtgacc ggctgtccct    1080
gcagtcgctg cagccgccgc cgcacggctt cgccgcccct ccgcagtcgg cggcgccggc    1140
gatcggcagc agcagcgcca gtccttctg gcagcaccag cagcagcacc acctcatggg    1200
cccccggggtg cagcttctgt ctcacgagtc gctggccctc ctgcaccagc agcaccagca    1260
ggcgcagcag cactcgcacg tggtcctgca cgtggcgccg ccgttcctgc agcagcacca    1320
ccagaacccg caccaccagc acctgatggt gcagctggaa ggcgccggcg ccggtgcacc    1380
tgccggcgcc ttccagctgc aacaccacca gcacctgcac ccgcaccacg tccagggctc    1440
aggccctgcc gacggcagca gcggcccccgt cctgctcatg ggccccgccg gccccacgc    1500
cgcggcgctg cagctgctgg gctcccaccc gcaccaccag caccagcacc accagcagct    1560
cgtgctcctg ccctcgtctg tccccggtgc acctccgcag catgtgctgc tgcctatggc    1620
cgtccgcccg ccgcacctgc ttcagtacgg cggtgcacac ggtgccagtg ccgctgcatc    1680
tgctgccgcc gctgctccgt ctgcgggcat gggcgccttc gtcttccacc ctcacccgca    1740
gcagcagcag ctgccgcctg ctgccgccgc tgccttgct gccgcctccg ccgcgccgtc    1800
gcagccccgcc gcagttgcgg ccgccgtgca ctcgctggca cccgccgcct ccgcagccct    1860
```

```
gtccctcagc ggcagctcgg tcctggaggc gaccaccacc accacccgca tcacaaccac    1920
cactgccgcg gctgttgcgg ccgctgctgc tggcgccgca gtggctgctg ggtcaagac    1980 cgagcccgcc tcagccgagg cggccactgg ctgggcccag cagcagcaac agaaggcgca    2040
tgctggcgtt agccgcagct gcagtagcag cagcagcagc agcgccgcct gcggcgcctg    2100
cagcacatgc accgccggtg tcggcgctac tcctgccaca gcaacccagc tgccgcaaca    2160
ccagcaggat caccagcttc tgggcgacga ctggtgcgcc ggtgacgagg agtgggccga    2220
gctcgggcgc atcctgcttg gctgaagcag tgctgatgat ggtggcacct tgcgaaggtt    2280
gcatgaacga atgacacaaa cgcatactag tgtactgtag cctaaatggc cggcctgaat    2340
tctttgaaga caataagtaa tttttgagcg tgagcgttct atggtaccta gggcgccacc    2400
atgcaaactc cacatgagtg agtggtatat tacaaggcct ggtccggaca ctgtgaaacc    2460
ggttgaccta ccgaacctaa atgtgagttg ctcaaattcg gagtagcttg aggtaggcgc    2520
atgaatgcat atggttcctg cagctgactt gctgcagcgt gggatgggat ggcaaacgag    2580
ttgtgtagcc agcagcccaa gggtgtctgg atgtgttcaa cctcctaatc gcatgcatgc    2640
gtgttggagt ttgcaagcat gctcgcatgc cgcactagcc gcacacatac acaagaagac    2700
tggagcaggc gagaattgca ctgacacaga gccaagcaag cccataaaaa gtggtagctg    2760
tataagatga ggtgtacagt ggatgggcag tgcccaaagc aagcaggggc gacagtgcaa    2820
gccgcgggca ctgccgtaca gagtgctgtg tactgctgag atgctgcaaa cggcagaagt    2880
agagcagccg ggaaggctgt gggcggggaa gagcgaacgt cggcatgtgt gagcgtcggt    2940
gtttacctag tgcggatgtg atgacgagcg agagagttga ccacagcgga catgcacggc    3000
cttcggcccc accccatttt tagggctgga gttttcccac catctctgga gttgactcgc    3060
gaatgtgtca accacccgaa agaatggtcg catgcttgtg agagttgctg gaagactgct    3120
gagagcgaga ccggatcccg cgtcaggggt gaaggtgcaa acggcacgaa tgaacgcact    3180
tcatccaagg ctcggaacag cacgcacgca tgtgcagttg taaggcgctg cagcgatacg    3240
atgtaacttc cttctcatgc agtcgtgtca cattgggctc agagcagcct tgaaagacgc    3300
agtggtgcgg gcagcaggtg cgcctggggc ctctctggct gcccacggac tgtaaatgta    3360
cggcgcc                                                              3367
```

<210> SEQ ID NO 43
<211> LENGTH: 2022
<212> TYPE: DNA
<213> ORGANISM: Chlamydomonas reinhardtii

<400> SEQUENCE: 43

```
atgacggaga ccgaccaccg ccgaagccgt ccggactggt ctcgcgcaca gtcccttcgt      60
ctaattcagc tccacgtcaa gctgggtaac agttggaccg agatcgctaa gcagctgccc     120
ggccgcactc agaatgactg caagaatttc ttcttcggag ccctgcgcgc aaagcgcggc     180
taccgtgaca acctggtcta cgcctacgcg cgcgcgttgc cgcccgcctc cgcctctgct     240
tgcgggtcgt gggagcagga caagcgcggc cccgacgccc tcaccccgtgc cgccgcctac     300 aaggcagcca tgcaacaagt ggcggcgcaa gaagtggccg agcagatgga gaagcagcag    360
cgtagccagc agcaagaggg agaggacggc ggctgcggct cgggtgccgc tggtgctact    420
gccgaggacg cgggggagcc gggtgctgta ccgctgccca gccgccgcag tagcagtgtg    480
tcagtgggcg ctgacggcgc ggcgcccacg gctcagggcg acggcatgga cacgcaagag    540
```

```
gacgccgcgt ccgcgcctgc ctgccccgcc tcggctgccg cgagcccggt tggtcctggt    600
gacgtcagcg tccgccggct ctcatccact ggtgataccg tcgtcactga tgccgccggc    660
accaggactg ttgttgccgc tggtgttgtt gctggcggtt ggcgctccgt tgccgccgcg    720
gcgtcaatgc cggcccaccc tgccgccgtg tgtcgatgc cgccggtggt gcccgcctct     780
gttgtggcgg cggccagcgg cgtgcttggc gccgccgcgg tgcccgctgc tggtgcccct    840
ggtgaccggc tgtccctgca gtcgctgcag ccgccgccgc acggcttcgc cgcccttccg    900
cagtcggcgg cgccggcgat cggcagcagc agcgccagtc ccttctggca gcaccagcag    960
cagcaccacc tcatgggccc ccgggtgcag cttctgtctc acgagtcgct ggccctcctg   1020
caccagcagc accagcaggc gcagcagcac tcgcacgtgg tcctgcacgt ggcgccgccg   1080
ttcctgcagc agcaccacca gaacccgcac caccagcacc tgatggtgca gctggaaggc   1140
gccggcgccg gtgcacctgc cggcgccttc cagctgcaac accaccagca cctgcacccg   1200
caccacgtcc agggctcagg ccctgccgac ggcagcagcg gccccgtcct gctcatgggc   1260
cccgccggcc ccacgccgc ggcgctgcag ctgctgggct cccaccccgca ccaccagcac   1320 cagcaccacc agcagctcgt gctcctgccc tcgtctgtcc ccggtgcacc tccgcagcat   1380
gtgctgctgc ctatgccgt ccgccgccg cacctgcttc agtacggcgg tgcacacggt     1440
gccagtgccg ctgcatctgc tgccgccgct gctccgtctg cgggcatggg cgccttcgtc   1500
ttccaccctc acccgcagca gcagcagctg ccgcctgctg ccgccgctgc ctttgctgcc   1560
gcctccgccg cgccgtcgca gcccgccgca gttgcggccg ccgtgcactc gctggcaccc   1620
gccgcctccg cagccctgtc cctcagcggc agctcggtcc tggaggcgac caccaccacc   1680
acccgcatca caaccaccac tgccgcggct gttgcggccg ctgctgctgg cgccgcagtg   1740
gctgctgggg tcaagaccga gcccgcctca gccgaggcgg ccactggctg ggcccagcag   1800
cagcaacaga aggcgcatgc tggcgttagc cgcagctgca gtagcagcag cagcagcagc   1860
gccgcctgcg gcgcctgcag cacatgcacc gccggtgtcg gcgctactcc tgccacagca   1920
acccagctgc cgcaacacca gcaggatcac cagcttctgg gcgacgactg tgtgcgccggt  1980 gacgaggagt gggccgagct cgggcgcatc ctgcttggct ga                      2022
```

<210> SEQ ID NO 44
<211> LENGTH: 673
<212> TYPE: PRT
<213> ORGANISM: Chlamydomonas reinhardtii

<400> SEQUENCE: 44

```
Met Thr Glu Thr Asp His Arg Arg Ser Arg Pro Asp Trp Ser Arg Ala
1               5                   10                  15

Gln Ser Leu Arg Leu Ile Gln Leu His Val Lys Leu Gly Asn Ser Trp
            20                  25                  30

Thr Glu Ile Ala Lys Gln Leu Pro Gly Arg Thr Gln Asn Asp Cys Lys
        35                  40                  45

Asn Phe Phe Gly Ala Leu Arg Ala Lys Arg Gly Tyr Arg Asp Asn
    50                  55                  60

Leu Val Tyr Ala Tyr Ala Arg Ala Leu Pro Pro Ala Ser Ala Ser Ala
65                  70                  75                  80

Cys Gly Ser Trp Glu Gln Asp Lys Arg Gly Pro Asp Ala Leu Thr Arg
                85                  90                  95

Ala Ala Ala Tyr Lys Ala Ala Met Gln Gln Val Ala Ala Gln Glu Val
            100                 105                 110
```

```
Ala Glu Gln Met Glu Lys Gln Gln Arg Ser Gln Gln Glu Gly Glu
            115                 120                 125

Asp Gly Gly Cys Gly Ser Gly Ala Ala Gly Ala Thr Ala Glu Asp Gly
130                 135                 140

Gly Glu Pro Gly Ala Val Ala Ala Ala Ser Arg Arg Ser Ser Ser Val
145                 150                 155                 160

Ser Val Gly Ala Asp Gly Ala Ala Pro Thr Ala Gln Gly Asp Gly Met
                    165                 170                 175

Asp Thr Gln Glu Asp Ala Ala Ser Ala Pro Ala Cys Pro Ala Ser Ala
            180                 185                 190

Ala Ala Ser Pro Val Gly Pro Gly Asp Val Ser Val Arg Arg Leu Ser
            195                 200                 205

Ser Thr Gly Asp Thr Val Val Thr Asp Ala Ala Gly Thr Arg Thr Val
    210                 215                 220

Val Ala Ala Gly Val Val Ala Gly Gly Trp Arg Ser Val Ala Ala Ala
225                 230                 235                 240

Ala Ser Met Pro Ala His Pro Ala Ala Val Val Ser Met Pro Pro Val
            245                 250                 255

Val Pro Ala Ser Val Val Ala Ala Ala Ser Gly Val Leu Gly Ala Ala
            260                 265                 270

Ala Val Pro Ala Ala Gly Ala Pro Gly Asp Arg Leu Ser Leu Gln Ser
            275                 280                 285

Leu Gln Pro Pro Pro His Gly Phe Ala Ala Leu Pro Gln Ser Ala Ala
            290                 295                 300

Pro Ala Ile Gly Ser Ser Ser Ala Ser Pro Phe Trp Gln His Gln Gln
305                 310                 315                 320

Gln His His Leu Met Gly Pro Arg Val Gln Leu Leu Ser His Glu Ser
                325                 330                 335

Leu Ala Leu Leu His Gln His Gln Gln Ala Gln Gln His Ser His
                340                 345                 350

Val Val Leu His Val Ala Pro Pro Phe Leu Gln Gln His His Gln Asn
            355                 360                 365

Pro His His Gln His Leu Met Val Gln Leu Glu Gly Ala Gly Ala Gly
370                 375                 380

Ala Pro Ala Gly Ala Phe Gln Leu Gln His His Gln His Leu His Pro
385                 390                 395                 400

His His Val Gln Gly Ser Gly Pro Ala Asp Gly Ser Ser Gly Pro Val
                405                 410                 415

Leu Leu Met Gly Pro Ala Gly Pro His Ala Ala Leu Gln Leu Leu
                420                 425                 430

Gly Ser His Pro His His Gln His Gln His His Gln Leu Val Leu
            435                 440                 445

Leu Pro Ser Ser Val Pro Gly Ala Pro Pro Gln His Val Leu Leu Pro
    450                 455                 460

Met Ala Val Arg Pro Pro His Leu Leu Gln Tyr Gly Gly Ala His Gly
465                 470                 475                 480

Ala Ser Ala Ala Ala Ser Ala Ala Ala Ala Pro Ser Ala Gly Met
            485                 490                 495

Gly Ala Phe Val Phe His Pro His Pro Gln Gln Gln Gln Leu Pro Pro
                500                 505                 510

Ala Ala Ala Ala Ala Phe Ala Ala Ala Ser Ala Ala Pro Ser Gln Pro
            515                 520                 525

Ala Ala Val Ala Ala Ala Val His Ser Leu Ala Pro Ala Ala Ser Ala
```

```
     530                 535                 540
Ala Leu Ser Leu Ser Gly Ser Ser Val Leu Glu Ala Thr Thr Thr Thr
545                 550                 555                 560

Thr Arg Ile Thr Thr Thr Ala Ala Ala Val Ala Ala Ala Ala Ala Ala
                565                 570                 575

Gly Ala Ala Val Ala Ala Gly Val Lys Thr Glu Pro Ala Ser Ala Glu
                580                 585                 590

Ala Ala Thr Gly Trp Ala Gln Gln Gln Gln Lys Ala His Ala Gly
                595                 600                 605

Val Ser Arg Ser Cys Ser Ser Ser Ser Ser Ala Ala Cys Gly
610                 615                 620

Ala Cys Ser Thr Cys Thr Ala Gly Val Gly Ala Thr Pro Ala Thr Ala
625                 630                 635                 640

Thr Gln Leu Pro Gln His Gln Gln Asp His Gln Leu Leu Gly Asp Asp
                645                 650                 655

Trp Cys Ala Gly Asp Glu Glu Trp Ala Glu Leu Gly Arg Ile Leu Leu
                660                 665                 670

Gly

<210> SEQ ID NO 45
<211> LENGTH: 4772
<212> TYPE: DNA
<213> ORGANISM: Chlamydomonas reinhardtii

<400> SEQUENCE: 45
```

| | | | | | |
|---|---|---|---|---|---|
| ctgacgcgac | ctactttcga | tttccaaaga | gtcgtctgaa | accccgtat | tggcccatgc | 60 |
| ctgatgcccc | acgatttatg | cgccagctgg | gcgccggttc | tgcttccggg | agcgggagcg | 120 |
| ggacgcagca | tgtgtgctca | aaacacctca | gctttccaat | tcggaaatcg | agtgcggtga | 180 |
| aagtgaaacc | ccacgtggtg | ccattcagag | cacttaggcg | cctaacgcag | ggttaaatca | 240 |
| cgctcagacc | cggtaaccga | taggcacgta | tgtgcggacc | attgaaggct | gaacggattg | 300 |
| tactgcgcct | aactatgcaa | aaaggcctgt | gtaatcctaa | gccctagacc | tgaacgctca | 360 |
| cgcgttctct | cgcttactgc | attattggtg | gcagggctac | atacacgctc | cgagtgaagt | 420 |
| ctataccgct | caggagctcc | gccaagggag | cgcgagcaag | ttttgagcaa | acgcgcagtt | 480 |
| aggacgccgt | acgccataga | ttccattctg | atgccttgcg | cagagtcctt | tgcaaaggtg | 540 |
| gtgtacgcgc | caagttgacg | actggcatgc | gtctgcgggg | ccgcagcaag | ctttcgatcc | 600 |
| aggcgacgtt | ccaatttcac | gaactagcgc | cgcttgtcag | tttcaaggtc | gcacctatcg | 660 |
| ctatgcaacg | atctacgttt | tgcggccttc | ttatacttga | tagagcatag | aacggatgga | 720 |
| agcgagctgg | ttggaatcgc | catttagtag | acctgccctg | gggcccgatg | acaaagctg | 780 |
| aacgcgctgc | tggtggccct | aacgctgcaa | gcgaggacga | ctggctgctg | gagttttggc | 840 |
| cggagcctgc | agcggacttt | cctgcaccgg | tcgctccgat | gctgtcgcag | catcaagacg | 900 |
| cagcacagct | gcctgaggcc | atgccgcagc | agcaaggact | ggcgctgggt | ggatatggtc | 960 |
| tcacgcagca | gccttctgac | tttatgcaaa | cgggcatgcc | cggcttcgac | gcgttcagca | 1020 |
| gcggaaaggc | tgcaaccctc | gggctgcccc | tgcttgccga | ccccagcgc | gcctccaccg | 1080 |
| acggcgcctc | tgcgcttatg | aacgcggcgc | agcagtcctc | agagtacatg | ctggcccccg | 1140 |
| gcatgggcgg | catgccgcat | ctactagcac | cgagcgttgg | cacggcgctg | ccggcactg | 1200 |
| ggcacaccgg | cttcgcggac | ctgtccatgg | ggggcatggc | gggggcatc | ccgggcctcg | 1260 |
| gggggccagg | cattatgcat | gggcagtact | tcatgcagcc | gcagcgagca | gccacgggcc | 1320 |

-continued

```
ccgccaagag ccggctgcgc tggacgccgg agctgcacaa ccgcttcgtc aacgcggtga    1380
actcgctggg ggggccggac aaggccacgc ccaagggcat ccttaagctc atgggcgtcg    1440
acggcctcac catctaccac atcaagtcgc acctgcagaa gtaccgcctc aacatccggc    1500
tgccgggaga gagcggcctc gcgggcgact cggcggacgg ctcggacggc gagcgctcgg    1560
acggcgaggg cggcgtgcgg cgcgccacct cgctggagcg ggcagacacc atgtcgggga    1620 tggcggggagg ggccgccgca gcgttaggga gagcgggcgg gacgccgggc ggtgcgctaa    1680
tctcccccgg ccttgccggc gggacgtcaa gcaccggtgg gatggcagcc ggcggcggcg    1740
ggggtggcgg cttggtgact gagcccagca tctctagggg cacggtcctc aacgcggccg    1800
gcgcagttgc caccgccgcg ccggctgcgg cggcgcctgc cggcgggtcc gccgccgtga    1860
agcggccggc gggtacgtct ctgagcagcg gcagcactgc ctcggctact cggcgcaatc    1920
tggaggaggc gctgctgttc caaatggagc tgcagaagaa gctgcacgag cagctggaga    1980
cgcagcgtca actgcagctg agcttggagg cgcacgggcg ctacatcgcc agcctcatgg    2040
agcaggaggg actcacctcg cgactgcccg agctcagcgg cggcgcgccg cggcggcgc    2100 ctgtggccgc aggcggcgca gcgggcggca tgattgcgcc gccgccaccg cagcagcagc    2160
tgcagcacca gccgcagctg ctgcagccgc agggcagctt gccagccggc ggttcctctg    2220
aagcccatgc cgcagccggc gccggcacga tggtggtgca ccagcagcag cagcagcacg    2280
tgcaccatca tcaccagcag cagcaggtgc agatgcagca gcatgcccgc cactgcgaca    2340
cgtgtggcgc cggtggcgct ggggggtgcgc ccagcggcgg cagcagcatg cagcagcttc    2400
aggctgcgga gcagcagcgc acggagcttg ttgtggcggg gcggctaggc tccatgccgg    2460
cgcccgcctc ttcgtcgccg ctagcagggc aggcacacca gcagcagccg ctggccggcg    2520
gggcggcgca cttggtgcac gtgcactcgc acacgcctgg ggggcagccg cacgtgcagc    2580
accaggacgc gttttgccggc gcggctacgg cggcagcgca cgcttcgccg gggctgccgc    2640
agtcacattc gcacctgctc ccagccgacc tctccagcaa cgccggtcct gacacaagcg    2700
cggggcagat taagcctgag cctgatatgt cgcagcaaca gcagcaacaa gagcaacagg    2760
aggcggagca gcttgcgcag ggtttgctca atgacagcag cgctggcgcg ggggctgtca    2820
gcggcagcga tggtggggc cttggggact ttgacttcgg tgatttcggg gacctggacg    2880
ggggagccca gggcggccta ctaggccccg gagacctcat tggcatcgcc gagctggagg    2940
cagcggccgc gcacgagcag cagcaagagc aagagcacga cccactagat gcggatcgcg    3000
caaagcggca gcgagtggag ccataggttc agagctagca ggtgtgttag gcagcggaac    3060
agcagctgtt gcgctcccga caggctaacc agccaagcca cagacgtctg gtgccccagt    3120
cggttgcgcg tgcagctgtg gcgccagggg cccctgcctg gtagacagag cccctcgtcc    3180
gctgaaagga gagcgagcac gggacgcgac gagccgtcgc caagttggca gaaggcacct    3240
gcgcatgcat ctgttgactc tgtctttctg ttgttggctg atgtcttgaa gtgtcattga    3300
ctaccgtcct gcatacgttc acgtggtaca tgctgggtgc cgccgccatc tggcgctccc    3360 gccgtttttga gctgattgcg ctcggcgcca gacagcggtt ggcccttgct ttggggctcg    3420
tgtcgattgc gtttgtatgc cgctcgtttg gccggcagag cgcgccggcc cacggggccg    3480
tgcggacgtt acgtgtgtga ggccccagcc gaagtaccgc agtgtgctgt cgctcactcg    3540
cgcactgccg ctcgacttgc ggtgtgtgga cgggtgctct caggtgcctg cgcatgctgc    3600
gtagttgcat tgcgcccgct ccgcgcttga ggtcagaggc ggggctgtgc agcctgctgg    3660
```

| | | | | |
|---|---|---|---|---|
| agtgtgcggc | agggggtgcg | tgtgccagga | ccctcacgac | aggaggagga cgcgttgcgc | 3720 |
| cccgctggtg | tggccggctg | ctcgggccgg | ccattgtacc | attcttaccg gtttgtactg | 3780 |
| ttcacggcag | ccgtgcgcac | ggggtggccg | gccgcgaggc | ctcagtattt gaggctgaca | 3840 |
| tgcgtgtgtg | tttggtgcgt | cgtggtgcga | ttgactcaga | gcctgccggt tgagactcag | 3900 |
| gagggcccag | tgtgcatgga | aaggttgcat | gagagtccgg | cggccgcttt gcgacgagtt | 3960 |
| gccagtcgaa | tcatagttgg | tggggcttct | ggcggagcga | tgggtgaggc atggttgtgt | 4020 |
| gaacaggaag | ggggttgagt | cgccaatgac | cgccaatgaa | cgatgatcac gaaacattag | 4080 |
| taagtggaac | gcgttggttg | gcatgtgtgc | cgattaggag | ccggtagggg aaattataac | 4140 |
| gtcatggcaa | acatgagggg | aggaacaaac | tggatgcggg | gcatagtcaa cagctgaaca | 4200 |
| acctagcatt | tgcttttat | cggggacgac | gctcaatcga | aagggcaatg cacggaaagg | 4260 |
| tcacagcatg | ggcaagggac | tgggagaggg | cgctgtgtga | gtcgctcctg cgagctggtg | 4320 |
| gccacagggg | ctcctggcac | aggcgagcgg | ctgaagttgt | gcgcgcggcc ggcgtctgga | 4380 |
| tggcgtgtca | acactgcacg | tgcatctaga | tgtcgacact | gcggccgaat aacattgcag | 4440 |
| gagcaacggt | aatgagggag | cgctaaggag | agagcgtcct | cggagtgttc gaaggcggca | 4500 |
| aggcatgggc | atgggctgtt | gcgcctgcat | gcgtggtcag | caggctgctt ctcaatgcca | 4560 |
| gggggttgcg | gtgaggtatg | cgccggcgcc | acgctcggag | caccgcgccg agtcgcctca | 4620 |
| gaagtcaggc | gtgttggatt | tgctgcgaga | ggagagggag | cggaattgga gacgcgctat | 4680 |
| tgtcatgaca | catgcgtgcg | ccgtacaccg | tgcgtgcggt | tccaggagtt caggtcgaat | 4740 |
| gtaagggagc | ccgtgaatgt | ctttccgcgc | gg | | 4772 |

<210> SEQ ID NO 46
<211> LENGTH: 2259
<212> TYPE: DNA
<213> ORGANISM: Chlamydomonas reinhardtii

<400> SEQUENCE: 46

| | | | | |
|---|---|---|---|---|
| atggacaaag | ctgaacgcgc | tgctggtggc | cctaacgctg | caagcgagga cgactggctg | 60 |
| ctggagtttt | ggccggagcc | tgcagcggac | tttcctgcac | cggtcgctcc gatgctgtcg | 120 |
| cagcatcaag | acgcagcaca | gctgcctgag | gccatgccgc | agcagcaagg actggcgctg | 180 |
| ggtggatatg | gtctcacgca | gcagccttct | gactttatgc | aaacgggcat gcccggcttc | 240 |
| gacgcgttca | gcagcgggaa | ggctgcaacc | ctcgggctgc | ccctgcttgc cgaccccag | 300 |
| cgcgcctcca | ccgacggcgc | ctctgcgctt | atgaacgcgg | cgcagcagtc ctcagagtac | 360 |
| atgctggccc | ccggcatggg | cggcatgccg | catctactag | caccgagcgt tggcacggcg | 420 |
| ctgcccggca | ctgggcacac | cggcttcgcg | gacctgtcca | tgggggggcat ggcgggggc | 480 |
| atcccgggcc | tcgggggggcc | aggcattatg | catgggcagt | acttcatgca gccgcagcga | 540 |
| gcagccacgg | gccccgccaa | gagccggctg | cgctggacgc | cggagctgca caaccgcttc | 600 |
| gtcaacgcgg | tgaactcgct | gggggggccg | gacaaggcca | cgcccaaggg catccttaag | 660 |
| ctcatgggcg | tcgacggcct | caccatctac | cacatcaagt | cgcacctgca gaagtaccgc | 720 |
| ctcaacatcc | ggctgccggg | agagagcggc | ctcgcgggcg | actcggcgga cggctcggac | 780 |
| ggcgagcgct | cggacggcga | gggcggcgtg | cggcgcgcca | cctcgctgga gcgggcagac | 840 |
| accatgtcgg | ggatgcgggg | aggggccgcc | gcagcgttag | ggagagcggg cgggacgccg | 900 |
| ggcggtgcgc | taatctcccc | cggccttgcc | ggcgggacgt | caagcaccgg tgggatggca | 960 |
| gccggcggcg | gcggggggtgg | cggcttggtg | actgagccca | gcatctctag gggcacggtc | 1020 |

-continued

```
ctcaacgcgg ccggcgcagt tgccaccgcc gcgccggctg cggcggcgcc tgccggcggg    1080
tccgccgccg tgaagcggcc ggcgggtacg tctctgagca gcggcagcac tgcctcggct    1140
actcggcgca atctggagga ggcgctgctg ttccaaatgg agctgcagaa gaagctgcac    1200
gagcagctgg agacgcagcg tcaactgcag ctgagcttgg aggcgcacgg cgctacatc     1260 gccagcctca tggagcagga gggactcacc tcgcgactgc ccgagctcag cggcggcgcg    1320 ccggcggcg cgcctgtggc cgcaggcggc gcagcgggcg catgattgc gccgccgcca     1380 ccgcagcagc agctgcagca ccagccgcag ctgctgcagc cgcagggcag cttgccagcc    1440
ggcggttcct ctgaagccca tgccgcagcc ggcgccggca cgatggtggt gcaccagcag    1500
cagcagcagc acgtgcacca tcatccaccag cagcagcagg tgcagatgca gcagcatgcc   1560
cgccactgcg acacgtgtgg cgccggtggc gctgggggtg cgcccagcgg cggcagcagc    1620
atgcagcagc ttcaggctgc ggagcagcag cgcacggagc ttgttgtggc ggggcggcta    1680
ggctccatgc cggcgcccgc ctcttcgtcg ccgctagcag ggcaggcaca ccagcagcag    1740
ccgctggccg gcggggcggc gcacttggtg cacgtgcact cgcacacgcc tgggggcag    1800 ccgcacgtgc agcaccagga gcgtttgcc ggcgcggcta cggcggcagc gcacgcttcg    1860
ccggggctgc cgcagtcaca ttcgcacctg ctcccagccg acctctccag caacgccggt    1920
cctgacacaa gcgcggggca gattaagcct gagcctgata tgtcgcagca acagcagcaa    1980
caagagcaac aggaggcgga gcagcttgcg cagggtttgc tcaatgacag cagcgctggc    2040 gcggggctg tcagcggcag cgatggtggg ggccttgggg actttgactt cggtgatttc     2100
ggggacctgg acggggagc ccagggcggc ctactaggcc ccggagacct cattggcatc     2160
gccgagctgg aggcagcggc cgcgcacgag cagcagcaag agcaagagca cgacccacta    2220
gatgcggatc gcgcaaagcg gcagcgagtg gagccatag                            2259
```

<210> SEQ ID NO 47
<211> LENGTH: 752
<212> TYPE: PRT
<213> ORGANISM: Chlamydomonas reinhardtii

<400> SEQUENCE: 47

```
Met Asp Lys Ala Glu Arg Ala Ala Gly Gly Pro Asn Ala Ala Ser Glu
1               5                   10                  15

Asp Asp Trp Leu Leu Glu Phe Trp Pro Glu Pro Ala Ala Asp Phe Pro
            20                  25                  30

Ala Pro Val Ala Pro Met Leu Ser Gln His Gln Asp Ala Ala Gln Leu
        35                  40                  45

Pro Glu Ala Met Pro Gln Gln Gln Gly Leu Ala Leu Gly Gly Tyr Gly
    50                  55                  60

Leu Thr Gln Gln Pro Ser Asp Phe Met Gln Thr Gly Met Pro Gly Phe
65                  70                  75                  80

Asp Ala Phe Ser Ser Gly Lys Ala Ala Thr Leu Gly Leu Pro Leu Leu
                85                  90                  95

Ala Asp Pro Gln Arg Ala Ser Thr Asp Gly Ala Ser Ala Leu Met Asn
            100                 105                 110

Ala Ala Gln Gln Ser Ser Glu Tyr Met Leu Ala Pro Gly Met Gly Gly
        115                 120                 125

Met Pro His Leu Leu Ala Pro Ser Val Gly Thr Ala Leu Pro Gly Thr
    130                 135                 140

Gly His Thr Gly Phe Ala Asp Leu Ser Met Gly Gly Met Ala Gly Gly
```

-continued

```
            145                 150                 155                 160
        Ile Pro Gly Leu Gly Gly Pro Gly Ile Met His Gly Gln Tyr Phe Met
                        165                 170                 175
        Gln Pro Gln Arg Ala Ala Thr Gly Pro Ala Lys Ser Arg Leu Arg Trp
                        180                 185                 190
        Thr Pro Glu Leu His Asn Arg Phe Val Asn Ala Val Asn Ser Leu Gly
                        195                 200                 205
        Gly Pro Asp Lys Ala Thr Pro Lys Gly Ile Leu Lys Leu Met Gly Val
                210                 215                 220
        Asp Gly Leu Thr Ile Tyr His Ile Lys Ser His Leu Gln Lys Tyr Arg
        225                 230                 235                 240
        Leu Asn Ile Arg Leu Pro Gly Glu Ser Gly Leu Ala Gly Asp Ser Ala
                        245                 250                 255
        Asp Gly Ser Asp Gly Glu Arg Ser Asp Gly Glu Gly Val Arg Arg
                260                 265                 270
        Ala Thr Ser Leu Glu Arg Ala Asp Thr Met Ser Gly Met Ala Gly Gly
                275                 280                 285
        Ala Ala Ala Ala Leu Gly Arg Ala Gly Gly Thr Pro Gly Gly Ala Leu
                290                 295                 300
        Ile Ser Pro Gly Leu Ala Gly Gly Thr Ser Ser Thr Gly Met Ala
        305                 310                 315                 320
        Ala Gly Gly Gly Gly Gly Gly Leu Val Thr Glu Pro Ser Ile Ser
                        325                 330                 335
        Arg Gly Thr Val Leu Asn Ala Ala Gly Ala Val Ala Thr Ala Ala Pro
                        340                 345                 350
        Ala Ala Ala Ala Pro Ala Gly Gly Ser Ala Ala Val Lys Arg Pro Ala
                        355                 360                 365
        Gly Thr Ser Leu Ser Ser Gly Ser Thr Ala Ser Ala Thr Arg Arg Asn
                370                 375                 380
        Leu Glu Glu Ala Leu Leu Phe Gln Met Glu Leu Gln Lys Lys Leu His
        385                 390                 395                 400
        Glu Gln Leu Glu Thr Gln Arg Gln Leu Gln Leu Ser Leu Glu Ala His
                        405                 410                 415
        Gly Arg Tyr Ile Ala Ser Leu Met Glu Gln Glu Gly Leu Thr Ser Arg
                        420                 425                 430
        Leu Pro Glu Leu Ser Gly Gly Ala Pro Ala Ala Ala Pro Val Ala Ala
                        435                 440                 445
        Gly Gly Ala Ala Gly Gly Met Ile Ala Pro Pro Pro Gln Gln Gln
                450                 455                 460
        Leu Gln His Gln Pro Gln Leu Leu Gln Pro Gln Gly Ser Leu Pro Ala
        465                 470                 475                 480
        Gly Gly Ser Ser Glu Ala His Ala Ala Ala Gly Ala Gly Thr Met Val
                        485                 490                 495
        Val His Gln Gln Gln Gln His Val His His His Gln Gln
                        500                 505                 510
        Gln Val Gln Met Gln Gln His Ala Arg His Cys Asp Thr Cys Gly Ala
                        515                 520                 525
        Gly Gly Ala Gly Gly Ala Pro Ser Gly Gly Ser Ser Met Gln Gln Leu
                530                 535                 540
        Gln Ala Ala Glu Gln Gln Arg Thr Glu Leu Val Val Ala Gly Arg Leu
        545                 550                 555                 560
        Gly Ser Met Pro Ala Pro Ala Ser Ser Ser Pro Leu Ala Gly Gln Ala
                        565                 570                 575
```

```
His Gln Gln Gln Pro Leu Ala Gly Gly Ala Ala His Leu Val His Val
                580                 585                 590

His Ser His Thr Pro Gly Gly Gln Pro His Val Gln His Gln Asp Ala
            595                 600                 605

Phe Ala Gly Ala Ala Thr Ala Ala Ala His Ala Ser Pro Gly Leu Pro
        610                 615                 620

Gln Ser His Ser His Leu Leu Pro Ala Asp Leu Ser Ser Asn Ala Gly
625                 630                 635                 640

Pro Asp Thr Ser Ala Gly Gln Ile Lys Pro Glu Pro Asp Met Ser Gln
                645                 650                 655

Gln Gln Gln Gln Gln Glu Gln Gln Glu Ala Glu Gln Leu Ala Gln Gly
            660                 665                 670

Leu Leu Asn Asp Ser Ser Ala Gly Ala Gly Ala Val Ser Gly Ser Asp
        675                 680                 685

Gly Gly Gly Leu Gly Asp Phe Asp Phe Gly Asp Phe Gly Asp Leu Asp
    690                 695                 700

Gly Gly Ala Gln Gly Gly Leu Leu Gly Pro Gly Asp Leu Ile Gly Ile
705                 710                 715                 720

Ala Glu Leu Glu Ala Ala Ala His Glu Gln Gln Gln Glu Gln Glu
                725                 730                 735

His Asp Pro Leu Asp Ala Asp Arg Ala Lys Arg Gln Arg Val Glu Pro
            740                 745                 750

<210> SEQ ID NO 48
<211> LENGTH: 4592
<212> TYPE: DNA
<213> ORGANISM: Chlamydomonas reinhardtii

<400> SEQUENCE: 48
gaacatcaag ctgttgggca aaactctcga tgcagcgaat ttctccattc caagggtcag      60
gcacgcgcat ccgattccca ggcaaactgg aagggcttgc tagtacctct gaggcacctg     120
tgatgcaaat acaaacatag acataatgca catttaagat gccatagggc tcaccgcaag     180
aacttcttcc caaccgaaaa ccctgtgctg ctgcgctggc cctggccagg agctggccat     240
ctaggacagc cgcaatcatt gcggaacaat tggcgaaaac catcagatag cctagatttg     300
gcctgtgggc accgacaatc ggcagggtgt tgcgcaacac agccttgggc ttgtcgcgtg     360
catttcggcc aaaactagtc attttgtgcc cattgcgcat gcgcgcaccg gcacggtagc     420
agcgccgagc tggagcagcc gtgcgaaccc gcgcccggac tgggagggat gtcgcgccgg     480
tccgcagctg gtggcccgcc gcggcaccca actgccaaac ttaaaggtgg atggagcccg     540
gaggaagatg ccctgctcac caggctggtt aagaagttcg gcgagggcaa ctggagcccc     600
atcgcgcgcg ccctgaacga ggccaccggc aagaccgagg ccactggccg catcggcaag     660
cagtgccgcg agcgatggaa ccaccacctg tcgccggggc tgcgcaagga cccctggacg     720
ccggaggagg aggtgctggt ggtggatgct cacaagaggc ttggcaacag gtggagcgac     780
atcgcgcgct gcatccccgg acgtagcgag aacgcagtca agaaccactg gaacgccacg     840
ctgcgcaagc gcgtcacgcc cgagaacccg cgggcccat tgaaggagta ccttgactca     900
ctcaacctga cagtggcgcc acgcaagagg ggcgcggcg gcgcggcgg cggcggtgga     960 ggcggcggcg ccaagcgcaa gcgcaacaac aggggcagcc aggaggagga cacgtccgag    1020 gacccctgacg aggacctgct gcctgacgac ctggatgact ctctggacga ctccaccacc    1080
agccgcaccg cacacaccgc agcagcggcc gcggcatcag gcggaggaag aggccggact    1140
```

-continued

```
gccagccgcg ctacaaccac tggcggcggc ggcggcagcc gcgctgcaca cgccgccgcc    1200
gcggcccgca caacctcggc gccgactgcc gccgccgccg tcactgccgc caccgtcgcc    1260
gccaacagcc cggacagctc gtcggctggc ggcgccgttg gcccggccgc ggccgacgcc    1320
gcgcactcgg ctggcggcgg cgccgttgtt tgcggcggcg cctacagcag cggcggcgtg    1380
gtcaccttcg ccggcgccgg cttgctgtgc agcgccgctg tccccaccac caccgtcacc    1440
accgcggcgg tgccgctggc gtcagacgcg ggtgtgggtg tggacgacgg tgcggacgac    1500
ctggcgcctg gcgtgcgccg ctcctcccgc cgcgccgcac agctgagcag ccagcgcctg    1560
cgcgacatgg tggaggcgga cgccgcctg atggacgagc tggccgagga cgaggaggcg     1620
caggagcagc agcagatgca ggccgcagag gcggcggagg cggctgcagg ggcggccgca    1680
gaggcggcag aggcggcaga gatgcaggct gagatgcagg tgaagcgagc ggaggcgggc    1740
gagcctgcgg gcgccagcgt cggctccggc cgcggccacg gcggcggcgg cggcggcggc    1800
ggcggcggcg gcgccagggc cgagtacggc gctgaggcgg aggtgtccag cggcggcgcg    1860
gccaagaggc ggcgccgcga cggcggaggt gcggcggcgg cggcggcggc gcaacgtgcc    1920
ggtgcgccgc agcggcgccc gcccgccgc agcgagagtg tgtgcgacag cgccggcatc     1980
cgcatggccc cgctccagaa gccgccgcag cccgccctgc ccagccagca tcaacagcaa    2040
gcgctccacc accaactcca gcaccagcat cagcagccag cgatgtcgcc ctttggctac    2100
gccgccagcc aggccgaacc caccgctgcc gccgccgcag cagccgccgc cggctgcatg    2160
gtaatgcccc gcgtcgcgtc cagcgccgcc ctggcgcctg gcgccgacgc cagcggcggc    2220
ggtggcgacc gtgcggccct ggcacccccc ggcagcatgc tggcgcacgc cgctactgcc    2280
gcctccggct tcccggcggc agcagctgct accgctgcta cagccggcag ccccgctaccac    2340 ccgcaccacc cgcaccagca gcagcagcac ccgggggtg gcggcggcgg ctggacgtcc    2400
atgctgccgt acaactggag caccaacaac atgcaacaca tggcggcggt ggcggcggcg    2460
cctggcggcc cggcgggcga ggaggacgag ttccaagcct atcgccgcag cagcagcggt    2520
ggcggcgggt gctacagcgg cggcggcggc ggcaaggtcc gacccaaggg ctcaccgcaa    2580
cacgagtcgg ccgcgccggc catgcgccac gtgagcagca gccaccgcct gcacggcccc    2640
gccgcctcgg cccagctgtc cctctccctg gaccccatgc ccgccgccac caccgtcacc    2700
acagccaccg gcgccggcgc ggccgccgcc gccgccgccg ctgccgccac cgccctggc    2760 gccgccggcg ccagggcggc cgccgccgcc gtggccgccg ccggccctgc tgacgacgac    2820
gacgagacgt gtctgttcct gtcgccggcc gctactgaga tgacgacggc gggtggcggc    2880
ggcggcctgc gccacgtggc cagcggcagc gccctgttca gctacgacac ctcggcgccg    2940
ccggccccgc cctggcgcc gccgccgcc ccggctcagg aggccaggca gcagcccacc    3000
atgcctgctg agcagcagca ggagctgcag cggcagccgt cagcgattgc ctgcccgcgg    3060
ccctccctgg cgcagccgca gcagcagcag ccgtacgcga acagcctgtg gcagcagcag    3120
ccgcaacagc cgcagcagcc gcaacagctg cagccgcagc accacatgca gcaccagcac    3180
atgcagcaca tgcacctgca acaataccag cagcgccagc agccgcaaca gcagcgccct    3240
caacagcagc accagcagcc gcaccagcac cagcagcacc agcagcagca ccaggcgggc    3300
ggccgccagc aacacgcgct ggcccacctg ttgcacctgg ctcccacgcc gctgccgctg    3360
cgcgcctgga cgccgcccaa cctgttcgac accgccacc tgcacctgga ctttggctgc    3420
cccgactcgc cgctcctgga cgccctggga gggtccggcg gcggcactgc cgcagccgcc    3480
```

-continued

| | |
|---|---|
| ggcgccggca gcggcggcgc ggccgccact gcctgtaccg ctggtgcggc tgctgctgct | 3540 |
| gctgctgctg aggcagctgc tgccgcggtg cctgctccag gtgcgggtgt tggtgcgggc | 3600 |
| ggtgacggca gcagctccac cagctcagcc ccgtcgggtg aggccggcgg cagcggcagc | 3660 |
| ggcagcggcg gggccgagcc cggcaccgcc cgcagcgtgc aggctggcgc agcagcagag | 3720 |
| gcggcggcgg accgcagcga cgcagccgtg atgcagatga tgaagcggga gagcagcttc | 3780 |
| ggcttccttg ctaacgccgc cggggctgcc gccgccgcca cgggcagcct tacggtcggc | 3840 |
| agcgcggccc ctgctgctgc tgctggtacg gctgctgccg cgccctctgc ggcttggccc | 3900 |
| ggggccctgc aggcctgcaa cgccgccgcc accgccgccg ctgctgcggc cgcaagcgct | 3960 |
| accgcctccg ccgccagctc gcaggccatg ccgtcagcgc cttcctcgcc gggcgtctgg | 4020 |
| ccgccggctg cgacggcggc gccagcgctg ccctacctgc cgccgctggc gcctctgggc | 4080 |
| gggccgccgg cgctgccgtc gccgccgtgc tcgccgctga tctggaacgg gctgggcatg | 4140 |
| gcggcgccgc tgccgccgca gatgcaccac gcgctgctcg gcagcacgtc ggcgccgccg | 4200 |
| cctcaacacc agcagcagca gcagcagcag cagcaccacc agcaggcagc gacggctgcg | 4260 |
| tctgccgacg ctgctgctag taccgctggt gcgggtgcgg gtgcgggtgc cgctcctgcc | 4320 |
| gcaccgtaca tgctgcctgc cggctactac taccaccccg gccccgtgcc gacttggcac | 4380 |
| cacccgtca gcagcttcca cggccccctg tacgggcccg tgacttaccc gcccatgccg | 4440 |
| gctgcagccg ctgcagtgcc cgcggctgcg gctgcgcag tgccgcagta acagccagc | 4500 |
| ggcagctgcg ctgctgccgc caacaggcac tgggcgcgag tgctggcagg cggggtggtt | 4560 |
| cgccgtgtga gcgtatgtaa taatagacca gc | 4592 |

<210> SEQ ID NO 49
<211> LENGTH: 4023
<212> TYPE: DNA
<213> ORGANISM: Chlamydomonas reinhardtii

<400> SEQUENCE: 49

| | |
|---|---|
| atgtcgcgcc ggtccgcagc tggtggcccg ccgcggcacc caactgccaa acttaaaggt | 60 |
| ggatggagcc cggaggaaga tgccctgctc accaggctgg ttaagaagtt cggcgagggc | 120 |
| aactggagcc ccatcgcgcg cgccctgaac gaggccaccg gcaagaccga ggccactggc | 180 |
| cgcatcggca gcagtgccg cgagcgatgg aaccaccacc tgtcgccggg gctgcgcaag | 240 |
| gaccccctgga cgccggagga ggaggtgctg gtggtggatg ctcacaagag gcttggcaac | 300 |
| aggtggagcg acatcgcgcg ctgcatcccc ggacgtagcg agaacgcagt caagaaccac | 360 |
| tggaacgcca cgctgcgcaa gcgcgtcacg cccgagaacc cggcgggccc attgaaggag | 420 |
| taccttgact cactcaacct gacagtggcc cacgcaagag ggggcggcgg cggcggcggc | 480 |
| ggcggcggtg gaggcggcgg cgccaagcgc aagcgcaaca acaggggcag ccaggaggag | 540 |
| gacacgtccg aggaccctga cgaggacctg ctgcctgacg acctggatga ctctctggac | 600 |
| gactccacca ccagccgcac cgcacacacc gcagcagcgg ccgcggcatc aggcggagga | 660 |
| agaggccgga ctgccagccg cgctacaacc actggcggcg gcggcggcag ccgcgctgca | 720 |
| cacgccgccg ccgcggcccg cacaacctcg cgccgactg ccgccgccgc cgtcactgcc | 780 |
| gccaccgtcg ccgccaacag cccggacagc tcgtcggctg gcgcgccgt tggcccggcc | 840 |
| gcggccgacg ccgcgcactc ggctggcggc ggcgccgttg tttgcggcgg cgcctacagc | 900 |
| agcggcggc tggtcacctt cgccggcgcc ggcttgctgt gcagcgccgc tgtccccacc | 960 |
| accaccgtca ccaccgcggc ggtgccgctg gcgtcagacg cgggtgtggg tgtggacgac | 1020 |

```
ggtgcggacg acctggcgcc tggcgtgcgc cgctcctccc gccgcgccgc acagctgagc   1080
agccagcgcc tgcgcgacat ggtggaggcg gagcgccgcc tgatggacga gctggccgag   1140
gacgaggagg cgcaggagca gcagcagatg caggccgcag aggcggcgga ggcggctgca   1200
ggggcggccg cagaggcggc agaggcggca gagatgcagg ctgagatgca ggtgaagcga   1260
gcggaggcgg gcgagcctgc gggcgccagc gtcggctccg gccgcggcca cggcggcggc   1320
ggcggcggcg gcggcggcgg cggcgccagg gccgagtacg cgctgaggc ggaggtgtcc   1380 agcggcggcg cggccaagag gcggcgccgc gacggcggag gtgcggcggc ggcggcggcg   1440
gcgcaacgtg ccggtgcgcc gcagcggcgc ccgcccgccc gcagcgagag tgtgtgcgac   1500
agcgccggca tccgcatggc cccgctccag aagccgccgc agcccgccct gcccagccag   1560
catcaacagc aagcgctcca ccaccaactc cagcaccagc atcagcagcc agcgatgtcg   1620 cccctttggct acgccgccag ccaggccgaa cccaccgctg ccgccgccgc agcagccgcc   1680
gccggctgca tggtaatgcc ccgcgtcgcg tccagcgccg ccctggcgcc tggcgccgac   1740
gccagcggcg gcggtggcga ccgtgcgcc ctggcaccc ccggcagcat gctggcgcac   1800
gccgctactg ccgcctccgg cttcccggcg gcagcagctg ctaccgctgc tacagccggc   1860 agccccctacc acccgcacca cccgcaccag cagcagcagc acccggggg tggcggcggc   1920 ggctggacgt ccatgctgcc gtacaactgg agcaccaaca acatgcaaca catggcggcg   1980
gtggcggcgg cgcctggcgg cccggcgggc gaggaggacg agttccaagc ctatcgccgc   2040
agcagcagcg gtggcggcgg gtgctacagc ggcggcggcg gcggcaaggt ccgacccaag   2100
ggctcaccgc aacacgagtc ggccgcgccg gccatgcgcc acgtgagcag cagccaccgc   2160
ctgcacggcc ccgccgcctc ggcccagctg tccctctccc tggacccat gcccgccgcc   2220 accaccgtca ccacagccac cggcgccggc gcggccgccgcc ccgccgccgc cgctgccgcc   2280
accgcccctg gcgccgccgg cgccaggggcg gccgccgccg ccgtggccgc cgccggcct   2340 gctgacgacg acgacgagac gtgtctgttc ctgtcgccgg ccgctactga gatgacgacg   2400
gcgggtggcg gcggcggcct gcgccacgtg ccagcggca gcgccctgtt cagctacgac   2460
acctcggcgc cgccggcccc gccctggcg ccgccgccgg ccccggctca ggaggccagg   2520
cagcagccca ccatgcctgc tgagcagcag caggagctgc agcggcagcc gtcagcgatt   2580 gcctgccgc ggccctccct ggcgcagccg cagcagcagc agccgtacgc gaacagcctg   2640
tggcagcagc agccgcaaca gccgcagcag ccgcaacagc tgcagccgca gcaccacatg   2700
cagcaccagc acatgcagca catgcacctg caacaatacc agcagcgcca gcagccgcaa   2760
cagcagcgcc ctcaacagca gcaccagcag ccgcaccagc accagcagca ccagcagcag   2820
caccaggcgg cggccgcca gcaacacgcg ctggcccacc tgttgcacct ggctcccacg   2880
ccgctgccgc tgcgcgcctg gacgccgccc aacctgttcg acaccgccca cctgcacctg   2940
gactttggct gccccgactc gccgctcctg gacgccctgg gagggtccgg cggcggcact   3000
gccgcagccg ccggcgccgg cagcggcggc gcggccgcca ctgcctgtac cgctggtgcg   3060
gctgctgctg ctgctgctgc tgaggcagct gctgccgcgg tgcctgctcc aggtgcgggt   3120
gttggtgcgg gcggtgacgg cagcagctcc accagctcag ccccgtcggg tgaggccggc   3180
ggcagcggca gcggcagcgg cggggccgag cccggcaccg cccgcagcgt gcaggctggc   3240
gcagcagcag aggcggcggc ggaccgcagc gacgcagccg tgatgcagat gatgaagcgg   3300
gagagcagct tcggcttcct tgctaacgcc gccggggctg ccgccgccgc cacgggcagc   3360
```

-continued

```
cttacggtcg gcagcgcggc ccctgctgct gctgctggta cggctgctgc cgcgccctct    3420
gcggcttggc ccggggccct gcaggcctgc aacgccgccg ccaccgccgc cgctgctgcg    3480
gccgcaagcg ctaccgcctc cgccgccagc tcgcaggcca tgccgtcagc gccttcctcg    3540
ccgggcgtct ggccgccggc tgcgacggcg gcgccagcgc tgccctacct gccgccgctg    3600
gcgcctctgg gcgggccgcc ggcgctgccg tcgccgccgt gctcgccgct gatctggaac    3660
gggctgggca tggcggcgcc gctgccgccg cagatgcacc acgcgctgct cggcagcacg    3720
tcggcgccgc cgcctcaaca ccagcagcag cagcagcagc agcagcacca ccagcaggca    3780
gcgacggctg cgtctgccga cgctgctgct agtaccgctg gtgcgggtgc gggtgcgggt    3840
gccgctcctg ccgcaccgta catgctgcct gccggctact actaccaccc cggccccgtg    3900
ccgacttggc accaccccgt cagcagcttc cacggccccc tgtacgggcc cgtgacttac    3960
ccgcccatgc cggctgcagc cgctgcagtg cccgcggctg cggctgcggc agtgccgcag    4020
taa                                                                  4023
```

<210> SEQ ID NO 50
<211> LENGTH: 1340
<212> TYPE: PRT
<213> ORGANISM: Chlamydomonas reinhardtii

<400> SEQUENCE: 50

```
Met Ser Arg Arg Ser Ala Ala Gly Gly Pro Pro Arg His Pro Thr Ala
1               5                   10                  15

Lys Leu Lys Gly Gly Trp Ser Pro Glu Glu Asp Ala Leu Leu Thr Arg
            20                  25                  30

Leu Val Lys Lys Phe Gly Glu Gly Asn Trp Ser Pro Ile Ala Arg Ala
        35                  40                  45

Leu Asn Glu Ala Thr Gly Lys Thr Glu Ala Thr Gly Arg Ile Gly Lys
    50                  55                  60

Gln Cys Arg Glu Arg Trp Asn His His Leu Ser Pro Gly Leu Arg Lys
65                  70                  75                  80

Asp Pro Trp Thr Pro Glu Glu Val Leu Val Asp Ala His Lys
                85                  90                  95

Arg Leu Gly Asn Arg Trp Ser Asp Ile Ala Arg Cys Ile Pro Gly Arg
            100                 105                 110

Ser Glu Asn Ala Val Lys Asn His Trp Asn Ala Thr Leu Arg Lys Arg
        115                 120                 125

Val Thr Pro Glu Asn Pro Ala Gly Pro Leu Lys Glu Tyr Leu Asp Ser
    130                 135                 140

Leu Asn Leu Thr Val Ala Pro Arg Lys Arg Gly Gly Gly Gly Gly
145                 150                 155                 160

Gly Gly Gly Gly Gly Gly Gly Ala Lys Arg Lys Arg Asn Asn Arg Gly
            165                 170                 175

Ser Gln Glu Glu Asp Thr Ser Glu Asp Pro Asp Glu Asp Leu Leu Pro
        180                 185                 190

Asp Asp Leu Asp Asp Ser Leu Asp Asp Ser Thr Thr Ser Arg Thr Ala
    195                 200                 205

His Thr Ala Ala Ala Ala Ala Ser Gly Gly Arg Gly Arg Thr
    210                 215                 220

Ala Ser Arg Ala Thr Thr Thr Gly Gly Gly Gly Ser Arg Ala Ala
225                 230                 235                 240

His Ala Ala Ala Ala Ala Arg Thr Thr Ser Ala Pro Thr Ala Ala Ala
                245                 250                 255
```

-continued

```
Ala Val Thr Ala Ala Thr Val Ala Ala Asn Ser Pro Asp Ser Ser Ser
                260                 265                 270

Ala Gly Gly Ala Val Gly Pro Ala Ala Asp Ala Ala His Ser Ala
            275                 280                 285

Gly Gly Gly Ala Val Val Cys Gly Gly Ala Tyr Ser Ser Gly Gly Val
            290                 295                 300

Val Thr Phe Ala Gly Ala Gly Leu Leu Cys Ser Ala Ala Val Pro Thr
305                 310                 315                 320

Thr Thr Val Thr Thr Ala Ala Val Pro Leu Ala Ser Asp Ala Gly Val
                325                 330                 335

Gly Val Asp Asp Gly Ala Asp Asp Leu Ala Pro Gly Val Arg Arg Ser
                340                 345                 350

Ser Arg Arg Ala Ala Gln Leu Ser Ser Gln Arg Leu Arg Asp Met Val
            355                 360                 365

Glu Ala Glu Arg Arg Leu Met Asp Glu Leu Ala Glu Asp Glu Glu Ala
370                 375                 380

Gln Glu Gln Gln Gln Met Gln Ala Ala Glu Ala Ala Glu Ala Ala Ala
385                 390                 395                 400

Gly Ala Ala Ala Glu Ala Ala Glu Ala Ala Glu Met Gln Ala Glu Met
                405                 410                 415

Gln Val Lys Arg Ala Glu Ala Gly Glu Pro Ala Gly Ala Ser Val Gly
                420                 425                 430

Ser Gly Arg Gly His Gly Gly Gly Gly Gly Gly Gly Gly Gly
            435                 440                 445

Ala Arg Ala Glu Tyr Gly Ala Glu Ala Glu Val Ser Ser Gly Gly Ala
            450                 455                 460

Ala Lys Arg Arg Arg Asp Gly Gly Gly Ala Ala Ala Ala Ala
465                 470                 475                 480

Ala Gln Arg Ala Gly Ala Pro Gln Arg Arg Pro Pro Ala Arg Ser Glu
            485                 490                 495

Ser Val Cys Asp Ser Ala Gly Ile Arg Met Ala Pro Leu Gln Lys Pro
                500                 505                 510

Pro Gln Pro Ala Leu Pro Ser Gln His Gln Gln Gln Ala Leu His His
            515                 520                 525

Gln Leu Gln His Gln His Gln Gln Pro Ala Met Ser Pro Phe Gly Tyr
            530                 535                 540

Ala Ala Ser Gln Ala Glu Pro Thr Ala Ala Ala Ala Ala Ala
545                 550                 555                 560

Ala Gly Cys Met Val Met Pro Arg Val Ala Ser Ser Ala Ala Leu Ala
                565                 570                 575

Pro Gly Ala Asp Ala Ser Gly Gly Gly Gly Asp Arg Ala Ala Leu Ala
            580                 585                 590

Pro Pro Gly Ser Met Leu Ala His Ala Ala Thr Ala Ala Ser Gly Phe
            595                 600                 605

Pro Ala Ala Ala Ala Thr Ala Thr Ala Gly Ser Pro Tyr His
            610                 615                 620

Pro His His Pro His Gln Gln Gln Gln His Pro Gly Gly Gly Gly
625                 630                 635                 640

Gly Trp Thr Ser Met Leu Pro Tyr Asn Trp Ser Thr Asn Asn Met Gln
                645                 650                 655

His Met Ala Ala Val Ala Ala Ala Pro Gly Gly Pro Ala Gly Glu Glu
                660                 665                 670
```

```
Asp Glu Phe Gln Ala Tyr Arg Arg Ser Ser Gly Gly Gly Cys
            675                 680                 685

Tyr Ser Gly Gly Gly Gly Lys Val Arg Pro Lys Gly Ser Pro Gln
    690                 695                 700

His Glu Ser Ala Ala Pro Ala Met Arg His Val Ser Ser His Arg
705                 710                 715                 720

Leu His Gly Pro Ala Ser Ala Gln Leu Ser Leu Ser Leu Asp Pro
                725                 730                 735

Met Pro Ala Ala Thr Thr Val Thr Thr Ala Thr Gly Ala Gly Ala Ala
                740                 745                 750

Ala Ala Ala Ala Ala Ala Ala Thr Ala Pro Gly Ala Ala Gly Ala
    755                 760                 765

Arg Ala Ala Ala Ala Val Ala Ala Ala Gly Pro Ala Asp Asp Asp
    770                 775                 780

Asp Glu Thr Cys Leu Phe Leu Ser Pro Ala Ala Thr Glu Met Thr Thr
785                 790                 795                 800

Ala Gly Gly Gly Gly Leu Arg His Val Ala Ser Gly Ser Ala Leu
                805                 810                 815

Phe Ser Tyr Asp Thr Ser Ala Pro Pro Ala Pro Pro Leu Ala Pro Pro
            820                 825                 830

Pro Ala Pro Ala Gln Glu Ala Arg Gln Gln Pro Thr Met Pro Ala Glu
    835                 840                 845

Gln Gln Gln Glu Leu Gln Arg Gln Pro Ser Ala Ile Ala Cys Pro Arg
    850                 855                 860

Pro Ser Leu Ala Gln Pro Gln Gln Gln Pro Tyr Ala Asn Ser Leu
865                 870                 875                 880

Trp Gln Gln Gln Pro Gln Gln Pro Gln Gln Pro Gln Gln Leu Gln Pro
                885                 890                 895

Gln His His Met Gln His Gln His Met Gln His Met His Leu Gln Gln
            900                 905                 910

Tyr Gln Gln Arg Gln Gln Pro Gln Gln Gln Arg Pro Gln Gln Gln His
    915                 920                 925

Gln Gln Pro His Gln His Gln Gln His Gln Gln Gln His Gln Ala Gly
    930                 935                 940

Gly Arg Gln Gln His Ala Leu Ala His Leu Leu His Leu Ala Pro Thr
945                 950                 955                 960

Pro Leu Pro Leu Arg Ala Trp Thr Pro Pro Asn Leu Phe Asp Thr Ala
                965                 970                 975

His Leu His Leu Asp Phe Gly Cys Pro Asp Ser Pro Leu Leu Asp Ala
            980                 985                 990

Leu Gly Gly Ser Gly Gly Gly Thr Ala Ala Ala Ala Gly Ala Gly Ser
            995                 1000                1005

Gly Gly Ala Ala Ala Thr Ala Cys Thr Ala Gly Ala Ala Ala Ala
    1010                1015                1020

Ala Ala Ala Ala Glu Ala Ala Ala Ala Ala Val Pro Ala Pro Gly
    1025                1030                1035

Ala Gly Val Gly Ala Gly Gly Asp Gly Ser Ser Ser Thr Ser Ser
    1040                1045                1050

Ala Pro Ser Gly Glu Ala Gly Gly Ser Gly Ser Gly Ser Gly Gly
    1055                1060                1065

Ala Glu Pro Gly Thr Ala Arg Ser Val Gln Ala Gly Ala Ala Ala
    1070                1075                1080

Glu Ala Ala Ala Asp Arg Ser Asp Ala Ala Val Met Gln Met Met
```

```
                1085                1090                1095
Lys Arg Glu Ser Ser Phe Gly Phe Leu Ala Asn Ala Ala Gly Ala
        1100                1105                1110
Ala Ala Ala Ala Thr Gly Ser Leu Thr Val Gly Ser Ala Ala Pro
        1115                1120                1125
Ala Ala Ala Ala Gly Thr Ala Ala Ala Pro Ser Ala Ala Trp
        1130                1135                1140
Pro Gly Ala Leu Gln Ala Cys Asn Ala Ala Thr Ala Ala Ala
        1145                1150                1155
Ala Ala Ala Ala Ser Ala Thr Ala Ser Ala Ala Ser Ser Gln Ala
        1160                1165                1170
Met Pro Ser Ala Pro Ser Ser Pro Gly Val Trp Pro Pro Ala Ala
        1175                1180                1185
Thr Ala Ala Pro Ala Leu Pro Tyr Leu Pro Pro Leu Ala Pro Leu
        1190                1195                1200
Gly Gly Pro Pro Ala Leu Pro Ser Pro Pro Cys Ser Pro Leu Ile
        1205                1210                1215
Trp Asn Gly Leu Gly Met Ala Ala Pro Leu Pro Pro Gln Met His
        1220                1225                1230
His Ala Leu Leu Gly Ser Thr Ser Ala Pro Pro Gln His Gln
        1235                1240                1245
Gln Gln Gln Gln Gln Gln Gln His His Gln Gln Ala Ala Thr Ala
        1250                1255                1260
Ala Ser Ala Asp Ala Ala Ala Ser Thr Ala Gly Ala Gly Ala Gly
        1265                1270                1275
Ala Gly Ala Ala Pro Ala Ala Pro Tyr Met Leu Pro Ala Gly Tyr
        1280                1285                1290
Tyr Tyr His Pro Gly Pro Val Pro Thr Trp His His Pro Val Ser
        1295                1300                1305
Ser Phe His Gly Pro Leu Tyr Gly Pro Val Thr Tyr Pro Pro Met
        1310                1315                1320
Pro Ala Ala Ala Ala Ala Val Pro Ala Ala Ala Ala Ala Val
        1325                1330                1335
Pro Gln
    1340

<210> SEQ ID NO 51
<211> LENGTH: 1873
<212> TYPE: DNA
<213> ORGANISM: Chlamydomonas reinhardtii

<400> SEQUENCE: 51
gacaccataa gaacacatat attgtattca taacctagga aagcatgttc gcaacctctt    60
tcggcctggc gcattcaggc cgggtgcttc ttgccccctc gcacaatgct gccgcatgca   120
gcacaagcta tattactcaa cgcgggcatc ctctacgagc gatcctgggc cattggcggt   180
ctgcgctgac gctagctcga agaaccctct cgagaggttg cgcgtcacgc tctgactga    240 gcgcggtgcg cgggcggctc ttctgcagga gcttgacctg acctggtcag agtgggagga   300
gcggtaccag cccacgccag cagagcgctg tctcgctgag gagctggggg tgggcaatc    360 cactgtgatg ctggcggcgg tgcagaaccc gggactgagt gctcttgacg cggccagcca   420
ggtccttccc tcggtgcggg cgctgcgctc ggccggcatt ggggcgcagg acgcctggtt   480
cctggtgtcc aagcgctggc agctcctggc acagccggcg cgctgtcgc gctggctgga   540
```

-continued

| | |
|---|---|
| cttcctgggg gtgtacggca tgcagccgcg cgactgccag aacttcctcc tgcgctccca | 600 |
| gccgtccttc ctggcggcca ccacactgta ccaggctggc caggtggtga ccttcctcaa | 660 |
| aggactgggc ctcaaagacg acatgctggc ggcgcgtgtg ctgtgcgtgt ggccggagct | 720 |
| gctggggcgg gacgtggacg cgcagctgcg cccagtggtc accttcctca tgagcctggg | 780 |
| gctggaggtg caggcgtgg gccgggcggt ggtgctgtgg cctgagatcc tgctcaagga | 840 |
| cgtggagggg cagttggcgc cctggtggc atacctgcga ggactgggct gcaccaccgc | 900 |
| ccaggtggcc gaggtcgtct gcctgtgccc acacctgctg ggcttcaagc ctgaggaggt | 960 |
| gtttggcggc gtgctggcgg cgctgtcaga cgtgggcatc agcgccgccg acgtgcgaga | 1020 |
| catggtgtcg gcctcgctcg cattcctcat cacgccctcc gcctccgcgg cggtgcgcgc | 1080 |
| ggcagtggac tgcctgcagc agcagggctt cacaaaggag cagattcgcg ccatggccct | 1140 |
| gacgcggccg gagctgctgg ccgtcaagcc gcatgacctg gatcgctcgc tgcgcttcgt | 1200 |
| gcgcgagacc atcggcggcg acaacggcac ggtgctgtcc tgcccgctgc tgttggccaa | 1260 |
| gccgctgggg caggtgctgg ggccgaggta cagcttcatc cagaagcagg gcctcgcgca | 1320 |
| caagtacacc aagagagacg tcgtcgccgg cggagccgac cgaactgacg gcgccagcgg | 1380 |
| cagcggcagt gacggcagtg ccagcagcag cggcaacagc acgggcgggt ttgagttcta | 1440 |
| caagctgctg atggcggagg acgatgcctg gtgtgcctcc ctgggcctgt ccgtaaacga | 1500 |
| gtaccagggc tttaaactgg tgtgggatga ggagtacagt ctgcagctgc accaggaggc | 1560 |
| ggcatcagag ttccaggctg aactcaaaaa gctgggcatt tacgagggta tctaggcact | 1620 |
| attgcccaag tgattgcatg cagctttcct tgggttcggg gtgaattttc aaaccgattg | 1680 |
| gggattacac ggaagatgtg tggattggcc tgtacggtga cggtgctact aagtaggagc | 1740 |
| aatcagcctg cccattgggc gggattgcca ttcatgtcgg gctgtgactg gttagcctgg | 1800 |
| ctgcttagct tggctgctta gcttcgactc gcggtagtta gcatgtcagc tacccttgta | 1860 |
| acaaacacac acg | 1873 |

<210> SEQ ID NO 52
<211> LENGTH: 1500
<212> TYPE: DNA
<213> ORGANISM: Chlamydomonas reinhardtii

<400> SEQUENCE: 52

| | |
|---|---|
| atgcagcaca agctatatta ctcaacgcgg gcatcctcta cgagcgatcc tgggccattg | 60 |
| gcggtctgcg ctgacgctag ctcgaagaac cctctcgaga ggttgcgcgt cacgcctctg | 120 |
| actgagcgcg gtgcgcgggc ggctcttctg caggagcttg acctgacctg gtcagagtgg | 180 |
| gaggagcggt accagcccac gccagcagag cgctgtctcg ctgaggagct gggggtgggg | 240 |
| caatccactg tgatgctggc ggcggtgcag aacccgggac tgagtgctct tgacgcggcc | 300 |
| agccaggtcc ttccctcggt gcgggcgctg cgctcggccg gcattggggc gcaggacgcc | 360 |
| tggttcctgg tgtccaagcg ctggcagctc ctggcacagc cggcggcgct gtcgcgctgg | 420 |
| ctggacttcc tgggggtgta cggcatgcag ccgcgcgact gccagaactt cctcctgcgc | 480 |
| tcccagccgt ccttcctggc ggccaccaca ctgtaccagg ctggccaggt ggtgaccttc | 540 |
| ctcaaaggac tgggcctcaa agacgacatg ctggcggcgc gtgtgctgtg cgtgtggccg | 600 |
| gagctgctgg gcgggacgt ggacgcgcag ctgcgcccag tggtcacctt cctcatgagc | 660 |
| ctggggctgg aggtggcagg cgtgggccgg cggtggtgc tgtggcctga gatcctgctc | 720 |
| aaggacgtgg aggggcagtt ggcgccctgg gtggcatacc tgcgaggact gggctgcacc | 780 |

```
accgcccagg tggccgaggt cgtctgcctg tgcccacacc tgctgggctt caagcctgag    840
gaggtgtttg cggcgtgct  ggcggcgctg tcagacgtgg gcatcagcgc cgccgacgtg    900
cgagacatgg tgtcggcctc gctcgcattc ctcatcacgc cctccgcctc gcggcggtg     960 cgcgcggcag tggactgcct gcagcagcag ggcttcacaa aggagcagat cgcgccatg    1020 gccctgacgc ggccggagct gctggccgtc aagccgcatg acctggatcg ctcgctgcgc   1080
ttcgtgcgcg agaccatcgg cggcgacaac ggcacggtgc tgtcctgccc gctgctgttg   1140
gccaagccgc tggggcaggt gctggggccg aggtacagct tcatccagaa gcagggcctc   1200
gcgcacaagt acaccaagag agacgtcgtc gccggcggag ccgaccgaac tgacggcgcc   1260
agcggcagcg gcagtgacgg cagtgccagc agcagcggca acagcacggg cgggtttgag   1320
ttctacaagc tgctgatggc ggaggacgat gcctggtgtg cctccctggg cctgtccgta   1380
aacgagtacc agggctttaa actggtgtgg gatgaggagt acagtctgca gctgcaccag   1440
gaggcggcat cagagttcca ggctgaactc aaaaagctgg gcatttacga gggtatctag   1500
```

<210> SEQ ID NO 53
<211> LENGTH: 499
<212> TYPE: PRT
<213> ORGANISM: Chlamydomonas reinhardtii

<400> SEQUENCE: 53

```
Met Gln His Lys Leu Tyr Tyr Ser Thr Arg Ala Ser Ser Thr Ser Asp
1               5                   10                  15

Pro Gly Pro Leu Ala Val Cys Ala Asp Ala Ser Ser Lys Asn Pro Leu
            20                  25                  30

Glu Arg Leu Arg Val Thr Pro Leu Thr Glu Arg Gly Ala Arg Ala Ala
        35                  40                  45

Leu Leu Gln Glu Leu Asp Leu Thr Trp Ser Glu Trp Glu Glu Arg Tyr
    50                  55                  60

Gln Pro Thr Pro Ala Glu Arg Cys Leu Ala Glu Leu Gly Val Gly
65                  70                  75                  80

Gln Ser Thr Val Met Leu Ala Ala Val Gln Asn Pro Gly Leu Ser Ala
                85                  90                  95

Leu Asp Ala Ala Ser Gln Val Leu Pro Ser Val Arg Ala Leu Arg Ser
            100                 105                 110

Ala Gly Ile Gly Ala Gln Asp Ala Trp Phe Leu Val Ser Lys Arg Trp
        115                 120                 125

Gln Leu Leu Ala Gln Pro Ala Leu Ser Arg Trp Leu Asp Phe Leu
    130                 135                 140

Gly Val Tyr Gly Met Gln Pro Arg Asp Cys Gln Asn Phe Leu Leu Arg
145                 150                 155                 160

Ser Gln Pro Ser Phe Leu Ala Ala Thr Thr Leu Tyr Gln Ala Gly Gln
                165                 170                 175

Val Val Thr Phe Leu Lys Gly Leu Gly Leu Lys Asp Asp Met Leu Ala
            180                 185                 190

Ala Arg Val Leu Cys Val Trp Pro Glu Leu Leu Gly Arg Asp Val Asp
        195                 200                 205

Ala Gln Leu Arg Pro Val Val Thr Phe Leu Met Ser Leu Gly Leu Glu
    210                 215                 220

Val Ala Gly Val Gly Arg Ala Val Val Leu Trp Pro Glu Ile Leu Leu
225                 230                 235                 240

Lys Asp Val Glu Gly Gln Leu Ala Pro Trp Val Ala Tyr Leu Arg Gly
```

```
            245                 250                 255
Leu Gly Cys Thr Thr Ala Gln Val Ala Glu Val Val Cys Leu Cys Pro
            260                 265                 270

His Leu Leu Gly Phe Lys Pro Glu Glu Val Phe Gly Gly Val Leu Ala
        275                 280                 285

Ala Leu Ser Asp Val Gly Ile Ser Ala Ala Asp Val Arg Asp Met Val
    290                 295                 300

Ser Ala Ser Leu Ala Phe Leu Ile Thr Pro Ser Ala Ser Ala Ala Val
305                 310                 315                 320

Arg Ala Ala Val Asp Cys Leu Gln Gln Gln Gly Phe Thr Lys Glu Gln
                325                 330                 335

Ile Arg Ala Met Ala Leu Thr Arg Pro Glu Leu Leu Ala Val Lys Pro
            340                 345                 350

His Asp Leu Asp Arg Ser Leu Arg Phe Val Arg Glu Thr Ile Gly Gly
        355                 360                 365

Asp Asn Gly Thr Val Leu Ser Cys Pro Leu Leu Leu Ala Lys Pro Leu
    370                 375                 380

Gly Gln Val Leu Gly Pro Arg Tyr Ser Phe Ile Gln Lys Gln Gly Leu
385                 390                 395                 400

Ala His Lys Tyr Thr Lys Arg Asp Val Val Ala Gly Ala Asp Arg
                405                 410                 415

Thr Asp Gly Ala Ser Gly Ser Gly Ser Asp Gly Ser Ala Ser Ser Ser
            420                 425                 430

Gly Asn Ser Thr Gly Gly Phe Glu Phe Tyr Lys Leu Leu Met Ala Glu
        435                 440                 445

Asp Asp Ala Trp Cys Ala Ser Leu Gly Leu Ser Val Asn Glu Tyr Gln
    450                 455                 460

Gly Phe Lys Leu Val Trp Asp Glu Glu Tyr Ser Leu Gln Leu His Gln
465                 470                 475                 480

Glu Ala Ala Ser Glu Phe Gln Ala Glu Leu Lys Lys Leu Gly Ile Tyr
                485                 490                 495

Glu Gly Ile
```

<210> SEQ ID NO 54
<211> LENGTH: 2263
<212> TYPE: DNA
<213> ORGANISM: Chlamydomonas reinhardtii

<400> SEQUENCE: 54

```
ggagtgatgc aggtcggcat gccgtgcata cgacttggtc gctctaccga gttcaccggt      60
cgcattcaag tcacctgtat gaaacaatga gagcgcttgt aggacaacgt tgtttggcgc     120
cacaacgcgc accaggttcg cttcatggca cgcttcgtgc ggtgcccagc gcggtggcgc     180
tgcggcgagc gcgtgctagc tgctcttatc cagaatcatc atcgaaccac tcggcgacag     240
cgaccaccac cacgctggag tcgcagctgt ctgaggtgaa cgccagcccg gtgctggtgc     300
tcggcagtcc tgcactgcag ggcgcagacc atgctcagat gtgtgccgcg ctggaggcgc     360
tgcgcgatgc tgtgccgcgg cgctcccctgg gcgggctgct ggagcgctac cccgccatcc     420
tcaccgcccc cgtggccacg tgggtggact tcctgggctc cttcggcttc agcgactgg       480
ccgtgcagga gctgctgttg aattcgccgg acgtgttggc caactcgtcc gtcttccggg      540
cgggccaggt gttcctgttc ctgaagcggc tgggtgtgcc caacgaccaa attgttggcc      600
ccatattcaa gtggcgggcg ctgctgtcgg agcaggtcga cttcgaggcg gccgccgact      660
```

```
tcctggctag cgaggctggc atcgcacccg agctgctggg tcaggtggcg tgccagtacc    720
cggcactgct ggcagccccc gttgccaccg agctggcccc ccggctggcc ttcctgcgcg    780
gcctcggccc cgaggcgccg ggcctgttgc gtggcgtgct gcatgaggac tggtacggct    840
gggtgcacgg cctggcgaac tggcccaccg cggtggcgcc caagttggcg cgcgctggagg   900 cggtggtgga gggcgggccg caggcggcgg cggcgctgct gcggcgagtg cccgaggcgc    960
tcaaataccc ccccgagagc cgcctggtgc ccaacctgag gctcttgcag ggagccatgg   1020
ggctggacca gcagtcgctg gcggcgctgc tgcgcggcgc ccccgagatc ctgtccctgg   1080
cgccggagca gctggagagc cgctggacct tcctgaccga ggccgcgaac ggcggagagg   1140
ctgacctgct cgcataccog ccctacctgc tggccagcct ggccaagacc tccgggcccc   1200
ggctcatgtt tgtggcgaca cgcggcctgg cggcacgcct ggcgacgccg ccggcgccgg   1260
cagctgtgca ggagggctcg gcggcagcgg ctgacgaggc ggggcaaagt gggagatggg   1320
gggaagcgga tgaggaggat ggggatgagg gcggtgacgt gggccagggg gcggtgctgg   1380
acctgagatg gttggtggag ggcagcgacg aggacttcct gcggcgggcg cgctggagc    1440 tgcgacgggc cggcgggcgg cgctcgcctt cgttgtcagc gggggcgttg ctgtacgcct   1500
cgtcaacctt ctcatcttca tcccgagcat caagcccagt gtctgggtct gcatctgggt   1560
cagcagcagc attggggtca ggggcaaggg caggagcggc gggtggggag gaggtgagtg   1620
aggaggagct gttattggtg cggggcgagt acgagacggc ggcggcagag tgggaatcgc   1680
tgttgggctg gtgcgcggac agggcgttca caaaggcggg gcggaagaag tttgaggagc   1740
agctttcgct gttttatttg ctagtgcagg gttgatgatg ttgcgggtgg tgctttgttt   1800
gttgtgcttg catgctttg tgttcacgga ttgagctcga tgccggcgga ctgacgggga   1860
ggacgtagcg gggccagcgc ttgtggcgtg cagtgctggg tgctgccggg cgcatctgtc   1920
ttaggctgat ttatacctag caatcctagt cagatgacta tctgtgtgcg tggcgtggtg   1980
gggcggtcag gcgcagggga gggtcaggcg gttgcagctg cggtgaagca gcgtggcgcc   2040
gtgacatcat gccacatccg aaaggctgta attttgcca actgcttaaa taagtgggcg    2100
tgtgaggtag tgaagctgtg aagcgccgta cactgccgtg gatggccgat ccaagtacgt   2160
tgccggtgcg tgtgtgcgga tacgtggcgg atactggcgg atatcattgt ggagcttcac   2220
gcggacgtgc cccgtagggt cccaaggcca gctacaacat ctt                    2263

<210> SEQ ID NO 55
<211> LENGTH: 1689
<212> TYPE: DNA
<213> ORGANISM: Chlamydomonas reinhardtii

<400> SEQUENCE: 55
atgagagcgc ttgtaggaca acgttgtttg gcgccacaac gcgcaccagg ttcgcttcat     60
ggcacgcttc gtgcggtgcc cagcgcggtg gcgctgcggc gagcgcgtgc tagctgctct   120
tatccagaat catcatcgaa ccactcggcg acagcgacca ccaccacgct ggagtcgcag   180
ctgtctgagg tgaacgccag cccggtgctg gtgctcggca gtcctgcact gcagggcgca   240
gaccatgctc agatgtgtgc cgcgctgag gcgctgcgcg atgctgtgcc gcggcgctcc    300
ctgggcgggc tgctggagcg ctaccccgcc atcctcaccg ccccgtggc cacgtggtg    360 gacttcctgg gctccttcgg cttccagcga ctggccgtgc aggagctgct gttgaattcg   420
ccggacgtgt tggccaactc gtccgtcttc cgggcgggcc aggtgttcct gttcctgaag   480
cggctgggtg tgcccaacga ccaaattgtt ggccccatat tcaagtggcg ggcgctgctg   540
```

```
tcggagcagg tcgacttcga ggcggccgcc gacttcctgg ctagcgaggc tggcatcgca      600
cccgagctgc tgggtcaggt ggcgtgccag tacccggcac tgctggcagc ccccgttgcc      660
accgagctgg cccccggct ggccttcctg cgcggcctcg ccccgaggc gcgggcctg        720 ttgcgtggcg tgctgcatga ggactggtac ggctgggtgc acggcctggc gaactggccc      780
accgcggtgg cgcccaagtt ggcggcgctg gaggcggtgg tggagggcgg ccgcaggcg       840 gcggcggcgc tgctgcggcg agtgcccgag gcgctcaaat accccccga gagccgcctg       900 gtgcccaacc tgaggctctt gcagggagcc atggggctgg accagcagtc gctggcggcg     960
ctgctgcgcg cgccccccga gatcctgtcc tggcgccgg agcagctgga gagccgctgg     1020
accttcctga ccgaggccgc gaacggcgga gaggctgacc tgctcgcata cccgccctac    1080
ctgctggcca gcctggccaa gacctccggg ccccggctca tgtttgtggc gacacgcggc    1140
ctggcggcac gcctggcgac gccgccggcg ccggcagctg tgcaggaggg ctcggcggca    1200
gcggctgacg aggcggggca aagtgggaga tgggggaag cggatgagga ggatggggat     1260
gagggcggtg acgtgggcca ggggcggtg ctggacctga gatggttggt ggagggcagc     1320
gacgaggact tcctgcggcg ggcggcgctg gagctgcgac gggccggcgg gcggcgctcg    1380
ccttcgttgt cagcggggc gttgctgtac gcctcgtcaa ccttctcatc ttcatcccga     1440
gcatcaagcc cagtgtctgg gtctgcatct gggtcagcag cagcattggg gtcaggggca    1500
agggcaggag cggcgggtgg ggaggaggtg agtgaggagg agctgttatt ggtgcgggc     1560 gagtacgaga cggcggcggc agagtgggaa tcgctgttgg gctggtgcgc ggacagggcg    1620
ttcacaaagg cggggcggaa gaagtttgag gagcagcttt cgctgttta tttgctagtg     1680 cagggttga                                                            1689

<210> SEQ ID NO 56
<211> LENGTH: 562
<212> TYPE: PRT
<213> ORGANISM: Chlamydomonas reinhardtii

<400> SEQUENCE: 56

Met Arg Ala Leu Val Gly Gln Arg Cys Leu Ala Pro Gln Arg Ala Pro
1               5                   10                  15

Gly Ser Leu His Gly Thr Leu Arg Ala Val Pro Ser Ala Val Ala Leu
            20                  25                  30

Arg Arg Ala Arg Ala Ser Cys Ser Tyr Pro Glu Ser Ser Asn His
        35                  40                  45

Ser Ala Thr Ala Thr Thr Thr Leu Glu Ser Gln Leu Ser Glu Val
    50                  55                  60

Asn Ala Ser Pro Val Leu Val Leu Gly Ser Pro Ala Leu Gln Gly Ala
65                  70                  75                  80

Asp His Ala Gln Met Cys Ala Ala Leu Glu Ala Leu Arg Asp Ala Val
                85                  90                  95

Pro Arg Arg Ser Leu Gly Gly Leu Leu Glu Arg Tyr Pro Ala Ile Leu
            100                 105                 110

Thr Ala Pro Val Ala Thr Trp Val Asp Phe Leu Gly Ser Phe Gly Phe
        115                 120                 125

Gln Arg Leu Ala Val Gln Glu Leu Leu Leu Asn Ser Pro Asp Val Leu
    130                 135                 140

Ala Asn Ser Ser Val Phe Arg Ala Gly Gln Val Phe Leu Phe Leu Lys
145                 150                 155                 160
```

-continued

```
Arg Leu Gly Val Pro Asn Asp Gln Ile Val Gly Pro Ile Phe Lys Trp
            165                 170                 175
Arg Ala Leu Leu Ser Glu Gln Val Asp Phe Glu Ala Ala Ala Asp Phe
        180                 185                 190
Leu Ala Ser Glu Ala Gly Ile Ala Pro Glu Leu Leu Gly Gln Val Ala
    195                 200                 205
Cys Gln Tyr Pro Ala Leu Leu Ala Ala Pro Val Ala Thr Glu Leu Ala
210                 215                 220
Pro Arg Leu Ala Phe Leu Arg Gly Leu Gly Pro Glu Ala Pro Gly Leu
225                 230                 235                 240
Leu Arg Gly Val Leu His Glu Asp Trp Tyr Gly Trp Val His Gly Leu
            245                 250                 255
Ala Asn Trp Pro Thr Ala Val Ala Pro Lys Leu Ala Ala Leu Glu Ala
        260                 265                 270
Val Val Glu Gly Gly Pro Gln Ala Ala Ala Leu Leu Arg Arg Val
    275                 280                 285
Pro Glu Ala Leu Lys Tyr Pro Pro Glu Ser Arg Leu Val Pro Asn Leu
    290                 295                 300
Arg Leu Leu Gln Gly Ala Met Gly Leu Asp Gln Gln Ser Leu Ala Ala
305                 310                 315                 320
Leu Leu Arg Gly Ala Pro Glu Ile Leu Ser Leu Ala Pro Glu Gln Leu
            325                 330                 335
Glu Ser Arg Trp Thr Phe Leu Thr Glu Ala Ala Asn Gly Gly Glu Ala
        340                 345                 350
Asp Leu Leu Ala Tyr Pro Pro Tyr Leu Leu Ala Ser Leu Ala Lys Thr
    355                 360                 365
Ser Gly Pro Arg Leu Met Phe Val Ala Thr Arg Gly Leu Ala Ala Arg
370                 375                 380
Leu Ala Thr Pro Pro Ala Pro Ala Ala Val Gln Glu Gly Ser Ala Ala
385                 390                 395                 400
Ala Ala Asp Glu Ala Gly Gln Ser Gly Arg Trp Gly Glu Ala Asp Glu
            405                 410                 415
Glu Asp Gly Asp Glu Gly Gly Asp Val Gly Gln Gly Ala Val Leu Asp
        420                 425                 430
Leu Arg Trp Leu Val Glu Gly Ser Asp Glu Asp Phe Leu Arg Arg Ala
    435                 440                 445
Ala Leu Glu Leu Arg Arg Ala Gly Gly Arg Arg Ser Pro Ser Leu Ser
    450                 455                 460
Ala Gly Ala Leu Leu Tyr Ala Ser Ser Thr Phe Ser Ser Ser Ser Arg
465                 470                 475                 480
Ala Ser Ser Pro Val Ser Gly Ser Ala Ser Gly Ser Ala Ala Ala Leu
            485                 490                 495
Gly Ser Gly Ala Arg Ala Gly Ala Ala Gly Gly Glu Val Ser Glu
        500                 505                 510
Glu Glu Leu Leu Leu Val Arg Gly Glu Tyr Gly Thr Ala Ala Ala Glu
    515                 520                 525
Trp Glu Ser Leu Leu Gly Trp Cys Ala Asp Arg Ala Phe Thr Lys Ala
    530                 535                 540
Gly Arg Lys Lys Phe Glu Glu Gln Leu Ser Leu Phe Tyr Leu Leu Val
545                 550                 555                 560
Gln Gly
```

<210> SEQ ID NO 57

<211> LENGTH: 9174
<212> TYPE: DNA
<213> ORGANISM: Chlamydomonas reinhardtii

<400> SEQUENCE: 57

```
cgtcttattg cacgaccggc gcaaccctcc acctctcgcg tcgtctcgct tgcgtgacag      60
aggcttgaca acttgtcttt ttcctggtcc catgggagac tgaccttcac aaggcaatac     120
ctatgatgta cctataaggc agctgactct tgagtccgcg ttagcccccac gcaaactttg    180
agcgcgcgac ggggatcgtt gtcttggccg ggtcgcttca ccagcgtaga cgaaaatgcg     240
gcggcgtcaa ggccagctgc atccatgggg ttttctgctg cggcagcgcg atggcgggct     300
cgccgcgcca cccgtggcgt tagtccacga ccacgtcgcg ttaggtcgcg gcacggcgcc     360
tcccccgggc gcggcacatg ccgttgcggg catgcagcag tgcccctcc agttcattac      420
tatcgacgat gagcgcgtga ccgcctgca cgccgcgctc acagtgcact gcaacagcag     480
ccggtggccg ccgctggtga ctgtggagga ccgcagccgc aacggtacct acctcaacgg    540
ctcgccgctg cgccccggcg ccccccgccgt cctgtccagc ggcgacgtgc tgtcgctggt    600
gctgtgcgtc aaccccctca cgcagctgtg cttcgtgttt gaggagtgcc ccgtgccgcc     660
gcccaactgg acacgagccg ccaacgccca agaaggcgcc ggctcatcag cgcagagcgg    720
caacactgct gtccggcgac caaccgccac cggcggtgat gcgctgggag caggcggagc    780
agcaggagca gcggcagggg cagctcccta tccggtactg ccagtcggcc tgcctcgcgc    840
cagcggcaac ctgaacgcgg ccctgagcgc tgcagctgtt gctgctgcgc tggcggccgg    900
ccgtggcacg tcgcgcaaca gccgcggcca ccgcgccggc cgcagcaacc ggtctcccgc    960
cgccgccgcc acgtcgactg ctggcaccga gacgctgggg ctggtggacc cgctggcggc   1020
ggcggcgccg caccggctga gcggcacggg cttctctgag ggcggcgtgg agcagtggcc   1080
gtcgggagct gggccgcgcg aggtgaccag ccccagccg tcgctgccgc cggcctcgct    1140
gccgcagtcg cccgaccgcc gccgtatcac acggcagtcc acgggcagtg gtgtgcctcg   1200
ctcgctgtcg cctgacagca gtcccacctc ggtggtgggc gagtcggcac atggcttccc   1260
cctggaaggc ggcggcgggc ggcgccacag cgtcccggtc ggcggtgcct cctgggaccg   1320
gcacgacgac cactggccgg agccgcacag ccccactgcc actccccgct cgcgcgtgca   1380
caatcacacc gttgcgcagg tcctggcggc gctgcacccc aacccgctgt acgccgacca   1440
cctcaccgcg ctggagctag cgcccggcac ggcgccgccc gcctcgccgc cgcgcagccc   1500
ccgctcgacg cccctgcgtg cgccgtcac tggcgccgcc gcccgcgcca gccgccccag    1560
ccgccgcagc accggcagcg gcatggccgc ggctgacggc caccaccagc ggcaccagcg   1620
gcaccgccgc tcccggacag cgcacctggg agctcacctg cttgccttcg ccgcagcggg   1680
cgtggccgcg ccggcggact cggcggtgtc tgcggctcgc ggcggcattt cgctgagccg   1740
ctcgctcccc caactgctcc ccgtcgattt ggtcggcaac caccagtttc acgagctgcg   1800
gctgcagcag cactcgtccg cccaagccgg cggctacatg tcggctgcgg cggtgccctc   1860
gctgtcgtca gtgtccgact ccacacctgc ctacgccggc tggcccgtcc atggcctggc   1920
cggcagcgga ggcagtgccc ccgctaccag cgccgccacg agcacgagca gcagcagccg   1980
gcacagcttg cacagcccgc ttagtcagcc cagcctgcac agccgctacc tactgaccgg   2040
cggcgcggag gctgtgctca acagcccgcg cgccagcgc ttcagcactg gcagcggctt    2100
tggaccgccg ctgccggtgt tgccgccgcc gcccttgtca tcggcacctt cggcgtcatc   2160
tgcgtttgca gatccgaccc aggccgaagc cctggcccag gcccatcgcc gtccgcgcgc   2220
```

```
tctgtcctac ggctctggca gctttggcct ggaggaagag aacagcggtg gcggcagcgg    2280
cggcagcggc acccacacag ccctggttcc gaggatttca gccccacgc tggacgcgtt     2340 tgggtccgtg tccgatgccc ccatgctgac accggcgccg ccgtctgcgc ccctgccagc    2400
ctgcggctcc ggctccggct ctcctcgttc cgccccgcc gccgccgcag tcatcgtggg     2460
cggcggccca aggtccagcc gcagctcggc gtcgcggccg cagtcccgcc tgctgcgcgt    2520
cagccgcccc aactcgccgc tgcctgggta cgagaacagc ggtggcgtgg gctcaaccgg    2580
cttcgccgct gcatgggctg caggcggcgc tggtgctgct agctgccgcg gcggtgatgt    2640
tggtaccgct ggtgctggtg ctgtggatga gctggcgtat ggcatggaca tgcaagggca    2700
tgagggcgga aacaactgcg agctgctggc tccgttgcca agctcgccgc gctttgggcc    2760
tggaggccgc ggcggcgctg ggtcgttgcc tgatgctgca tcggagtttg gccagggtgc    2820
cagtggtgca ggttctggcg tggctggggc tggagtaggg gggacggcga ccgccgtgcc    2880
gctgcgtcgg ctgtgctccg cagcggtggc cgcgctggcg gccgccgccg aggccactgc    2940
gagtgagagc gacactccca gcgagatcac ttgcaaggag ttctccttct cctccctgtc    3000
ccgtcccaca ctctccgcgc ccgccgccgc cagcagcccg cccggtgcca accgcgaccc    3060
ctgctgcagc ccttcagtgc cggccatcgc gctcgagccc gcagcctccg tccctactgc    3120
cgccgccgcc tctgtcaacc ttgaggctag gctgcacacc gccgcagctg acggcggcag    3180
cgggggcagc ccgcgcttcc tccgccgcac ggtctccgcg aacgacggcc gcaggcaca    3240 gaccctgcac aggcaacagc agctacagct tcagcagcag cagcactttg gtaatgcctc    3300
tgatgcattt ctggtggcgg cggcggcggc aggagctcct ccaactctcc gtgtgtcagc    3360
gtcttccgta agggctgctg caccaggcc gcagcgcagc gtaagcgccg gctcgcacgg    3420
atgcagtagc agaagcgtgg ccagcagcgc ggactgtgct gctgccagtg aggtcagcgg    3480
cgcctacccg gaggggccgt ggctccagcg gggcggcgtg gaggcggcgc tccagcactc    3540
cccacaagcc gcaatggtgg ctgtagcagc cgcagcagca cagctgtacg gtggcggcgc    3600
cgccactggt ggcgccgcta gcagcctgcc cacggccagc cgccagctac agtgccgctg    3660
cagcggcact ggcggcggtg gtgagagcag cggcagcggc acggggctga gtgacgcgtc    3720
catgccctca cccaggtggg ctgggggcaca tggcgctgga aggacggggg gctccagcag    3780 caccccagt agcggccgcc cgcagcgcct ggccgcaggc cgccacccca accgccgcct    3840
cacgcgctac ggcgagtgcc tcgacacgcc ctcgccgcgc agccccgccg tcaccagcag    3900
tagccatgct ggcgccggcg cctcacccctt ccgtcacgca gactcgtatc gcctggcgg    3960 actcgcggct cttgccgctg cctccccggc cgccgccagc ccggtgccgg tgccagcggc    4020
tgcggcagta gctgcagcgg ctacccaggc ggcgccgtcc tggccgtcac cggcgcgcgc    4080
cacccggccg cgcggcgccg cctcccccgc ctgccgccga ctgcggctgg agggcgctga    4140
gccgcacgac gctgcggcgc cgtcgccttg ctctggggca agaagcagcc gcagctggct    4200
acagcatgat ctcagtggcg ggggcgccgt ggcggaaccg gcgcgcccgc tggcgcctgg    4260
agtggtgaca ttgcctgtat atgtggctcg ctccgagtcg gagggctcgg cgttgcggtc    4320
cgccgcgccc ccaccggcat ggccccgcgc gcaggccgct gccgcctgtc cctcgctgcc    4380
gtacacgccg tcctcgctgg tgcgatacct ggactcgcgc ctgggctccc tggcggcggc    4440
ggcggaggcg gcggtggcgg aggcgggtga agagattggc gcgcagctgg cgtcactgga    4500
ggcggctgca gctgtggctg cggctggcgg tgccgcgggc ggcggcgcac gctcacagtc    4560
```

```
gcgctcagcc gcggcgccgg gtctaaattt ggagctaggt ttggatctgg acctacctgc    4620
gttgccgccg gttccgatgc cgacagccat cggctttggc ggcgacggca ctctcggcaa    4680
ccgccgcttc aatgcggctg cgcccagctt ccgcggctac cagtcaccgg aggggatgct    4740
gacgcgtgcc ggcggcggcg gtgatgaggc cctgacgcca cggagtggcc atggcagtgt    4800
ctgtggcagc accggaggcg ccgccgcagc ttctttgat gaggcccgca gctctggcgc    4860
cggaggcgac ggtggccgca gccccgtcgg cagcagcggc agctgcgcgc gtagctgcgt    4920
gggcaacgcg gctgccggtg gcgcagcgtc gcgcttggcg cttggccgcg ccttgagcac    4980
aagcgcgaca gtgggctcgc cgcgcgcagg ccggcgtgct ccgctggcag cagccacgga    5040
cagcggctgt gacctggacc acagcccgcc gcacaagccc atcaactcta cctgcgccac    5100
cccgcgcaag caaagcccgc cgcacaagcc catcacgtcc acctgtgcca cgccgcggaa    5160
gcacacgccg cgcgcttcgt tcagccaaag ccactcccag gtattccacg aggaccaagg    5220
ctgcgaccac caccaccacg gccaccaccg ccagctctcc cggggcggcg gggactgcct    5280
gctgctgcac gaccaggccc agggacacag ccggacggct gctgcagcgg cggcctcagt    5340
cacggccgcc aggagcggca gcagctcaca gggcctgccc ctccagccct cgccctcagg    5400
ccgccctccc accgccgagt ccgacacact gccgctgcac gacgccggca gcggcagctg    5460
cggcaacagc agcggcggcg gctggagtgc gcaggccagc agccgcgagg ggtatgctta    5520
tgcgtacggg agcgccggct ggcccggcga gcagtgctac ccgcctgctg cccactacca    5580
ctaccagcag caccaggacc gacaggtgct gcagctgcac agccgtcggg tcagcggcgg    5640
cgcggccagc acactggagg cgccgccgcc gtcagaggtg gacgtggcca gggcgatgag    5700
caccggccgc ggctgcgaca acgccgaggg cgatggcggt ctcagtgtcg gtatgggcca    5760
cgcaggttgg gggccacagg cgcaggcggc ggcacagcag cagcagcagc agcagcagcg    5820
ccgtgtgtca ggtgtttcgc gtggcagcag cagcagctgt cggcccagca cgagcggcag    5880
cggctgtagc agcgagttct gggcggcggc ggttgtgccg gtggaccaat ccccgctgc    5940 cgccgccggt gcccgcggcg tggtgcagct ggcagttgcg cctgcgctgt cgcgctcgag    6000
cctgagcccc ctcaaggtgg acgtgcggca ggaggacggc gtcccagggg cggaggggcc    6060
cgccaccggc aggctggctg ggtccccagg tagctcgcag ctggtgtgcg gcctgtgtgc    6120
tggcggcttg cgggctgcgg tggcgctgac gccgtgcggc cactccttct gcgccgagtg    6180
tctggcaggg cacctggggt cggcagtgct gggcggatcg cgcgtgggct gccccaaccg    6240
gtgccctgct tttgaggcgg tcgtcatcaa ccatccggcc cgccgcctgg aaagcaagcg    6300
gtccaacgcg accaccgcta cagccgcccc acgctcccac gccccgccc gtgcccagcc    6360 cgacggtcaa tgtgagtcat ctcccttga agccccggct gcggctgccg ccgtcgcggc    6420
gcacgccgcc gcacgcgcaa gcgccgcctc gacgcccgtg cgcggtgcac gcggcggctc    6480
tgaccccggg cctgccgcat caccgcgct cgtgcggct ggtggcgcca ccagcaggct    6540
gcgcacgcgc atgggcagcc gcggcagtgg ctacggcccc agcccagcc ggcgccggga    6600 gggggcgggc acgggcagcg agccagggc gtggtcggag atgctggcgg acgcagcact    6660
gcccgtgccc gccatccgcc tgcacctgca gcagggcgag gtgctgctgc gcgccctcag    6720
ccagctcctg gacgacacgc cccagctgcc ggcgcccccg ccgccctcca tccccgccgc    6780
cacagccacc accaccacaa ccagcaccgc cgcagctgct gccgccgcgg caaccaccca    6840
ggcggcgaca gcagcggtgc gcgaggcccg tgctgcggtg gtggagtggc ggcgtgtggt    6900
gctggacgtg ttgggctgcc tgggccgcct ggcactggag cacgtgcggg tgcgggaggc    6960
```

-continued

```
gcttggcgcg gcgggcgcgt cccagggctg cgtgctggcg ctgcggcgg tgcaggcgca      7020 gatggcggcg gcggagctgt gcaccaaggg cggcgagcgg agtcttgtcg acaaggatgg      7080
cattgtcaag aagccaacag tggcggaagc cgagaaggag cagaggctg cgctggtagc      7140 ggaggagcgg gcgacggcgc aggacaccag ccgcgcgggc tgtgtgctgc tgtgccacct      7200
gctgaaccca ccggcgccgt cgccgccggc cgagacgggt gccacagatt cggagcaagc      7260
ggtgtgccgc cagcagtcca accaatgggc gctggcgcgc atgggcggcg cagaggcctt      7320
gctggcgctg ctcctgcctg cgcaggagcc aggcaagggg gccaccgacg ctggtggcga      7380
gggcgccggt ggcaatggca acgcggagcg gcggcggtgg tcagggcaga tggcggcggc      7440
gctgacggcg cttcagagga tggtcgtggg gaacatcatg actcagaccc acgtggccga      7500
gtgtgggtct gccgccgtca tccgcacgct ggccgccgcc acccgcgccg ccgccgcctc      7560
gggcgatgag gccgtacagg cggcggcgct gcggctgctg gctgacgtgg cccgtggcgg      7620
cgacgccgca cacgccgcag tgcggcagat gctgctagag gccggcgcac tgggggcggc      7680
gctggcggcg ctgcgcgaca gcgtggctgc tttcggcggc tgcaatggag aagagaagg      7740 atctgggaat agcggatgcg ctgacggcgg tagcgccgcc agctcgggga tggaggtcag      7800
cccggtgctg atggcggcgc tggacgcgat tcatgtgttg atgggtccgt cggagcagca      7860
cgtggacgga tctgagccgc cgctggcgct tcaggcggtg gtgcggcggg agttgcggcg      7920
gctgggcgcg ccgcgcctgc tggcggactg cgtgcgggag ctgcggctgc aacaggagga      7980
cgagcagggc gagggccggg cccaggagga gtgggagcgg gcgagcgggc gcacgggcca      8040
cagcaggcat gccctgatg gtcgcgtgct tcccggagca gtagcaggag caggagggaa      8100
gcagccgcat ccacggccct gggacgggtc gcggtcgcgg gaggagcggg gttcggcggg      8160
tggcgattgc ctcgggtgca gccccgtgct tcgggcgatg gccgagctgc aggcgcgcgt      8220
gtgtgcagta gcaggtggta cgggctgggt gcgttgtgtg gtgcagatgt tgggcgcaag      8280
tcccgacgga gtggggcagg ctgggcgtgg tggcgttgat ggcggtggtg cggcgatggc      8340
agcggtggcg gcgcatagg tgcagttgcg ccttctcgcg gtggcagcag gtggcgggtt      8400
tgcgctcggt gccgcggtga cggggcagt ggcagcgatg tggatggctt gattttgggg      8460
tggtgctagc aagtgcgttt gcgactttgg tgtgacattg caccttcagg agaaggcagg      8520
caagggttga ggtgtaggtt tggccgttgt ccggttggca agtgctggcc tgtttgttga      8580
gctgttgact ttatagtggc tgtacctttg ggggtcggc tttgttgaac acacgcccac      8640
cacattgttt gcgcatcggg acgctaagtt ggcgcaagcc acggttgccc acccaaaagc      8700
cggcagctgg tagggccatg tgcagcgtgg aagttgctct gctggtaggg ccgtatgcag      8760
atttgaaata gctctggtgt tggccgagga aggctgcgga ggggtccatg ggtgcggctg      8820
tgttggggca ggtgctagcc cggggactc cccgtgggga ctccctggac atgccgccgt      8880
gtgaatggtc atttgcagga cattgggttg cggggcgtag gggattctag tagatggatg      8940
caggcaggac agctctgaca ttcatcaatt gatgataggc tgcaggacgc agtatacggc      9000
tgtacttgca tgtgtgttga gccgatgggt tgttgacgtc tcctgatgcg ttgggtggct      9060
gggtcgccac ggagcaatta gcgccacggg ccaatcgtaa aggttacatg ttttgctaga      9120
caaaatgaat gaagagaaaa ccattgtcat tggtaggaaa acttctccgt cgag            9174
```

<210> SEQ ID NO 58
<211> LENGTH: 8217
<212> TYPE: DNA

<213> ORGANISM: Chlamydomonas reinhardtii

<400> SEQUENCE: 58

```
atgcggcggc gtcaaggcca gctgcatcca tggggttttc tgctgcggca gcgcgatggc      60
gggctcgccg cgccacccgt ggcgttagtc cacgaccacg tcgcgttagg tcgcggcacg     120
gcgcctcccc cgggcgcggc acatgccgtt gcgggcatgc agcagtgccc cctccagttc     180
attactatcg acgatgagcg cgtgagccgc ctgcacgccg cgctcacagt gcactgcaac     240
agcagccggt ggccgccgct ggtgactgtg gaggaccgca gccgcaacgg tacctacctc     300
aacggctcgc cgctgcgccc cggcgccccc gccgtcctgt ccagcggcga cgtgctgtcg     360
ctggtgctgt gcgtcaaccc cctcacgcag ctgtgcttcg tgtttgagga gtgcccgtg     420
ccgccgccca actggacacg agccgccaac gcccaagaag gcgccggctc atcagcgcag     480
agcggcaaca ctgctgtccg cgaccaacc gccaccggcg gtgatgcgct gggagcaggc     540
ggagcagcag gagcagcggc aggggcagct ccctatccgg tactgccagt cggcctgcct     600
cgcgccagcg gcaacctgaa cgcggccctg agcgctgcag ctgttgctgc tgcgctggcg     660
gccggccgtg gcacgtcgcg caacagccgc ggccaccgcg ccggccgcag caaccggtct     720
cccgccgccg ccgccacgtc gactgctggc accgagacgc tggggctggt ggacccgctg     780
gcggcggcgg cgccgcaccg gctgagcggc acgggcttct ctgagggcgg cgtggagcag     840
tggccgtcgg gagctgggcc gcgcgaggtg accagccccc agccgtcgct gccgccggcc     900
tcgctgccgc agtcgcccga ccgccgccgt atcacacggc agtccacggg cagtggtgtg     960
cctcgctcgc tgtcgcctga cagcagtccc acctcggtgg tgggcgagtc ggcacatggc    1020
ttcccctggg aaggcggcgg cgggcggcgc cacagcgtcc cggtcggcgg tgcctcctgg    1080
gaccggcacg acgaccactg gccggagccg cacagcccca ctgccactcc cgctcgcgc    1140
gtgcacaatc acaccgttgc gcaggtcctg gcggcgctgc accccaaccc gctgtacgcc    1200
gaccacctca ccgcgctgga gctagcgccc ggcacggcgc cgcccgcctc gccgccgcgc    1260
agcccccgct cgacgcccct gcgtgcgccc gtcactggcg ccgccgcccg cccagccgc    1320
cccagccgcc gcagcaccgg cagcggcatg gccgcggctg acggccacca ccagcggcac    1380
cagcggcacc gccgctcccg gacagcgcac ctgggagctc acctgcttgc cttcgccgca    1440
gcgggcgtgg ccgcgccggc ggactcggcg gtgtctgcgg ctcgcggcgg catttcgctg    1500
agccgctcgc tcccccaact gctccccgtc gatttggtcg gcaaccacca gtttcacgag    1560
ctgcggctgc agcagcactc gtccgcccaa gccggcggct acatgtcggc tgcggcggtg    1620
ccctcgctgt cgtcagtgtc cgactccaca cctgcctacg ccggctggcc cgtccatggc    1680
ctggccggca gcggaggcag tgcccccgct accagcgccg ccacgagcac gagcagcagc    1740
agccggcaca gcttgcacag cccgcttagt cagcccagcc tgcacagccg ctacctactg    1800
accggcggcg cggaggctgt gctcaacagc ccgcggcgcc agcgcttcag cactggcagc    1860
ggctttggac cgccgctgcc ggtgttgccg ccgccgccct tgtcatcggc accttcggcg    1920
tcatctgcgt ttgcagatcc gacccaggcc gaagccctgg cccaggccca tcgccgtccg    1980
cgcgctctgt cctacggctc tggcagcttt ggcctggagg aagagaacag cggtggcggc    2040
agcggcggca gcggcaccca cacagccctg gttccgagga tttcagcccc cacgctggac    2100
gcgtttgggt ccgtgtccga tgcccccatg ctgacaccgg cgccgccgtc tgcgccctg    2160
ccagcctgcg gctccggctc cggctctcct cgttccgccc ccgccgccgc cgcagtcatc    2220
gtgggcggcg gcccaaggtc cagccgcagc tcggcgtcgc ggccgcagtc ccgcctgctg    2280
```

```
cgcgtcagcc gccccaactc gccgctgcct gggtacgaga acagcggtgg cgtgggctca   2340
accggcttcg ccgctgcatg ggctgcaggc ggcgctggtg ctgctagctg ccgcggcggt   2400
gatgttggta ccgctggtgc tggtgctgtg gatgagctgg cgtatggcat ggacatgcaa   2460
gggcatgagg gcggaaacaa ctgcgagctg ctggctccgt tgccaagctc gccgcgcttt   2520
gggcctggag gccgcggcgg cgctgggtcg ttgcctgatg ctgcatcgga gtttggccag   2580
ggtgccagtg gtgcaggttc tggcgtggct ggggctggag tagggggggac ggcgaccgcc   2640 gtgccgctgc gtcggctgtg ctccgcagcg gtggccgcgc tggcggccgc cgccgaggcc   2700
actgcgagtg agagcgacac tcccagcgag atcacttgca aggagttctc cttctcctcc   2760
ctgtcccgtc ccacactctc cgcgcccgcc gccgccagca gcccgcccgg tgccaaccgc   2820 gaccctgct gcagcccttc agtgccggcc atcgcgctcg agcccgcagc ctccgtccct   2880
actgccgccg ccgcctctgt caaccttgag gctaggctgc acaccgccgc agctgacggc   2940
ggcagcgggg gcagcccgcg cttcctccgc cgcacggtct ccgcgaacga cggcccgcag   3000
gcacagaccc tgcacaggca acagcagcta cagcttcagc agcagcagca ctttggtaat   3060
gcctctgatg catttctggt ggcggcgcg cggcaggag ctcctccaac tctccgtgtg   3120
tcagcgtctt ccgtaagggc tgctgcacca ggcccgcagc gcagcgtaag cgccggctcg   3180
cacggatgca gtagcagaag cgtggccagc agcgcggact gtgctgctgc cagtgaggtc   3240
agcggcgcct acccggaggg gccgtggctc cagcggggcg gcgtggaggc ggcgctccag   3300
cactccccac aagccgcaat ggtggctgta gcagccgcag cagcacagct gtacggtggc   3360
ggcgccgcca ctggtggcgc cgctagcagc ctgcccacgg ccagccgcca gctacagtgc   3420
cgctgcagcg gcactggcgg cggtggtgag agcagcggca gcggcacggg gctgagtgac   3480
gcgtccatgc cctcacccag gtgggctggg gcacatggcg ctggagagga cggggctcc   3540 agcagcaccc ccagtagcgg ccgcccgcag cgcctggccg caggccgcca ccccaaccgc   3600
cgcctcacgc gctacggcga gtgcctcgac acgccctcgc cgcgcagccc cgccgtcacc   3660
agcagtagcc atgctggcgc cggcgcctca cccttccgtc acgcagactc gtatcgcctg   3720
gcggcactcg cggctcttgc cgctgcctcc ccggccgccg ccagcccggt gccggtgcca   3780
gcggctgcgg cagtagctgc agcggctacc caggcggcgc cgtcgtggcc gtcaccggcg   3840
cgcgccaccc ggccgcgcgg cgccgcctcc cccgcctgcc gccgactgcg gctggagggc   3900
gctgagccgc acgacgctgc ggcgccgtcg ccttgctctg gggcaagaag cagccgcagc   3960
tggctacagc atgatctcag tggcgggggc ccgtggcgg aaccggcgcg cccgctggcg   4020
cctggagtgg tgacattgcc tgtatatgtg gctcgctccg agtcggaggg ctcggcgttg   4080
cggtccgccg cgccgccacc ggcatggccc cgcgcgcagg ccgctgccgc ctgtccctcg   4140
ctgccgtaca cgccgtcctc gctggtgcga tacctggact cgcgcctggg ctccctggcg   4200 gcggcggcg aggcggcggt ggcggaggcg ggtgaagaga ttggcgcgca gctggcgtca   4260
ctggaggcgg ctgcagctgt ggctgcggct ggcggtgccg cgggcggcgg cgcacgctca   4320
cagtcgcgct cagccgcggc gccgggtcta aatttggagc taggtttgga tctggaccta   4380
cctgcgttgc cgccggttcc gatgccgaca gccatcggct ttgcggcga cggcactctc   4440 ggcaaccgcc gcttcaatgc ggctgcgccc agcttccgcg gctaccagtc accggagggg   4500
atgctgacgc gtgccggcgg cggcggtgat gaggccctga cgccacggag tggccatggc   4560
agtgtctgtg gcagcaccgg aggcgccgcc gcagcttctt ttgatgaggc ccgcagctct   4620
```

```
ggcgccggag gcgacggtgg ccgcagcccc gtcggcagca gcggcagctg cgcgcgtagc    4680
tgcgtgggca acgcggctgc cggtggcgca gcgtcgcgct tggcgcttgg ccgcgccttg    4740
agcacaagcg cgacagtggg ctcgccgcgc gcaggccggc gtgctccgct ggcagcagcc    4800
acggacagcg gctgtgacct ggaccacagc ccgccgcaca agcccatcaa ctctacctgc    4860 gccacccccgc gcaagcaaag cccgccgcac aagcccatca cgtccacctg tgccacgccg    4920
cggaagcaca cgccgcgcgc ttcgttcagc caaagccact cccaggtatt ccacgaggac    4980
caaggctgcg accaccacca ccacggccac caccgccagc tctcccgggg cggcggggac    5040
tgcctgctgc tgcacgacca ggcccaggga cacagccgga cggctgctgc agcggcggcc    5100
tcagtcacgg ccgccaggag cggcagcagc tcacagggcc tgcccctcca gccctcgccc    5160
tcaggccgcc ctcccaccgc cgagtccgac acactgccgc tgcacgacgc cggcagcggc    5220
agctgcggca acagcagcgg cggcggctgg agtgcgcagg ccagcagccg cgaggggtat    5280
gcttatgcgt acggcagcgc cggctggccc ggcgagcagt gctaccgcc tgctgcccac    5340 taccactacc agcagcacca ggaccgacag gtgctgcagc tgcacagccg tcgggtcagc    5400
ggcggcgcgg ccagcacact ggaggcgccg ccgccgtcag aggtggacgt ggccagggcg    5460
atgagcaccg gccgcggctg cgacaacgcc gagggcgatg gcggtctcag tgtcggtatg    5520
ggccacgcag gttggggggcc acaggcgcag gcggcggcac agcagcagca gcagcagcag    5580
cagcgccgtg tgtcaggtgt ttcgcgtggc agcagcagca gctgtcggcc cagcacgagc    5640
ggcagcggct gtagcagcga gttctgggcg gcggcggttg tgccggtgga ccaatccccc    5700
gctgccgccg ccgtgcccg cggcgtggtg cagctggcag ttgcgcctgc gctgtcgcgc    5760
tcgagcctga gccccctcaa ggtggacgtg cggcaggagg acggcgtccc aggggcggag    5820
gggcccgcca ccggcaggct ggctgggtcc ccaggtagct cgcagctggt gtgcggcctg    5880
tgtgctggcg gcttgcgggc tgcggtggcg ctgacgccgt gcggccactc cttctgcgcc    5940
gagtgtctgg cagggcacct ggggtcggca gtgctgggcg gatcgcgcgt gggctgcccc    6000
aaccggtgcc ctgcttttga ggcggtcgtc atcaaccatc cggcccgccg cctggaaagc    6060
aagcggtcca acgcgaccac cgctacagcc gccccacgct cccacgcccc cgcccgtgcc    6120
cagcccgacg gtcaatgtga gtcatctccc tttgaagccc cggctgcggc tgccgccgtc    6180
gcggcgcacg ccgccgcacg cgcaagcgcc gcctcgacgc ccgtgcgcgg tgcacgcggc    6240
ggctctgacc ccgggcctgc cgcatcaccc gcgctgcgtg cggctggtgg cgccaccagc    6300
aggctgcgca cgcgcatggg cagccgcggc agtggctacg gccccagccc cagccggcgc    6360
cgggaggggg cgggcacggg cagcgagcca ggggcgtggt cggagatgct ggcggacgca    6420
gcactgcccg tgcccgccat ccgcctgcac ctgcagcagg gcgaggtgct gctgcgcgcc    6480
ctcagccagc tcctggacga cacgcccag ctgccgccgc cccgccgcc ctccatcccc    6540 gccgccacag ccaccaccac cacaaccagc accgccgcag ctgctgccgc gcggcaacc    6600 acccaggcgg cgacagcagc ggtgcgcgag gcccgtgctg cggtggtgga gtggcggcgt    6660
gtggtgctgg acgtgttggg ctgcctgggc cgcctggcac tggagcacgt gcgggtgcgg    6720
gaggcgcttg gcgcggcggg cgcgtcccag ggctgcgtgc tggcgctgcg ggcggtgcag    6780
gcgcagatgg cggcggcgga gctgtgcacc aagggcggcg agcggagtct tgtcgacaag    6840
gatggcattg tcaagaagcc aacagtggcg gaagccgaga aggaggcaga ggctgcgctg    6900
gtagcggagg agcgggcgac ggcgcaggac accagccgcg cggcgtgtgt gctgctgtgc    6960
cacctgctga acccaccggc gccgtcgccg ccggccgaga cgggtgccac agattcggag    7020
```

-continued

```
caagcggtgt gccggcagca gtccaaccaa tgggcgctgg cgcgcatggg cggcgcagag      7080
gccttgctgg cgctgctcct gcctgcgcag gagccaggca aggggccac  cgacgctggt      7140 ggcgagggcg ccggtggcaa tggcaacgcg gagcggcggc ggtggtcagg gcagatggcg      7200
gcggcgctga cggcgcttca gaggatggtc gtggggaaca tcatgactca gacccacgtg      7260
gccgagtgtg ggtctgccgc cgtcatccgc acgctggccg ccgccacccg cgccgccgcc      7320
gcctcgggcg atgaggccgt acaggcggcg gcgctgcggc tgctggctga cgtggcccgt      7380
ggcggcgacg ccgcacacgc cgcagtgcgg cagatgctgc tagaggccgg cgcactgggg      7440
gcggcgctgg cggcgctgcg cgacagcgtg gctgctttcg gcggctgcaa tggaggaaga      7500
gaaggatctg ggaatagcgg atgcgctgac ggcggtagcg ccgccagctc ggggatggag      7560
gtcagcccgt gctgatggc  ggcgctggac gcgattcatg tgttgatggg tccgtcggag      7620
cagcacgtgg acggatctga ccgccgctg  gcgcttcagg cggtggtgcg gcgggagttg      7680
cggcggctgg gcgcgccgcg cctgctggcg gactgcgtgc gggagctgcg gctgcaacag      7740
gaggacgagc agggcgaggg ccgggcccag gaggagtggg agcgggcgag cgggcgcacg      7800
ggccacagca ggcatgcccc tgatggtcgc gtgcttcccg gagcagtagc aggagcagga      7860
gggaagcagc cgcatccacg gccctgggac gggtcgcggt cgcgggagga gcggggttcg      7920
gcgggtggcg attgcctcgg gtgcagcccc gtgcttcggg cgatggccga gctgcaggcg      7980
cgcgtgtgtg cagtagcagg tggtacgggc tgggtgcgtt gtgtggtgca gatgttgggc      8040
gcaagtcccg acggagtggg gcaggctggg cgtggtggcg ttgatggcgg tggtgcggcg      8100
atggcagcgg tggcggcgca tagggtgcag ttgcgccttc tcgcggtggc agcaggtggc      8160
gggtttgcgc tcggtgccgc ggtgacgggg gcagtggcag cgatgtggat ggcttga        8217
```

<210> SEQ ID NO 59
<211> LENGTH: 2738
<212> TYPE: PRT
<213> ORGANISM: Chlamydomonas reinhardtii

<400> SEQUENCE: 59

```
Met Arg Arg Arg Gln Gly Gln Leu His Pro Trp Gly Phe Leu Leu Arg
1               5                   10                  15

Gln Arg Asp Gly Gly Leu Ala Ala Pro Pro Val Ala Leu Val His Asp
            20                  25                  30

His Val Ala Leu Gly Arg Gly Thr Ala Pro Pro Gly Ala Ala His
        35                  40                  45

Ala Val Ala Gly Met Gln Gln Cys Pro Leu Gln Phe Ile Thr Ile Asp
    50                  55                  60

Asp Glu Arg Val Ser Arg Leu His Ala Ala Leu Thr Val His Cys Asn
65                  70                  75                  80

Ser Ser Arg Trp Pro Pro Leu Val Thr Val Glu Asp Arg Ser Arg Asn
                85                  90                  95

Gly Thr Tyr Leu Asn Gly Ser Pro Leu Arg Pro Gly Ala Pro Ala Val
            100                 105                 110

Leu Ser Ser Gly Asp Val Leu Ser Leu Val Leu Cys Val Asn Pro Leu
        115                 120                 125

Thr Gln Leu Cys Phe Val Phe Glu Glu Cys Pro Val Pro Pro Asn
    130                 135                 140

Trp Thr Arg Ala Ala Asn Ala Gln Glu Gly Ala Gly Ser Ser Ala Gln
145                 150                 155                 160
```

-continued

```
Ser Gly Asn Thr Ala Val Arg Arg Pro Thr Ala Gly Gly Asp Ala
            165                 170                 175
Leu Gly Ala Gly Gly Ala Ala Gly Ala Ala Gly Ala Ala Pro Tyr
        180                 185                 190
Pro Val Leu Pro Val Gly Leu Pro Arg Ala Ser Gly Asn Leu Asn Ala
    195                 200                 205
Ala Leu Ser Ala Ala Ala Val Ala Ala Ala Leu Ala Ala Gly Arg Gly
    210                 215                 220
Thr Ser Arg Asn Ser Arg Gly His Arg Ala Gly Arg Ser Asn Arg Ser
225                 230                 235                 240
Pro Ala Ala Ala Ala Thr Ser Thr Ala Gly Thr Glu Thr Leu Gly Leu
                245                 250                 255
Val Asp Pro Leu Ala Ala Ala Pro His Arg Leu Ser Gly Thr Gly
            260                 265                 270
Phe Ser Glu Gly Gly Val Glu Gln Trp Pro Ser Gly Ala Gly Pro Arg
        275                 280                 285
Glu Val Thr Ser Pro Gln Pro Ser Leu Pro Pro Ala Ser Leu Pro Gln
    290                 295                 300
Ser Pro Asp Arg Arg Arg Ile Thr Arg Gln Ser Thr Gly Ser Gly Val
305                 310                 315                 320
Pro Arg Ser Leu Ser Pro Asp Ser Ser Pro Thr Ser Val Val Gly Glu
                325                 330                 335
Ser Ala His Gly Phe Pro Leu Glu Gly Gly Gly Arg Arg His Ser
            340                 345                 350
Val Pro Val Gly Gly Ala Ser Trp Asp Arg His Asp Asp His Trp Pro
        355                 360                 365
Glu Pro His Ser Pro Thr Ala Thr Pro Arg Ser Arg Val His Asn His
    370                 375                 380
Thr Val Ala Gln Val Leu Ala Ala Leu His Pro Asn Pro Leu Tyr Ala
385                 390                 395                 400
Asp His Leu Thr Ala Leu Glu Leu Ala Pro Gly Thr Ala Pro Pro Ala
                405                 410                 415
Ser Pro Pro Arg Ser Pro Arg Ser Thr Pro Leu Arg Ala Pro Val Thr
            420                 425                 430
Gly Ala Ala Ala Arg Ala Ser Arg Pro Ser Arg Arg Ser Thr Gly Ser
        435                 440                 445
Gly Met Ala Ala Ala Asp Gly His His Gln Arg His Gln Arg His Arg
    450                 455                 460
Arg Ser Arg Thr Ala His Leu Gly Ala His Leu Leu Ala Phe Ala Ala
465                 470                 475                 480
Ala Gly Val Ala Ala Pro Ala Asp Ser Ala Val Ser Ala Ala Arg Gly
                485                 490                 495
Gly Ile Ser Leu Ser Arg Ser Leu Pro Gln Leu Leu Pro Val Asp Leu
            500                 505                 510
Val Gly Asn His Gln Phe His Glu Leu Arg Leu Gln Gln His Ser Ser
        515                 520                 525
Ala Gln Ala Gly Gly Tyr Met Ser Ala Ala Val Pro Ser Leu Ser
    530                 535                 540
Ser Val Ser Asp Ser Thr Pro Ala Tyr Ala Gly Trp Pro Val His Gly
545                 550                 555                 560
Leu Ala Gly Ser Gly Gly Ser Ala Pro Ala Thr Ser Ala Ala Thr Ser
                565                 570                 575
Thr Ser Ser Ser Ser Arg His Ser Leu His Ser Pro Leu Ser Gln Pro
```

-continued

```
                580                 585                 590
    Ser Leu His Ser Arg Tyr Leu Leu Thr Gly Gly Ala Glu Ala Val Leu
                    595                 600                 605
    Asn Ser Pro Arg Arg Gln Arg Phe Ser Thr Gly Ser Gly Phe Gly Pro
                610                 615                 620
    Pro Leu Pro Val Leu Pro Pro Leu Ser Ser Ala Pro Ser Ala
    625                 630                 635                 640
    Ser Ser Ala Phe Ala Asp Pro Thr Gln Ala Glu Ala Leu Ala Gln Ala
                    645                 650                 655
    His Arg Arg Pro Arg Ala Leu Ser Tyr Gly Ser Gly Ser Phe Gly Leu
                660                 665                 670
    Glu Glu Glu Asn Ser Gly Gly Gly Ser Gly Gly Ser Gly Thr His Thr
                    675                 680                 685
    Ala Leu Val Pro Arg Ile Ser Ala Pro Thr Leu Asp Ala Phe Gly Ser
                690                 695                 700
    Val Ser Asp Ala Pro Met Leu Thr Pro Ala Pro Pro Ser Ala Pro Leu
    705                 710                 715                 720
    Pro Ala Cys Gly Ser Gly Ser Gly Ser Pro Arg Ser Ala Pro Ala Ala
                    725                 730                 735
    Ala Ala Val Ile Val Gly Gly Pro Arg Ser Ser Arg Ser Ser Ala
                740                 745                 750
    Ser Arg Pro Gln Ser Arg Leu Leu Arg Val Ser Arg Pro Asn Ser Pro
                    755                 760                 765
    Leu Pro Gly Tyr Glu Asn Ser Gly Gly Val Gly Ser Thr Gly Phe Ala
                770                 775                 780
    Ala Ala Trp Ala Ala Gly Gly Ala Gly Ala Ala Ser Cys Arg Gly Gly
    785                 790                 795                 800
    Asp Val Gly Thr Ala Gly Ala Gly Ala Val Asp Glu Leu Ala Tyr Gly
                    805                 810                 815
    Met Asp Met Gln Gly His Glu Gly Gly Asn Asn Cys Glu Leu Leu Ala
                820                 825                 830
    Pro Leu Pro Ser Ser Pro Arg Phe Gly Pro Gly Gly Arg Gly Gly Ala
                    835                 840                 845
    Gly Ser Leu Pro Asp Ala Ala Ser Glu Phe Gly Gln Gly Ala Ser Gly
                850                 855                 860
    Ala Gly Ser Gly Val Ala Gly Ala Gly Val Gly Gly Thr Ala Thr Ala
    865                 870                 875                 880
    Val Pro Leu Arg Arg Leu Cys Ser Ala Ala Val Ala Ala Leu Ala Ala
                    885                 890                 895
    Ala Ala Glu Ala Thr Ala Ser Glu Ser Asp Thr Pro Ser Glu Ile Thr
                900                 905                 910
    Cys Lys Glu Phe Ser Phe Ser Ser Leu Ser Arg Pro Thr Leu Ser Ala
                    915                 920                 925
    Pro Ala Ala Ala Ser Ser Pro Gly Ala Asn Arg Asp Pro Cys Cys
    930                 935                 940
    Ser Pro Ser Val Pro Ala Ile Ala Leu Glu Pro Ala Ala Ser Val Pro
    945                 950                 955                 960
    Thr Ala Ala Ala Ala Ser Val Asn Leu Glu Ala Arg Leu His Thr Ala
                    965                 970                 975
    Ala Ala Asp Gly Gly Ser Gly Gly Ser Pro Arg Phe Leu Arg Arg Thr
                980                 985                 990
    Val Ser Ala Asn Asp Gly Pro Gln Ala Gln Thr Leu His Arg Gln Gln
                    995                 1000                1005
```

```
Gln Leu Gln Leu Gln Gln Gln Gln His Phe Gly Asn Ala Ser Asp
    1010            1015               1020

Ala Phe Leu Val Ala Ala Ala Ala Gly Ala Pro Pro Thr Leu
    1025            1030            1035

Arg Val Ser Ala Ser Ser Val Arg Ala Ala Ala Pro Gly Pro Gln
    1040            1045               1050

Arg Ser Val Ser Ala Gly Ser His Gly Cys Ser Ser Arg Ser Val
    1055            1060               1065

Ala Ser Ser Ala Asp Cys Ala Ala Ala Ser Glu Val Ser Gly Ala
    1070            1075               1080

Tyr Pro Glu Gly Pro Trp Leu Gln Arg Gly Gly Val Glu Ala Ala
    1085            1090               1095

Leu Gln His Ser Pro Gln Ala Ala Met Val Ala Val Ala Ala Ala
    1100            1105               1110

Ala Ala Gln Leu Tyr Gly Gly Gly Ala Ala Thr Gly Gly Ala Ala
    1115            1120               1125

Ser Ser Leu Pro Thr Ala Ser Arg Gln Leu Gln Cys Arg Cys Ser
    1130            1135               1140

Gly Thr Gly Gly Gly Gly Glu Ser Ser Gly Ser Gly Thr Gly Leu
    1145            1150               1155

Ser Asp Ala Ser Met Pro Ser Pro Arg Trp Ala Gly Ala His Gly
    1160            1165               1170

Ala Gly Glu Asp Gly Gly Ser Ser Ser Thr Pro Ser Ser Gly Arg
    1175            1180               1185

Pro Gln Arg Leu Ala Ala Gly Arg His Pro Asn Arg Arg Leu Thr
    1190            1195               1200

Arg Tyr Gly Glu Cys Leu Asp Thr Pro Ser Pro Arg Ser Pro Ala
    1205            1210               1215

Val Thr Ser Ser Ser His Ala Gly Ala Gly Ala Ser Pro Phe Arg
    1220            1225               1230

His Ala Asp Ser Tyr Arg Leu Ala Ala Leu Ala Ala Leu Ala Ala
    1235            1240               1245

Ala Ser Pro Ala Ala Ala Ser Pro Val Pro Val Pro Ala Ala Ala
    1250            1255               1260

Ala Val Ala Ala Ala Ala Thr Gln Ala Ala Pro Ser Trp Pro Ser
    1265            1270               1275

Pro Ala Arg Ala Thr Arg Pro Arg Gly Ala Ala Ser Pro Ala Cys
    1280            1285               1290

Arg Arg Leu Arg Leu Glu Gly Ala Glu Pro His Asp Ala Ala Ala
    1295            1300               1305

Pro Ser Pro Cys Ser Gly Ala Arg Ser Ser Arg Ser Trp Leu Gln
    1310            1315               1320

His Asp Leu Ser Gly Gly Gly Ala Val Ala Glu Pro Ala Arg Pro
    1325            1330               1335

Leu Ala Pro Gly Val Val Thr Leu Pro Val Tyr Val Ala Arg Ser
    1340            1345               1350

Glu Ser Glu Gly Ser Ala Leu Arg Ser Ala Ala Pro Pro Pro Ala
    1355            1360               1365

Trp Pro Arg Ala Gln Ala Ala Ala Ala Cys Pro Ser Leu Pro Tyr
    1370            1375               1380

Thr Pro Ser Ser Leu Val Arg Tyr Leu Asp Ser Arg Leu Gly Ser
    1385            1390               1395
```

```
Leu Ala Ala Ala Glu Ala Ala Val Ala Glu Ala Gly Glu Glu
    1400            1405            1410

Ile Gly Ala Gln Leu Ala Ser Leu Glu Ala Ala Ala Val Ala
    1415            1420            1425

Ala Ala Gly Gly Ala Ala Gly Gly Gly Ala Arg Ser Gln Ser Arg
    1430            1435            1440

Ser Ala Ala Ala Pro Gly Leu Asn Leu Glu Leu Gly Leu Asp Leu
    1445            1450            1455

Asp Leu Pro Ala Leu Pro Pro Val Pro Met Pro Thr Ala Ile Gly
    1460            1465            1470

Phe Gly Gly Asp Gly Thr Leu Gly Asn Arg Arg Phe Asn Ala Ala
    1475            1480            1485

Ala Pro Ser Phe Arg Gly Tyr Gln Ser Pro Glu Gly Met Leu Thr
    1490            1495            1500

Arg Ala Gly Gly Gly Gly Asp Glu Ala Leu Thr Pro Arg Ser Gly
    1505            1510            1515

His Gly Ser Val Cys Gly Ser Thr Gly Gly Ala Ala Ala Ala Ser
    1520            1525            1530

Phe Asp Glu Ala Arg Ser Ser Gly Ala Gly Gly Asp Gly Gly Arg
    1535            1540            1545

Ser Pro Val Gly Ser Ser Gly Ser Cys Ala Arg Ser Cys Val Gly
    1550            1555            1560

Asn Ala Ala Gly Gly Ala Ala Ser Arg Leu Ala Leu Gly Arg
    1565            1570            1575

Ala Leu Ser Thr Ser Ala Thr Val Gly Ser Pro Arg Ala Gly Arg
    1580            1585            1590

Arg Ala Pro Leu Ala Ala Ala Thr Asp Ser Gly Cys Asp Leu Asp
    1595            1600            1605

His Ser Pro Pro His Lys Pro Ile Asn Ser Thr Cys Ala Thr Pro
    1610            1615            1620

Arg Lys Gln Ser Pro Pro His Lys Pro Ile Thr Ser Thr Cys Ala
    1625            1630            1635

Thr Pro Arg Lys His Thr Pro Arg Ala Ser Phe Ser Gln Ser His
    1640            1645            1650

Ser Gln Val Phe His Glu Asp Gln Gly Cys Asp His His His His
    1655            1660            1665

Gly His His Arg Gln Leu Ser Arg Gly Gly Asp Cys Leu Leu
    1670            1675            1680

Leu His Asp Gln Ala Gln Gly His Ser Arg Thr Ala Ala Ala Ala
    1685            1690            1695

Ala Ala Ser Val Thr Ala Ala Arg Ser Gly Ser Ser Ser Gln Gly
    1700            1705            1710

Leu Pro Leu Gln Pro Ser Pro Ser Gly Arg Pro Pro Thr Ala Glu
    1715            1720            1725

Ser Asp Thr Leu Pro Leu His Asp Ala Gly Ser Gly Ser Cys Gly
    1730            1735            1740

Asn Ser Ser Gly Gly Gly Trp Ser Ala Gln Ala Ser Ser Arg Glu
    1745            1750            1755

Gly Tyr Ala Tyr Ala Tyr Gly Ser Ala Gly Trp Pro Gly Glu Gln
    1760            1765            1770

Cys Tyr Pro Pro Ala Ala His Tyr His Tyr Gln Gln His Gln Asp
    1775            1780            1785

Arg Gln Val Leu Gln Leu His Ser Arg Arg Val Ser Gly Gly Ala
```

```
                1790                1795                1800

Ala Ser Thr Leu Glu Ala Pro Pro Ser Glu Val Asp Val Ala
    1805            1810            1815

Arg Ala Met Ser Thr Gly Arg Gly Cys Asp Asn Ala Glu Gly Asp
1820                1825                1830

Gly Gly Leu Ser Val Gly Met Gly His Ala Gly Trp Gly Pro Gln
    1835            1840            1845

Ala Gln Ala Ala Ala Gln Gln Gln Gln Gln Gln Gln Arg Arg
    1850            1855            1860

Val Ser Gly Val Ser Arg Gly Ser Ser Ser Cys Arg Pro Ser
    1865            1870            1875

Thr Ser Gly Ser Gly Cys Ser Ser Glu Phe Trp Ala Ala Val
    1880            1885            1890

Val Pro Val Asp Gln Ser Pro Ala Ala Ala Gly Ala Arg Gly
    1895            1900            1905

Val Val Gln Leu Ala Val Ala Pro Ala Leu Ser Arg Ser Ser Leu
1910                1915                1920

Ser Pro Leu Lys Val Asp Val Arg Gln Glu Asp Gly Val Pro Gly
    1925            1930            1935

Ala Glu Gly Pro Ala Thr Gly Arg Leu Ala Gly Ser Pro Gly Ser
    1940            1945            1950

Ser Gln Leu Val Cys Gly Leu Cys Ala Gly Gly Leu Arg Ala Ala
    1955            1960            1965

Val Ala Leu Thr Pro Cys Gly His Ser Phe Cys Ala Glu Cys Leu
    1970            1975            1980

Ala Gly His Leu Gly Ser Ala Val Leu Gly Gly Ser Arg Val Gly
    1985            1990            1995

Cys Pro Asn Arg Cys Pro Ala Phe Glu Ala Val Val Ile Asn His
2000                2005                2010

Pro Ala Arg Arg Leu Glu Ser Lys Arg Ser Asn Ala Thr Thr Ala
    2015            2020            2025

Thr Ala Ala Pro Arg Ser His Ala Pro Ala Arg Ala Gln Pro Asp
    2030            2035            2040

Gly Gln Cys Glu Ser Ser Pro Phe Glu Ala Pro Ala Ala Ala Ala
    2045            2050            2055

Ala Val Ala Ala His Ala Ala Ala Arg Ala Ser Ala Ala Ser Thr
    2060            2065            2070

Pro Val Arg Gly Ala Arg Gly Gly Ser Asp Pro Gly Pro Ala Ala
    2075            2080            2085

Ser Pro Ala Leu Arg Ala Ala Gly Gly Ala Thr Ser Arg Leu Arg
    2090            2095            2100

Thr Arg Met Gly Ser Arg Gly Ser Gly Tyr Gly Pro Ser Pro Ser
    2105            2110            2115

Arg Arg Arg Glu Gly Ala Gly Thr Gly Ser Glu Pro Gly Ala Trp
    2120            2125            2130

Ser Glu Met Leu Ala Asp Ala Ala Leu Pro Val Pro Ala Ile Arg
    2135            2140            2145

Leu His Leu Gln Gln Gly Glu Val Leu Leu Arg Ala Leu Ser Gln
    2150            2155            2160

Leu Leu Asp Asp Thr Pro Gln Leu Pro Pro Pro Pro Pro Ser
    2165            2170            2175

Ile Pro Ala Ala Thr Ala Thr Thr Thr Thr Ser Thr Ala Ala
    2180            2185            2190
```

-continued

Ala Ala Ala Ala Ala Ala Thr Thr Gln Ala Ala Thr Ala Ala Val
            2195                2200                2205

Arg Glu Ala Arg Ala Ala Val Val Glu Trp Arg Arg Val Val Leu
2210                2215                2220

Asp Val Leu Gly Cys Leu Gly Arg Leu Ala Leu Glu His Val Arg
2225                2230                2235

Val Arg Glu Ala Leu Gly Ala Ala Gly Ala Ser Gln Gly Cys Val
2240                2245                2250

Leu Ala Leu Arg Ala Val Gln Ala Gln Met Ala Ala Ala Glu Leu
2255                2260                2265

Cys Thr Lys Gly Gly Glu Arg Ser Leu Val Asp Lys Asp Gly Ile
2270                2275                2280

Val Lys Lys Pro Thr Val Ala Glu Ala Glu Lys Glu Ala Glu Ala
2285                2290                2295

Ala Leu Val Ala Glu Glu Arg Ala Thr Ala Gln Asp Thr Ser Arg
2300                2305                2310

Ala Ala Cys Val Leu Leu Cys His Leu Leu Asn Pro Pro Ala Pro
2315                2320                2325

Ser Pro Pro Ala Glu Thr Gly Ala Thr Asp Ser Glu Gln Ala Val
2330                2335                2340

Cys Arg Gln Gln Ser Asn Gln Trp Ala Leu Ala Arg Met Gly Gly
2345                2350                2355

Ala Glu Ala Leu Leu Ala Leu Leu Leu Pro Ala Gln Glu Pro Gly
2360                2365                2370

Lys Gly Ala Thr Asp Ala Gly Gly Glu Gly Ala Gly Gly Asn Gly
2375                2380                2385

Asn Ala Glu Arg Arg Arg Trp Ser Gly Gln Met Ala Ala Ala Leu
2390                2395                2400

Thr Ala Leu Gln Arg Met Val Val Gly Asn Ile Met Thr Gln Thr
2405                2410                2415

His Val Ala Glu Cys Gly Ser Ala Ala Val Ile Arg Thr Leu Ala
2420                2425                2430

Ala Ala Thr Arg Ala Ala Ala Ala Ser Gly Asp Glu Ala Val Gln
2435                2440                2445

Ala Ala Ala Leu Arg Leu Leu Ala Asp Val Ala Arg Gly Gly Asp
2450                2455                2460

Ala Ala His Ala Ala Val Arg Gln Met Leu Leu Glu Ala Gly Ala
2465                2470                2475

Leu Gly Ala Ala Leu Ala Ala Leu Arg Asp Ser Val Ala Ala Phe
2480                2485                2490

Gly Gly Cys Asn Gly Gly Arg Glu Gly Ser Gly Asn Ser Gly Cys
2495                2500                2505

Ala Asp Gly Gly Ser Ala Ala Ser Ser Gly Met Glu Val Ser Pro
2510                2515                2520

Val Leu Met Ala Ala Leu Asp Ala Ile His Val Leu Met Gly Pro
2525                2530                2535

Ser Glu Gln His Val Asp Gly Ser Glu Pro Pro Leu Ala Leu Gln
2540                2545                2550

Ala Val Val Arg Arg Glu Leu Arg Arg Leu Gly Ala Pro Arg Leu
2555                2560                2565

Leu Ala Asp Cys Val Arg Glu Leu Arg Leu Gln Gln Glu Asp Glu
2570                2575                2580

| | | | | | | | | | | | |
|---|---|---|---|---|---|---|---|---|---|---|---|
| Gln | Gly | Glu | Gly | Arg | Ala | Gln | Glu | Trp | Glu | Arg | Ala Ser Gly |
| | | 2585 | | | | 2590 | | | | 2595 | |
| Arg | Thr | Gly | His | Ser | Arg | His | Ala | Pro | Asp | Gly | Arg Val Leu Pro |
| | 2600 | | | | | 2605 | | | | | 2610 |
| Gly | Ala | Val | Ala | Gly | Ala | Gly | Gly | Lys | Gln | Pro | His Pro Arg Pro |
| | 2615 | | | | | 2620 | | | | | 2625 |
| Trp | Asp | Gly | Ser | Arg | Ser | Arg | Glu | Glu | Arg | Gly | Ser Ala Gly Gly |
| | 2630 | | | | | 2635 | | | | | 2640 |
| Asp | Cys | Leu | Gly | Cys | Ser | Pro | Val | Leu | Arg | Ala | Met Ala Glu Leu |
| | 2645 | | | | | 2650 | | | | | 2655 |
| Gln | Ala | Arg | Val | Cys | Ala | Val | Ala | Gly | Gly | Thr | Gly Trp Val Arg |
| | 2660 | | | | | 2665 | | | | | 2670 |
| Cys | Val | Val | Gln | Met | Leu | Gly | Ala | Ser | Pro | Asp | Gly Val Gly Gln |
| | 2675 | | | | | 2680 | | | | | 2685 |
| Ala | Gly | Arg | Gly | Gly | Val | Asp | Gly | Gly | Gly | Ala | Ala Met Ala Ala |
| | 2690 | | | | | 2695 | | | | | 2700 |
| Val | Ala | Ala | His | Arg | Val | Gln | Leu | Arg | Leu | Leu | Ala Val Ala Ala |
| | 2705 | | | | | 2710 | | | | | 2715 |
| Gly | Gly | Gly | Phe | Ala | Leu | Gly | Ala | Ala | Val | Thr | Gly Ala Val Ala |
| | 2720 | | | | | 2725 | | | | | 2730 |
| Ala | Met | Trp | Met | Ala | | | | | | | |
| | 2735 | | | | | | | | | | |

<210> SEQ ID NO 60
<211> LENGTH: 2780
<212> TYPE: DNA
<213> ORGANISM: Chlamydomonas reinhardtii

<400> SEQUENCE: 60

```
ttagttatca tatcctttga agcagacttg ctattcgcaa cccaccgcca cgctgtgctg     60
tgtgcgaaac acagtacgct cactttggca cggagagagc gcgcagctgc ttaactactc    120
tgtatttgct ctagaatgcg acatggtatt aaccggtttg atctttgctc gcactgataa    180
ttgtcggcat ttggtttcct cgcaaactgg acgcatgctg taattcacac ctgagatggc    240
gcacgagcag cagctcataa caaaacgcgc ctggctgggc ccgggcggtc cggagggcta    300
cctcacggtc gcgagcgcca gcctaaagtg gcagcctgca gccagcggag ccacgggtgt    360
gcaggagctg cgcattcccc tgtcatgcat tacaaataat cagcgcgcca aggacaagcc    420
gctggtgcgc atcactttca ccaatggcac cggcggcgcc gcggcgcatg tgttccagtt    480
tgagagcgtg gcgaccgtg atgcggccct ggacgtgctc acaaaggtca ttgcggcggt    540
ggcggcagcg gcgtcaggca gcggcacggc agccagtggc ggcggcggcg gtggtgatgc    600
tgggccagca gtggcgggcg gcttcaccag gcagcagcgg cagcagatgg ttgcacggga    660
cgctgacctc aaggccctgt acgacgagct ggtgggcggc ggggtggtgg gcgaggccga    720
cttctggggc ggcgtggcgg cacgctggcc ggcggcaaag ccggccagct ggggcacggc    780
ggcggcgggg ccggcggggg cgggcgggct gccggggcgg cggcgcctgg gcctgagcaa    840
catcctgcag cgagtggagg ccgaggtgga cgggcggcac caacgtgtgc tgcgtgtgag    900
cctgacgccc gagcaggtgg cgcagatctt tgccgagcag ccggcggtgc tgcgcgccta    960
ccgcgagcac gtgccgcacc gcatggcgga ggaggacttc tggcggcgat acgtccggca   1020
tgagatgcaa aaggagtcga agcgcaaggc ccggctgag gcatcaacc ccaatgccgc    1080
ggcggcgggc ggcggcgcca tggcggatga cgccggcggc gacatcttca gggaggcggc   1140
```

```
ggcggcggtg gcggcggagg cggcgcggcg gccgggccag gcggcggcgc accgtgaggc    1200
agtggatccg gagctggacc tggcggcggc ggcggcggag aggtacagcg gacacggcac    1260
cgcacacgcg gcagcccggg acccgagat ggagctggcg gcgggcagtg gcggcggagg    1320 cagcggggc catcaccacc cgctggccgc cgaccccgac ccggacgacc tggcggccgc     1380
catcaacaag cacggcgagg tggtgctgca gggtgtggag gctttggccc gggtggaggc    1440
gcagctcaaa ggcaccgcac cggcagcagc aggcggccac cacggccacc acggacatca    1500
ccaacacaac caccacaacc acaaccacaa ccaccataga gcggacggcg cggacccggg    1560
gccaggcagc aacggcggcg acccacacg ggaggggcag ggcggcgggg ggctgctggg     1620
tcggcggcgg cggcgacaca gcgcgggtct tgaggacctg cacgagccgc ccgcacgcca    1680
gttggacgcc ctcagcattg ccgaccccg caggtacttt gagcgcagcg ggcagcaggg     1740
cggcggggcg gcgccagcag cacacatggg cggcggctgg ggtggggccg gcggaggtgg    1800
gggcggcggg ccgggcctgt cgggcgctgc agcggtgctg gctgtgtgt ctcccggctg     1860 cctgccgctg ccgccgctgc aggggtgtgc ggcggaggag gcgctgctgg aggccacacc    1920
gctggcccga gcgctggcgg aggaggaggc tgcgggtccg ggcggcgccg cgactgcctc    1980
tggccccggg ggcgccagtg cgctgctgcg cgaccccgcc tcctccgtgc cgcccgagac    2040
actggccttc ctgcggcgca ccgtgctgtc cgtcaacgag gcgtgccggc acctgtggcg    2100
ctgcctgccc gccaacacac ccgcgcggag agacaaggcc gggcggctgg ctcgtctgct    2160
tgagtccaag cgcggcgagg tggaggccct gaacgaccgc gcccggggag tggaggggcg    2220
cttcatccgg cagctgctca agccgcccat ggacatgctg ctggcggcgc tggtcaggtg    2280
ggatgaggag cagcagaagc ggccggccgg agcgtcatga tgaacggcct gacggcagca    2340
gcgcggggta tgactctggc gtgggcggct cagtgatgcg gcgctggacg ttggcatgtg    2400
caggcataag gaactgggag cagggttgag cgcgcttggt tatgtgagcg tactagctcg    2460
gagctctttg acctggggct aggtgcatgc cgtctgcccc gatgagttgt gacccagata    2520
tgtctgaact ggccggactg agggcgagag gagttacaga gagtcgtgac atcgcctcct    2580
ctagcaagat caagtgcgta agctacgcac agtctgcctt tgacctgct tacggtgccc     2640 caggcgcctg acacacgcga ccatctccct gttccgtggt acaacgacca ctttctctgt    2700
cggccggcta tgacggaagt attgacagct gaagccttc gcaccgaagt caagatgcat     2760
ctacatatcc acttcaacgg                                                2780
```

<210> SEQ ID NO 61
<211> LENGTH: 2085
<212> TYPE: DNA
<213> ORGANISM: Chlamydomonas reinhardtii

<400> SEQUENCE: 61

```
atggcgcacg agcagcagct cataacaaaa cgcgcctggc tgggcccggg cggtccggag     60
ggctacctca cggtcgcgag cgccagccta aagtggcagc ctgcagccag cggagccacg    120
ggtgtgcagg agctgcgcat tcccctgtca tgcattacaa ataatcagcg cgccaaggac    180
aagccgctgg tgcgcatcac tttcaccaat ggcaccggcg gcgccgcggc gcatgtgttc    240
cagtttgaga gcgtggcgga ccgtgatgcg gccctggacg tgctcacaaa ggtcattgcg    300
gcggtggcgg cagcagcgtc aggcagcggc acgcagcca gtggcggcgg cggcggtggt     360
gatgctgggc cagcagtggc gggcggcttc accaggcagc agcggcagca gatggttgca    420
cgggacgctg acctcaaggc cctgtacgac gagctggtgg gcggcggggt ggtgggcgag    480
```

```
gccgacttct ggggcggcgt ggcggcacgg ctggcggcgg cgaagccggc cagctggggc      540
acggcggcgg cggggccggc gggggcgggc gggctgccgg ggcggcggcg cctgggcctg      600
agcaacatcc tgcagcgagt ggaggccgag gtggacgggc ggcaccaacg tgtgctgcgt      660
gtgagcctga cgcccgagca ggtggcgcag atctttgcgg agcagccggc ggtgctgcgc      720
gcctaccgcg agcacgtgcc gcaccgcatg gcggaggagg acttctggcg gcgatacgtc      780
cggcatgaga tgcacaagga gtcgaagcgc aaggcccggg ctgagggcat caaccccaat      840
gccgcggcgg cgggcggcgg cgccatggcg gatgacgccg gcggcgacat cttcagggag      900
gcggcggcgg cggtggcggc ggaggcggcg cggcggccgg gccaggcggc ggcgcaccgt      960
gaggcagtgg atccggagct ggacctggcg gcggcggcgg cggagaggta cagcggacac     1020
ggcaccgcac acgcggcagc ccgggacccc gagatggagc tggcggcggg cagtggcggc     1080
ggaggcagcg ggggccatca ccacccgctg gccgccgacc ccgacccgga cgacctggcg     1140
gccgccatca acaagcacgg cgaggtggtg ctgcagggtg tggaggcttt ggcccgggtg     1200
gaggcgcagc tcaaaggcac cgcaccggca gcagcaggcg gccaccacgg ccaccacgga     1260
catcaccaac acaaccacca caaccacaac cacaaccacc atagagcgga cggcgcggac     1320
ccggggccag gcagcaacgg cggcgaccca cacggggagg ggcagggcgg cggggggctg     1380
ctgggtcggc ggcggcggcg acacagcgcg ggtcttgagg acctgcacga gccgcccgca     1440
cgccagttgg acgccctcag cattgccgac ccccgcaggt actttgagcg cagcgggcag     1500
cagggcggcg gggcggcgcc agcagcacac atgggcggcg gctggggtgg ggccggcgga     1560
ggtgggggcg gcgggccggg cctgtcgggc gctgcagcgg tgctgggctg tgtgtctccc     1620
ggctgcctgc cgctgccgcc gctgcagggg tgtgcggcgg aggaggcgct gctgcaggcc     1680
acaccgctgg cccgagcgct ggcggaggag gaggctgcgg gtccgggcgg cgccgcgact     1740
gcctctggcc cgggcggcgc cagtgcgctg ctgcgcgacc ccgcctcctc cgtgccgccc     1800
gagacactgg ccttcctgcg gcgcaccgtg ctgtccgtca acgaggcgtg ccggcacctg     1860
tggcgctgcc tgcccgccaa cacacccgcg cggagagaca aggccgggcg gctggctcgt     1920
ctgcttgagt ccaagcgcgg cgaggtggag gccctgaacg accgcgcccg gggagtggag     1980
gggcgcttca tccggcagct gctcaagccg cccatggaca tgctgctggc ggcgctggtc     2040
aggtgggatg aggagcagca gaagcggccg gccggagcgt catga                    2085
```

<210> SEQ ID NO 62
<211> LENGTH: 694
<212> TYPE: PRT
<213> ORGANISM: Chlamydomonas reinhardtii

<400> SEQUENCE: 62

Met Ala His Glu Gln Gln Leu Ile Thr Lys Arg Ala Trp Leu Gly Pro
1               5                   10                  15

Gly Gly Pro Glu Gly Tyr Leu Thr Val Ala Ser Ala Ser Leu Lys Trp
            20                  25                  30

Gln Pro Ala Ala Ser Gly Ala Thr Gly Val Gln Glu Leu Arg Ile Pro
        35                  40                  45

Leu Ser Cys Ile Thr Asn Asn Gln Arg Ala Lys Asp Lys Pro Leu Val
    50                  55                  60

Arg Ile Thr Phe Thr Asn Gly Thr Gly Gly Ala Ala His Val Phe
65                  70                  75                  80

Gln Phe Glu Ser Val Ala Asp Arg Asp Ala Ala Leu Asp Val Leu Thr

-continued

```
                    85                  90                  95
Lys Val Ile Ala Ala Val Ala Ala Ala Ser Gly Ser Gly Thr Ala
                100                 105                 110
Ala Ser Gly Gly Gly Gly Gly Asp Ala Gly Pro Ala Val Ala Gly
            115                 120                 125
Gly Phe Thr Arg Gln Gln Arg Gln Gln Met Val Ala Arg Asp Ala Asp
        130                 135                 140
Leu Lys Ala Leu Tyr Asp Glu Leu Val Gly Gly Val Val Gly Glu
145                 150                 155                 160
Ala Asp Phe Trp Gly Val Ala Ala Arg Leu Ala Ala Lys Pro
            165                 170                 175
Ala Ser Trp Gly Thr Ala Ala Gly Pro Ala Gly Ala Gly Gly Leu
            180                 185                 190
Pro Gly Arg Arg Arg Leu Gly Leu Ser Asn Ile Leu Gln Arg Val Glu
        195                 200                 205
Ala Glu Val Asp Gly Arg His Gln Arg Val Leu Arg Val Ser Leu Thr
    210                 215                 220
Pro Glu Gln Val Ala Gln Ile Phe Ala Glu Gln Pro Ala Val Leu Arg
225                 230                 235                 240
Ala Tyr Arg Glu His Val Pro His Arg Met Ala Glu Glu Asp Phe Trp
            245                 250                 255
Arg Arg Tyr Val Arg His Glu Met His Lys Glu Ser Lys Arg Lys Ala
        260                 265                 270
Arg Ala Glu Gly Ile Asn Pro Asn Ala Ala Ala Gly Gly Gly Ala
    275                 280                 285
Met Ala Asp Asp Ala Gly Gly Asp Ile Phe Arg Glu Ala Ala Ala Ala
    290                 295                 300
Val Ala Ala Glu Ala Ala Arg Arg Pro Gly Gln Ala Ala Ala His Arg
305                 310                 315                 320
Glu Ala Val Asp Pro Glu Leu Asp Leu Ala Ala Ala Ala Glu Arg
            325                 330                 335
Tyr Ser Gly His Gly Thr Ala His Ala Ala Arg Asp Pro Glu Met
        340                 345                 350
Glu Leu Ala Ala Gly Ser Gly Gly Gly Ser Gly Gly His His His
    355                 360                 365
Pro Leu Ala Ala Asp Pro Asp Pro Asp Leu Ala Ala Ala Ile Asn
    370                 375                 380
Lys His Gly Glu Val Val Leu Gln Gly Val Glu Ala Leu Ala Arg Val
385                 390                 395                 400
Glu Ala Gln Leu Lys Gly Thr Ala Pro Ala Ala Ala Gly Gly His His
            405                 410                 415
Gly His His Gly His His Gln His Asn His His Asn His Asn His Asn
        420                 425                 430
His His Arg Ala Asp Gly Ala Asp Pro Gly Pro Gly Ser Asn Gly Gly
    435                 440                 445
Asp Pro His Gly Glu Gly Gln Gly Gly Gly Leu Leu Gly Arg Arg
    450                 455                 460
Arg Arg Arg His Ser Ala Gly Leu Glu Asp Leu His Glu Pro Pro Ala
465                 470                 475                 480
Arg Gln Leu Asp Ala Leu Ser Ile Ala Asp Pro Arg Arg Tyr Phe Glu
            485                 490                 495
Arg Ser Gly Gln Gln Gly Gly Gly Ala Ala Pro Ala Ala His Met Gly
        500                 505                 510
```

Gly Gly Trp Gly Gly Ala Gly Gly Gly Gly Gly Pro Gly Leu
        515                 520                 525

Ser Gly Ala Ala Ala Val Leu Gly Cys Val Ser Pro Gly Cys Leu Pro
    530                 535                 540

Leu Pro Pro Leu Gln Gly Cys Ala Ala Glu Glu Ala Leu Leu Glu Ala
545                 550                 555                 560

Thr Pro Leu Ala Arg Ala Leu Ala Glu Glu Glu Ala Ala Gly Pro Gly
                565                 570                 575

Gly Ala Ala Thr Ala Ser Gly Pro Gly Gly Ala Ser Ala Leu Leu Arg
            580                 585                 590

Asp Pro Ala Ser Ser Val Pro Pro Glu Thr Leu Ala Phe Leu Arg Arg
        595                 600                 605

Thr Val Leu Ser Val Asn Glu Ala Cys Arg His Leu Trp Arg Cys Leu
    610                 615                 620

Pro Ala Asn Thr Pro Ala Arg Arg Asp Lys Ala Gly Arg Leu Ala Arg
625                 630                 635                 640

Leu Leu Glu Ser Lys Arg Gly Glu Val Glu Ala Leu Asn Asp Arg Ala
                645                 650                 655

Arg Gly Val Glu Gly Arg Phe Ile Arg Gln Leu Leu Lys Pro Pro Met
            660                 665                 670

Asp Met Leu Leu Ala Ala Leu Val Arg Trp Asp Glu Glu Gln Gln Lys
        675                 680                 685

Arg Pro Ala Gly Ala Ser
        690

<210> SEQ ID NO 63
<211> LENGTH: 2293
<212> TYPE: DNA
<213> ORGANISM: Chlamydomonas reinhardtii

<400> SEQUENCE: 63
cttactccca aactcaaaag aagcactgaa tttaactaca actgatagcc atatgttcgg      60
ctcagacgta gggcaccgtg cttagaccca cgcccaagac aatcggtccc cagttataag     120
ggcctgaagg cccgagcgtt cccttagagc ggcaatggac tctgatagcg acgatgagcg     180
tgcggcgggc tacgtgccag tgttggcagc atcaatgcca cgagctgctg cagcggcggc     240
agtggccagc cccgcggcga agcaaccttc aacgttcta caagatggtg tttcgcttta     300
caccaatgag ctgttcaccg acaacaacgg ggatgtgctg ggcgagggtc ctgggctcgc     360
gtctcccagc ggagcggcgc ccggcagcgc acgaaaaggc ctggctgcga aacggcagga     420
gcggttgcag gggaacgcat acacgccaaa ctcgctccta agaacgcct cactgcgtaa      480
ccccggtgcc cctgcgtcgc cgggtatgcg ggactcgccc tcctccttcc ggccatccac     540
cctgtcgcaa acgggaccg ccaccacagt ggaaacgaca ttggtcagcc caaccgcaa      600
cagcaacaac cagggcatcg ccgggggcgt gggaatggtg cacggcttgc cgccagcta     660
cgaccccaac gaggggcagg aggagcctgt gccctccacg cggtacgtgg cgccggcagc     720
ggtgccggtg gcacgcgccg tgccccagct ggaccttca gacatgccgg cattcctgca     780
gcagccgggg cctaagaatg gccggtgca gtgcgtcatc gtgcgcgacc gcgggtctgc     840
aaagatgtac ccgcggtact cgctgttcct ggaggagggg cggcgctttc tgctgtcagc     900
gcgcaagcgg aagaagcaga ccaccagcaa ctacatcata tccatggact acgaggacct     960
cagccgggag agcgggtcgt tctttgggaa ggtccgcgcc aacttcgtgg gtacggagtt    1020

| | |
|---|---|
| cacggtgtat gaccgggggg ttaaggcggg caagaaggac gcccagggcg acggccagcg | 1080 |
| cgaggagctg ggggcggtga cgtaccagta caacgtgctg ggcacgcggg ggccgcgcaa | 1140 |
| gatgatggcg gccatccccg gggtggacgg cagcgggcgg cgcatgttca accccagcgg | 1200 |
| cgacgcggac accatcctgg agcggctcaa acaccggaag ggactggagg agctggtggt | 1260 |
| gatgggcaac aagccgccgc gctggaatga cgagctgaac gcctactgcc tgaacttcaa | 1320 |
| cgggcgcgtg acggaggcgt ccgtgaagaa cttccagctg gtgtcggacg acaaccacaa | 1380 |
| ccacgtcatc ctgcagttcg gcaaggtcgg caaggacacg ttcaccatgg actaccagtg | 1440 |
| gcccatctcc gcgtttcagg cgttcgccat ctgcatgtcg tcctttgaca caagctggc | 1500 |
| gtgcgagtaa tgaagtggtg atgcagcagt cagcggcaga atgtggctgg gagtcgcgtg | 1560 |
| gaggagcgca gagcggaggg tgctgcagat tttggagcct aaagtggact cgtgatggag | 1620 |
| ccggaggttg gccatctggc cggaggtaca tctggcagct gccagggctt ggggagcttg | 1680 |
| ggtaggaatg ccgccgtgtg ctgtaaggcg caggttacag gctcgggagc tttgtctaga | 1740 |
| caaatgatag caacccgtgc ctacacttgg gtgtgcatgg ctgaagagcg gtgcatacgg | 1800 |
| taggacagat cagggcgtgg cgatggggtg ttaggtagct cggaggtaac gggtgcagcg | 1860 |
| gcttgggacg gcccgatggg caaggttttgc tgcatgtact gccgacaggg gcacaagaag | 1920 |
| aaattgtata atgtatgttc taggacagct ccgactaacc cccaactaac tcgcgtacgg | 1980 |
| caccctcagc cgtacaggag ttgactaggg agtcggcagc tgcgcgagtg ggagcgggta | 2040 |
| gttgtacggt tgcccagctc gcaagctacc tgactgtcgt gacgcacacg ggcagttgcc | 2100 |
| acgagtcagc aggcgcgcga gtgggagctg gcactcagta gagagctcac gcgtgtggga | 2160 |
| agctgcggtt gagcataatg gagcacggcg gaggctgccg gttggcgcgg cgcgcgattg | 2220 |
| gtagtgcata gtcgcgcgcg tgcgtgctgt gtgggaagcc ccgtgtgtga gctacgtgta | 2280 |
| aactcagaga gac | 2293 |

<210> SEQ ID NO 64
<211> LENGTH: 1356
<212> TYPE: DNA
<213> ORGANISM: Chlamydomonas reinhardtii

<400> SEQUENCE: 64

| | |
|---|---|
| atggactctg atagcgacga tgagcgtgcg gcgggctacg tgccagtgtt ggcagcatca | 60 |
| atgccacgag ctgctgcagc ggcggcagtg gccagccccg cggcgaagca accttccaac | 120 |
| gttctacaag atggtgtttc gctttacacc aatgagctgt tcaccgacaa caacggggat | 180 |
| gtgctgggcg agggtcctgg gctcgcgtct cccagcggag cggcgcccgg cagcgcacga | 240 |
| aaaggcctgg ctgcgaaacg gcaggagcgg ttgcagggga acgcatacac gccaaactcg | 300 |
| ctcctaaaga acgcctcact gcgtaacccc ggtgcccctg cgtcgccggg tatgcgggac | 360 |
| tcgccctcct ccttccggcc atccaccctg tcgcaaacgg ggaccgccac cacagtggaa | 420 |
| acgacattgg tcagccccaa ccgcaacagc aacaaccagg gcatcgccgg gggcgtggga | 480 |
| atggtgcacg gcttgcgcgc cagctacgac cccaacgagg ggcaggagga gcctgtgccc | 540 |
| tccacgcggt acgtggcgcc ggcagcggtg ccggtgcac gcgccgtgcc ccagctggac | 600 |
| ctttcagaca tgccggcatt cctgcagcag ccggggccta gaatgggcc ggtgcagtgc | 660 |
| gtcatcgtgc gcgaccgcgg gtctgcaaag atgtacccgc ggtactcgct gttcctggag | 720 |
| gaggggcggg gctttctgct gtcagcgcgc aagcggaaga agcagaccac cagcaactac | 780 |
| atcatatcca tggactacga ggacctcagc cgggagagcg ggtcgttctt tgggaaggtc | 840 |

-continued

```
cgcgccaact tcgtgggtac ggagttcacg gtgtatgacc ggggggttaa ggcgggcaag      900
aaggacgccc agggcgacgg ccagcgcgag gagctggggg cggtgacgta ccagtacaac      960
gtgctgggca cgcgggggcc gcgcaagatg atggcggcca tccccggggt ggacggcagc     1020
gggcggcgca tgttcaaccc cagcggcgac gcggacacca tcctggagcg gctcaaacac     1080
cggaagggac tggaggagct ggtggtgatg ggcaacaagc cgccgcgctg aatgacgag      1140 ctgaacgcct actgcctgaa cttcaacggg cgcgtgacgg aggcgtccgt gaagaacttc     1200
cagctggtgt cggacgacaa ccacaaccac gtcatcctgc agttcggcaa ggtcggcaag     1260
gacacgttca ccatggacta ccagtggccc atctccgcgt ttcaggcgtt cgccatctgc     1320
atgtcgtcct ttgacaacaa gctggcgtgc gagtaa                              1356
```

<210> SEQ ID NO 65
<211> LENGTH: 451
<212> TYPE: PRT
<213> ORGANISM: Chlamydomonas reinhardtii

<400> SEQUENCE: 65

```
Met Asp Ser Asp Ser Asp Asp Glu Arg Ala Ala Gly Tyr Val Pro Val
1               5                  10                  15

Leu Ala Ala Ser Met Pro Arg Ala Ala Ala Ala Ala Val Ala Ser
            20                  25                  30

Pro Ala Ala Lys Gln Pro Ser Asn Val Leu Gln Asp Gly Val Ser Leu
        35                  40                  45

Tyr Thr Asn Glu Leu Phe Thr Asp Asn Gly Asp Val Leu Gly Glu
    50                  55                  60

Gly Pro Gly Leu Ala Ser Pro Ser Gly Ala Ala Pro Gly Ser Ala Arg
65                  70                  75                  80

Lys Gly Leu Ala Ala Lys Arg Gln Glu Arg Leu Gln Gly Asn Ala Tyr
                85                  90                  95

Thr Pro Asn Ser Leu Leu Lys Asn Ala Ser Leu Arg Asn Pro Gly Ala
            100                 105                 110

Pro Ala Ser Pro Gly Met Arg Asp Ser Pro Ser Ser Phe Arg Pro Ser
        115                 120                 125

Thr Leu Ser Gln Thr Gly Thr Ala Thr Thr Val Glu Thr Thr Leu Val
    130                 135                 140

Ser Pro Asn Arg Asn Ser Asn Asn Gln Gly Ile Ala Gly Gly Val Gly
145                 150                 155                 160

Met Val His Gly Leu Arg Ala Ser Tyr Asp Pro Asn Glu Gly Gln Glu
                165                 170                 175

Glu Pro Val Pro Ser Thr Arg Tyr Val Ala Pro Ala Ala Val Pro Val
            180                 185                 190

Ala Arg Ala Val Pro Gln Leu Asp Leu Ser Asp Met Pro Ala Phe Leu
        195                 200                 205

Gln Gln Pro Gly Pro Lys Asn Gly Pro Val Gln Cys Val Ile Val Arg
    210                 215                 220

Asp Arg Gly Ser Ala Lys Met Tyr Pro Arg Tyr Ser Leu Phe Leu Glu
225                 230                 235                 240

Glu Gly Arg Arg Phe Leu Leu Ser Ala Arg Lys Arg Lys Lys Gln Thr
                245                 250                 255

Thr Ser Asn Tyr Ile Ile Ser Met Asp Tyr Glu Asp Leu Ser Arg Glu
            260                 265                 270

Ser Gly Ser Phe Phe Gly Lys Val Arg Ala Asn Phe Val Gly Thr Glu
```

```
                275                 280                 285
Phe Thr Val Tyr Asp Arg Gly Val Lys Ala Gly Lys Lys Asp Ala Gln
    290                 295                 300
Gly Asp Gly Gln Arg Glu Glu Leu Gly Ala Val Thr Tyr Gln Tyr Asn
305                 310                 315                 320
Val Leu Gly Thr Arg Gly Pro Arg Lys Met Met Ala Ala Ile Pro Gly
                325                 330                 335
Val Asp Gly Ser Gly Arg Arg Met Phe Asn Pro Ser Gly Asp Ala Asp
            340                 345                 350
Thr Ile Leu Glu Arg Leu Lys His Arg Lys Gly Leu Glu Glu Leu Val
                355                 360                 365
Val Met Gly Asn Lys Pro Pro Arg Trp Asn Asp Glu Leu Asn Ala Tyr
    370                 375                 380
Cys Leu Asn Phe Asn Gly Arg Val Thr Glu Ala Ser Val Lys Asn Phe
385                 390                 395                 400
Gln Leu Val Ser Asp Asp Asn His Asn His Val Ile Leu Gln Phe Gly
                405                 410                 415
Lys Val Gly Lys Asp Thr Phe Thr Met Asp Tyr Gln Trp Pro Ile Ser
            420                 425                 430
Ala Phe Gln Ala Phe Ala Ile Cys Met Ser Ser Phe Asp Asn Lys Leu
    435                 440                 445
Ala Cys Glu
    450

<210> SEQ ID NO 66
<211> LENGTH: 3036
<212> TYPE: DNA
<213> ORGANISM: Chlamydomonas reinhardtii

<400> SEQUENCE: 66
gtatcagtcg tgggcaattg tagaagacgc cctgactgtg cgataggaca catttgctta      60
ggcttcttct tcagccggaa attgtggtcg ccaccgactt gcgctttctc acaccagcaa     120
acatggcgct tccaggctcc acaatgaacc ttacaacccg ctgctctact acaccgcggt     180
cggctgtggt tgcgcgcgcg gtggctgcgc ccacgcgacc caccaccaag tctgcggtgc     240
cagagctgct ggatagccgg ccaggcgagc gcaatctcaa cttcatggag tatgctcagg     300
cgactcagat gctggaccgg ctcaagggcc aggcctctga cctggaattg ctgctggacc     360
agctcaacgc gctggaggcc agcctcgacg agagcgttct ggcgccgccc acggtggacg     420
accccaagga gcgggctgcg cgacaagcac ggcgcgctgc caagcgtgca gagcgtaggg     480
cccaggcgac atccgcaaca gtcgcggccg cggctgggcc ggcaatgtca gcagtggtct     540
cgcattccac gccgacgaag gctgctgctg cgccggccac gtcaacagcg agcagcagct     600
ccagcgatag tggtttgcta gacctggtga gctttgttgg cggctttgac acgcggccga     660
tcccggcaac gacgtctgca ccccctgctg gcgccagcag ctccgacgtg cagcacctgg     720
aggacctctt caaactcagc gtcggcgagc ccgacatccc ccgggcctcc gcttcagcag     780
cgcctgcggt gctgcggcca cgcaagctca ccaaagaa gccctctgcg gcaccctccg     840
cggcggtgac ggcagcaccc tcgccggcac ccacgctccc cagcacgccc agcaccagcg     900
cgcgcattgc gcccgcgccc ggctccctcg cggatgagct ggagcggtta ctggggccca     960
ccacgtcacg ggaggcggct gagtctgagg acgaggacag cttcgcgggg ccgtctgagg    1020
acgacctgct ggcgctggag caggaggtgt cgcgcaagtc gtcacggctg cctgtgctag    1080
```

| | |
|---|---|
| acgaggaaga cgaggaggat gagcagcagc agctggagga caacgaggag gacgcggtgg | 1140 |
| cggggcccgg ctctttggag gcgtcggcaa tggcgactcg gacgtccagc cagctgtcca | 1200 |
| tcatgcagac ggggccgtcg ctgcttagcc tggtcccagc atccgcggcg ccaggccgca | 1260 |
| gcgccaaggc gcgcgcctcc cggcgcgcgg gcgcaacgg tcacgctagc gggcggctgg | 1320 |
| gtggcgcgac agctaacgcg gcggggcggg gcaaggtggg cagcaaggac gggaccatga | 1380 |
| acttcctggg caaggtggag tcattgtcaa cgctggacgt ggagaaggaa cgcgaggtga | 1440 |
| cggcagtttg ccgcgacttc ctgttcctgg agaaggtgaa gcggcagtgc gagaagacgc | 1500 |
| tgcaccggcc cgccacgtct gaggagattg cggcggccgt ggccatggat gtcgagagcc | 1560 |
| tgaagctccg ctatgacgcc ggtctgaagg ccaaggagct gctgctcaag tccaactaca | 1620 |
| agctggtcat gacggtgtgc aagtcgtttg tgggcaaggg cccgcacatc caggacctgg | 1680 |
| tgtcggaggg cgtcaagggc ctgctcaagg gcgtggaaaa gtacgacgcc accaagggct | 1740 |
| tccgcttcgg cacgtacgcg cactggtgga tccgccaggc cgtgtcgcgc tcgctggcgg | 1800 |
| agacgggccg cgcagtcagg ctgcccatgc acatgatcga gcagctgacg cggctcaaga | 1860 |
| acctgtccgc caagctgcag acgcagctgg cgcgagagcc cacgctgccc gagctggcca | 1920 |
| aggcggctgg tctgcctgtg acgcgcgttc agatgctcat ggagacgcg cgctccgccg | 1980 |
| cgtccctgga cacgcccatc ggcggcaacg agctgggccc gaccgtgaag gactccgtgg | 2040 |
| aggacgagcg cgaggcggcg gacgaggagt ttggcagcga cagtctgcgc aacgacatgg | 2100 |
| aggcgatgtt gttggagctg ccggagcgcg aggcgcgcgt ggtgcggctg cgcttcgggc | 2160 |
| tggacgacgg caaggagtgg acgctggagg agattggaga ggcgctgaac gtaacacgcg | 2220 |
| agcgcatccg tcagattgag gccaaggcgc tgcgcaagct gcgtgtgaag actattgacg | 2280 |
| tgagcggcaa gctgatggag tacgcgagaa acctggagat gctgatggac ggctcgcgcg | 2340 |
| agatggctgc gcgcaccagc agcggcaccc gcaagacgta agctggctgc tgtaggaggc | 2400 |
| ggaggcggca ggaggcggag gcagcaatag ggatgtcaac agtagctgag gtagcgggtg | 2460 |
| atgcgtgggt tggtggcggt aatagcagca tgtagcgtgc aggcttgggc cgggaagcta | 2520 |
| gattcccgtg aggttctatg cgctggtagc gagtgcgttc atagctagcc gtccatgtct | 2580 |
| tgtaggatgt agtcattgca tgaggtagcg tgccacgggg tcaaatgtgc catcctgaat | 2640 |
| cagcggtgc ttgctcgcat ataaatgaga gcaagattgc aggccctgcg ctatgccagg | 2700 |
| ccgcagacag tgtcagcact aagagagcgt tagagcacct gagcgcgggt aagggacacc | 2760 |
| gtgtatgtgc ttgtttaatc aggataccgt atgctatggc atgggatcgg tcagctgcaa | 2820 |
| gtgggagata tagtgtatgc actcacgccc ggattcgagg gctgtataac atgattgctg | 2880 |
| atttctgaaa ctatgccaat cctgaattta gtttctcacg atggacatgg gcggcagttg | 2940 |
| agacagatac gttcccgacg agaaattgac catccatagc tgcttttgtc tgcagccaag | 3000 |
| ttgcttttgc atgatggctt gtaaattcat gccgac | 3036 |

```
<210> SEQ ID NO 67
<211> LENGTH: 2259
<212> TYPE: DNA
<213> ORGANISM: Chlamydomonas reinhardtii

<400> SEQUENCE: 67
```

| | |
|---|---|
| atggcgcttc caggctccac aatgaaccttt acaacccgct gctctactac accgcggtcg | 60 |
| gctgtggttg cgcgcgcggt ggctgcgccc acgcgaccca ccaccaagtc tgcggtgcca | 120 |
| gagctgctgg atagccggcc aggcgagcgc aatctcaact tcatggagta tgctcaggcg | 180 |

```
actcagatgc tggaccggct caagggccag gcctctgacc tggaattgct gctggaccag      240
ctcaacgcgc tggaggccag cctcgacgag agcgttctgg cgccgcccac ggtggacgac      300
cccaaggagc gggctgcgcg acaagcacgg cgcgctgcca agcgtgcaga gcgtagggcc      360
caggcgacat ccgcaacagt cgcggccgcg gctgggccgg caatgtcagc agtggtctcg      420
cattccacgc cgacgaaggc tgctgctgcg ccggccacgt caacagcgag cagcagctcc      480
agcgatagtg gtttgctaga cctggtgagc tttgttggcg gctttgacac gcggccgatc      540
ccggcaacga cgtctgcacc ccctgctggc gccagcagct ccgacgtgca gcacctggag      600
gacctcttca aactcagcgt cggcgagccc gacatccccc gggcctccgc ttcagcagcg      660
cctgcggtgc tgcggccacg caagctcaca ccaaagaagc cctctgcggc accctccgcg      720
gcggtgacgg cagcaccctc gccggcaccc acgctcccca gcacgcccag caccagcgcg      780
cgcattgcgc ccgcgcccgg ctccctcgcg gatgagctgg agcggttact ggggcccacc      840
acgtcacggg aggcggctga gtctgaggac gaggacagct tcgcggggcc gtctgaggac      900
gacctgctgg cgctggagca ggaggtgtcg cgcaagtcgt cacggctgcc tgtgctagac      960
gaggaagacg aggaggatga gcagcagcag ctggaggaca cgaggaggaa gcgcgtggcg     1020 gggccccggct ctttggaggc gtcggcaatg gcgactcgga cgtccagcca gctgtccatc     1080
atgcagacgg ggccgtcgct gcttagcctg gtcccagcat ccgcggcgcc aggccgcagc     1140
gccaaggcgc gcgcctcccg gcgcgcggcg cgcaacggtc acgctagcgg gcggctgggt     1200
ggcgcgacga ctaacgcggc ggggcggggc aaggtgggca gcaaggacgg gaccatgaac     1260
ttcctgggca aggtggagtc attgtcaacg ctggacgtgg agaaggaacg cgaggtgacg     1320
gcagtttgcc gcgacttcct gttcctggag aaggtgaagc ggcagtgcga aagacgctg      1380 caccggcccg ccacgtctga ggagattgcg gcggccgtgg ccatggatgt cgagagcctg     1440
aagctccgct atgacgccgg tctgaaggcc aaggagctgc tgctcaagtc caactacaag     1500
ctggtcatga cggtgtgcaa gtcgtttgtg ggcaagggcc cgcacatcca ggacctggtg     1560
tcggagggcg tcaagggcct gctcaagggc gtggaaaagt acgacgccac caagggcttc     1620
cgcttcggca cgtacgcgca ctggtggatc cgccaggccg tgtcgcgctc gctggcggag     1680
acgggccgcg cagtcaggct gcccatgcac atgatcgagc agctgacgcg gctcaagaac     1740
ctgtccgcca agctgcagac gcagctggcg cgagagccca cgctgcccga gctggccaag     1800
gcggctggtc tgcctgtgac gcgcgttcag atgctcatgg agacggcgcg ctccgccgcg     1860
tccctggaca cgcccatcgg cggcaacgag ctgggcccga ccgtgaagga ctccgtggag     1920
gacgagcgcg aggcggcgga cgaggagttt ggcagcgaca gtctgcgcaa cgacatggag     1980
gcgatgttgt tggagctgcc ggagcgcgag gcgcgcgtgg tgcggctgcg cttcgggctg     2040
gacgacggca aggagtggac gctggaggag attggagagg cgctgaacgt aacacgcgag     2100
cgcatccgtc agattgaggc caaggcgctg cgcaagctgc gtgtgaagac tattgacgtg     2160
agcggcaagc tgatggagta cggcgagaac ctggagatgc tgatggacgg ctcgcgcgag     2220
atggctgcgc gcaccagcag cggcacccgc aagacgtaa                            2259
```

<210> SEQ ID NO 68
<211> LENGTH: 752
<212> TYPE: PRT
<213> ORGANISM: Chlamydomonas reinhardtii

<400> SEQUENCE: 68

-continued

```
Met Ala Leu Pro Gly Ser Thr Met Asn Leu Thr Thr Arg Cys Ser Thr
1               5                   10                  15

Thr Pro Arg Ser Ala Val Val Ala Arg Ala Val Ala Ala Pro Thr Arg
            20                  25                  30

Pro Thr Thr Lys Ser Ala Val Pro Glu Leu Leu Asp Ser Arg Pro Gly
            35                  40                  45

Glu Arg Asn Leu Asn Phe Met Glu Tyr Ala Gln Ala Thr Gln Met Leu
        50                  55                  60

Asp Arg Leu Lys Gly Gln Ala Ser Asp Leu Glu Leu Leu Leu Asp Gln
65                  70                  75                  80

Leu Asn Ala Leu Glu Ala Ser Leu Asp Glu Ser Val Leu Ala Pro Pro
                85                  90                  95

Thr Val Asp Asp Pro Lys Glu Arg Ala Ala Arg Gln Ala Arg Arg Ala
                100                 105                 110

Ala Lys Arg Ala Glu Arg Arg Ala Gln Ala Thr Ser Ala Thr Val Ala
            115                 120                 125

Ala Ala Ala Gly Pro Ala Met Ser Ala Val Val Ser His Ser Thr Pro
        130                 135                 140

Thr Lys Ala Ala Ala Ala Pro Ala Thr Ser Thr Ala Ser Ser Ser Ser
145                 150                 155                 160

Ser Asp Ser Gly Leu Leu Asp Leu Val Ser Phe Val Gly Gly Phe Asp
                165                 170                 175

Thr Arg Pro Ile Pro Ala Thr Thr Ser Ala Pro Pro Ala Gly Ala Ser
                180                 185                 190

Ser Ser Asp Val Gln His Leu Glu Asp Leu Phe Lys Leu Ser Val Gly
            195                 200                 205

Glu Pro Asp Ile Pro Arg Ala Ser Ala Ser Ala Ala Pro Ala Val Leu
        210                 215                 220

Arg Pro Arg Lys Leu Thr Pro Lys Lys Pro Ser Ala Ala Pro Ser Ala
225                 230                 235                 240

Ala Val Thr Ala Ala Pro Ser Pro Ala Pro Thr Leu Pro Ser Thr Pro
                245                 250                 255

Ser Thr Ser Ala Arg Ile Ala Pro Ala Pro Gly Ser Leu Ala Asp Glu
                260                 265                 270

Leu Glu Arg Leu Leu Gly Pro Thr Thr Ser Arg Glu Ala Ala Glu Ser
            275                 280                 285

Glu Asp Glu Asp Ser Phe Ala Gly Pro Ser Glu Asp Asp Leu Leu Ala
        290                 295                 300

Leu Glu Gln Glu Val Ser Arg Lys Ser Ser Arg Leu Pro Val Leu Asp
305                 310                 315                 320

Glu Glu Asp Glu Glu Asp Glu Gln Gln Leu Glu Asp Asn Glu Glu
                325                 330                 335

Asp Ala Val Ala Gly Pro Gly Ser Leu Glu Ala Ser Ala Met Ala Thr
            340                 345                 350

Arg Thr Ser Ser Gln Leu Ser Ile Met Gln Thr Gly Pro Ser Leu Leu
        355                 360                 365

Ser Leu Val Pro Ala Ser Ala Pro Gly Arg Ser Ala Lys Ala Arg
    370                 375                 380

Ala Ser Arg Arg Ala Ala Arg Asn Gly His Ala Ser Gly Arg Leu Gly
385                 390                 395                 400

Gly Ala Thr Ala Asn Ala Ala Gly Arg Gly Lys Val Gly Ser Lys Asp
                405                 410                 415

Gly Thr Met Asn Phe Leu Gly Lys Val Glu Ser Leu Ser Thr Leu Asp
```

```
                420               425               430
Val Glu Lys Glu Arg Glu Val Thr Ala Val Cys Arg Asp Phe Leu Phe
            435               440               445

Leu Glu Lys Val Lys Arg Gln Cys Glu Lys Thr Leu His Arg Pro Ala
        450               455               460

Thr Ser Glu Glu Ile Ala Ala Val Ala Met Asp Val Glu Ser Leu
465             470              475               480

Lys Leu Arg Tyr Asp Ala Gly Leu Lys Ala Lys Glu Leu Leu Lys
            485               490               495

Ser Asn Tyr Lys Leu Val Met Thr Val Cys Lys Ser Phe Val Gly Lys
        500               505               510

Gly Pro His Ile Gln Asp Leu Val Ser Glu Val Lys Gly Leu Leu
            515               520               525

Lys Gly Val Glu Lys Tyr Asp Ala Thr Lys Gly Phe Arg Phe Gly Thr
        530               535               540

Tyr Ala His Trp Trp Ile Arg Gln Ala Val Ser Arg Ser Leu Ala Glu
545             550               555               560

Thr Gly Arg Ala Val Arg Leu Pro Met His Met Ile Glu Gln Leu Thr
            565               570               575

Arg Leu Lys Asn Leu Ser Ala Lys Leu Gln Thr Gln Leu Ala Arg Glu
        580               585               590

Pro Thr Leu Pro Glu Leu Ala Lys Ala Ala Gly Leu Pro Val Thr Arg
        595               600               605

Val Gln Met Leu Met Glu Thr Ala Arg Ser Ala Ala Ser Leu Asp Thr
        610               615               620

Pro Ile Gly Gly Asn Glu Leu Gly Pro Thr Val Lys Asp Ser Val Glu
625             630               635               640

Asp Glu Arg Glu Ala Ala Asp Glu Glu Phe Gly Ser Asp Ser Leu Arg
            645               650               655

Asn Asp Met Glu Ala Met Leu Leu Glu Leu Pro Glu Arg Glu Ala Arg
            660               665               670

Val Val Arg Leu Arg Phe Gly Leu Asp Asp Gly Lys Glu Trp Thr Leu
        675               680               685

Glu Glu Ile Gly Glu Ala Leu Asn Val Thr Arg Glu Arg Ile Arg Gln
        690               695               700

Ile Glu Ala Lys Ala Leu Arg Lys Leu Arg Val Lys Thr Ile Asp Val
705             710               715               720

Ser Gly Lys Leu Met Glu Tyr Gly Glu Asn Leu Glu Met Leu Met Asp
            725               730               735

Gly Ser Arg Glu Met Ala Ala Arg Thr Ser Ser Gly Thr Arg Lys Thr
            740               745               750

<210> SEQ ID NO 69
<211> LENGTH: 8296
<212> TYPE: DNA
<213> ORGANISM: Chlamydomonas reinhardtii

<400> SEQUENCE: 69
atgactgggc gtacacacgt aacgtgtgag tctgcgaggc tcgggggggcg attgccctca    60 ctccgaagac gggcattggc gtctaccagt attgcgctct aatatgagtc caggttttgaa   120 gctatgtgga gattttcaga tggagcgagc ggctggcagc gctctggcta gcggggcgtg   180
aacgccggca gcgacgacgg tgcgcaaagc tatctgggca ccaccggtgc aatcatggac   240
atgtttatgc atggaggctc gccagagcct caaggtcggg gcggctatga agacgaccgc   300
```

```
gctggcacaa acgaacttgc agcaaatcga tgccaggccg atggctgcat ggcggacctc    360
tcaggactga agcgctactt ccgccgctac catgtgtgcg agatgcacat ccgggcgcag    420
gtggtgttga tctcggggcg tcaggtgcgc ttctgcgacc agtgcagcac attccacccc    480
ctggccttct ttgacggagt gcgcaggacg tgtcgtgaga agctggagca caaccgacaa    540
aagcggcgcg cgcgcaaggc tgcgcacggc ggcggcggtg gtggcggcgg aggcggcgct    600
gagcgcacaa caggcggcgg cggcggcggt cggcccgctg gctccggccg cggcgcacgc    660
agcggcggcg ccggaaacga cgacgatgac gatggtggcg gcgagtctga aggagagccg    720
ggtggcggcg gcagtgacga tggcggctcg gggtctgggc gggggcaggc gcgcaagcgg    780
ccgccgagcg tgtcgtcgtc gcaacagcag caggcggctg cggcggcgca gcggcggcgc    840
atgggcagcg gcccaatgcc gggctccgcg caggacctag ctctggcggc ggcggtggcg    900
gcggcggcgg cggcgggcat gtcagttgcc agccctggtg ccgcgccgg cgccggacct    960 gggcccggcg cggggcgct gggcttgggt ccgggctata gccgtatggg gtcggaggca    1020
cggaccggtg cgatgccggg gccggcgccg gggccggggc cgcgtggtgt ctcgcccggg    1080
tttgagggcg aggatgacga gtactacgcc ggccgcaccg ccacccgca cacgtacacg    1140 catcatcaac atccgcatcc acagcagctg ccgcagcagc agcaatcacg agagggctac    1200
atggggggcg ccaacgcgcg ggactccttg tcgggcgggc ccgtggtggc ggggcagggc    1260
gggtcggctg gcgcacaccc gcacccgcac ctgccggcac agggcgggcc gccgccgccg    1320
ccaccgaggg cagggctatt cggggcccct ctcgggtcag cggcgggagc caacggcgca    1380
gccgctgcgg cggggctgct gcgcggcggc tccgccccg gtgcagagca cctgcggccg    1440
ccgctgaggg aggctagcgg cgtgctgggg gcgccgtcgg gcgatggcct tggtggtggt    1500
ggtggcggtg gtggtggtgg tggtggtggt ggtggtggcg gtggtgtgct gcctgcggga    1560
ctgagtgagg aggaggcgct gcagcggcag ttggaggagc tgcgcagtgc gatcacgtgg    1620
cgtcagcagg agctgcagca gcaccagcac cagcgctacc aacatcatca ccaacagcaa    1680
caacaacatc aacaacaaca ccagcaacag caacagcagc accaacagat tggcttgaag    1740
caggaggggc gggagcagga agcctgggcg cgcgggccgg ggccggggcc gggaggggac    1800
gagccgcgct ggcagcagca gcagcagcag cagcagcagc aggcgcggca tgggtacccg    1860
gcaccaggca tggggcaagg gccggggctc ggcctgggc ggcagggagc gcctgtgccc    1920
gcaatgccgg caattgcagg cgccgccaat ggcgccaacg tgtcggtgg cgtcaatggc    1980 gttcgcgtgg cacgtgacgg cgcgtttgca ccgccgccgc tagaccctgc gcgccggcgg    2040
ccgggggcac ccggcggccc ccctccgccg ccgcacctgc cacagcaccc gcaccaccac    2100
catcaccacc accaagatgt ggagatggcg ctgcaggagc agcagctgct gcaggagctg    2160
cgccggcagc aacaacagca gcagcagcag cagcaacaac aacaacaaga caacaacaa    2220 cggcagcagc aacaacaaca cggcagcag caacagttgc aggagcagca caacatgcag    2280
cacgggcatc agcagcagct gcggccgccg ccgccggttc caggggcgac tgcgggctgg    2340
agttacgccc acacggggac tcgcccgcca gtggaggtga agatggaggt ggaggcagac    2400
gttggggcag gcgcggcgg cctggcgggg accggcgggt tgcgcaagga actaacactc    2460
ggccccgccg gcttcaccag cgccggcgct ccgcctccct accaccccca acacccctcg    2520
ccgcacgctt cctcgcctcg tgggcccctc gtgggccgct cctgggacgg ccgcggccca    2580
ccgtcagatc cctcggcgcg accgccgccg ccgccgccgc cgggcgtgtc gctggccggc    2640
```

```
tttccctccg acgtaccagc ccggctgcag ctgccgggct cggcccgcgg cccggcgccc    2700
ggcgccgccg ccgggaggcc caccggagat ggcatggcgg cggcggcggc ggccgtgcga    2760
cagcaccagc agcaccagta ccagctgcac caacagcagc aagagcacca acagcaacag    2820
cagcaccaac agcaacagca ccagcagcat caccagcacc aacagcagtt gctcctggcg    2880
gaggcggagg cggagctgca gcggcagcgg cagctgcagg cgatggcggc ggcgggcggc    2940
cccatggcgg cggcgatgcg actgcgcgcc ggcgccggcc tcggcggcgc gtggcagcag    3000
caccagcacc agcacccgca gcaccagcac cagcagcaac agccgcagca acagccgcag    3060
ccgcaatcga gccggcggtc agaggactgg acgccgctca cggacgtgcc cacgcttggc    3120
gcggctctgc ctgagggtct cagcctggaa ctcagcttcg gcggcgccgc cggcgccgca    3180
ggtgccgccg gtctcacgcc tctggtggc ggcggcggcg gcgccgccgc caccgccggg    3240
ctgctgccta gcgccggcag cctgatcagc ctgccgttga gtgtgctaca ggaggactcg    3300
tcgttgtgga gcgacggcga cctgcgcgcg ctgatggcgg cgggcagtgt cctgccgccg    3360
ccgccggcct cggcgacgtc gtcgttgtac acggctgacg acgacggcca cctgcgcggc    3420
gaggacggcg aggaggtgga gatggcggtg gcggcggcgg tggggccggt ggggccggtg    3480
gggatggtgg ggatggggat gcctggcggc gccctggcgg cggcggcggc ggcggcggtg    3540
gacgccgagg cggcggagtt ggaattggac agcctagcgg cggcgggcgc gcatttgggc    3600
caccggccgt cgtttggcgg cggcggcggc ggtggcggcg gcggcttgca tcggctgatg    3660
gcgctgcgcg ccctgcccag cggcggcagc agcgcgcagt cgcttgcgca cctggccctc    3720
ccgcaccagg cccccatgc acacggccac ggtggcggcg gcgccgccgc cgcgtacggc    3780
agcggcggcg gaagtggcgg cggcgcagcg ctggcggagg cctactccac caggagcgag    3840
gccagcgagg ctccggagat ctgcctcacg gaatctttta aggcggaggt gctgtcgctg    3900
cagcggctgg cgcaggcgca gcaggggcat ccagggccgc atggctcgga gttcgggccg    3960
cagcatggac cgcacggctt ccccggcccg catgctgggg ccgccgcggc agcaacgccc    4020
aaccagctgc cgccgtcggt acggctacac ctgccgccca gcattttggg gcgcggcggt    4080
accagctacg gcggcggcag cggccctggc ggccccgacg gcggcggcgc cgtataccac    4140
cagcaccagc accagccgta ccagctgcag taccagcacc agctccagca gcagcagcgc    4200
gtggcgctga tgcagcacca ccatcagcaa caacagtacc agcagcagca cttgcaatac    4260
aggccgcctc tgcagcagca gcaccagcag cagcagcagc tgcaccagca gccggccgcg    4320
gcgccgccgc tgttcggcga ggggcgggtg tccgccttcc acctgctggg gccggggac    4380 ctggacgatg aagaagagga cgggcccgcc ctcgggcccg gctggcagct gcacccgcac    4440
cagcacccgc acccgcagca gccgtatggc ggcatgggc gcccccagca gcaaccgcag    4500
cagcaccagc aaccgcagca ccagcaccag cagcaggctg gcgggctgga ctcgcgccct    4560
tcccacctcg ccggcgccgg cttcggtgcc ggcactggtg cgcgtgcagg tggcggcggc    4620
gccgccgcag ttgcctcagc cggggctggg gctggggctg ggctgggc ccgcagatc    4680 ctgttgctgc ccggcggccc ggcggcgggg agtcagccgg ggcgactgct gggctcggcg    4740
gcggcgctgg gcctaggcgg tgcgcgaggc ggcggcggcg gcggcggtgg cgagcacacg    4800
ctcgtgcagc ctagcctgcg ccgcctcagc caacaggagc aggacggccg cggggcgcag    4860
ggggcggcgt cggctgacag cgagccgccg ccgccggcgc agcagcagca gatgcagcag    4920
cagcagcagc agcagcagac tgccaacggc ccgactggaa aagtaggagg aggggcccg    4980 ggcgctgggt tggcgcgggc gccggcggcg ccgcgggagg cgcctcagca ggcgcagcag    5040
```

```
ccgcgcgcaa acggggaagt gcgccacccc acaggcgcgg cgcaggcgtg gagcggcggc      5100
gtcgcttctg gcgccccggc ggcagcggct gacggcaacc tgggcagcgc ggcggcggtg      5160
gcggcggtgg cggcggcggc ggcggaagca gaggcggacg gcgaggtggg tgaggaggag      5220
gaggaggtgg atccttctga gctgttgcgt caggcctact ccgccggact cacagagctg      5280
cctgggatgc tggggatgc ggaggcggag gaggaggagg agcaggaggc ggccgcggcg       5340
gcgggcgatg aggtgacgga tccggggacg gggtccgggt cgggccaggc aggccgccgc      5400
cgcggcggtg gtggtggggg cagcggcagc gctcaggcgg cggatgccac gccgcctcct      5460
gagggcgagg gcacggagat cgtcggctcc gtcggcagcg gccgtgccgc cactggctta      5520
cgcagtggcg gcggcgccgt cggcgacgcg tccttcatcc ggcccggcgg cggcggcggc      5580
atgtctttcc tggccagtgc cgttggtggt ggcggcggcg gcggcggagg gcaacagatg      5640
acgacgacgg ttgactttc gggattggat ggaggcggcg gcggctcgtg gtggctcagc       5700
aagggcagtg gcgagggcga gggcgaggag aggagtgtgg tgtcgtcagg cgctatggcg      5760
gcggtggcgg cggggcacg gcgggagggg ctcagtggtg gcggcggcgt tggcggcggc       5820
gtggtcatga tgctgagga tgtggacatg gatgacacaa cgtcactggc cgctgaggcg       5880
gcggcggcgg cggcggctga cctggcggcg gcggcggcag gtccggctgt cggcgccgtt      5940
ggggttcgct cgtgaaccgt tgttgggagg agtgcattca agttggtgat gacggtggct      6000
gactgcatgg ctgcatgcct gcatggctgc acaaggcggc atgcctgcac ggctgctcaa      6060
ggcgcgccgc tggggcaggc agatgcatat gtgggcgggc gcagcggtgg cgacagcgcg      6120
gacgcagctg tgcccgacac aatgcggcgg cggcggcgtc tgctccgata ctgccaccgt      6180
ctgcaccccg ttggcatccc gtcggatcag catacaggca tagggccagg gatgcgtgt     6240 caactgcgtg aactgctttc cctggcgttt cccacccggg ttcccacaca cttcacttgc      6300
taccacgctg ctgcgacgac ttggcgtggg cgcaaacagg tgtggcaagg acgtacagta      6360
ccggggtgat gtgttgctgc acctaaggcg ctgagttgtt cataaggaat tttggcgtgt      6420
cactcgtgct tcatgggctt gatgaacgtg atgcctggaa attgcgaagt tgcggccacc      6480
aagggccggc acgactgcac gagcacagga agcggtgaat tgtattgcgg aggggttgt      6540 tgccatgcct cgtatgttgg gagctgccgc gggaagccat acctcttcca gtgcgcatcg      6600
ggaaaaccgg gaggcacaac aaaaaactac tacacggtac cggggcttgt cccggcgcaa      6660
gcgagggaga aagtatacgg catgcaaatt tattgatgat cgaacgccca tgcaggacaa      6720
gaacgatgac ttgtctgcgg cggggttgcc attgtgttct tgtaattgtt gttggctggg      6780
gcgtgctgtg cgggtcgttg caagctgtgt aatttgcatg tcctgctcgc taggactctg      6840
tgggctcaag cgggagacgg tggcggcgcg gggcttggcg gtagctgcgc atgcgccagg      6900
cgtgttgggc ggttgtgggc acggccgcat acaagggcg cgaatggagc tgctgttcac       6960
gaggcggcgc cggccggcac ctgcacttga gccggccgct gttcctgcac cccagccggc      7020
cgcgggctat agcagagctg gggtgggggc atggccgtgg ggccaattgg caggacgcag      7080
cagaggcaga ggcgtggggg taccttgttt gctgctgtgg ctcctctgcg ctgttggctg      7140
cggtcgggca tgtcgtaagc atttggggc gggcggcgct tgtggtgcca attcatcagg       7200 cttgccgcg ggcacgtgcg gcgcagctgg cggacccgcg ggctgagact ttggaggtcg       7260
tgtgggcgtg tgcgtgcagc ccatttcttg cgtgcttgcg cggaaagcgt tactgcattt      7320
gttcttaatg atgactgtgg tgttggtgtt gctggggtcc gggagtggcg gcacggcgga      7380
```

```
gagcctgttt gcgctgcacc tgcgacccat gccattaccg cggactcttg ggcgccctac    7440
attgtgggct tggtgttggt gccggttgag gggatggccc gcaatgcaac aaggcttgag    7500
gagtcggcga tgtttaatta agttctttca tgcgaccggg tggtgtgttg gcaagttgtc    7560
acatacactg tatcgcttgg aacgatttgg ggcttctgtg tgtgtatgtc tttatgtggt    7620
ctgttaaagc tgtggtctgt taaagctgga gcggcgaggg gcgagggcgc gaatgtgatg    7680
agggttgagg gctgcaaatt gcggagggaa gatgcgcact tgtccgagat gcgtcccagg    7740
gtaccaaggc actggcagtg tgcgcattgg gtgttgacac atgctggggg ccgcgctgcg    7800
gggggtgggg cgtgtggggg ttaccgaaat gcgggcgcag caggggtgaa acgaggacac    7860
ccctggctgg agcagagctg agaaacgtcg ggggccggca gcaacaacgt gaatgatgat    7920
tgtcccaaca cacggcatgc aatgctagat gtatggtaaa tttgggaccc atcgcaaaga    7980
tgtgcgatat aatgcaactg gtggcaacga ttctagggc gtcacagcgg ccgcacttgg     8040
gaattacacg gcaacgcta acagcatgcc gcaggcgatg cggcggggca gatccgcaga    8100
tgcggtcggg tgggtagtgg gcaacccgct ttggagtggt gtgtgtgtgt gtgtgtgtgt    8160
gtgtgtgtgt gtgtgtgtgt gtgtgtgtgt gtgtgtgtgt gtgtgtgtgt gtgtgtgtgt    8220
gtgtgtgtgt gtgtgtgtgt gtgtgtgtgt gtgtgtgtgt gtgtgcattt gtatacaact    8280
gtaaatgccg ggcaat                                                    8296

<210> SEQ ID NO 70
<211> LENGTH: 5721
<212> TYPE: DNA
<213> ORGANISM: Chlamydomonas reinhardtii

<400> SEQUENCE: 70
atggacatgt ttatgcatgg aggctcgcca gagcctcaag gtcggggcgg ctatgaagac      60
gaccgcgctg gcacaaacga acttgcagca aatcgatgcc aggccgatgg ctgcatggcg     120
gacctctcag gactgaagcg ctacttccgc cgctaccatg tgtgcgagat gcacatccgg     180
gcgcaggtgg tgttgatctc ggggcgtcag gtgcgcttct gcgaccagtg cagcacattc     240 cacccctgg ccttctttga cggagtgcgc aggacgtgtc gtgagaagct ggagcacaac      300
cgacaaaagc ggcgcgcgcg caaggctgcg cacggcggcg gcggtggtgg cggcggaggc     360
ggcgctgagc gcacaacagg cggcggcggc ggcggtcggc ccgctggctc cggccgcggc     420
gcacgcagcg gcggcgccgg aaacgacgac gatgacgatg gtggcggcga gtctgaagga     480
gagccgggtg gcggcggcag tgacgatggc ggctcgggt ctgggcgggg caggcgcgc       540 aagcggccgc cgagcgtgtc gtcgtcgcaa cagcagcagg cggctgcggc ggcgcagcgg     600
cggcgcatgg gcagcggccc aatgccgggc tccgcgcagg acctagctct ggcggcggcg     660
gtggcggcgg cggcggcggc gggcatgtca gttgccagcc ctggtgccgg cgccggcgcc     720
ggacctgggc ccggcgcggg ggcgctgggc ttgggtccgg gctatagccg tatgggtcg     780 gaggcacgga ccggtgcgat gccggggccg gcgccgggc cggggccgcg tggtgtctcg     840
cccgggtttg agggcgagga tgacgagtac tacgccggcc gcaccggcca ccgcacacg     900 tacacgcatc atcaacatcc gcatccacag cagctgccgc agcagcagca atcacgagag    960
ggctacatgg ggggcgccaa cgcgcgggac tccttgtcgg gcgggcccgt ggtggcgggg   1020
cagggcgggt cggctggcgc acaccccgcac ccgcacctgc cggcacaggg cgggccgccg   1080
ccgccgccac cgagggcagg gctattcggg ggcccgctcg ggtcagcggc gggagccaac    1140
ggcgcagccg ctgcggcggg gctgctgcgc ggcggctccg gccccggtgc agagcacctg    1200
```

```
cggccgccgc tgagggaggc tagcggcgtg ctgggggcgc cgtcgggcga tggccttggt    1260
ggtggtggtg gcggtggtgg tggtggtggt ggtggtggtg gtggcggtgg tgtgctgcct    1320
gcgggactga gtgaggagga ggcgctgcag cggcagttgg aggagctgcg cagtgcgatc    1380
acgtggcgtc agcaggagct gcagcagcac cagcaccagc gctaccaaca tcatcaccaa    1440
cagcaacaac aacatcaaca acaacaccag caacagcaac agcagcacca acagattggc    1500
ttgaagcagg aggggcggga gcaggaagcc tgggcgcgcg ggccggggcc ggggccggga    1560
ggggacgagc cgcgctggca gcagcagcag cagcagcagc agcagcaggc gcggcatggg    1620
tacccggcac caggcatggg gcaagggccg ggctcggcc  tggggcggca gggagcgcct    1680
gtgcccgcaa tgccggcaat tgcaggcgcc gccaatggcg ccaacggtgt cggtggcgtc    1740
aatggcgttc gcgtggcacg tgacggcgcg tttgcaccgc cgccgctaga ccctgcgcgc    1800
cggcggccgg gggcacccgg cggccccct  ccgccgccgc acctgccaca gcacccgcac    1860
caccaccatc accaccacca agatgtggag atggcgctgc aggagcagca gctgctgcag    1920
gagctgcgcc ggcagcaaca acagcagcag cagcagcagc aacaacaaca caagaacaa     1980 caacaacggc agcagcaaca acaacaacgg cagcagcaac agttgcagga gcagcacaac    2040
atgcagcacg ggcatcagca gcagctgcgg ccgccgccgc cggttccagg ggcgactgcg    2100
ggctggagtt acgcccacac ggggactcgc ccgccagtgg aggtgaagat ggaggtggag    2160
gcagacgttg gggcaggcgg cggcggcctg ggcgggaccg gcggcttgcg caaggaacta    2220
acactcggcc ccgccggctt caccagcgcc ggcgctccgc ctccctacca cccccaacac    2280
ccctcgccgc acgcttcctc gcctcgtggg ccctcgtgg  gccgctcctg ggacggccgc    2340
ggcccaccgt cagatccctc ggcgcgaccg ccgccgccgc cgccgccggg cgtgtcgctg    2400
gccggctttc cctccgacgt accagcccgg ctgcagctgc cgggctcggc ccgcggcccg    2460
gcgcccggcg ccgccgccgg gagccccacc ggagatggca tggcggcggc ggcggcggcc    2520
gtgcgacagc accagcagca ccagtaccag ctgcaccaac agcagcaaga gcaccaacag    2580
caacagcagc accaacagca acagcaccag cagcatcacc agcaccaaca gcagttgctc    2640
ctggcggagg cggaggcgga gctgcagcgg cagcggcagc tgcaggcgat ggcggcggcg    2700
ggcggcccca tggcggcggc gatgcgactg cgcgccggcg ccggcctcgg cggcgcgtgg    2760
cagcagcacc agcaccagca cccgcagcac cagcaccagc agcaacagcc gcagcaacag    2820
ccgcagccgc aatcgagccg gcggtcagag gactggacgc cgctcacgga cgtgcccacg    2880
cttggcgcgg ctctgcctga gggtctcagc ctggaactca gcttcggcgg cgccgccggc    2940
gccgcaggtg ccgccggtct cacgcctctg ggtggcggcg gcggcggcgc cgccgccacc    3000
gccgggctgc tgcctagcgc cggcagcctg atcagcctgc cgttgagtgt gctacaggag    3060
gactcgtcgt tgtggagcga cggcgacctg gcgcggctga tggcggcggg cagtgtcctg    3120
ccgccgccgc cggcctcggc gacgtcgtcg ttgtacacgg ctgacgacga cggccacctg    3180
cgcggcgagg acggcgagga ggtggagatg gcggtggcgg cggcggtggg gccggtgggg    3240
ccggtgggga tggtggggat ggggatgcct ggcggcgccc tggcggcggc ggcggcggcg    3300
gcggtggacg ccgaggcggc ggagttggaa ttggacagcc tagcggcggc gggcgcgcat    3360
ttgggccacc ggccgtcgtt tggcggcggc ggcggcggtg gcggcggcgg cttgcatcgg    3420
ctgatggcgc tgcgcgccct gcccagcggc ggcagcagcg cgcagtcgct tgcgcacctg    3480
gccctcccgc accaggcccc ctatgcacac ggccacggtg gcggcggcgc cgccgccgcg    3540
```

| | |
|---|---|
| tacggcagcg gcggcggaag tggcggcggc gcagcgctgg cggaggccta ctccaccagg | 3600 |
| agcgaggcca gcgaggctcc ggagatctgc ctcacggaat cttttaaggc ggaggtgctg | 3660 |
| tcgctgcagc ggctggcgca ggcgcagcag gggcatccag ggccgcatgg ctcggagttc | 3720 |
| gggccgcagc atggaccgca cggcttcccc ggcccgcatg ctggggccgc cgcggcagca | 3780 |
| acgcccaacc agctgccgcc gtcggtacgg ctacacctgc cgcccagcat tttggggcgc | 3840 |
| ggcggtacca gctacggcgg cggcagcggc cctggcgggc ccgacggcgg cggcgccgta | 3900 |
| taccaccagc accagcacca gccgtaccag ctgcagtacc agcaccagct ccagcagcag | 3960 |
| cagcgcgtgg cgctgatgca gcaccaccat cagcaacaac agtaccagca gcagcacttg | 4020 |
| caatacaggc cgcctctgca gcagcagcac cagcagcagc agcagctgca ccagcagccg | 4080 |
| gccgcggcgc cgccgctgtt cggcgagggg cgggtgtccg ccttccacct gctggggccg | 4140 |
| ggggacctgg acgatgaaga agaggacggg cccgccctcg ggcccggctg gcagctgcac | 4200 |
| ccgcaccagc acccgcaccc gcagcagccg tatggcggca tggggcgccc ccagcagcaa | 4260 |
| ccgcagcagc accagcaacc gcagcaccag caccagcagc aggctggcgg gctggactcg | 4320 |
| cgcccttccc acctcgccgg cgccggcttc ggtgccggca ctggtgcgcg tgcaggtggc | 4380 |
| ggcggcgccc ccgcagttgc ctcagccggg gctggggctg gggctggggc tggggcgccg | 4440 |
| cagatcctgt tgctgcccgg cggcccggcg gcggggagtc agccggggcg actgctgggc | 4500 |
| tcggcggcgc cgctgggcct aggcggtgcg cgaggcggcg gcggcggcgg cggtggcgag | 4560 |
| cacacgctcg tgcagcctag cctgcgccgc ctcagccaac aggagcagga cggccgcggg | 4620 |
| gcgcagggggg cggcgtcggc tgacagcgag ccgccgccgc cggcgcagca gcagcagatg | 4680 |
| cagcagcagc agcagcagca gcagactgcc aacgcccga ctggaaaagt aggaggaggg | 4740 |
| ggcccggggc ctgggttggc gcgggcgccg cgggcgccgc gggaggcgcc tcagcaggcg | 4800 |
| cagcagccgc gcgcaaacgg ggaagtgcgc caccccacag gcgcggcgca ggcgtggagc | 4860 |
| ggcggcgtcg cttctggcgg cccggcggca gcggctgacg gcaacctggg cagcgcggcg | 4920 |
| gcggtggcgg cggtggcggc ggcggcggcg gaagcagagg cggacggcga ggtgggtgag | 4980 |
| gaggaggagg aggtggatcc ttctgagctg ttgcgtcagg cctactccgc cggactcaca | 5040 |
| gagctgcctg ggatgctggg ggatgcggag gcggaggagg aggaggagca ggaggcggcc | 5100 |
| gcggcggcgg gcgatgaggt gacggatccg gggacggggt ccgggtcggg ccaggcaggc | 5160 |
| cgccgccgcg gcggtggtgg tgggggcagc ggcagcgctc aggcggcgga tgccacgccg | 5220 |
| cctcctgagg gcgagggcac ggagatcgtc ggctccgtcg gcagcggccg tgccgccact | 5280 |
| ggcttacgca gtggcggcgg cgccgtcggc gacgcgtcct tcatccggcc cggcggcggc | 5340 |
| ggcggcatgt ctttcctggc cagtgccgtt ggtggtggcg gcggcggcgg cggagggcaa | 5400 |
| cagatgacga cgacggttga cttttcggga ttggatggag gcggcggcgg ctcgtggtgg | 5460 |
| ctcagcaagg gcagtggcga gggcgagggc gaggagagga gtgtggtgtc gtcaggcgct | 5520 |
| atggcggcgt ggcggcggg ggcacggcgg gagggctca gtggtggcgg cggcgttggc | 5580 |
| ggcggcgtgg tcatggatgc tgaggatgtg gacatggatg acacaacgtc actggccgct | 5640 |
| gaggcggcgc cggcggcggc ggctgacctg gcggcggcgg cggcaggtcc ggctgtcggc | 5700 |
| gccgttgggg ttcgctcgtg a | 5721 |

<210> SEQ ID NO 71
<211> LENGTH: 1906
<212> TYPE: PRT
<213> ORGANISM: Chlamydomonas reinhardtii

<400> SEQUENCE: 71

```
Met Asp Met Phe Met His Gly Gly Ser Pro Glu Pro Gln Gly Arg Gly
1               5                   10                  15

Gly Tyr Glu Asp Asp Arg Ala Gly Thr Asn Glu Leu Ala Ala Asn Arg
            20                  25                  30

Cys Gln Ala Asp Gly Cys Met Ala Asp Leu Ser Gly Leu Lys Arg Tyr
        35                  40                  45

Phe Arg Arg Tyr His Val Cys Glu Met His Ile Arg Ala Gln Val Val
    50                  55                  60

Leu Ile Ser Gly Arg Gln Val Arg Phe Cys Asp Gln Cys Ser Thr Phe
65                  70                  75                  80

His Pro Leu Ala Phe Phe Asp Gly Val Arg Arg Thr Cys Arg Glu Lys
                85                  90                  95

Leu Glu His Asn Arg Gln Lys Arg Arg Ala Arg Lys Ala Ala His Gly
            100                 105                 110

Gly Gly Gly Gly Gly Gly Gly Gly Ala Glu Arg Thr Thr Gly Gly
        115                 120                 125

Gly Gly Gly Gly Arg Pro Ala Gly Ser Gly Arg Gly Ala Arg Ser Gly
    130                 135                 140

Gly Ala Gly Asn Asp Asp Asp Asp Gly Gly Glu Ser Glu Gly
145                 150                 155                 160

Glu Pro Gly Gly Gly Ser Asp Asp Gly Ser Gly Ser Gly Arg
                165                 170                 175

Gly Gln Ala Arg Lys Arg Pro Pro Ser Val Ser Ser Gln Gln Gln
            180                 185                 190

Gln Ala Ala Ala Ala Gln Arg Arg Arg Met Gly Ser Gly Pro Met
        195                 200                 205

Pro Gly Ser Ala Gln Asp Leu Ala Leu Ala Ala Val Ala Ala Ala
    210                 215                 220

Ala Ala Ala Gly Met Ser Val Ala Ser Pro Gly Ala Gly Ala Gly Ala
225                 230                 235                 240

Gly Pro Gly Pro Gly Ala Gly Ala Leu Gly Leu Gly Pro Gly Tyr Ser
                245                 250                 255

Arg Met Gly Ser Glu Ala Arg Thr Gly Ala Met Pro Gly Pro Ala Pro
            260                 265                 270

Gly Pro Gly Pro Arg Gly Val Ser Pro Gly Phe Glu Gly Glu Asp Asp
        275                 280                 285

Glu Tyr Tyr Ala Gly Arg Thr Gly His Pro His Thr Tyr Thr His His
    290                 295                 300

Gln His Pro His Pro Gln Gln Leu Pro Gln Gln Gln Ser Arg Glu
305                 310                 315                 320

Gly Tyr Met Gly Gly Ala Asn Ala Arg Asp Ser Leu Ser Gly Pro
                325                 330                 335

Val Val Ala Gly Gln Gly Ser Ala Gly Ala His Pro His Pro His
            340                 345                 350

Leu Pro Ala Gln Gly Gly Pro Pro Pro Pro Arg Ala Gly Leu
        355                 360                 365

Phe Gly Gly Pro Leu Gly Ser Ala Ala Gly Ala Asn Gly Ala Ala Ala
    370                 375                 380

Ala Ala Gly Leu Leu Arg Gly Gly Ser Gly Pro Gly Ala Glu His Leu
385                 390                 395                 400

Arg Pro Pro Leu Arg Glu Ala Ser Gly Val Leu Gly Ala Pro Ser Gly
```

```
              405                 410                 415
Asp Gly Leu Gly Gly Gly Gly Gly Gly Gly Gly Gly Gly Gly
            420                 425                 430
Gly Gly Gly Gly Gly Val Leu Pro Ala Gly Leu Ser Glu Glu Ala
            435                 440                 445
Leu Gln Arg Gln Leu Glu Glu Leu Arg Ser Ala Ile Thr Trp Arg Gln
    450                 455                 460
Gln Glu Leu Gln Gln His Gln His Gln Arg Tyr Gln His His His Gln
465                 470                 475                 480
Gln Gln Gln Gln His Gln Gln His Gln Gln Gln Gln Gln His
                485                 490                 495
Gln Gln Ile Gly Leu Lys Gln Glu Gly Arg Glu Gln Glu Ala Trp Ala
            500                 505                 510
Arg Gly Pro Gly Pro Gly Pro Gly Gly Asp Glu Pro Arg Trp Gln Gln
            515                 520                 525
Gln Gln Gln Gln Gln Gln Gln Ala Arg His Gly Tyr Pro Ala Pro
            530                 535                 540
Gly Met Gly Gln Gly Pro Gly Leu Gly Leu Gly Arg Gln Gly Ala Pro
545                 550                 555                 560
Val Pro Ala Met Pro Ala Ile Ala Gly Ala Ala Asn Gly Ala Asn Gly
                565                 570                 575
Val Gly Gly Val Asn Gly Val Arg Val Ala Arg Asp Gly Ala Phe Ala
            580                 585                 590
Pro Pro Pro Leu Asp Pro Ala Arg Arg Arg Pro Gly Ala Pro Gly Gly
            595                 600                 605
Pro Pro Pro Pro His Leu Pro Gln His Pro His His His His
            610                 615                 620
His His Gln Asp Val Glu Met Ala Leu Gln Gln Gln Leu Leu Gln
625                 630                 635                 640
Glu Leu Arg Arg Gln Gln Gln Gln Gln Gln Gln Gln Gln Gln
                645                 650                 655
Gln Gln Glu Gln Gln Gln Arg Gln Gln Gln Gln Gln Arg Gln Gln
            660                 665                 670
Gln Gln Leu Gln Glu Gln His Asn Met Gln His Gly His Gln Gln Gln
            675                 680                 685
Leu Arg Pro Pro Pro Val Pro Gly Ala Thr Ala Gly Trp Ser Tyr
    690                 695                 700
Ala His Thr Gly Thr Arg Pro Pro Val Glu Val Lys Met Glu Val
705                 710                 715                 720
Ala Asp Val Gly Ala Gly Gly Gly Leu Gly Gly Thr Gly Leu
                725                 730                 735
Arg Lys Glu Leu Thr Leu Gly Pro Ala Gly Phe Thr Ser Ala Gly Ala
            740                 745                 750
Pro Pro Pro Tyr His Pro Gln His Pro Ser Pro His Ala Ser Ser Pro
            755                 760                 765
Arg Gly Pro Leu Val Gly Arg Ser Trp Asp Gly Arg Gly Pro Pro Ser
            770                 775                 780
Asp Pro Ser Ala Arg Pro Pro Pro Pro Pro Gly Val Ser Leu
785                 790                 795                 800
Ala Gly Phe Pro Ser Asp Val Pro Ala Arg Leu Gln Leu Pro Gly Ser
                805                 810                 815
Ala Arg Gly Pro Ala Pro Gly Ala Ala Ala Gly Arg Pro Thr Gly Asp
            820                 825                 830
```

-continued

```
Gly Met Ala Ala Ala Ala Ala Val Arg Gln His Gln Gln His Gln
        835                 840                 845

Tyr Gln Leu His Gln Gln Gln Glu His Gln Gln Gln Gln His
    850                 855                 860

Gln Gln Gln Gln His Gln His His Gln His Gln Gln Gln Leu Leu
865                 870                 875                 880

Leu Ala Glu Ala Glu Ala Glu Leu Gln Arg Gln Arg Gln Leu Gln Ala
                885                 890                 895

Met Ala Ala Gly Gly Pro Met Ala Ala Met Arg Leu Arg Ala
        900                 905                 910

Gly Ala Gly Leu Gly Gly Ala Trp Gln Gln His Gln His Gln His Pro
        915                 920                 925

Gln His Gln His Gln Gln Gln Pro Gln Gln Pro Gln Pro Gln
        930                 935                 940

Ser Ser Arg Arg Ser Glu Asp Trp Thr Pro Leu Thr Asp Val Pro Thr
945                 950                 955                 960

Leu Gly Ala Ala Leu Pro Glu Gly Leu Ser Leu Glu Leu Ser Phe Gly
                965                 970                 975

Gly Ala Ala Gly Ala Ala Gly Ala Ala Gly Leu Thr Pro Leu Gly Gly
        980                 985                 990

Gly Gly Gly Gly Ala Ala Ala Thr Ala Gly Leu Leu Pro Ser Ala Gly
        995                 1000                1005

Ser Leu Ile Ser Leu Pro Leu Ser Val Leu Gln Glu Asp Ser Ser
    1010                1015                1020

Leu Trp Ser Asp Gly Asp Leu Ala Arg Leu Met Ala Ala Gly Ser
    1025                1030                1035

Val Leu Pro Pro Pro Pro Ala Ser Ala Thr Ser Ser Leu Tyr Thr
    1040                1045                1050

Ala Asp Asp Asp Gly His Leu Arg Gly Glu Asp Gly Glu Glu Val
    1055                1060                1065

Glu Met Ala Val Ala Ala Ala Val Gly Pro Val Gly Pro Val Gly
    1070                1075                1080

Met Val Gly Met Gly Met Pro Gly Gly Ala Leu Ala Ala Ala Ala
    1085                1090                1095

Ala Ala Ala Val Asp Ala Glu Ala Ala Glu Leu Glu Leu Asp Ser
    1100                1105                1110

Leu Ala Ala Ala Gly Ala His Leu Gly His Arg Pro Ser Phe Gly
    1115                1120                1125

Gly Gly Gly Gly Gly Gly Gly Gly Leu His Arg Leu Met Ala
    1130                1135                1140

Leu Arg Ala Leu Pro Ser Gly Gly Ser Ser Ala Gln Ser Leu Ala
    1145                1150                1155

His Leu Ala Leu Pro His Gln Ala Pro Tyr Ala His Gly His Gly
    1160                1165                1170

Gly Gly Gly Ala Ala Ala Ala Tyr Gly Ser Gly Gly Gly Ser Gly
    1175                1180                1185

Gly Gly Ala Ala Leu Ala Glu Ala Tyr Ser Thr Arg Ser Glu Ala
    1190                1195                1200

Ser Glu Ala Pro Glu Ile Cys Leu Thr Glu Ser Phe Lys Ala Glu
    1205                1210                1215

Val Leu Ser Leu Gln Arg Leu Ala Gln Ala Gln Gln Gly His Pro
    1220                1225                1230
```

Gly Pro His Gly Ser Glu Phe Gly Pro Gln His Gly Pro His Gly
    1235                1240                1245

Phe Pro Gly Pro His Ala Gly Ala Ala Ala Ala Thr Pro Asn
    1250                1255                1260

Gln Leu Pro Pro Ser Val Arg Leu His Leu Pro Pro Ser Ile Leu
    1265                1270                1275

Gly Arg Gly Gly Thr Ser Tyr Gly Gly Ser Gly Pro Gly Gly
    1280                1285                1290

Pro Asp Gly Gly Gly Ala Val Tyr His Gln His Gln His Gln Pro
    1295                1300                1305

Tyr Gln Leu Gln Tyr Gln His Gln Leu Gln Gln Gln Arg Val
    1310                1315                1320

Ala Leu Met Gln His His His Gln Gln Gln Gln Tyr Gln Gln Gln
    1325                1330                1335

His Leu Gln Tyr Arg Pro Leu Gln Gln Gln His Gln Gln Gln
    1340                1345                1350

Gln Gln Leu His Gln Gln Pro Ala Ala Ala Pro Pro Leu Phe Gly
    1355                1360                1365

Glu Gly Arg Val Ser Ala Phe His Leu Leu Gly Pro Gly Asp Leu
    1370                1375                1380

Asp Asp Glu Glu Glu Asp Gly Pro Ala Leu Gly Pro Gly Trp Gln
    1385                1390                1395

Leu His Pro His Gln His Pro His Pro Gln Gln Pro Tyr Gly Gly
    1400                1405                1410

Met Gly Arg Pro Gln Gln Gln Pro Gln Gln His Gln Gln Pro Gln
    1415                1420                1425

His Gln His Gln Gln Ala Gly Gly Leu Asp Ser Arg Pro Ser
    1430                1435                1440

His Leu Ala Gly Ala Gly Phe Gly Ala Gly Thr Gly Ala Arg Ala
    1445                1450                1455

Gly Gly Gly Gly Ala Ala Ala Val Ala Ser Ala Gly Ala Gly Ala
    1460                1465                1470

Gly Ala Gly Ala Gly Ala Pro Gln Ile Leu Leu Leu Pro Gly Gly
    1475                1480                1485

Pro Ala Ala Gly Ser Gln Pro Gly Arg Leu Leu Gly Ser Ala Ala
    1490                1495                1500

Ala Leu Gly Leu Gly Gly Ala Arg Gly Gly Gly Gly Gly Gly Gly
    1505                1510                1515

Gly Glu His Thr Leu Val Gln Pro Ser Leu Arg Arg Leu Ser Gln
    1520                1525                1530

Gln Glu Gln Asp Gly Arg Gly Ala Gln Gly Ala Ala Ser Ala Asp
    1535                1540                1545

Ser Glu Pro Pro Pro Pro Ala Gln Gln Gln Gln Met Gln Gln Gln
    1550                1555                1560

Gln Gln Gln Gln Gln Thr Ala Asn Gly Pro Thr Gly Lys Val Gly
    1565                1570                1575

Gly Gly Gly Pro Gly Ala Gly Leu Ala Arg Ala Pro Ala Ala Pro
    1580                1585                1590

Arg Glu Ala Pro Gln Gln Ala Gln Gln Pro Arg Ala Asn Gly Glu
    1595                1600                1605

Val Arg His Pro Thr Gly Ala Ala Gln Ala Trp Ser Gly Gly Val
    1610                1615                1620

Ala Ser Gly Gly Pro Ala Ala Ala Ala Asp Gly Asn Leu Gly Ser

```
                1625                1630                1635
Ala  Ala  Ala  Val  Ala  Ala  Val  Ala  Ala  Ala  Ala  Glu  Ala  Glu
          1640                1645                1650

Ala  Asp  Gly  Glu  Val  Gly  Glu  Glu  Glu  Glu  Val  Asp  Pro  Ser
          1655                1660                1665

Glu  Leu  Leu  Arg  Gln  Ala  Tyr  Ser  Ala  Gly  Leu  Thr  Glu  Leu  Pro
          1670                1675                1680

Gly  Met  Leu  Gly  Asp  Ala  Glu  Ala  Glu  Glu  Glu  Glu  Gln  Glu
          1685                1690                1695

Ala  Ala  Ala  Ala  Ala  Gly  Asp  Glu  Val  Thr  Asp  Pro  Gly  Thr  Gly
          1700                1705                1710

Ser  Gly  Ser  Gly  Gln  Ala  Gly  Arg  Arg  Arg  Gly  Gly  Gly  Gly
          1715                1720                1725

Gly  Ser  Gly  Ser  Ala  Gln  Ala  Ala  Asp  Ala  Thr  Pro  Pro  Pro  Glu
          1730                1735                1740

Gly  Glu  Gly  Thr  Glu  Ile  Val  Gly  Ser  Val  Gly  Ser  Gly  Arg  Ala
          1745                1750                1755

Ala  Thr  Gly  Leu  Arg  Ser  Gly  Gly  Gly  Ala  Val  Gly  Asp  Ala  Ser
          1760                1765                1770

Phe  Ile  Arg  Pro  Gly  Gly  Gly  Gly  Gly  Met  Ser  Phe  Leu  Ala  Ser
          1775                1780                1785

Ala  Val  Gly  Gly  Gly  Gly  Gly  Gly  Gly  Gly  Gln  Gln  Met  Thr
          1790                1795                1800

Thr  Thr  Val  Asp  Phe  Ser  Gly  Leu  Asp  Gly  Gly  Gly  Gly  Gly  Ser
          1805                1810                1815

Trp  Trp  Leu  Ser  Lys  Gly  Ser  Gly  Glu  Gly  Glu  Gly  Glu  Glu  Arg
          1820                1825                1830

Ser  Val  Val  Ser  Ser  Gly  Ala  Met  Ala  Ala  Val  Ala  Ala  Gly  Ala
          1835                1840                1845

Arg  Arg  Glu  Gly  Leu  Ser  Gly  Gly  Gly  Gly  Val  Gly  Gly  Gly  Val
          1850                1855                1860

Val  Met  Asp  Ala  Glu  Asp  Val  Asp  Met  Asp  Asp  Thr  Thr  Ser  Leu
          1865                1870                1875

Ala  Ala  Glu  Ala  Ala  Ala  Ala  Ala  Ala  Ala  Asp  Leu  Ala  Ala  Ala
          1880                1885                1890

Ala  Ala  Gly  Pro  Ala  Val  Gly  Ala  Val  Gly  Val  Arg  Ser
          1895                1900                1905

<210> SEQ ID NO 72
<211> LENGTH: 12099
<212> TYPE: DNA
<213> ORGANISM: Chlamydomonas reinhardtii

<400> SEQUENCE: 72
gagcaacacg catcaaccaa gaaagataca agcttgcaga ggtcgccgtg aggaaatagt    60
cccagctaaa atgcgtgcag gtctcaacct gccacgactc ccagtttcgg cgaattaacc   120
gctgtcaccc tcgtcaaggc ttccctacgc gtttacgtat actcctatgt aacttagttg   180
tagtgggcgt gctttcagac gcgtatacga gcgttgtgtc ggttttggaa cgtggtgaat   240
ccagcagtct gccacgccga acgccggaga cgctctctcg tcttgccaac actgccgcga   300
gtaaagtcct cagaattgag cttaaatata tcattaaagt gggcgtcgtc gctggtctgg   360
cgccacaccg ctttgggagt tgggtgttgc gcaaggcgct aatcgaattc gttccgcctg   420
catatcgcac atatcggggt acatgtgaag gtatacattg aactctagcc actcagtaac   480
```

```
tccatgctac cagtgcaagg cgctccgtac aggtattagc ggcactagtg caagcggagg    540
ggaagaggac ggaagcctgc ctactaccgc cgcgatagcc gtcgtgtgac ctactagctc    600
catgcaaaag atatagaaaa tggaaggcga atgctcagac acttgcactc cgcaatttgt    660
gacgagcttt tacatactag tattcagtca caagggtagt ggcccctaggt cacgacgctt    720 atgcatatca ttgtgagttg tcgaaccagg aagtcctggc gagcgtgctg ccgcggacag    780
gagggctaaa ggcagagcat ggccacggtc ggtgaaccgc cgctggagca gctccgcgag    840
ctcttccatc tttcggctcg cgacgcctgc atcacgctaa atatcagcca atcgcggctt    900
aagaagatat gccgtcagca cggcatctcg cgatggccgc accgcaagct ggccagcctg    960
gactcgctgc ggcagcagct gaagggcgac agcggcctta ccacgcagga cagagcggtg   1020
cttctggcgc ggctggaggc ccaggtggcg gcggtcattg cggagccgga caggccgctg   1080
gagaagctgt tcgaggacat gcggcagacc agctacaagg tgcgttacca cgcacgcaac   1140
aagctgcgtc gcggcacggg agcagctggg gagggcgctg atgatggtga tgctgccggc   1200
accgcttctg ggggcgacgc atcctctcca gcggggcgcg ccctgtcgac ggagcgcggc   1260
ggaggcaggc ggggccggcg cggcgctgcc agtccccgta gggggccgca gcgccggggcg   1320 gcgtcctcgg gcccagccag cggcagccgg cttagacggg ccgggagacg tcgaggcagt   1380
gattggggcg gctcctcagg cgaggaagag gcggcatcgg actcgactga agccgcctcg   1440
gatgacgagg agcaggcggc gggtggcgct gcagccggcg gctactcgga gcgggacgat   1500
gacgaagacg acgagggcga tgacggcgag gacagcgatg aggatgacga ggacgacgag   1560
gaggatgagg actgggtggc gggcggcagg gctggcaagg caggggggccg ccaggcacgt   1620 gcggacatgg cggcagctgc tacagccggg ggcagtgctg ggcgagccga tcgccttcgc   1680
cgccgggcga cagggttaca ggggctgcgt gtgccggcgg cggcatcccc cgcaactcca   1740
cgcagccggc ggcggcggcg aagcgccgcc ccgctggact cggggggacac agagccttcg   1800 ccaggcggaa ggagcgccgc cgctgcagcc ccgcttgcga caaccgcctg tggtggaggc   1860
gataccaaca gcagtgacag cgcaggcagg agcctggagc agcggcagcc ggcggcaagg   1920
gagggtgccg gtgacgcagc cggacggccg cctacgcgc cacagccgca gctgagcggc   1980
cgctcccgca cagtggcctc ccgctcggcg tccgcccgcg cgggcgcgcc agcggggctg   2040
cccggcttca gccctgtgcg cgatgcgccc acgcccagca gccacaccgg ccctgccgct   2100
gccagccgcg gccggctgca ctccgggggga cacgggcacg ggcacgcaca cgggcgcgcc   2160
gccaagccgg agcgcggcgg cgcagccgcc acactgtcag cctttgcggc ggcggagcgc   2220
gcagtggccg gtgcatctgc tgcaggtgct gctggtggtg gtggtggtgg tggtggtggt   2280
ggtggttctg ctgtgaagca ggagcgggag cagagtgctg ggcagctggt gggcccgggc   2340
ggcggtggcg gcgttgccgg cgctgctggc cgcggggccg acggcgcggc ggcaagggac   2400
gacgctcgtg cggcagctgg tgacgttgct gttgaggcag gtgccggtac aggcggatcg   2460
agccagctgg acgggtccag ccagtggggc atgaagcgag cccggtctgc gccgcagccc   2520
cagcctctgg gcgcagctgg tgtggcgggc acgacttcct cccaccagac cacctcttca   2580
gatcgctcgc agcaccagca gcaacaggcg ccgctgccgc cgctccaggc caggacgtcg   2640
agggaatggc cgcccatgga catgatgccc tcaggctggc agcagcccta ccgtcagccc   2700
atgccgctgg acgcaacccg cactacgcct gcaacggcca ccaccgccac gactgctgct   2760
ggcggaggtg ccgacgttgg ctcgggccgc caccaagacc gccgcttaga ccacccgtcg   2820
```

```
cacctgcagc aggcgccgca gcacccccac cctcaggaac ccctgcatca gcgggcgcag    2880
cgccctgcct cgtcgcccac ggcctccatg ggcgggcctg caacaaagca gcaggcccac    2940
ggcagctacg gcgccgcagc gcccctccat cacacggcgg cccaaagcca tagccatagc    3000
tacagccacg ccccgccgac ggcaaccacc gcgccgccgg cggagccgca tcctttcttt    3060
tcaccagccg cagccgcagc cgcggccgct gctgccggac cgggaatcga atctagcctg    3120
ggcctggggt cgtctgtgcc caggtcaggg gcgctggagc atggtgttga ggactgggag    3180
tggcgctggc gggaggaagg ccagcagcgg catcagcgcg ccctcctgca gcagcaacaa    3240
cagcagcagg agtacatgcc gccagcaccg caccaccaca tgcctcatga acagcagcag    3300
cggcatcaac agctgctgca gtcacagtcg cagtcgcagt cacagtcgca gtcgcagcca    3360
cagtcacagc agcaacgcca tgacttgcac cgggagcagc tgccaccgct gccgccgcaa    3420
ccagaggcgc tgtcgcgtca acagcaggag cagcggcaac aggagcactt tgagttgcag    3480
cagctgcagt tgctgcagca acagcagcag tcgcagcagc tgcagcagcc gcaacagcac    3540
ctgatgccgt cgtcctcctc cttccaacgc gactggatcc cgccgccgca gccggatccg    3600
cagcctctgc cgtcctggcg ccagtcagag ccgctgcatg ctgaaccgca gccacgtgcc    3660
agccggtcgc agcaacagcc tcaacagctg cagagcccgg ggcatgtgca gcagggccag    3720
ccgctacaac acggcggcgc gtccggcagc gctcctacgt accgcggcgg cggcttcggc    3780
tcagagctgg atggcggttg gcactggcag cagcagcagc agcagcagca acagcagcag    3840
cagctgctgc agcaacaaca ggcggcatct ctgtcgcacc aactgcagga acgtgaacag    3900
caggagctgc agcggcaaca ggcgcaagcc cgacaccaca tgcagctgca gcagcaacaa    3960
caaggcgctc cgccgtcttc gtcatggcac gggcagtacc cgccactcca ccagcgcccc    4020
gaccaggcgc acgcgcagta cccccacctg cagcagccgc aagagcacca gcacccacag    4080
caagagcggt acccgccact gcaccagcag acgcaacagc agctgcagca gcagcagcag    4140
cagccacagc tgcaacagca gcaacaggca cagtggccag gtgcggaccc tcgcctgctt    4200
gcgcctggca ggcagccact gccgccccg ccttcctggt cagcccgcca aggtcccggc    4260
tcggcgccgc cgtctaccc tgccggccac ccgacactgc agcagcaact gtacccgcca    4320
atgtaccaac agcagacgca acagcagccg cagccgcaac aacaaacgc aggccagcaa    4380
cccgcctatc accaccaccc gcttttgtcg ccgcactctc cgcagtacca gcagcggatg    4440
caggcgtcgg cgcccgtcgg cagcggcggt gctcaccgac agagccaaag catcatcccg    4500
ggacctccaa gcgctctgct gtcgctgccg agccccgcct ccaatgagcc cagccccga    4560
gacttcgcct acccctcgcc cctgcctccg catcaccagc caccgcacca accccacccg    4620
caccaccact ctctgtcggg cagcggcttc gactcggagg gcggcgctga cgccgcggct    4680
gctgcccgcc gcccgtccaa ccagtcccag tcctttgacc agcagcacca ggcggcggcg    4740
attgcgagcg gcacgctgcg caattggtcg tcctcctcct cggcctcatc gctgctggtg    4800
tggggctcgg cgtggccccc gggcagcggg ctcggcggca tgggccctgg aggcatgggc    4860
cccggaggcg tgggttctgg aggcatgggc cccgggccgc tgggccgggc ggctcgaac    4920
ccacacggcg ctgcgggcag cggcggcggc agcgcctacg gcgcggctgg cttccgcagc    4980
ggcctacaca gcggcggcgg tgtgggtggt gccggaggcg ccggtttcgg cggctcagcg    5040
ggcggcgggt atgggtggag ctctgggggc agttcatatt cggcggcgg ctttgcgcat    5100
gcaatgggcc ttccgtcgtc gggcggcggc cagcggctg ccagcggcac cggtggtgac    5160
ggcggcggtg gagacgagaa ccggatgctg cacgagggc tgcgggggcg cagtgcttac    5220
```

```
gtgtccgatg caggggaccg gcgggatgag gcggtggcag aggcggccgc agccgcagcc    5280
gccacggttg cggctggacc cggcggtgga cgcatgggcg gaaggatgc cgcaggcact     5340 cgtggcggtg gtggcggaac tggcagcggc gcggccacaa ccgcagccgt ggcagccgcc    5400
gccgctgcgg ctgcggccgt ggcagcggtt cgggctacct cgggcgctgc cgaccatgaa    5460
acgcgccatc gctcgccagc actgcagcca ccgacgcacc atggcgcccc caccgacctg    5520
ctctcaagtc ggcaccacgc gcgccattcg cacgtgctgc cgcccgccgg aatgaactac    5580
gccgcctacc tgcctccgcc cttgtcactg cctccggcgt tggactcgcc gcaccagccg    5640
ccatacagcg cgtcccacgg accggcccac ggccggctca acccgccgc ctactcccgt     5700 gtcgtctcca ccggcttccc tgggattcac cccgggtcgc tgcctggcag cagcagccca    5760
agccccagcg gcggcggcgg tggcggaggt gccaatgcag gcggaggtcg tgtcggtggc    5820
ggctcgggca ccgccgcccg ccgccgcggt ggtgatcgtg cagccagccc gcttggctcg    5880
tatggcagcg gtgctgctgg cggcggggc ggtatcgctg ccggcgtaaa ggcagaggac      5940
aggggcccta gcggcggcag cggcggcgat ggcggctttg gcgggacga cactcgggac     6000 gtggagccac atcttggtca cgtagcattc catggcggca atgcagggca gcagcaaaca    6060
gccgcctacc gccgcacgtc ggccccagca gccgcagctg ccgccacggc ggacccacga    6120
gcgcaatctg ccagcggcga gcgcgacagc ggcggcggcg tggcagtaga ccttcggcgc    6180
gtgccgtaca cggggcggct cagcgagccc gtgatgcggg cgccgcttcg ggcattgctg    6240
gggcttgggt ccgacctggc tgacgagggc gaggcgagg cggagctcgc ggcgtccatg     6300
gcggcggcgg cgcgtgatga agagcggttc cgcatgctga gcaccggcag cagcaccgtc    6360
gcgatatttg caccggaggc tcagccccag ccgcaccagc aaacgcagca ccaacagccg    6420
caccagccgt cacggccggt ggagggacgg ccgcaccacg gctacggttt gccgcggctg    6480
cagcagggcg cgcccgaggg ccgtgtggct agcgccagtg ctgcagacag aggcggcagg    6540
cgcaccagcg gcgacatgga aagggcggt aacggcggcc ggcggcccca cactgtgccg     6600
gacgcccgcg gctgggctgg gccgctgac ctgctgctag cctgccagga aacggacgcc     6660
attgcgcagg ccgaggcggc agacggcgta cgcggcgccc ttggccacct acaccaagca    6720
acgtaccaag ccgccgcttc gcttcacgta gcgcagcagc cgcgcggtgg ggctgcttat    6780
gaggaaccac ccccgcgtcg tcagccccac caggcagcgg gtgcaggcgg gccctcacct    6840
gtgtgctccg ccgacctcac cacacccacc gcagcccatc aacgcccca gcagctacgg     6900 ccgcacgccg cagcgccgcc ttctgccacc tccagccgcc accaagtctc gcgccgcgct    6960
gcggctgctg aggctgcagt cgttactgcc acgcccgtgg cggcgaccgg ctcctcgggt    7020
cggccgggtc ccgctgcagg cccctctcct gccgcagccc ctgttaccgc cgctgcagct    7080
tctggtgccg ccttcctgtc gccagtcgcc tcggtggctg cgggcagcgg cgtggcgggt    7140
ggccctgcca ccagcagcgc cagcagcggc cgccgtagca gcgtggcgg cagtagcagc     7200 agcggcggca ggacgctgct ggtgtggacg ggatcacagc cgcgctgggg gcaggtgctg    7260
ccgccgctgc aacaccagtc acagccacag cagcagcagc cacagcagca gcagcagcca    7320
cagcagcagc cggagctgca gtccccaagt atgcggccgc cgcagctaca gccgctgccc    7380
ctgatgccgt cctcggcgcc gctgcgcacc ggccccagc gccgcatcag tggcgccggc      7440
gcagctggtg ctgaggtcac caccggcaca gcgactgcat ctggcccagg gcaggagtcc    7500
accagcgcag cagccgcagg cgccgccggt gcgcttccgc ccatgccgcc tctgccagca    7560
```

```
tcgctgctag cagcgctggc tgccggcggc ggcgcaggcg gcgacctctc cccagatgcc    7620
taccccgtga cggcgctgca gccgccggca gttggcgccg ctgaccgcgg cactgatgcc    7680
ggtcagcgcg aacaggaccg cccgcagggc cgcagggcct cgccgcctcc cgccgccacc    7740
gaccccgcca acgccacaac cgcgggcgga gtgccactgt ccattctgga gtacctgcgc    7800
catggatccg gatccgagcc gccgctggat ctcgaggcgc tggaggacct ggacatggat    7860
ctggatctgg attttcagac gccgcaggcc ggcgacgcgg ccgccgcgct ggcgctgatg    7920
cggccgtggc tgacgagcac accgggtttg ggccccacgc caatggagat atcgccgcgt    7980
gctgctttgc cggctacgcg ccgtatcagt gccgcgggaa cagaggcacc tgcgccccag    8040
cgccagcagg cgccgccagc aaccgggcag cctacttgtg aggacgccgc tggctcaact    8100
gctgccggcg ggggcactgc tgcagcacct gctgcgcgca tgacgtcagc gggccaagcg    8160
gctgccagca ccgccctgtc gctttctgcc tctgccgccg gccaagccg gccgcccat    8220 gccacctgtg ccgctgcaga cgctacaacg tttgcctcac ctgtcgccgc ggccgcagct    8280
gacgccgcac ggcagcacga gttcgcatct cccgccccgc acgccgcagc agccacggca    8340
gcagcacccg cggcagtgtc accctgcacg cctgcagccg ccgtgatacc gggtagcggg    8400
gccggtgggg ccgctggtgc cggtgcgccc gcgtcgccgc cgccggcgcc cgtcaagcga    8460
cctccgccgg cgcggctgtt cttgcacacc gtgcggcggc actcgggtac aggcgaaggg    8520
cctgctgctg agcccacggc tgcgcgtgcg catgcccctg cagctcatgc ggagggtggc    8580
ggcatggacg cgcctccgct gccacaccac cagtcacagc agcagcacca gtcacagcag    8640
cacccccagc accaccacca gcaggcatcc ccgtacggag gcgcagcggc gcacatgtac    8700
gcggcctggt gcagcagtcc tgccgccacg cccacccgcc acaacgcatc tggtggcggc    8760
gccgccgccg ctgccgcagg cagcaccgga ggcgctgcct tcgctgccgc gcccgcgccg    8820
ccacaggcgc ccagggccgc agccgcagcc gacgctgata cgcggagcgt cagcgtcacc    8880
gggggcctcg gtgggagcgg cagtggaggc tctgcacacg gcggggcac tggggtctc    8940 ggaggcgtct caccgcgcag ccgcgctgcg ctcttggtgg atgtggccga gcctcttggc    9000
ccgtacgggc cccagcagcc cacaactgcc acctcgactg ctgcagctgc tgtagctgcg    9060
ggtgaggcgg gtggcgcaag cggcaggcag ctccagccgg ctccggcacc tccaactgcg    9120
gccagccgct acccgtggaa catgggctgg ggtgcggggg caagcggtgc agcgggcagg    9180
gagaacacac cgctgcgcca gcttccgccc ttcccgccgc cgcagcctga gctggcagcc    9240
ctgccgctgc accgtgcgca agcgacgggc acagtggcga caggcaccgc tggacctgga    9300 gagcagggc cgcaagggta ccagcaacgt agtggcggcg gcgacacgac ggaggcccat    9360
gtgccaccac cgctgctgca gccgccgcca gcgccacct cgcctaccgg ctacgcggtt    9420
gcgtcctatc gccgggacag tgagggcggc ggcgtcatac cggtggtgtc gccgccgccg    9480
cagctgatgc cgcagtcggt gcggccgccg ccgcgcctgg cgccgctagt ggcgccgact    9540
gccgcggcgg gaccgcctca gccgccgccg ctgacgtcgc cacctgcgcc gcgcaagcca    9600
gccaagcagc ccgcgctcat ggctcctggg ccgccggcgg ccagcgtcg cagtagtggc    9660 ggcagtgtcg acaccggcgg cagtgccgga ggtgcggctg gccgcaactc cccagcatcg    9720
cttgccgggg cggcaccgg cgcggctggg ccgctgccca gctaccacc acacgtgctg    9780 gagcggccgc tgccgccgcg tatgcaggtg cacatgcccg cgcccgcgcc ttcgccggca    9840
gccgtccaag ggcctgtcgg cgcaacagct cactctggcg cagcagctcc cggcagccgg    9900
ctactagcgg cggccatgtc gcctgtcggt ggcacaaacg cgggtggggc agccgccggc    9960
```

-continued

```
gcatcgccgc cgcccctgct caaggtaacc attggcggcc gcccaggctc gctgcagtca      10020
gccataggca gcttctccgt gcagcctacg cagctgccgc agccgccgca gctgccggca      10080
ttgcctcagt cacagcacca gtcacagcga cagcaccagg tcgcagagca ggggcgtttt      10140
gggatgccag gcgcggcggg ctgggccgtg ccgggcgctg ctgtgggcgc ggccggctcc      10200
cacctgccgc agctgcacca gcaccagcat gccgctgcag ggatcttgga cggcgataca      10260
cagtctgccg gcggtactgg tggcggtggc gtcagcagca agcgcaagcg ggagggcgat      10320
tcagagtagg atgggcgaca tgggtcttca cgcgcggtgc acattgatgc aaacgcatga      10380
gtggggcaac atgaatgccg gcagcactac ctgtcgaaga tcgtgagtcg attgcatgtg      10440
gccgtgtgac tagcaagcac ttatatccgt gcatggaaag catggcaggt tggtgcattg      10500
gaatgcaaat acgtacact cggcggtagc tgttcaggcg gtggccctgc aactggacga      10560
gaatgtgtgt agactgaagt caggcagcat ttagatcggc tgctgacaac ataccttccc      10620
attcaagggg attcatggga cagtagcgat gccttgaact cgtattgacg tagttggtgg      10680
cgagcgtgtg aggaccagca gcaggtttag cgcaggatgc aaagcgcatc aacgtccagg      10740
cacatgtcat actcacattt gttgacgcgt aatcaagcaa cgcagaaaga gcaagcggcg      10800
cagggtgacc acacaaccag cacgatgtca ctacgcggtg aggatgcgag gtactgctgt      10860
cacaggtcgc gcgcgtacgt tcgcagatgt agggggttgc atgcatgtcc tgccagctgt      10920
aaaggcgcat ggcgtcaatt gcaccatgtg cggcgccgtg ccaccacaga cccatgggcc      10980
tggactgggc ctgagcgcct tggacatggc cgtctattct gccctgtgta tggggtcagg      11040
gaaaatgtgg gtccgggtgc ttgtatgttg acttgggccg cggcacgtaa gccgtcatgc      11100
cgtctgcatt catagcacag ccatggtgtg caggccgggg gcttttcgat ggcacgtttt      11160
tgcgctgtcg gcgtgtgttc aggcttgggg acgtggttgc atcggtttgc attaaaagcg      11220
aaggctggtg tgaggcgcgc gctcatatca tcagcccagc aagccacgcg gtcgctctgg      11280
cccctactat cgccgttgct catcaggcat gctgtcataa ggtttcgctc tctttctttg      11340
gactgcgctc actccctctt cttctctcaa gcagcatact ggtgctctca tgtttgacag      11400
ggtcatacag ccccggcaag cagagaacct ctttctaact attatgcgtg tgttttgtgc      11460
actgcaatgg tctatgcgta gtcttgatta gcctgtgggc agtccatgaa tgactcattg      11520
gtgttatgcg tcttgcaagt gagggtagag aggttcactg atcaagggca taagatcagg      11580
cccaccagca cgtaattcaa gtctttgcgg caccgcattc ctaagcgttt tgcaagctgt      11640
ctgtaggtgc gcgtgggctg gcgtgcctgt ggtgcgtgaa acattactgc cattctgaga      11700
ctggagctgg ggctgcatcc cctgtgtcac acgcggtgac tagtatgttg tatcaagtcg      11760
tagcaagtaa aactctgctt attctggctt gtcttccgta gcatgcaccg gcctgatgcc      11820
aatttgtgct ggtgttggaa ttgcgcactg atgaaggagg catggtctgt cggttaggcg      11880
tcggcggtag ctggacatgc cagcaccgcc tcacaccaga tcgatgaaga actttgcaca      11940
atcaaaatga ttagcagcta gcactggcac gtcgtgtggc atgggatgtt gagtgttgtg      12000
gcctcgcgaa tggatgtagg gagcagtgta ctgctttccg tgctgtgggg cacttcacat      12060
gttgtggcgg gccgggtggc catgtaattt caagtccga                            12099
```

<210> SEQ ID NO 73
<211> LENGTH: 9531
<212> TYPE: DNA
<213> ORGANISM: Chlamydomonas reinhardtii

<400> SEQUENCE: 73

```
atggccacgg tcggtgaacc gccgctggag cagctccgcg agctcttcca tctttcggct        60
cgcgacgcct gcatcacgct aaatatcagc caatcgcggc ttaagaagat atgccgtcag       120
cacggcatct cgcgatggcc gcaccgcaag ctggccagcc tggactcgct gcggcagcag       180
ctgaagggcg acagcggcct taccacgcag gacagagcgg tgcttctggc gcggctggag       240
gcccaggtgg cggcggtcat tgcggagccg gacaggccgc tggagaagct gttcgaggac       300
atgcggcaga ccagctacaa ggtgcgttac cacgcacgca acaagctgcg tcgcggcacg       360
ggagcagctg gggagggcgc tgatgatggt gatgctgccg gcaccgcttc tgggggcgac       420
gcatcctctc cagcggggcg cgccctgtcg acggagcgcg gcggaggcag gcggggccgg       480
cgcggcgctg ccagtcccCg taggggGccg cagcgccggg cggcgtcctc gggcccagcc       540
agcggcagcc ggcttagacg ggccgggaga cgtcgaggca gtgattgggg cggctcctca       600
ggcgaggaag aggcggcatc ggactcgact gaagccgcct cggatgacga ggagcaggcg       660
gcgggtggcg ctgcagccgg cggctactcg gagcgggacg atgacgaaga cgacgagggc       720
gatgacggcg aggacagcga tgaggatgac gaggacgacg aggaggatga ggactgggtg       780
gcgggcggca gggctggcaa ggcagggggc cgccaggcac gtgcggacat ggcggcagct       840
gctacagccg ggggcagtgc tgggcgagcc gatcgccttc gccgccgggc gacagggtta       900
caggggctgc gtgtgccggc ggcggcatcc cccgcaactc cacgcagccg gcggcggcgg       960
cgaagcgccg ccccgctgga ctcggggGac acagagcctt cgccaggcgg aaggagcgcc      1020
gccgctgcag ccccgcttgc gacaaccgcc tgtggtggag gcgataccaa cagcagtgac      1080
agcgcaggca ggagcctgga gcagcggcag ccggcggcaa gggagggtgc cggtgacgca      1140
gccgacggc cgcctacggc gccacagccg cagctgagcg gccgctcccg cacagtggcc      1200
tcccgctcgg cgtccgcccg cgcgggcgcg ccagcggggc tgcccggctt cagccctgtg      1260
cgcgatgcgc ccacgcccag cagccacacc ggccctgccg ctgccagccg cggccggctg      1320
cactccgggg gacacgggca cggcacgca cacgggcgcg ccgccaagcc ggagcgcggc      1380
ggcgcagccg ccacactgtc agcctttgcg cggcggagc gcgcagtggc cggtgcatct      1440
gctgcaggtg ctgctggtgg tggtggtggt ggtggtggtg gtggtggttc tgctgtgaag      1500
caggagcggg agcagagtgc tgggcagctg gtgggcccgg gcggcggtgg cggcgttgcc      1560
ggcgctgctg gccgcggggc cgacggcgcg gcggcaaggg acgacgctcg tgcggcagct      1620
ggtgacgttg ctgttgaggc aggtgccggt acaggcggat cgagccagct ggacgggtcc      1680
agccagtggg gcatgaagcg agcccggtct gcgccgcagc cccagcctct gggcgcagct      1740
ggtgtggcgg gcacgacttc ctcccaccag accacctctt cagatcgctc gcagcaccag      1800
cagcaacagg cgccgctgcc gccgctccag gccaggacgt cgagggaatg gccgcccatg      1860
gacatgatgc cctcaggctg gcagcagccc taccgtcagc ccatgccgct ggacgcaacc      1920
cgcactacgc ctgcaacggc caccaccgcc acgactgctg ctggcggagg tgccgacgtt      1980
ggctcgggcc gccaccaaga ccgccgctta gaccacccgt cgcacctgca gcaggcgccg      2040
cagcaccccc accctcagga accctgcat cagcgggcgc agcgccctgc ctcgtcgccc      2100
acggcctcca tgggcgggcc tgcaacaaag cagcaggccc acggcagcta cggcgccgca      2160
gcgcccctcc atcacacggc ggcccaaagc catagccata gctacagcca cgccccgccg      2220
acggcaacca ccgcgccgcc ggcggagccg catcctttct tttcaccagc cgcagccgca      2280
gccgcggccg ctgctgccgg accgggaatc gaatctagcc tgggcctggg gtcgtctgtg      2340
```

-continued

```
cccaggtcag gggcgctgga gcatggtgtt gaggactggg agtggcgctg gcgggaggaa    2400
ggccagcagc ggcatcagcg cgccctcctg cagcagcaac aacagcagca ggagtacatg    2460
ccgccagcac cgcaccacca catgcctcat gaacagcagc agcggcatca acagctgctg    2520
cagtcacagt cgcagtcgca gtcacagtcg cagtcgcagc cacagtcaca gcagcaacgc    2580
catgacttgc accgggagca gctgccaccg ctgccgccgc aaccagaggc gctgtcgcgt    2640
caacagcagg agcagcggca acaggagcac tttgagttgc agcagctgca gttgctgcag    2700
caacagcagc agtcgcagca gctgcagcag ccgcaacagc acctgatgcc gtcgtcctcc    2760
tccttccaac gcgactggat cccgccgccg cagccggatc cgcagcctct gccgtcctgg    2820
cgccagtcag agccgctgca tgctgaaccg cagccacgtg ccagccggtc gcagcaacag    2880
cctcaacagc tgcagagccc ggggcatgtg cagcagggcc agccgctaca cacggcggc    2940
gcgtccggca cgctcctac gtaccgcggc ggcggcttcg gctcagagct ggatggcggt    3000
tggcactggc agcagcagca gcagcagcag caacagcagc agcagctgct gcagcaacaa    3060
caggcggcat ctctgtcgca ccaactgcag gaacgtgaac agcaggagct gcagcggcaa    3120
caggcgcaag cccgacacca catgcagctg cagcagcaac aacaaggcgc tccgccgtct    3180
tcgtcatggc acgggcagta cccgccactc caccagcgcc ccgaccaggc gcacgcgcag    3240
tacccccacc tgcagcagcc gcaagagcac cagcacccac agcaagagcg gtacccgcca    3300
ctgcaccagc agacgcaaca gcagctgcag cagcagcagc agcagccaca gctgcaacag    3360
cagcaacagg cacagtggcc aggtgcggac cctcgcctgc ttgcgcctgg caggcagcca    3420
ctgccgcccc cgccttcctg gtcagcccgc caaggtcccg gctcggcgcc gccgtctacc    3480
tctgccggcc acccgacact gcagcagcaa ctgtacccgc caatgtacca acagcagacg    3540
caacagcagc cgcagccgca acaacaaaac gcaggccagc aacccgccta tcaccaccac    3600
ccgcttttgt cgccgcactc tccgcagtac cagcagcgga tgcaggcgtc ggcgcccgtc    3660
ggcagcggcg gtgctcaccg acagagccaa agcatcatcc cgggacctcc aagcgctctg    3720
ctgtcgctgc cgagcccgc ctccaatgag cccagcccc gagacttcgc ctaccccctcg    3780
cccctgcctc cgcatcacca gccaccgcac caaccccacc cgcaccacca ctctctgtcg    3840
ggcagcggct tcgactcgga gggcggcgct gacgccgcgg ctgctgcccg ccgcccgtcc    3900
aaccagtccc agtcctttga ccagcagcac caggcggcgg cgattgcgag cggcacgctg    3960
cgcaattggt cgtcctcctc ctcggcctca tcgctgctgg tgtggggctc ggcgtggccc    4020
ccgggcagcg ggctcggcgg catgggccct ggaggcatgg gccccggagg cgtgggttct    4080
ggaggcatgg gccccgggcc gctggggccg gcggctcga acccacacgg cgctgcgggc    4140
agcggcggc gcagcgccta cggcgcggct ggcttccgca gcggcctaca cagcggcggc    4200
ggtgtgggtg gtgccggagg cgccggtttc ggcggctcag cgggcggcgg gtatgggtgg    4260
agctctgggg gcagttcata ttcgggcggc ggctttgcgc atgcaatggg ccttccgtcg    4320
tcgggcggcg gcgcagcggc tgccagcggc accggtggtg acggcggcgg tggagacgag    4380
aaccggatgc tgcacgaggg gctgcggggg cgcagtgctt acgtgtccga tgcagggac    4440
cggcgggatg aggcggtggc agaggcggcc gcagccgcag ccgccacggt tgcggctgga    4500
cccggcggtg gacgcatggg cggaagggat gccgcaggca ctcgtggcgg tggtggcgga    4560
actggcagcg gcgcggccac aaccgcagcc gtggcagccg ccgccgctgc ggctgcggcc    4620
gtggcagcgg ttgcggctac ctcgggcgct gccgaccatg aaacgcgcca tcgctcgcca    4680
```

```
gcactgcagc caccgacgca ccatggcgcc cccaccgacc tgctctcaag tcggcaccac    4740
gcgcgccatt cgcacgtgct gccgcccgcc ggaatgaact acgccgccta cctgcctccg    4800
cccttgtcac tgcctccggc gttggactcg ccgcaccagc cgccatacag cgcgtcccac    4860
ggaccggccc acggccggct caacccggcc gcctactccc gtgtcgtctc caccggcttc    4920
cctgggattc accccgggtc gctgcctggc agcagcagcc caagcccag cggcggcggc     4980 ggtggcggag gtgccaatgc aggcggaggt cgtgtcggtg gcggctcggg caccgccgcc    5040
cgccgccgcg gtggtgatcg tgcagccagc ccgcttggct cgtatggcag cggtgctgct    5100
ggcggcgggg gcggtatcgc tgccggcgta aaggcagagg acaggggccc tagcggcggc    5160
agcggcggcg atggcggctt tggcggggac gacactcggg acgtggagcc acatcttggt    5220
cacgtagcat tccatggcgg caatgcaggg cagcagcaaa cagccgccta ccgccgcacg    5280
tcggccccag cagccgcagc tgccgccacg gcggacccac gagcgcaatc tgccagcggc    5340
gagcgcgaca gcggcggcgg cgtggcagta gaccttcggc gcgtgccgta cacggggcgg    5400
ctcagcgagc ccgtgatgcg ggcgccgctt cgggcattgc tggggcttgg gtccgacctg    5460
gctgacgagg gcgagggcga ggcggagctc gcggcgtcca tggcggcggc ggcgcgtgat    5520
gaagagcggt tccgcatgct gagcaccggc agcagcaccg tcgcgatatt tgcaccggag    5580
gctcagcccc agccgcacca gcaaacgcag caccaacagc cgcaccagcc gtcacggccg    5640
gtggagggac ggccgcacca cggctacggt ttgccgcggc tgcagcaggg cgcgcccgag    5700
ggccgtgtgg ctagcgccag tgctgcagac agaggcggca ggcgcaccag cggcgacatg    5760
gaaaggggcg gtaacggcgg ccggcggccc cacactgtgc cggacgcccg cggctgggct    5820
gggcccgctg acctgctgct agcctgccag gaaacggacg ccattgcgca ggccgaggcg    5880
gcagacggcg tacgcggcgc cgttggccac ctacaccaag caacgtacca agccgccgct    5940
tcgcttcacg tagcgcagca gccgcgcggt ggggctgctt atgaggaacc accccgcgt     6000 cgtcagcccc accaggcagc gggtgcaggc gggccctcac ctgtgtgctc cgccgacctc    6060
accacaccca ccgcagccca tcaacgcccc cagcagctac ggccgcacgc cgcagcgccg    6120
ccttctgcca cctccagccg ccaccaagtc tcgcgccgcg ctgcggctgc tgaggctgca    6180
gtcgttactg ccacgcccgt ggcggcgacc ggctcctcgg gtcggccggg tcccgctgca    6240 ggccctctc ctgccgcagc ccctgttacc gccgctgcag cttctggtgc cgccttcctg     6300
tcgccagtcg cctcggtggc tgcgggcagc ggcgtggcgg gtggccctgc caccagcagc    6360
gccagcagcg gccgccgtag cagcggtggc ggcagtagca gcagcggcgg caggacgctg    6420
ctggtgtgga cgggatcaca gccgcgctgg gggcaggtgc tgccgccgct gcaacaccag    6480
tcacagccac agcagcagca gccacagcag cagcagcagc cacagcagca gccggagctg    6540
cagtccccaa gtatgcggcc gccgcagcta cagccgctgc ccctgatgcc gtcctcggcg    6600
ccgctgcgca ccggcccca gcgccgcatc agtggcgccg gcgcagctgg tgctgaggtc     6660
accaccggca cagcgactgc atctggccca gggcaggagt ccaccagcgc agcagccgca    6720
ggcgccgccg gtgcgcttcc gcccatgccg cctctgccag catcgctgct agcagcgctg    6780
gctgccggcg gcggcgcagg cggcgacctc tccccagatg cctacccgt gacgcgctg      6840 cagccgccgg cagttggcgc cgctgaccgc ggcactgatg ccggtcagcg cgaacaggac    6900
cgcccgcagg gccgcagggc ctcgccgcct cccgccgcca ccgaccccgc caacgccaca    6960
accgcgggcg gagtgccact gtccattctg gagtacctgc gccatggatc cggatccgag    7020
ccgccgctgg atctcgaggc gctggaggac ctggacatgg atctggatct ggattttcag    7080
```

```
acgccgcagg ccggcgacgc ggccgccgcg ctggcgctga tgcggccgtg gctgacgagc    7140
acaccgggtt tgggccccac gccaatggag atatcgccgc gtgctgcttt gccggctacg    7200
cgccgtatca gtgccgcggg aacagaggca cctgcgcccc agcgccagca ggcgccgcca    7260
gcaaccgggc agcctacttg tgaggacgcc gctggctcaa ctgctgccgg cgggggcact    7320
gctgcagcac ctgctgcgcg catgacgtca gcgggccaag cggctgccag caccgccctg    7380
tcgctttctg cctctgccgc cggcccaagc cggccgcccc atgccacctg tgccgctgca    7440
gacgctacaa cgtttgcctc acctgtcgcc gcggccgcag ctgacgccgc acggcagcac    7500
gagttcgcat ctcccgcccc gcacgccgca gcagccacgg cagcagcacc cgcggcagtg    7560
tcaccctgca cgcctgcagc cgccgtgata ccgggtagcg gggccggtgg ggccgctggt    7620
gccggtgcgc ccgcgtcgcc gccgccggcg cccgtcaagc gacctccgcc ggcgcggctg    7680
ttcttgcaca ccgtgcggcg gcactcgggt acaggcgaag ggcctgctgc tgagcccacg    7740
gctgcgcgtg cgcatgcccc tgcagctcat gcggagggtg gcggcatgga cgcgcctccg    7800
ctgccacacc accagtcaca gcagcagcac cagtcacagc agcaccccca gcaccaccac    7860
cagcaggcat ccccgtacgg aggcgcagcg gcgcacatgt acgcggcctg gtgcagcagt    7920
cctgccgcca cgcccacccg ccacaacgca tctggtggcg gcgccgccgc cgctgccgca    7980
ggcagcaccg gaggcgctgc cttcgctgcc gcgcccgcgc cgccacaggc gcccagggcc    8040
gcagccgcag ccgacgctga tacgcggagc gtcagcgtca ccgggggcct cggtgggagc    8100
ggcagtggag gctctgcaca cggcggggc actgggggtc tcggaggcgt ctcaccgcgc    8160
agccgcgctg cgctcttggt ggatgtggcc gagcctcttg gccgtacgg ccccagcag     8220 cccacaactg ccacctcgac tgctgcagct gctgtagctg cgggtgaggc gggtggcgca    8280
agcggcaggc agctccagcc ggctccggca cctccaactg cggccagccg ctacccgtgg    8340
aacatgggct ggggtgcggg ggcaagcggt gcagcgggca gggagaacac accgctgcgc    8400
cagcttccgc ccttcccgcc gccgcagcct gagctggcag ccctgccgct gcaccgtgcg    8460
caagcgacgg gcacagtggc gacaggcacc gctggacctg gagagcaggg gccgcaaggg    8520
taccagcaac gtagtggcgg cggcgacacg acggaggccc atgtgccacc accgctgctg    8580
cagccgccgc cacgcgccac ctcgcctacc ggctacgcgg ttgcgtccta tcgccgggac    8640
agtgagggcg gcggcgtcat accggtggtg tcgccgccgc cgcagctgat gccgcagtcg    8700
gtgcggccgc cgccgcgcct ggcgccgcta gtggcgccga ctgccgcggc gggaccgcct    8760
cagccgccgc cgctgacgtc gccacctgcg ccgcgcaagc cagccaagca gcccgcgctc    8820
atggctcctg ggccgccggc gggccagcgt cgcagtagtg gcggcagtgt cgacaccggc    8880
ggcagtgccg gaggtgcggc tggccgcaac tccccagcat cgcttgccgg ggcgggcacc    8940
ggcgcggctg gccgctgcc caagctacca ccacacgtgc tggagcggcc gctgccgccg    9000
cgtatgcagg tgcacatgcc cgcgcccgcg ccttcgccgg cagccgtcca agggcctgtc    9060
ggcgcaacag ctcactctgg cgcagcagct cccggcagcc ggctactagc ggcggccatg    9120
tcgcctgtcg gtggcacaaa cgcgggtggg gcagccgccg gcgcatcgcc gccgcccctg    9180
ctcaaggtaa ccattggcgg ccgcccaggc tcgctgcagt cagccatagg cagcttctcc    9240
gtgcagccta cgcagctgcc gcagccgccg cagctgccgg cattgcctca gtcacagcac    9300
cagtcacagc gacagcacca ggtcgcagag caggggcgtt ttgggatgcc aggcgcggcc    9360
ggctgggccg tgccgggcgc tgctgtgggc gcggccggct cccacctgcc gcagctgcac    9420
```

```
cagcaccagc atgccgctgc agggatcttg gacggcgata cacagtctgc cggcggtact    9480
ggtggcggtg gcgtcagcag caagcgcaag cgggagggcg attcagagta g             9531
```

<210> SEQ ID NO 74
<211> LENGTH: 3176
<212> TYPE: PRT
<213> ORGANISM: Chlamydomonas reinhardtii

<400> SEQUENCE: 74

```
Met Ala Thr Val Gly Glu Pro Pro Leu Glu Gln Leu Arg Glu Leu Phe
1               5                   10                  15

His Leu Ser Ala Arg Asp Ala Cys Ile Thr Leu Asn Ile Ser Gln Ser
            20                  25                  30

Arg Leu Lys Lys Ile Cys Arg Gln His Gly Ile Ser Arg Trp Pro His
        35                  40                  45

Arg Lys Leu Ala Ser Leu Asp Ser Leu Arg Gln Gln Leu Lys Gly Asp
    50                  55                  60

Ser Gly Leu Thr Thr Gln Asp Arg Ala Val Leu Leu Ala Arg Leu Glu
65                  70                  75                  80

Ala Gln Val Ala Ala Val Ile Ala Glu Pro Asp Arg Pro Leu Glu Lys
                85                  90                  95

Leu Phe Glu Asp Met Arg Gln Thr Ser Tyr Lys Val Arg Tyr His Ala
            100                 105                 110

Arg Asn Lys Leu Arg Arg Gly Thr Gly Ala Ala Gly Glu Gly Ala Asp
        115                 120                 125

Asp Gly Asp Ala Ala Gly Thr Ala Ser Gly Gly Asp Ala Ser Ser Pro
    130                 135                 140

Ala Gly Arg Ala Leu Ser Thr Glu Arg Gly Gly Arg Arg Gly Arg
145                 150                 155                 160

Arg Gly Ala Ala Ser Pro Arg Arg Gly Pro Gln Arg Arg Ala Ala Ser
                165                 170                 175

Ser Gly Pro Ala Ser Gly Ser Arg Leu Arg Arg Ala Gly Arg Arg Arg
            180                 185                 190

Gly Ser Asp Trp Gly Gly Ser Ser Gly Glu Glu Glu Ala Ala Ser Asp
        195                 200                 205

Ser Thr Glu Ala Ala Ser Asp Asp Glu Glu Gln Ala Ala Gly Gly Ala
    210                 215                 220

Ala Ala Gly Gly Tyr Ser Glu Arg Asp Asp Asp Glu Asp Glu Asp Gly
225                 230                 235                 240

Asp Asp Gly Glu Asp Ser Asp Glu Asp Glu Asp Glu Asp Glu Glu Asp
                245                 250                 255

Glu Asp Trp Val Ala Gly Gly Arg Ala Gly Lys Ala Gly Gly Arg Gln
            260                 265                 270

Ala Arg Ala Asp Met Ala Ala Ala Thr Ala Gly Gly Ser Ala Gly
        275                 280                 285

Arg Ala Asp Arg Leu Arg Arg Ala Thr Gly Leu Gln Gly Leu Arg
    290                 295                 300

Val Pro Ala Ala Ala Ser Pro Ala Thr Pro Arg Ser Arg Arg Arg Arg
305                 310                 315                 320

Arg Ser Ala Ala Pro Leu Asp Ser Gly Asp Thr Glu Pro Ser Pro Gly
                325                 330                 335

Gly Arg Ser Ala Ala Ala Ala Pro Leu Ala Thr Thr Ala Cys Gly
            340                 345                 350

Gly Gly Asp Thr Asn Ser Ser Asp Ser Ala Gly Arg Ser Leu Glu Gln
```

```
              355                 360                 365
Arg Gln Pro Ala Ala Arg Glu Gly Ala Gly Asp Ala Ala Gly Arg Pro
            370                 375                 380
Pro Thr Ala Pro Gln Pro Gln Leu Ser Gly Arg Ser Arg Thr Val Ala
385                 390                 395                 400
Ser Arg Ser Ala Ser Ala Arg Ala Gly Ala Pro Ala Gly Leu Pro Gly
                405                 410                 415
Phe Ser Pro Val Arg Asp Ala Ala Thr Pro Ser Ser His Thr Gly Pro
                420                 425                 430
Ala Ala Ala Ser Arg Gly Arg Leu His Ser Gly Gly His Gly His Gly
                435                 440                 445
His Ala His Gly Arg Ala Ala Lys Pro Glu Arg Gly Gly Ala Ala Ala
            450                 455                 460
Thr Leu Ser Ala Phe Ala Ala Ala Glu Arg Ala Val Ala Gly Ala Ser
465                 470                 475                 480
Ala Ala Gly Ala Ala Gly Gly Gly Gly Gly Gly Gly Gly Gly Gly Gly
                485                 490                 495
Ser Ala Val Lys Gln Glu Arg Glu Gln Ser Ala Gly Gln Leu Val Gly
                500                 505                 510
Pro Gly Gly Gly Gly Val Ala Gly Ala Ala Gly Arg Gly Ala Asp
                515                 520                 525
Gly Ala Ala Arg Asp Asp Ala Arg Ala Ala Gly Asp Val Ala
            530                 535                 540
Val Glu Ala Gly Ala Gly Thr Gly Gly Ser Ser Gln Leu Asp Gly Ser
545                 550                 555                 560
Ser Gln Trp Gly Met Lys Arg Ala Arg Ser Ala Pro Gln Pro Gln Pro
                565                 570                 575
Leu Gly Ala Ala Gly Val Ala Gly Thr Thr Ser Ser His Gln Thr Thr
                580                 585                 590
Ser Ser Asp Arg Ser Gln His Gln Gln Gln Ala Pro Leu Pro Pro
            595                 600                 605
Leu Gln Ala Arg Thr Ser Arg Glu Trp Pro Pro Met Asp Met Pro
            610                 615                 620
Ser Gly Trp Gln Gln Pro Tyr Arg Gln Pro Met Pro Leu Asp Ala Thr
625                 630                 635                 640
Arg Thr Thr Pro Ala Thr Ala Thr Ala Thr Ala Ala Gly Gly
                645                 650                 655
Gly Ala Asp Val Gly Ser Gly Arg His Gln Asp Arg Arg Leu Asp His
                660                 665                 670
Pro Ser His Leu Gln Gln Ala Pro Gln His Pro His Pro Gln Glu Pro
            675                 680                 685
Leu His Gln Arg Ala Gln Arg Pro Ala Ser Ser Pro Thr Ala Ser Met
            690                 695                 700
Gly Gly Pro Ala Thr Lys Gln Gln Ala His Gly Ser Tyr Gly Ala Ala
705                 710                 715                 720
Ala Pro Leu His His Thr Ala Ala Gln Ser His Ser His Ser Tyr Ser
                725                 730                 735
His Ala Pro Pro Thr Ala Thr Thr Ala Pro Pro Ala Glu Pro His Pro
                740                 745                 750
Phe Phe Ser Pro Ala Ala Ala Ala Ala Ala Ala Ala Gly Pro
                755                 760                 765
Gly Ile Glu Ser Ser Leu Gly Leu Gly Ser Ser Val Pro Arg Ser Gly
                770                 775                 780
```

-continued

```
Ala Leu Glu His Gly Val Glu Asp Trp Glu Trp Arg Trp Glu Glu
785                 790                 795                 800

Gly Gln Gln Arg His Gln Arg Ala Leu Leu Gln Gln Gln Gln Gln
            805                 810                 815

Gln Glu Tyr Met Pro Pro Ala Pro His His Met Pro His Glu Gln
        820                 825                 830

Gln Gln Arg His Gln Gln Leu Leu Gln Ser Gln Ser Gln Ser Gln Ser
            835                 840                 845

Gln Ser Gln Ser Gln Pro Gln Ser Gln Gln Arg His Asp Leu His
    850                 855                 860

Arg Glu Gln Leu Pro Pro Leu Pro Pro Gln Pro Glu Ala Leu Ser Arg
865                 870                 875                 880

Gln Gln Gln Glu Gln Arg Gln Gln Glu His Phe Glu Leu Gln Gln Leu
            885                 890                 895

Gln Leu Leu Gln Gln Gln Gln Ser Gln Gln Leu Gln Gln Pro Gln
            900                 905                 910

Gln His Leu Met Pro Ser Ser Ser Phe Gln Arg Asp Trp Ile Pro
    915                 920                 925

Pro Pro Gln Pro Asp Pro Gln Pro Leu Pro Ser Trp Arg Gln Ser Glu
    930                 935                 940

Pro Leu His Ala Glu Pro Gln Pro Arg Ala Ser Arg Ser Gln Gln
945                 950                 955                 960

Pro Gln Gln Leu Gln Ser Pro Gly His Val Gln Gln Gly Pro Leu
            965                 970                 975

Gln His Gly Gly Ala Ser Gly Ser Ala Pro Thr Tyr Arg Gly Gly
            980                 985                 990

Phe Gly Ser Glu Leu Asp Gly Gly Trp His Trp Gln Gln Gln Gln Gln
            995                 1000                1005

Gln Gln Gln Gln Gln Gln Gln Leu Leu Gln Gln Gln Gln Ala Ala
    1010                1015                1020

Ser Leu Ser His Gln Leu Gln Glu Arg Glu Gln Gln Glu Leu Gln
    1025                1030                1035

Arg Gln Gln Ala Gln Ala Arg His His Met Gln Leu Gln Gln Gln
    1040                1045                1050

Gln Gln Gly Ala Pro Pro Ser Ser Ser Trp His Gly Gln Tyr Pro
    1055                1060                1065

Pro Leu His Gln Arg Pro Asp Gln Ala His Ala Gln Tyr Pro His
    1070                1075                1080

Leu Gln Gln Pro Gln Glu His Gln His Pro Gln Gln Glu Arg Tyr
    1085                1090                1095

Pro Pro Leu His Gln Gln Thr Gln Gln Gln Leu Gln Gln Gln Gln
    1100                1105                1110

Gln Gln Pro Gln Leu Gln Gln Gln Gln Ala Gln Trp Pro Gly
    1115                1120                1125

Ala Asp Pro Arg Leu Leu Ala Pro Gly Arg Gln Pro Leu Pro Pro
    1130                1135                1140

Pro Pro Ser Trp Ser Ala Arg Gln Gly Pro Gly Ser Ala Pro Pro
    1145                1150                1155

Ser Thr Ser Ala Gly His Pro Thr Leu Gln Gln Gln Leu Tyr Pro
    1160                1165                1170

Pro Met Tyr Gln Gln Gln Thr Gln Gln Gln Pro Gln Pro Gln Gln
    1175                1180                1185
```

```
Gln Asn Ala Gly Gln Gln Pro Ala Tyr His His His Pro Leu Leu
    1190            1195                1200

Ser Pro His Ser Pro Gln Tyr Gln Gln Arg Met Gln Ala Ser Ala
    1205            1210                1215

Pro Val Gly Ser Gly Gly Ala His Arg Gln Ser Gln Ser Ile Ile
    1220            1225                1230

Pro Gly Pro Pro Ser Ala Leu Leu Ser Leu Pro Ser Pro Ala Ser
    1235            1240                1245

Asn Glu Pro Ser Pro Arg Asp Phe Ala Tyr Pro Ser Pro Leu Pro
    1250            1255                1260

Pro His His Gln Pro Pro His Gln Pro His Pro His His His Ser
    1265            1270                1275

Leu Ser Gly Ser Gly Phe Asp Ser Glu Gly Gly Ala Asp Ala Ala
    1280            1285                1290

Ala Ala Ala Arg Arg Pro Ser Asn Gln Ser Gln Ser Phe Asp Gln
    1295            1300                1305

Gln His Gln Ala Ala Ile Ala Ser Gly Thr Leu Arg Asn Trp
    1310            1315                1320

Ser Ser Ser Ser Ser Ala Ser Ser Leu Leu Val Trp Gly Ser Ala
    1325            1330                1335

Trp Pro Pro Gly Ser Gly Leu Gly Gly Met Pro Gly Gly Met
    1340            1345                1350

Gly Pro Gly Gly Val Gly Ser Gly Gly Met Gly Pro Gly Pro Leu
    1355            1360                1365

Gly Pro Gly Gly Ser Asn Pro His Gly Ala Ala Gly Ser Gly Gly
    1370            1375                1380

Gly Ser Ala Tyr Gly Ala Ala Gly Phe Arg Ser Gly Leu His Ser
    1385            1390                1395

Gly Gly Gly Val Gly Gly Ala Gly Gly Ala Gly Phe Gly Gly Ser
    1400            1405                1410

Ala Gly Gly Gly Tyr Gly Trp Ser Ser Gly Gly Ser Ser Tyr Ser
    1415            1420                1425

Gly Gly Gly Phe Ala His Ala Met Gly Leu Pro Ser Ser Gly Gly
    1430            1435                1440

Gly Ala Ala Ala Ala Ser Gly Thr Gly Gly Asp Gly Gly Gly Gly
    1445            1450                1455

Asp Glu Asn Arg Met Leu His Glu Gly Leu Arg Gly Arg Ser Ala
    1460            1465                1470

Tyr Val Ser Asp Ala Gly Asp Arg Arg Asp Glu Ala Val Ala Glu
    1475            1480                1485

Ala Ala Ala Ala Ala Ala Ala Thr Val Ala Ala Gly Pro Gly Gly
    1490            1495                1500

Gly Arg Met Gly Gly Arg Asp Ala Ala Gly Thr Arg Gly Gly Gly
    1505            1510                1515

Gly Gly Thr Gly Ser Gly Ala Ala Thr Thr Ala Ala Val Ala Ala
    1520            1525                1530

Ala Ala Ala Ala Ala Ala Ala Val Ala Ala Val Ala Ala Thr Ser
    1535            1540                1545

Gly Ala Ala Asp His Glu Thr Arg His Arg Ser Pro Ala Leu Gln
    1550            1555                1560

Pro Pro Thr His His Gly Ala Pro Thr Asp Leu Leu Ser Ser Arg
    1565            1570                1575

His His Ala Arg His Ser His Val Leu Pro Pro Ala Gly Met Asn
```

```
            1580                1585                1590
Tyr Ala Ala Tyr Leu Pro Pro Pro Leu Ser Leu Pro Pro Ala Leu
            1595                1600                1605
Asp Ser Pro His Gln Pro Pro Tyr Ser Ala Ser His Gly Pro Ala
            1610                1615                1620
His Gly Arg Leu Asn Pro Ala Ala Tyr Ser Arg Val Val Ser Thr
            1625                1630                1635
Gly Phe Pro Gly Ile His Pro Gly Ser Leu Pro Gly Ser Ser Ser
            1640                1645                1650
Pro Ser Pro Ser Gly Gly Gly Gly Gly Gly Ala Asn Ala Gly
            1655                1660                1665
Gly Gly Arg Val Gly Gly Gly Ser Gly Thr Ala Ala Arg Arg Arg
            1670                1675                1680
Gly Gly Asp Arg Ala Ala Ser Pro Leu Gly Ser Tyr Gly Ser Gly
            1685                1690                1695
Ala Ala Gly Gly Gly Gly Ile Ala Ala Gly Val Lys Ala Glu
            1700                1705                1710
Asp Arg Gly Pro Ser Gly Gly Ser Gly Gly Asp Gly Gly Phe Gly
            1715                1720                1725
Gly Asp Asp Thr Arg Asp Val Glu Pro His Leu Gly His Val Ala
            1730                1735                1740
Phe His Gly Gly Asn Ala Gly Gln Gln Gln Thr Ala Ala Tyr Arg
            1745                1750                1755
Arg Thr Ser Ala Pro Ala Ala Ala Ala Ala Thr Ala Asp Pro
            1760                1765                1770
Arg Ala Gln Ser Ala Ser Gly Glu Arg Asp Ser Gly Gly Gly Val
            1775                1780                1785
Ala Val Asp Leu Arg Arg Val Pro Tyr Thr Gly Arg Leu Ser Glu
            1790                1795                1800
Pro Val Met Arg Ala Pro Leu Arg Ala Leu Leu Gly Leu Gly Ser
            1805                1810                1815
Asp Leu Ala Asp Glu Gly Glu Gly Glu Ala Glu Leu Ala Ala Ser
            1820                1825                1830
Met Ala Ala Ala Arg Asp Glu Glu Arg Phe Arg Met Leu Ser
            1835                1840                1845
Thr Gly Ser Ser Thr Val Ala Ile Phe Ala Pro Glu Ala Gln Pro
            1850                1855                1860
Gln Pro His Gln Gln Thr Gln His Gln Gln Pro His Gln Pro Ser
            1865                1870                1875
Arg Pro Val Glu Gly Arg Pro His His Gly Tyr Gly Leu Pro Arg
            1880                1885                1890
Leu Gln Gln Gly Ala Pro Glu Gly Arg Val Ala Ser Ala Ser Ala
            1895                1900                1905
Ala Asp Arg Gly Gly Arg Arg Thr Ser Gly Asp Met Glu Arg Gly
            1910                1915                1920
Gly Asn Gly Gly Arg Arg Pro His Thr Val Pro Asp Ala Arg Gly
            1925                1930                1935
Trp Ala Gly Pro Ala Asp Leu Leu Leu Ala Cys Gln Glu Thr Asp
            1940                1945                1950
Ala Ile Ala Gln Ala Glu Ala Ala Asp Gly Val Arg Gly Ala Val
            1955                1960                1965
Gly His Leu His Gln Ala Thr Tyr Gln Ala Ala Ala Ser Leu His
            1970                1975                1980
```

```
Val Ala Gln Gln Pro Arg Gly Gly Ala Ala Tyr Glu Glu Pro Pro
    1985                1990                1995

Pro Arg Arg Gln Pro His Gln Ala Ala Gly Ala Gly Gly Pro Ser
    2000                2005                2010

Pro Val Cys Ser Ala Asp Leu Thr Thr Pro Thr Ala Ala His Gln
    2015                2020                2025

Arg Pro Gln Gln Leu Arg Pro His Ala Ala Ala Pro Pro Ser Ala
    2030                2035                2040

Thr Ser Ser Arg His Gln Val Ser Arg Arg Ala Ala Ala Ala Glu
    2045                2050                2055

Ala Ala Val Val Thr Ala Thr Pro Val Ala Ala Thr Gly Ser Ser
    2060                2065                2070

Gly Arg Pro Gly Pro Ala Ala Gly Pro Ser Pro Ala Ala Ala Pro
    2075                2080                2085

Val Thr Ala Ala Ala Ala Ser Gly Ala Ala Phe Leu Ser Pro Val
    2090                2095                2100

Ala Ser Val Ala Ala Gly Ser Gly Val Ala Gly Gly Pro Ala Thr
    2105                2110                2115

Ser Ser Ala Ser Ser Gly Arg Arg Ser Ser Gly Gly Gly Ser Ser
    2120                2125                2130

Ser Ser Gly Gly Arg Thr Leu Leu Val Trp Thr Gly Ser Gln Pro
    2135                2140                2145

Arg Trp Gly Gln Val Leu Pro Pro Leu Gln His Gln Ser Gln Pro
    2150                2155                2160

Gln Gln Gln Gln Pro Gln Gln Gln Gln Gln Pro Gln Gln Gln Pro
    2165                2170                2175

Glu Leu Gln Ser Pro Ser Met Arg Pro Pro Gln Leu Gln Pro Leu
    2180                2185                2190

Pro Leu Met Pro Ser Ser Ala Pro Leu Arg Thr Gly Pro Gln Arg
    2195                2200                2205

Arg Ile Ser Gly Ala Gly Ala Ala Gly Ala Glu Val Thr Thr Gly
    2210                2215                2220

Thr Ala Thr Ala Ser Gly Pro Gly Gln Glu Ser Thr Ser Ala Ala
    2225                2230                2235

Ala Ala Gly Ala Ala Gly Ala Leu Pro Pro Met Pro Pro Leu Pro
    2240                2245                2250

Ala Ser Leu Leu Ala Ala Leu Ala Ala Gly Gly Gly Ala Gly Gly
    2255                2260                2265

Asp Leu Ser Pro Asp Ala Tyr Pro Val Thr Ala Leu Gln Pro Pro
    2270                2275                2280

Ala Val Gly Ala Ala Asp Arg Gly Thr Asp Ala Gly Gln Arg Glu
    2285                2290                2295

Gln Asp Arg Pro Gln Gly Arg Arg Ala Ser Pro Pro Ala Ala
    2300                2305                2310

Thr Asp Pro Ala Asn Ala Thr Thr Ala Gly Gly Val Pro Leu Ser
    2315                2320                2325

Ile Leu Glu Tyr Leu Arg His Gly Ser Gly Ser Glu Pro Pro Leu
    2330                2335                2340

Asp Leu Glu Ala Leu Glu Asp Leu Asp Met Asp Leu Asp Leu Asp
    2345                2350                2355

Phe Gln Thr Pro Gln Ala Gly Asp Ala Ala Ala Ala Leu Ala Leu
    2360                2365                2370
```

```
Met Arg Pro Trp Leu Thr Ser Thr Pro Gly Leu Gly Pro Thr Pro
2375                2380                2385

Met Glu Ile Ser Pro Arg Ala Ala Leu Pro Ala Thr Arg Arg Ile
2390                2395                2400

Ser Ala Ala Gly Thr Glu Ala Pro Ala Pro Gln Arg Gln Gln Ala
2405                2410                2415

Pro Pro Ala Thr Gly Gln Pro Thr Cys Glu Asp Ala Ala Gly Ser
2420                2425                2430

Thr Ala Ala Gly Gly Gly Thr Ala Ala Pro Ala Ala Arg Met
2435                2440                2445

Thr Ser Ala Gly Gln Ala Ala Ala Ser Thr Ala Leu Ser Leu Ser
2450                2455                2460

Ala Ser Ala Ala Gly Pro Ser Arg Pro Pro His Ala Thr Cys Ala
2465                2470                2475

Ala Ala Asp Ala Thr Thr Phe Ala Ser Pro Val Ala Ala Ala Ala
2480                2485                2490

Ala Asp Ala Ala Arg Gln His Glu Phe Ala Ser Pro Ala Pro His
2495                2500                2505

Ala Ala Ala Ala Thr Ala Ala Ala Pro Ala Ala Val Ser Pro Cys
2510                2515                2520

Thr Pro Ala Ala Ala Val Ile Pro Gly Ser Gly Ala Gly Gly Ala
2525                2530                2535

Ala Gly Ala Gly Ala Pro Ala Ser Pro Pro Pro Ala Pro Val Lys
2540                2545                2550

Arg Pro Pro Pro Ala Arg Leu Phe Leu His Thr Val Arg Arg His
2555                2560                2565

Ser Gly Thr Gly Glu Gly Pro Ala Ala Glu Pro Thr Ala Ala Arg
2570                2575                2580

Ala His Ala Pro Ala Ala His Ala Glu Gly Gly Gly Met Asp Ala
2585                2590                2595

Pro Pro Leu Pro His His Gln Ser Gln Gln Gln His Gln Ser Gln
2600                2605                2610

Gln His Pro Gln His His His Gln Gln Ala Ser Pro Tyr Gly Gly
2615                2620                2625

Ala Ala Ala His Met Tyr Ala Ala Trp Cys Ser Ser Pro Ala Ala
2630                2635                2640

Thr Pro Thr Arg His Asn Ala Ser Gly Gly Gly Ala Ala Ala Ala
2645                2650                2655

Ala Ala Gly Ser Thr Gly Gly Ala Ala Phe Ala Ala Ala Pro Ala
2660                2665                2670

Pro Pro Gln Ala Pro Arg Ala Ala Ala Ala Ala Asp Ala Asp Thr
2675                2680                2685

Arg Ser Val Ser Val Thr Gly Gly Leu Gly Gly Ser Gly Ser Gly
2690                2695                2700

Gly Ser Ala His Gly Gly Gly Thr Gly Gly Leu Gly Gly Val Ser
2705                2710                2715

Pro Arg Ser Arg Ala Ala Leu Leu Val Asp Val Ala Glu Pro Leu
2720                2725                2730

Gly Pro Tyr Gly Pro Gln Gln Pro Thr Thr Ala Thr Ser Thr Ala
2735                2740                2745

Ala Ala Ala Val Ala Ala Gly Glu Ala Gly Gly Ala Ser Gly Arg
2750                2755                2760

Gln Leu Gln Pro Ala Pro Ala Pro Pro Thr Ala Ala Ser Arg Tyr
```

```
            2765                2770                2775
Pro Trp Asn Met Gly Trp Gly Ala Gly Ala Ser Gly Ala Ala Gly
        2780                2785                2790

Arg Glu Asn Thr Pro Leu Arg Gln Leu Pro Pro Phe Pro Pro Pro
        2795                2800                2805

Gln Pro Glu Leu Ala Ala Leu Pro Leu His Arg Ala Gln Ala Thr
        2810                2815                2820

Gly Thr Val Ala Thr Gly Thr Ala Gly Pro Gly Glu Gln Gly Pro
        2825                2830                2835

Gln Gly Tyr Gln Gln Arg Ser Gly Gly Gly Asp Thr Thr Glu Ala
        2840                2845                2850

His Val Pro Pro Pro Leu Leu Gln Pro Pro Pro Arg Ala Thr Ser
        2855                2860                2865

Pro Thr Gly Tyr Ala Val Ala Ser Tyr Arg Arg Asp Ser Glu Gly
        2870                2875                2880

Gly Gly Val Ile Pro Val Val Ser Pro Pro Pro Gln Leu Met Pro
        2885                2890                2895

Gln Ser Val Arg Pro Pro Arg Leu Ala Pro Leu Val Ala Pro
        2900                2905                2910

Thr Ala Ala Ala Gly Pro Pro Gln Pro Pro Pro Leu Thr Ser Pro
        2915                2920                2925

Pro Ala Pro Arg Lys Pro Ala Lys Gln Pro Ala Leu Met Ala Pro
        2930                2935                2940

Gly Pro Pro Ala Gly Gln Arg Arg Ser Ser Gly Gly Ser Val Asp
        2945                2950                2955

Thr Gly Gly Ser Ala Gly Gly Ala Ala Gly Arg Asn Ser Pro Ala
        2960                2965                2970

Ser Leu Ala Gly Ala Gly Thr Gly Ala Ala Gly Pro Leu Pro Lys
        2975                2980                2985

Leu Pro Pro His Val Leu Glu Arg Pro Leu Pro Pro Arg Met Gln
        2990                2995                3000

Val His Met Pro Ala Pro Ala Pro Ser Pro Ala Ala Val Gln Gly
        3005                3010                3015

Pro Val Gly Ala Thr Ala His Ser Gly Ala Ala Ala Pro Gly Ser
        3020                3025                3030

Arg Leu Leu Ala Ala Ala Met Ser Pro Val Gly Gly Thr Asn Ala
        3035                3040                3045

Gly Gly Ala Ala Ala Gly Ala Ser Pro Pro Pro Leu Leu Lys Val
        3050                3055                3060

Thr Ile Gly Gly Arg Pro Gly Ser Leu Gln Ser Ala Ile Gly Ser
        3065                3070                3075

Phe Ser Val Gln Pro Thr Gln Leu Pro Gln Pro Pro Gln Leu Pro
        3080                3085                3090

Ala Leu Pro Gln Ser Gln His Gln Ser Gln Arg Gln His Gln Val
        3095                3100                3105

Ala Glu Gln Gly Arg Phe Gly Met Pro Gly Ala Ala Gly Trp Ala
        3110                3115                3120

Val Pro Gly Ala Ala Val Gly Ala Ala Gly Ser His Leu Pro Gln
        3125                3130                3135

Leu His Gln His Gln His Ala Ala Ala Gly Ile Leu Asp Gly Asp
        3140                3145                3150

Thr Gln Ser Ala Gly Gly Thr Gly Gly Gly Gly Val Ser Ser Lys
        3155                3160                3165
```

Arg Lys Arg Glu Gly Asp Ser Glu
    3170                3175

<210> SEQ ID NO 75
<211> LENGTH: 3470
<212> TYPE: DNA
<213> ORGANISM: Chlamydomonas reinhardtii

<400> SEQUENCE: 75

```
aaaaaccagg tatactgtat gctttaggtt cttgcgcaac ctgacgagtc aggcagactc    60
ctgtccttgc tttatcaaaa acacgcactg tacatagtta tacacgaaga ctgatttgat   120
tttatcgtaa gcacgcttgg gcgcaagctg aggtcaggtt cgctcacaag gcaggcaagc   180
tttccgttca tcctggagct aacaggagag ctgtggagag aaatgggcac aatgacctga   240
gactggcccg agcgcaaaat ggactcggag cagcagccgg ccagcccgag ggctgcgcct   300
ggtgcaagcg gaggccgacg cttgcctggt cggacacctt ctggtctatt gggacaggca   360
gcgcaggggc cgcagcaacc tcagcccaa cttggcaagg agcacttca gctcaatcag     420
tccagcagcg cagcgacaac cgcgttgccg gtgaaacgtc gggggagttt ccagcagttg   480
aagaaaatag gtgccgccgg ggggcagat ggcagctctt cgcacctgga ctcggactcg    540
gcaccatcaa ttttcgccat tgtgaaaaag tccacacact gggaaaagta tggcacggtg   600
ctcgtgctgc tcgttgccga cgagctcagc agtgacaagg aggcggtggt gcagatgctg   660
agcgcagagg gatacgatga ccagacgtcg gacagcatcg aggaggcggt gaagttgttt   720
tcggaaaggg aggtgtaccc ggacattgtt attgttgatt cagacaatga gctggtggac   780
accaaacagc tcatcaaggc gctgcaggcg ctgaacccca cggtggcggt gctggtactg   840
ggcagccgcg gcgggcccat gggcgcggtg gcggcgctgc aggcgggcgc ggcggactac   900
atggtgaagc cgctggatct ggatgaggtg gttgcccgcg tggagcgaca cgtgcagcga   960
cagcactgca tcaagttgga aatggaaaag gcgctggagc acgccaagga gatgatgcag  1020
cagctcatgc cggcatcact actcggggac gtgatgttgc ggaaagacgg cagcgccgcg  1080
ggcggcgcgc cggcgggcgg caaggcgagt ctcaacagcg tggcggagac cgactttgag  1140
gagcagatga gcgagctgag cgaggagaac caccgcttgg ccagaaggt gcaggagatg   1200
gagcgcaagc ttgagctcaa ggaccaggag aaccgcgacc tggaagccaa actcaacgcc  1260
atcgaccgca agtcagcgc gctggccgcc agccgcgaga tgggcggcgg caacggcggc  1320
ggcaacggcg gcggcggggg gtcgggctgc acggccgtgg ggcctgagca gcgtgccgcg  1380
gcgcagcagg cggcgcaggc ggcccaggcc tcgttgcagg gcagctgaa cagcgtggca   1440
caggccaacg aggacctccg acataaagtg gacgagctgg agcggctgat gcagtcgcac  1500
acaggcgtca ccagcgccag caaccaaaac ctgcgcctga gcgtcaacgg tgggcagcag  1560
cagggctagc tgcagcccgc gggcctgtcg cacagcggca gcggtgctgt cgagcagcat  1620
tagcagcggc gctggcggcc gcattagcat tagcattagc agcaggagca gcagcggaac  1680
gctgcaggcg gcaggcaggc tttgcaatgg gcaaagggc tcctgctgcg tgtggccacg   1740
ggcaggagct ctagaactgc actgagtcgt agaggcactg ccgcccctgc tctcggagca  1800
gcaccgggat ggccgggcac gctgtggccg gactggtgac aggtggcgca gcggaccgct  1860
gctcttgtac ccaagtgctg ccgccggcga tgcatcaggc gctggcgagc gtcagttaca  1920
tcatcggaat tgaacggagc gctgcagtct cggcgaggag taaagcagca cgacaaggac  1980
tgcggcagaa gtcacgctgg gcagtgcagc gcaacggcat tgcatgagcg gtggtggctg  2040
```

```
gcgcgcggct gcagctggcc gcccggactg tcgagcttct ggtgggctta catggcctgg    2100
cccagcaacc aggagcgtgt gcatggcgtc acagctgccg ttctggggct gcatgcacgt    2160
gctaggtgca ccgggcgctc gggcagtagc gcgctgcctg gagatgcgtg tggtcgggtg    2220
gcatcacgcg cagacagctg ttcgtacttg cgacccactt acagggcatc aacaagtctt    2280
ctttacgtgc tccaacttgc tgcagaactg ggagttgagg atggggattt aagcataagc    2340
accgtgtggg gtgcaaggca aaagtgtcg tactgtactt ctgaccccgt agcagcagac     2400
ccgggccccg cataggcctc tgccaggtct gaagctggcc aggtggagga actcaactgc    2460
ttgcttccag ttgcagcccg cgcaatgtg gcaggagag cgagaggctt tcggcaccgc      2520
tggaggtgtc acagaacatg ttcggtgatt atcggcgtac gagaagggggg gcgctgtaaa  2580 cggggcgcga gttagagtca gagtccccat gcaactcgga gtcaaataca tgaggtataa    2640
aatggttgtt gtgtgggcaa cagaccggga tgtgcgtcgt cagaaatggc actcgctcca    2700
tggcgaaatt tggtctcaac ccggagtctt tcctaacaca ggtccactgc attggtattt    2760
gcgtatgtgt gcgtgcgtgc gcgtgcctgt gttgcgcata ttcgcggtga aggggtgtgg    2820
gcggtagcgg ctcacaatgg gagtgatggg gcggcggacg gtagacctcg cgccgtcaca    2880
aatgctctaa ttaggggacc tcctggcgct aatggcttgt gcgcgcccct tccccggaag    2940
ctcactgcaa cagacaatgt gcgttggcac ggtgaactgc attacttggc tagggaggct    3000
gtgccttctc gagtacgatg gcaaaagctg cctggagcgt gctcagagag gaagtgtgag    3060
tgtgatggac caggcgaagt gggaggtatg aacattcgtc agcaagcatc atcatcgtgc    3120
ggctggtacg cgtgcttcca tttgaaatgc tgcaatgtat cacaacacag ttggcctcgt    3180
cacaagaatg tatgacgtgg gcgaccctct gcacgtgatt ttcagtgcca tgagcgggtc    3240
gtgtgcaatg aagcatacag tgacaggcaa ctcttgaaga tgacgcagcg cttggctgac    3300
aggcgctgaa aggatgcggg tagacaatga gctggggcac agctactggt gttacgatga    3360
taccgatacg ggagcagcac gtaggtcgcg tgttctcgtg gtctgtgtgc tgggccatca    3420
atgatatgcg cagcctgaca ggttgcaggg gtcgtgcagg aatgagcagc                3470
```

<210> SEQ ID NO 76
<211> LENGTH: 1311
<212> TYPE: DNA
<213> ORGANISM: Chlamydomonas reinhardtii

<400> SEQUENCE: 76

```
atggactcgg agcagcagcc ggccagcccg agggctgcgc ctggtgcaag cggaggccga      60
cgcttgcctg gtcggacacc ttctggtcta ttgggacagg cagcgcaggg gccgcagcaa    120
cctcagcccc aacttggcaa gggagcactt cagctcaatc agtccagcag cgcagcgaca    180
accgcgttgc cggtgaaacg tcgggggagt ttccagcagt tgaagaaaat aggtgccgcc    240 gggggggcgag atggcagctc ttcgcacctg gactcggact cggcaccatc aattttcgcc    300
attgtgaaaa agtccacaca ctgggaaaag tatggcacgg tgctcgtgct gctcgttgcc    360
gacgagctca gcagtgacaa ggaggcggtg gtgcagatgc tgagcgcaga gggatacgat    420
gaccagacgt cggacagcat cgaggaggcg gtgaagttgt tttcggaaag ggaggtgtac    480
ccggacattg ttattgttga ttcagacaat gagctggtgg acaccaaaca gctcatcaag    540
gcgctgcagg cgctgaaccc cacggtgcg tgtctggtac tgggcagccg cggcgggccc     600
atgggcgcgg tggcggcgct gcaggcgggc gggcggactg acatggtgaa gccgctggat    660
```

-continued

```
ctggatgagg tggttgcccg cgtggagcga cacgtgcagc gacagcactg catcaagttg    720
gaaatggaaa aggcgctgga gcacgccaag gagatgatgc agcagctcat gccggcatca    780
ctactcgggg acgtgatgtt gcggaaagac ggcagcgccg cgggcggcgc gccggcgggc    840
ggcaaggcga gtctcaacag cgtggcggag accgactttg aggagcagat gagcgagctg    900
agcgaggaga accaccgctt gggccagaag gtgcaggaga tggagcgcaa gcttgagctc    960
aaggaccagg agaaccgcga cctggaagcc aaactcaacg ccatcgaccg caaagtcagc   1020
gcgctggccg ccagccgcga gatgggcggc ggcaacggcg gcgcaacgg cggcggcggg    1080
gggtcgggct gcacggccgt ggggcctgag cagcgtgccg cggcgcagca ggcggcgcag   1140
gcggcccagg cctcgttgca ggggcagctg aacagcgtgg cacaggccaa cgaggacctc   1200
cgacataaag tggacgagct ggagcggctg atgcagtcgc acacaggcgt caccagcgcc   1260
agcaaccaaa acctgcgcct gagcgtcaac ggtgggcagc agcagggcta g            1311
```

<210> SEQ ID NO 77
<211> LENGTH: 436
<212> TYPE: PRT
<213> ORGANISM: Chlamydomonas reinhardtii

<400> SEQUENCE: 77

```
Met Asp Ser Glu Gln Gln Pro Ala Ser Pro Arg Ala Ala Pro Gly Ala
1               5                   10                  15

Ser Gly Gly Arg Arg Leu Pro Gly Arg Thr Pro Ser Gly Leu Leu Gly
                20                  25                  30

Gln Ala Ala Gln Gly Pro Gln Gln Pro Gln Pro Gln Leu Gly Lys Gly
            35                  40                  45

Ala Leu Gln Leu Asn Gln Ser Ser Ser Ala Ala Thr Thr Ala Leu Pro
        50                  55                  60

Val Lys Arg Arg Gly Ser Phe Gln Gln Leu Lys Lys Ile Gly Ala Ala
65                  70                  75                  80

Gly Gly Arg Asp Gly Ser Ser His Leu Asp Ser Asp Ser Ala Pro
                85                  90                  95

Ser Ile Phe Ala Ile Val Lys Lys Ser Thr His Trp Glu Lys Tyr Gly
            100                 105                 110

Thr Val Leu Val Leu Leu Val Ala Asp Glu Leu Ser Ser Asp Lys Glu
        115                 120                 125

Ala Val Val Gln Met Leu Ser Ala Glu Gly Tyr Asp Asp Gln Thr Ser
    130                 135                 140

Asp Ser Ile Glu Glu Ala Val Lys Leu Phe Ser Glu Arg Glu Val Tyr
145                 150                 155                 160

Pro Asp Ile Val Ile Val Asp Ser Asp Asn Glu Leu Val Asp Thr Lys
                165                 170                 175

Gln Leu Ile Lys Ala Leu Gln Ala Leu Asn Pro Thr Val Ala Val Leu
            180                 185                 190

Val Leu Gly Ser Arg Gly Gly Pro Met Gly Ala Val Ala Ala Leu Gln
        195                 200                 205

Ala Gly Ala Ala Asp Tyr Met Val Lys Pro Leu Asp Leu Asp Glu Val
    210                 215                 220

Val Ala Arg Val Glu Arg His Val Gln Arg Gln His Cys Ile Lys Leu
225                 230                 235                 240

Glu Met Glu Lys Ala Leu Glu His Ala Lys Glu Met Met Gln Gln Leu
                245                 250                 255

Met Pro Ala Ser Leu Leu Gly Asp Val Met Leu Arg Lys Asp Gly Ser
```

```
                260               265               270
Ala Ala Gly Gly Ala Pro Ala Gly Gly Lys Ala Ser Leu Asn Ser Val
            275               280               285
Ala Glu Thr Asp Phe Glu Glu Gln Met Ser Glu Leu Ser Glu Glu Asn
            290               295               300
His Arg Leu Gly Gln Lys Val Gln Glu Met Glu Arg Lys Leu Glu Leu
305               310               315               320
Lys Asp Gln Glu Asn Arg Asp Leu Glu Ala Lys Leu Asn Ala Ile Asp
                325               330               335
Arg Lys Val Ser Ala Leu Ala Ala Ser Arg Glu Met Gly Gly Gly Asn
            340               345               350
Gly Gly Gly Asn Gly Gly Gly Gly Ser Gly Cys Thr Ala Val Gly
            355               360               365
Pro Glu Gln Arg Ala Ala Ala Gln Gln Ala Ala Gln Ala Ala Gln Ala
            370               375               380
Ser Leu Gln Gly Gln Leu Asn Ser Val Ala Gln Ala Asn Glu Asp Leu
385               390               395               400
Arg His Lys Val Asp Glu Leu Glu Arg Leu Met Gln Ser His Thr Gly
                405               410               415
Val Thr Ser Ala Ser Asn Gln Asn Leu Arg Leu Ser Val Asn Gly Gly
            420               425               430
Gln Gln Gln Gly
        435

<210> SEQ ID NO 78
<211> LENGTH: 3846
<212> TYPE: DNA
<213> ORGANISM: Chlamydomonas reinhardtii

<400> SEQUENCE: 78
gcgacgcacg gctgggccaa attcgccaac ggcaggagac caaatcgatc gaggcgatct     60
tgcgaagttc tcggacaaat cgatcgcacc catagtgatt taagcattac atttgcccaa    120
ggcgtgagaa gtgcgaggcc cgaacggcta tgacgccaat gcgcagctta cgacatttaa    180
agcaaattat tcatacatca tacagcacgc ttatgtgaag aaagccagga ttttaggctc    240
tcgccccgat caagacgatc tccccattgc gaagttctcg gtttctttcc ggttcgcctg    300
ctccgtatga tttacctttg cgctacaaca gcgacttaaa cgacctacgt cgccttactg    360
tgtgcgcgta cgtgtttgta gctgtgagat agttttgtcc gcagcgtacc gcaaatagaa    420
atgctcgcga gcacttacac gccctgtggc gttcgccagg tggcaggccg cacggttgca    480
gtgcccagca gcttggtcgc gccagtggca gtcgctcggt cgctggggtt ggcgccctac    540
gtccctgtat gtgagccttc tgcggcgctt ccggcctgcc agcagcctag cgggcgtcgt    600
catgttcaga ctgctgccac tctccgtgcc gacaaccccca gctcggtcgc gcagctggtg    660
catcagaatg gaaaggggat gaaggttatt atcgccggcg cgggcatcgg cggcctggtg    720
ctagccgttg cacttctgaa gcagggcttc caggttcagg tctttgagcg cgacctgacg    780
gccatccgcg gcgagggcaa gtaccgtgga cccatccagg ttcaaagcaa tgcgctcgct    840
gcgctggagg ctatcgatcc cgaggtgccc gcggaggtgc tgcgcgaggg ctgcatcact    900
ggcgaccgta tcaacgggct ctgcgacggc ctgactggcg agtggtacgt caagttcgac    960
acgttccacc cggcggtcag caagggcctg ccggtgaccc cgtcatcag ccgcctcacg   1020
ctgcagcaga tcctggccaa agccgtggag cgctacggcg cccccggcac catccagaac   1080
```

```
ggctgcaacg tgaccgagtt cacggagcgc cgcaacgaca ccaccggcaa caacgaggtg    1140
actgtgcagc tggaggacgg gcgcacgttt gcggccgacg tgctggtggg cgccgacggc    1200
atctggtcca agatccgtaa gcagctcatt ggcgagacca aggccaacta cagcgggtac    1260
acctgctaca ccggcatctc ggactttacg ccggcggaca ttgacattgt gggctaccgc    1320
gtgttcctgg gcaacggcca gtactttgtc agcagcgacg tgggcaacgg caagatgcag    1380
tggtacggct ccacaaggga gccgtctggc ggcaccgacc ccgagggcag ccgcaaggcg    1440
cgcctgctgc agatctttgg ccactggaac gacaacgtgg tggacctgat caaggccacg    1500
cccgaggagg acgtgctgcg ccgcgacatc tttgacaggc cgcccatctt cacctggagc    1560
aagggccgcg tggccctgct gggcgacagc gcgcacgcca tgcagcccaa cctgggccag    1620
ggcggctgca tggccattga ggacgcctac gagctggcca tcgacctcag ccgcgccgtg    1680
tccgacaagg ccggaaacgc ggcggcggtg gacgtggagg gcgtgctgcg cagctaccag    1740
gacagccgca ttttgcgcgt cagcgccatt cacggcatgg cgggcatggc tgccttcatg    1800
gccagcacct acaagtgcta cctgggcgag ggctggagca gtgggttga ggggctgcgc     1860 atcccgcacc ccggccgcgt ggtggggcgg ctggtgatgc tgctcaccat gcccagcgtg    1920
ctggagtggg tgctgggcgg caacaccgac cacgtggcgc cgcaccgcac cagctactgc    1980
tcgctgggcg acaagcccaa ggcttttcccc gagagccgct tccccgagtt catgaacaac    2040
gacgcctcca tcatccgctc ctcccacgcc gactggctgc tggtggcgga gcgcgacgcc    2100
gccacggccg ccgccgccaa cgtgaacgcc gccaccggca gcagcgccgc cgcggccgcc    2160
gccgccgacg tgaacagcag ctgccagtgc aagggcatct acatggcgga ctcggcggcc    2220
ctggtgggcc gctgcggcgc cacctcgcgc cccgcgctgg ccgtggacga cgtgcacgtc    2280
gccgagagtc acgcgcaggt ctggcgcggc ctcgccggcc tccccccctc ctcgtcgtcc    2340
gcctccaccg ccgccgcctc tgcgtccgcc gcctcctctg ccgccagcgg caccgccagc    2400
accctgggca gctcggaggg ctactggctc cgcgacctgg gcagcggccg cggcacctgg    2460
gtcaacggca agcgcctgcc cgacggcgcc acggtgcagc tgtggcccgg cgacgcggtg    2520
gagttcggcc ggcaccccag ccacgaggtg ttcaaggtga agatgcagca cgtgacgctg    2580
cgcagcgacg agctcagcgg ccaggcctac accacgctca tggtgggcaa gatccggaac    2640
aacgactacg tcatgcccga gtcgcggccg gacggcggca gccagcagcc gggccgcctg    2700
gtgacggctt aagcggcgcc gtgcgtaagg gccggcttac gggggcggca gtgtcgctgt    2760
ggagggatgg tctgggtgg gaggaatggg aggagagcgg cgggagcccg aggagcggag    2820
cgctggaggc ttgcggagcg gcagcttggg aagagctgcg gagagaggaa ggagcgcagg    2880
gcgcttggag cacgcgccag attacgatca cggcagcgcg aggcgcgcgt ctgacttcga    2940
agtggtaagg aagatttcat gtatgattgc gtcgagggac accgcaagtt ttacgcgcgg    3000
cggagggagc cttggggcat acaacagtac gagcgggcgt tggtgagaag gtggtcactc    3060
cgtatgagaa gatggttact ccgtaccttc gtgagaagct gctgcgcaca agttacgaac    3120
ctatctgtgt ggagagcccg gtagtatatc aggggcgagg gtcatgaacg cgagtggcga    3180
gtctgtgagc gccaatttgt tatgcggcat aatttcgcat cggggtatta cgtctacaaa    3240
atgttgagct ggcttagcgc aggaggcaac acctcaggca gaatgtacga atgtgtgcag    3300
aagggcagag tcaaggcaga ggcggagaag ttgtcagggc tgtgtgtggt ttggtcaggg    3360
cgtggctaga tggatatgag acccgccgcc gtctccagat tgtggcggag gtggaactct    3420
cggcccccgc gccagtcccc gcggccagcg catcccgcca tgcgggttgt tggctggtgc    3480
```

```
atcgcgcggg gtgtgctatg agtgtggaaa cactatgtcg cgtgtcgtgc tgaggtctgt    3540
tgagaggttt cgtcgtttgt gcatgtcctg tcccggttgg agtttgagcg aggtggttca    3600 aagttttgg atcgcgtggg agagactgaa acggtttggt gagaatggtt gagacagagg    3660
ttgggcttgg aaactggagg agaggagcag cgtaactcga ggacgatgca gtagatgcac    3720
cacaacagtt gtggtgggcg cctggagtaa cacgcgtgcc accaacacgc aattacagag    3780
atccgtcata caggagggat catatgcgat ttaattttgg ttttgcattt gtaagacgtt    3840
ttcaca                                                               3846
```

<210> SEQ ID NO 79
<211> LENGTH: 2292
<212> TYPE: DNA
<213> ORGANISM: Chlamydomonas reinhardtii

<400> SEQUENCE: 79

```
atgctcgcga gcacttacac gccctgtggc gttcgccagg tggcaggccg cacggttgca      60
gtgcccagca gcttggtcgc gccagtggca gtcgctcggt cgctggggtt ggcgccctac     120
gtccctgtat gtgagccttc tgcggcgctt ccggcctgcc agcagcctag cgggcgtcgt     180
catgttcaga ctgctgccac tctccgtgcc gacaacccca gctcggtcgc gcagctggtg     240
catcagaatg gaaagggat gaaggttatt atcgccggcg cgggcatcgg cggcctggtg     300
ctagccgttg cacttctgaa gcagggcttc caggttcagg tctttgagcg cgacctgacg     360
gccatccgcg gcgagggcaa gtaccgtgga cccatccagg ttcaaagcaa tgcgctcgct     420
gcgctggagg ctatcgatcc cgaggtggcc gcggaggtgc tgcgcgaggg ctgcatcact     480
ggcgaccgta tcaacgggct ctgcgacggc ctgactggcg agtggtacgt caagttcgac     540
acgttccacc cggcggtcag caagggcctg ccggtgaccc gcgtcatcag ccgcctcacg     600
ctgcagcaga tcctggccaa agccgtggag cgctacggcg gccccggcac catccagaac     660
ggctgcaacg tgaccgagtt cacggagcgc cgcaacgaca ccaccggcaa caacgaggtg     720
actgtgcagc tggaggacgg cgcacgtttt gcggccgacg tgctggtggg cgccgacggc     780
atctggtcca agatccgtaa gcagctcatt ggcgagacca aggccaacta cagcgggtac     840
acctgctaca ccggcatctc ggactttacg ccggcggaca ttgacattgt gggctaccgc     900
gtgttcctgg caacggcca gtactttgtc agcagcgacg tgggcaacgg caagatgcag     960
tggtacggct ccacaagga gccgtctggc ggcaccgacc ccgagggcag ccgcaaggcg    1020
cgcctgctgc agatctttgg ccactggaac gacaacgtgg tggacctgat caaggccacg    1080
cccgaggagg acgtgctgcg ccgcgacatc tttgacaggc cgcccatctt cacctggagc    1140
aagggccgcg tggccctgct gggcgacagc gcgcacgcca tgcagcccaa cctgggccag    1200
ggcggctgca tggccattga ggacgcctac gagctggcca tcgacctcag ccgcgccgtg    1260
tccgacaagg ccggaaacgc ggcggcgtg acgtggagg cgtgctgcg cagctaccag    1320 gacagccgca ttttgcgcgt cagcgccatt cacggcatgg cgggcatggc tgccttcatg    1380
gccagcacct acaagtgcta cctgggcgag ggctggagca agtgggttga ggggctgcgc    1440
atcccgcacc ccggccgcgt ggtggggcgg ctggtgatgc tgctcaccat gcccagcgtg    1500
ctggagtggg tgctgggcgg caacaccgac cacgtggcgc cgcaccgcac cagctactgc    1560
tcgctgggcg acaagcccaa ggcttttccc gagagccgct tccccgagtt catgaacaac    1620
gacgcctcca tcatccgctc ctcccacgcc gactggctgc tggtggcgga gcgcgacgcc    1680
```

| | | |
|---|---|---|
| gccacggccg ccgccgccaa cgtgaacgcc gccaccggca gcagcgccgc cgcggccgcc | 1740 | |
| gccgccgacg tgaacagcag ctgccagtgc aagggcatct acatggcgga ctcggcggcc | 1800 | |
| ctggtgggcc gctgcggcgc cacctcgcgc cccgcgctgg ccgtggacga cgtgcacgtc | 1860 | |
| gccgagagtc acgcgcaggt ctggcgcggc ctcgccggcc tccccccctc ctcgtcgtcc | 1920 | |
| gcctccaccg ccgccgcctc tgcgtccgcc gcctcctctg ccgccagcgg caccgccagc | 1980 | |
| accctgggca gctcggaggg ctactggctc cgcgacctgg gcagcggccg cggcacctgg | 2040 | |
| gtcaacggca gcgcctgcc cgacggcgcc acggtgcagc tgtggcccgg cgacgcggtg | 2100 | |
| gagttcggcc ggcaccccag ccacgaggtg ttcaaggtga agatgcagca cgtgacgctg | 2160 | |
| cgcagcgacg agctcagcgg ccaggcctac accacgctca tggtgggcaa gatccggaac | 2220 | |
| aacgactacg tcatgcccga gtcgcggccg gacggcggca gcagcagcc gggccgcctg | 2280 | |
| gtgacggctt aa | 2292 | |

<210> SEQ ID NO 80
<211> LENGTH: 763
<212> TYPE: PRT
<213> ORGANISM: Chlamydomonas reinhardtii

<400> SEQUENCE: 80

Met Leu Ala Ser Thr Tyr Thr Pro Cys Gly Val Arg Gln Val Ala Gly
1               5                   10                  15

Arg Thr Val Ala Val Pro Ser Ser Leu Val Ala Pro Val Ala Val Ala
            20                  25                  30

Arg Ser Leu Gly Leu Ala Pro Tyr Val Pro Val Cys Glu Pro Ser Ala
        35                  40                  45

Ala Leu Pro Ala Cys Gln Gln Pro Ser Gly Arg Arg His Val Gln Thr
    50                  55                  60

Ala Ala Thr Leu Arg Ala Asp Asn Pro Ser Ser Val Ala Gln Leu Val
65                  70                  75                  80

His Gln Asn Gly Lys Gly Met Lys Val Ile Ile Ala Gly Ala Gly Ile
                85                  90                  95

Gly Gly Leu Val Leu Ala Val Ala Leu Leu Lys Gln Gly Phe Gln Val
            100                 105                 110

Gln Val Phe Glu Arg Asp Leu Thr Ala Ile Arg Gly Glu Gly Lys Tyr
        115                 120                 125

Arg Gly Pro Ile Gln Val Gln Ser Asn Ala Leu Ala Ala Leu Glu Ala
    130                 135                 140

Ile Asp Pro Glu Val Ala Ala Glu Val Leu Arg Glu Gly Cys Ile Thr
145                 150                 155                 160

Gly Asp Arg Ile Asn Gly Leu Cys Asp Gly Leu Thr Gly Glu Trp Tyr
                165                 170                 175

Val Lys Phe Asp Thr Phe His Pro Ala Val Ser Lys Gly Leu Pro Val
            180                 185                 190

Thr Arg Val Ile Ser Arg Leu Thr Leu Gln Gln Ile Leu Ala Lys Ala
        195                 200                 205

Val Glu Arg Tyr Gly Gly Pro Gly Thr Ile Gln Asn Gly Cys Asn Val
    210                 215                 220

Thr Glu Phe Thr Glu Arg Arg Asn Asp Thr Thr Gly Asn Asn Glu Val
225                 230                 235                 240

Thr Val Gln Leu Glu Asp Gly Arg Thr Phe Ala Ala Asp Val Leu Val
                245                 250                 255

Gly Ala Asp Gly Ile Trp Ser Lys Ile Arg Lys Gln Leu Ile Gly Glu

```
            260                 265                 270
Thr Lys Ala Asn Tyr Ser Gly Tyr Thr Cys Tyr Thr Gly Ile Ser Asp
            275                 280                 285

Phe Thr Pro Ala Asp Ile Asp Ile Val Gly Tyr Arg Val Phe Leu Gly
            290                 295                 300

Asn Gly Gln Tyr Phe Val Ser Ser Asp Val Gly Asn Gly Lys Met Gln
305                 310                 315                 320

Trp Tyr Gly Phe His Lys Glu Pro Ser Gly Thr Asp Pro Glu Gly
                325                 330                 335

Ser Arg Lys Ala Arg Leu Leu Gln Ile Phe Gly His Trp Asn Asp Asn
            340                 345                 350

Val Val Asp Leu Ile Lys Ala Thr Pro Glu Glu Asp Val Leu Arg Arg
            355                 360                 365

Asp Ile Phe Asp Arg Pro Pro Ile Phe Thr Trp Ser Lys Gly Arg Val
            370                 375                 380

Ala Leu Leu Gly Asp Ser Ala His Ala Met Gln Pro Asn Leu Gly Gln
385                 390                 395                 400

Gly Gly Cys Met Ala Ile Glu Asp Ala Tyr Glu Leu Ala Ile Asp Leu
                405                 410                 415

Ser Arg Ala Val Ser Asp Lys Ala Gly Asn Ala Ala Val Asp Val
            420                 425                 430

Glu Gly Val Leu Arg Ser Tyr Gln Asp Ser Arg Ile Leu Arg Val Ser
                435                 440                 445

Ala Ile His Gly Met Ala Gly Met Ala Ala Phe Met Ala Ser Thr Tyr
            450                 455                 460

Lys Cys Tyr Leu Gly Glu Gly Trp Ser Lys Trp Val Glu Gly Leu Arg
465                 470                 475                 480

Ile Pro His Pro Gly Arg Val Val Gly Arg Leu Val Met Leu Leu Thr
                485                 490                 495

Met Pro Ser Val Leu Glu Trp Val Leu Gly Gly Asn Thr Asp His Val
            500                 505                 510

Ala Pro His Arg Thr Ser Tyr Cys Ser Leu Gly Asp Lys Pro Lys Ala
            515                 520                 525

Phe Pro Glu Ser Arg Phe Pro Glu Phe Met Asn Asn Asp Ala Ser Ile
            530                 535                 540

Ile Arg Ser Ser His Ala Asp Trp Leu Leu Val Ala Glu Arg Asp Ala
545                 550                 555                 560

Ala Thr Ala Ala Ala Asn Val Asn Ala Thr Gly Ser Ser Ala
            565                 570                 575

Ala Ala Ala Ala Ala Asp Val Asn Ser Ser Cys Gln Cys Lys Gly
            580                 585                 590

Ile Tyr Met Ala Asp Ser Ala Ala Leu Val Gly Arg Cys Gly Ala Thr
            595                 600                 605

Ser Arg Pro Ala Leu Ala Val Asp Asp Val His Val Ala Glu Ser His
            610                 615                 620

Ala Gln Val Trp Arg Gly Leu Ala Gly Leu Pro Ser Ser Ser Ser
625                 630                 635                 640

Ala Ser Thr Ala Ala Ser Ala Ser Ala Ser Ser Ala Ala Ser
            645                 650                 655

Gly Thr Ala Ser Thr Leu Gly Ser Ser Glu Gly Tyr Trp Leu Arg Asp
                660                 665                 670

Leu Gly Ser Gly Arg Gly Thr Trp Val Asn Gly Lys Arg Leu Pro Asp
            675                 680                 685
```

```
Gly Ala Thr Val Gln Leu Trp Pro Gly Asp Ala Val Glu Phe Gly Arg
            690                 695                 700

His Pro Ser His Glu Val Phe Lys Val Lys Met Gln His Val Thr Leu
705                 710                 715                 720

Arg Ser Asp Glu Leu Ser Gly Gln Ala Tyr Thr Thr Leu Met Val Gly
                725                 730                 735

Lys Ile Arg Asn Asn Asp Tyr Val Met Pro Glu Ser Arg Pro Asp Gly
            740                 745                 750

Gly Ser Gln Gln Pro Gly Arg Leu Val Thr Ala
            755                 760

<210> SEQ ID NO 81
<211> LENGTH: 16122
<212> TYPE: DNA
<213> ORGANISM: Chlamydomonas reinhardtii

<400> SEQUENCE: 81
```

| | | | | | |
|---|---|---|---|---|---|
| cacattcaac | actgccacga | tgaagcaaac | tgaacgggtt | atgcaggagt | cgcttgaagg | 60 |
| ggaagtacac | ggccccactt | caggctctta | agcctcaggg | gttcgtgtag | gcgttgtatt | 120 |
| atcatgagtg | ctagatataa | gacggtatta | tgtgtaaact | gggagggagg | gagctgcaag | 180 |
| tatggagacg | cttgccagtt | tgcgcacgga | gcgcacgagc | tacgatctcg | ggcgaacag | 240 |
| gttgcgactg | gcttggtggt | cgcgccagta | aggaccacac | caaagcttgc | aggtcaacct | 300 |
| gctcagtcgc | tgcagaaaag | gcagctctgc | aaatggcacc | aagtgggcgc | ctgcagcttt | 360 |
| ggcgcccgct | gcaagttcgc | gcacagcgag | catgagctgt | gcgccccagg | cggagcctac | 420 |
| ggtggcagca | acagtcatgg | gtcggcagtc | tcccagaacg | gcggtggagc | ctttccgaca | 480 |
| tcaccgcagc | ccgaggccgc | gtcttctccc | acgtcccaga | ccccgcctcc | ccgcctcct | 540 |
| ccgcttcccc | tgccgcgcct | gagccccgtg | gaagttcata | agatttacaa | ggaggcactg | 600 |
| gtggcggcgc | ggtcgggtga | tgcggtcaag | gtggggagca | aggctggcga | gctgctagcc | 660 |
| cgcgggccgg | cgccgcacta | cggcctgtcg | cgcaaccagg | tggccgacct | gatcgccgcc | 720 |
| gccaccgccg | agtaccccag | cctgcccgtc | ctgaaggccc | tgctgccgct | ggcccagccc | 780 |
| ttcggcgact | ggaccctcct | gcaccggcag | taccccacgg | cctcccacca | acaggccacc | 840 |
| ggccaggcca | tgtactgcgg | gctactgcac | caggccgctc | tgatgctgct | ggagtggcac | 900 |
| aaggcgggcc | tcgcgcaggc | agccaccacc | gggctggagg | tgctgcgagc | catctgtgcc | 960 |
| gcgcggcccg | ccgccgtcgt | ggacatgaag | gcgccgggca | tcctgtccac | gccgctggag | 1020 |
| acggtgctgc | tagccggcca | ggagccgcgc | ggcttcgtgg | ctcggctgct | gcgcgaggtg | 1080 |
| tcacccatca | cctggctgca | cacggcgccg | gggcacgcgg | cgcacctgcg | cgcggtggag | 1140 |
| gtgtgcgagg | cgctggcgga | cgacgagggc | tgcctggtgg | cgcgcaacct | gggcttcagc | 1200 |
| caggcctact | tcctcacctg | cgcctcggtg | ctgcagggca | tctatgaccg | caagcggccc | 1260 |
| gcgtccgcct | cctacgaggc | ggtgccggag | ccggtgccgc | cgccggcgtc | cggctacatc | 1320 |
| cagctgccgg | ccctggagat | ccccggcatc | tcgcggacct | tcaccggcgt | acggacaggg | 1380 |
| gcgccgccgc | cgccaccacc | accgcatgca | gcagcaagca | gcgcttccgg | gcatgtcaag | 1440 |
| gtgcacagcc | agccggccac | ggcgccggcg | gctggcagca | ctgcctccag | cagctcagtg | 1500 |
| gcaaagcagc | cacacacgca | gcagctccag | ttgccgtcgg | gcgcacgcag | cggcgccgcc | 1560 |
| tcctccgctt | cctcggtgca | gaagggccct | gtggcagccg | cggtcaagac | gacagtcgcc | 1620 |
| agcgccgctg | tggccgcggc | tatcggtggc | gctgttgccg | ccgggcagcg | cggcgcgcgc | 1680 |

```
cagcggcagc agccgcagca agacgacgac gatgatgaag aggggccgcc cgcgctgctg   1740
gatgacaact cctcggatgg cgacggcgac agctcgggct ccgaagactt gctggggctg   1800
ctgctgcagc aaaagcagcc acccaactcc aaggctgctt tgaaacagca acggcaggc    1860 aagcagagca acggcgcagc ggcggccagc agcggcttcg cgcgcggctt ccttggcggg   1920
ggcggagcca gcacgggcgc tgcagcgggc gcgggggggca aggccgctgg gcctgctccc  1980
caacccgcag ccgcaagcaa gcccaaggc cagcagcaga atgcgatgca gcaacagggg   2040
cagcaggcac gacaatcgca gcagcagcag cagcagcagc agcagcagca gcagcagcag  2100
gcacaggcca agccagccag cggcggcctt gcacgcggct tcctggctgg cggcgcaaca   2160
gggtcttccg gcacagctca ggccgctgcc agtgcggcag gcaaagcacc cgcagccagc   2220
gctacaggtg caagtgctgg tgcgcaggcg ctcgccgcca agagagcggc gggctccgcc   2280
ggcgcggctg ccgccaaaac ggtagtagcg gccccgcgg cggcaacgac cccggccaaa    2340
ccggccaccg cgcagcccgc caaagcagtt gcagcagcag cggcagcagc cgccgccaag   2400
ccgttagcgc cgccgccgca gccggccggc gcgcaagtgc tgagggcact gctggcggag   2460 ctgacgcgg cggtggacgc gaacgccgcg ggcaaggtgg cagacgtcgt gaagcggctc    2520
aacaaggaga ccgcggcgtg cacgcctccg ctacctgtgg aaaaagcaat ccaggctcca   2580
tgctttgcgg ccacccatag cgcgaagcag aaggtcggag acctgacgcc gctgacgatc   2640
aaggatgacc cgctttgggc tgcggagaac gcggcgcggg ccgcggcgga gtctgccccg   2700
caggcggggc tgctggcgga actgcttgcc gcgctgcgca agtgcacctg gagggcggtg   2760
ctgggccaca tgtcgctctc catgctgcag gagctacgca taataaacat cccctgcggc   2820
attccatggt ggccggagat cctgcgtgac gcctctgtgc cggccgacca gccgtcaccc   2880
agcctgtttg agatgctgct ggagaagggc ggcgccgtcg ccagcgactt ggcggcgggc   2940
ctggtggaga agcacagcta cgtgctgctg tacgccaaca agagcccggt gtgcctggcc   3000
ctgacccgca agctgccgct gaacgacacc gactacatct tccgcatgag cctcgcctac   3060
cgctccaagg agaagggcgg cgccgccagg gagaccctca cggcggagct gcagctgccc   3120
gatccggccg cgccgcaggg ctggcgccgc cgccaagtga gcgccaccgc cttcggctgg   3180
tgggcgctgc tgccgcactg cagcaatgac gcccgggtgc tgtcgacgct gcgggccaag   3240 gtggaccccca aggtggagct gcccgccttc gagggcctgc cgccgctgca cgtgctggtg   3300
cagtacgggc ggcggccgtg ggatggggtg gcaacggtgg ccacggaccg gcggctcagc   3360
gcgctgctgt tcacggatga gggcgtgtta atctcccggc tgctggagca agtggcgggc   3420
ggcatcacac cgctgtacag ggcggtgcgc gtgggcgaca tcccggcagt gacgtggctg   3480
cggcagcggg gcgcgagccc gctggtcagc tgcacggagg agggcgcggg cggatacagc   3540
gatacgccgc tacacctggc ggtgacgcgc aagagcgccg aggccgtgga ggcaatcatt   3600
aagcactccg cgcccgacat cctcaagaag ctggacacca catacgacag cgacggcgcc   3660 acaccctca tgctcgcggc ggagctgggc tacacccgca tcgtggacct gctgctggcg   3720
gcaggtgccg accctccct gctgcacgac ctgccaaaca agggcgcgag caagtcaaag   3780
aaaggcggcg cggccggctc tacgacgcg ccgcggggca cacaccagtc ggtcctgtca    3840
cggacgctgc agctgcagga ggcggaggag gagcggcgga agaagcaggg cagcaacggt   3900
caggcgcagg gcgacgccaa gaagcccaac ccgcatgacg ctgtgctgga ggcgatcatc   3960
agcagttgga agcccctgtg gagtggtgcg gcgctgcagc gcgagctagg gccggacggg   4020
```

-continued

```
tgcgcacgtg tgcgggcctg gctgctgcag cacgcggaca cgacgctgtg gccagtgatc    4080
aaggagatgg gtgcgggcgg cgtgtcgcca ggcgtgctga cagccagcct cgtggcgctg    4140
ctgctggagg tgtgccgcac ggcaggtggc gccgactggc gcgtgccagg caccaccgac    4200
cccttcaagc ccgcgggcga aggcggcagc ggcagcagca cgtggacggg gccgaagggc    4260
acacacccgc ctcggtcgca gctgtcggtg tggtcactgg ttccggagtc agccgctgcc    4320
caggatcacg ccaaggccat agccgcaaag gagggcagcg gcagtttggc gccggcgtgg    4380
ctgacgctgc ccctgctgcg cgagatgctg cagcgcgggc tggcttcgcc gcatgagcgc    4440
ctgccgtcgt acggcatcat gtctgagctc tccaagggca gcaccctgct ccacaaggcc    4500
tgtttcatcg gcgacttgga catggcgctt ctgcttctgg aggcgggggc ggactggagc    4560
aggaaggacg acaacggcaa cacggtgctg cactacgtcg ccatgggcag cgccggttac    4620
ggcgagagcc gcgtgctggc gctgtggcgc ctcttcatgt ggggccgtgc ggaggggatt    4680
gcggcgggcg gcggcaaggg ctcggcagct gcggcgtcgg cgctgccgcc gctgctgatt    4740
gatccggagc gcctggcgct ggcgaccgca accaacacca agaagcgcat gccagaagac    4800
ctggcagccg ccaagatcaa gccggcgttg aagacagaga tacaggccct caagcagcgc    4860
gtgaacgcca agctgaagaa ccaggaggcc gcagccaagg ccggcggaaa ggccacaggc    4920
aactccagcg gcaaagcaga cagcaaggcg ggcgccgccg tggctgagca gccggccgct    4980
gacgcgggca cggccgccgc ggctgctgcc ccggaggccc cgggtgcggc tgcggccccg    5040
gctgtggccg tgctgagccc ggcggagcag ctgaaggcgc tgctggcgga cgacgaggcc    5100
ctggcctccg ctccgctggc gcaactggtg ggcgtgccgg aggagtcggc gctgcagcta    5160
gccacgcggc tggccaaggc cctgcccggt acgctgcttc gcggcaagcg ggcagcaggg    5220
gctcaaggag ccgcggcgg cgaggatggt ggcggcggcg acggcggcga tgacggcctg    5280
tcgcggctcc gggcggtggt ggaggagctg cgggaggagg acgacgaaca ggagaacggg    5340
gacgacggcc ccgagtacag cgaggacgac gcgccgccgc ccggtgagga gctgttggag    5400
gacgaggatg ccaacgcggc cgccatgcgg ggagtggccg gtgacgccgc ggctgcctca    5460
gcggccgccg cctccgccag cagcagcggc agcgcggccg cgaacggcgg cgcggcccag    5520
gcggtggcgg ctgcgaccga cttcgacaac cacccgctgc gcaacctggc ctggccgctg    5580
ctcatcacca aggaggccat cgcgggctgg ggcacgctga acgaccagtg gaggaagctg    5640
gtgatggccc ggctgcgcgt catcgggcag gggctgtggc cgcgctgccg cggcgccaag    5700
cgcatcacca gcgacgaccc actgctcatg ccgcaggagc tgtggcggct caagctcaca    5760
aagggcggcc gcatcctgtt cgaggtggcg gtggacgacc acgacagcaa gggcaccttc    5820
tgcgagatta tcagagtctg gtgcatcacg ctgaaccaca aggagtacga ggtgatgatt    5880
cagcgcgtgc agcgctcctt caccaactca ctgcgcatgc ggctgcgcaa gaagctgcag    5940
ccgctggagc aggaggggcc ggcagcggcc gcgaccgcgg ccggcacaaa gaaggcggcc    6000
ggcgccaagg cggcggcagc cggcgtcgtg gctgcgggcg cgaccgcac ccggactcgc    6060 ctgccgcggt tttacaagga ggcggggctg gtggacggca gcggcgctgg ggatgcgggc    6120
ggcagcaagg ggcaggagca gggccaggtg atggtgctgc gggagcacta cccgcccgca    6180
agctgggccg acgacacgta caccacgctc aagttctaca cggtggacgg gctgctggtg    6240
aaggcggtca tgtcggggct ggcggaggcg caggtggact tcatgttcaa gctgagcccg    6300
caggagcgcg acctcatcac catggtgccc agcccgccct cctccatcat cctgctgggc    6360
cgcagcggca ccggcaagac cacatgcgcc gtgttccgcc tgtggaccgc ctggctggcg    6420
```

-continued

```
ccctacctca gccgcgcgca cgagacgccg cacaccgtgt tcgtcaccgc gtcggccacg   6480
ctgcgggagc aggtggcccg cgccttccgc aagctgcagc gcgccgcact gcgcgaccac   6540
gagtgggagc gcgcctccgc ggccttcaac accacctatc acaccttcaa ggacgtgccg   6600
cccgaggcct tcccgctctt cctgtccagc cgcacctacc tgcgcatgct ggacggcacc   6660
accgagcgcc ccttcttccc gcgcgccgcc aacggctcca tcattcaggt ggcgggcgac   6720
ggcgaggaag cggaccccga cggcgcgcg ctggtggtgg ccctgaacga ggacctgagt   6780
gacgaggagg acgaggagga cggcgccgcc gcggaccagg agcggcagcg cggcgggccg   6840
gacgaggatg gcggcggcca ggagggcggc gcggcgctgt ttgaggagga ggtggcggcg   6900
gcggacgcgg cgcggcggga ggaggcggcg cgcgcgcggc tgctgatgga catggaggga   6960
gcggaggcgg gcggcgcggc ggacggctac gggctgggcg tggcgggtcg cgcgcggctg   7020
aaccgcgagg tgacgtacca gcacttcgtc agtgccatgt ggcccaagat cacaaccccc   7080
gagcagcgca accaggtggc gcccgggcgc gtgtaccagg agattgtgag ctacatcaag   7140
ggcagcgcag aagccatctc cagtcccgac ggccacctca gccgcgagca gtacatggcg   7200
ctgggccgca agcgcgccgc caacttcagc gccgacatgc gcggcgacgt ggtgtggccc   7260
atcttcgaga agtacgagcg gctgaagcga caggagtggc gctacgacat gttggacctg   7320
gtgggccaca tctaccgcga gatgaccacc acgcccgggg gctacgccgg cacgcccgtg   7380
cacgcgctgt atcgtgacga ggtccaggac ttcacccagg gcgagctgct gctggacatg   7440
gtggtggccg ccgaccccaa cagcctcttc tactgcggcg acacggcgca gaccattgcg   7500
cgaggcatcg ggttccgctt tgctgacacg cgcacgctgt tccacgagga gaacacgcgg   7560
cgccaggagg cggcggcgcg gcggctggcg gcggaggcgg cggacgagga gtcggtgggc   7620
aaggcgctgg cgcggcgcgg ccacggaatg accatcgcca cgcctcccgt cctccagctg   7680
accatgaact accggacgca ccagggcgtg ctggacgtgg cggcggtggt ggtggaggcg   7740
ctgaggcgct acttcccact gcagattgac aagctggagc gcgagagcgc gcagttcccg   7800
ggccctcacc cgctgctgct cggcagcatc tccgccgacg acctcaccta cctgctcagt   7860
ggctccgaca agaagacgtc gcaggtggag ttcgcgcgc accaggtgat cctggtccgc   7920
agcatggcgg cggtggacca gctgccggag gagatccggg acagcaacgc catcatcatg   7980
accgtgccgc aggccaaggg gctggagttc gacgatgtgt tcctggtgga cttctttgcg   8040
gacagccagg ccaccgccga gtggcgcgtg ctgtgctcct acctggccga gctgcaggag   8100
cggggcggca aggggctgga cggcttccag tacggcctgc agcaggtcgc cccgacggac   8160
ccgggcgcgg tgcggcctct ggagttgaac gagggcacgc acgtggtgct ggccgaggag   8220
ctcaagcacc tgtacaccgc catcacgcgc gccaagaaca acgtggtcat cttcgaccgc   8280
aacgccgcca gcgcgcgcc cttctaccac ctgctgcaga gcctgggcat ggcgcgcacc   8340
gtgcacaagt cgctgctgga ggacggcgcg gacgccgcca gttcgggct gacgcagaag   8400 gccaccagca gccggcacga gtgggccaag cgcgcgcgca acctcatggg caaccgcaac   8460
tacgccatgg cgcgcaaggc cttcctgcag gcggaggacc aggtgcgcgc cgaggtggcg   8520
gacgcactgc tcaagcgcca gcgcgccggc caggagtcca tgccgacgt cgacaagcgg   8580 cggctgctgg cggcgcggc gctgcagctg ctggcggcca ccgcccgctg cggcgagtcg   8640
ccggaccctg tggagccgga gggagctgcg cgctgggtgc gcgaggccag caagttcctg   8700
gagggttgcg gcaagagcat tgaggctgcg cagctcaagt tcaagctggg cacgcagcgc   8760
```

-continued

```
gccgtggcag cggcgctgcg cctgctggtg gacgccaagg agtacgccgc cgctgccgag    8820
tgctgcgtgc acatggcggc ggccgagctg cggcggcgc gcgcccgcgc cgcggaggag     8880
gacgcggcgg cggcgggcag catgcagcgg ctgctgatga cggaggcgga gctggcggcg    8940
cagcgggagg cgcaggcgca ccaggcggcg gtgccgtggc tggccaaagc agtggagcag    9000
ttccagttcg cgggcaacag cacggccgtg ctggcgctgc tcgcgccgcc tggcttcggc    9060
ggcagcaagg gtagcgccac aggcgcgcat gctccgcttg cagcagcagc cggcattgac    9120
tcggaggacg atgatgatgc ggcggaggat gcggcggagg atgcggcgga ggacgtggag    9180
gaggatgagc agcagcagcg cgagctagag gcgcaggagc ggacgggggcc gctggcactg    9240
tttgcgccgc tggcgccgcg gctgcacgcc atgctggcga ggcgctggca gggctacggc    9300
caggcgctga gggcggccgc catcgcgctg cactcgcgcg gctcgctgcg gcgggcgggc    9360
gccgtggcgc ggctggtgcc catgccgcag gagcgggaca cattgctgga gacgctcggc    9420
tactggcggg cgcggggcgcg ggcccgcagc gcggtggacc cgctgggcgc ggcgcaggtg    9480
ctgctggagc acggcgacac gcggcgggcg gtgcgcctgg tgctgcgctg cctggagccg    9540
ctgcccgcct cctcgggggg catggaggcg gccgaggccg ggggcgcggg cggcggcggc    9600
gaccggctga cccgggcggc gcggcagcag cagctgtatg agctgcagct gcggcaggag    9660
catgagcggc gtcagaagca ggtgctggag gccaacgcgc tggctgtgct gcaccggctc    9720
gtcgcggcgc agaccaaggc agcggaggcg acgcagctgc ggcgagcgct ggaggcttgg    9780
atggcgcggc aggcgaagtc ggaggagggc ggcaaggaag gtgaggaggg cgccggtctc    9840
accaagcgca tgctgcccat ccgcggccac gtgctgctgc tggaggcgcg cttgctgctg    9900
gagccatggg ccgcagccgc tgccgggggc gccaaaggcg ctgcaggtga cagcaaggag    9960
cagcaggcgg cggcagcggc ggtggccacc aacgcggcat gcgcgatgc cgcatggctt    10020
gaggcccggc cgctgctctt gacggcggtt gagtgcttcc tgcgctgtga ccagtggccg    10080
ggcttcatgg aggcggctga gctgctgctg cgggccgccc ccgacgcggc agtcgcaagc    10140
cacacggccg cagggcagct ggcagacttc gagcaggcgc tgctgcaggc tatgcagcga    10200
ggcgcagagc gcgccggtga cagcgccaca gtgcggccg cggcttcgtc tcgcacggcc    10260
gcagccaagc aggccctggc ccggagcctc gtggtgccgg aggcggcgct caagctgatg    10320
cggaccacgc agaccgcgtg tgatgcgctc agcgtgggggc taggcagcag tgcgggtagc    10380
aacgtctctc tccgcccagg cggtggactg gtgggccgcg ccgtggcgg cggcgaaagg    10440
tcgcgcgccg gcgccgcctc ttcattgagc aagccgcagc aggaggcgct gtcgcgcctg    10500
gaggggctgc tgctgctgcc gggcctgtcg cggccgactg aggcgaagct gtcggcgcgc    10560
aacgccagcc acagctggtg ggcggcgctg ggcagcagga acacggatgc ggtgcggcgc    10620
gcggctgggc ccaaggcagc agccggctcc ggacaggatg gcaaggagaa ggaaaagacg    10680
tctgggcagt cgagctgggc ggcggtggct gccaagggcg cggccgcaac ggcgatggtg    10740
tgggatccgg aggtgcccgc gctcgcaccc acctcgcacc tgctgctgcg ttgccaccag    10800
accgccatgg ccctgggcga aggtggagcc atggcggcag ccgtggaggc ggcgggtgct    10860
ggtgccagtc agatgccgct gccgcgtgcc gcgtcgcgg cggtcgcggc tcggagcctg    10920
actatccggg ctgcctgcct ggcacacctg gcggcacgcg gcgccctggc tgcctacttg    10980
caccctgcgc cgccgcctca gcccgccctg cccgcgggcg ccggcggcaa ggctgcggag    11040
gagggcacgg agggtgatgc cggcaagcag gagcagccgg cggaggccgc ggcgccgctc    11100
agctgtgagg tggtcctgga ccggctgcgg ccgctggtgt gcgctgcccg gcggtgcac    11160
```

```
ctggccaaga tgatggtcgg cagcgttggg caggccttct caatggccgc ggcggcgagc    11220
ctccgcaagt gcctagatgc gcagctgcgc tacttggcgg ctgctctggt cgcggcctcg    11280
ctgccgcctg cggctgcgcc cgagctgctc gcagagctgc tgcagccgcg gccgcagccg    11340
cagcgcaggc ctggcggcgg cggcgggccg cctcggcggg tcatgggcga tctgctagag    11400
ttgctggcgc gtgacggctt cccgcaccgc gagctggcgg actgggcgga gcacctgctg    11460
gtcaggtgca tgccgctgga actgcgcatg ccgctgcgcc ctgccgtgtc gtacctggcg    11520
tgccgcacga tgatgctggt ggcacccgac agcgaggacc gcgcctccaa gctgtggttg    11580
atcaaggaca gcagtgcgaa ggcgaccgga gacgtgcccc cggagcggct ggtgcatgac    11640
gacaagaaga cggggccggc ggaggcgctg ctggtgtccg ccttccgcgc catggacagc    11700
tccccgctcc gcgccgtggg ggacctgctc tactacctgg cgtggtgcgc ccggagagac    11760
gggctggcgg cggtgacgcc cactgacgct gcggcggaag gcgcgcaggc gccggctggt    11820
gcagctgccg gcggcagcaa gcccggaagc ggtgcagcgg cagcagccgg gcccgtgggc    11880
ctgtcgctgc cgcttgaggc ctacgccgag ctggtggagg tgacggtggg gcagctgctg    11940
ctggcggcct gcgacaacgc gctgctgccc ggcaacgtgg cgggcaccct ctcggggctg    12000
ccgcgcgtca gtgaccctca ggcgggcctg aacggcgtgg cggacacctg ggcgcgagag    12060
ctgggcttcc ggggccccgg ccgtgggcgaa ggagcaggcg gcggcggtgg cagcggctgg    12120
ggctggggcc gaggccgtgg cccgtcgccc aaggaggtgg cagaggctaa ggcgcgggcg    12180
gtgacggcgc gcaaggaggt ggcgggtcag ctgcgtctgg ccgcgcggat gacgttgttg    12240
ctggcgtccc acattgacca gcgcctgcag gacacggctg cgcccgctgc gggcggcgca    12300
ggcggcgact cggctgcgtc ccctccggag ctggagttgt tgcagcaaga ggtgctgccg    12360
ctgctggacg ccccggggcg gcgcgaggcg cacgagctgc tgaggcagcc cggcggccca    12420
ggggcgcagc ctcgccgggc gcagggcaag agtcgcggcg gtggagcgga ggccggcgtg    12480
ggctcgggtg cgtccgttgc accgccgtcc gcaggagcca gcgggctgcg cttgcgggcg    12540
attgcgcagc gcgtcctgct ggcggcaggc gcagcctacg tctcgctgga gctgcaagag    12600
agtgtggtga agccgcagcg gcagcagcag aaggcggcgg cggagcggca gcagaagctg    12660
gcgggcggcg gccctgtgcc ggagccgccg ccgctgcgcg ggggctggcc ggccgaggcc    12720
tccgcgggct ttcgggacgc atgcacgctg ctgcaggcgc gtgtggcgcc ggcctgcttc    12780
cagccggcca ccggcgcgac cgacctggcc tcggtggcgc aggctgcgga cgcgctggca    12840
cggctgtcgc agcgggtgtg ctaccccagc tcgcgcctga gcacgggcat gcggctggtg    12900
ggcccggacg ccaaccgcga gtacgagggc ctcagcggcg cgcggccgcc caagggcccc    12960
ctggcgctgc tgttccaggc ggcgcaggcc aagatgcagc tgcccaaggc ggcggcgac    13020
gcggggatag gaggccgcgt caaggccgcc agcgacgcgg tggcgcgtgt ggccgcccgc    13080
gacttccagg ccacggagga cgagcgcgtg cggcagcgcc acgcggcggc ggtgatccaa    13140
aagcggtggc gcgcctggag gcagcggcgc atcgaggcgg cggaggcaat gcggcggcgc    13200
cagctgcagg ccaacgcgct ggagaccctg cgccgctcca tacgcttccg ggtctgggtg    13260
cgtgcgcgcc ttgcaaacgc gcgcaaggcc ctggacgcgc ggcacttcgg ggagcgcttc    13320
accgcggggt gcgccgccgc ggtccagttc ggcgagcagg cgctgcacat ggcggacatc    13380
gaggcggtgc tgaaggcgcg gtttgtccag ttggaccggt gccgtgtgtg ctctggcgag    13440
acgctgcgca aacagacgga ggagctgaag cagcagatgg cgcagcgggc tgcgggcaag    13500
```

```
ctcaagggcg cagcagcgga gttccgaccg cacaagaaca cggttgatca cctggaggcc   13560
gccaactcct tcacaacctt ccgggacgtc tacaacggcg acctgccgac gcggctgggc   13620
ggcagcgccg cgcacatgga ccagctgcgt gccagcctag accgcttgga gcagctcggc   13680
gtcagcgacg cttcgctgat caagggccga ctcgtggcgg aggcggacct ggctctgcgc   13740
ggcgtggagc aggcccgtgc tgcgctggag gccagtctgc ggcagctggt ggaggagcgc   13800
gtctgggacg tgggtgtcct cgcatcgagg atgtttccgc agtacacctc gcttgacgcg   13860
gccgtgcagc gggttgacat gatgcgggtc cacgtggagg gactggccgc agctgcgcgc   13920
cgcacgcgcg tgctgccccc tgacgagcag ctggcagcca ttcagcccaa gcagcagccc   13980
cagccccagc tgcagcagcc acaggagcag gaccagcacc aggagcagga gcaggagcag   14040
gcgctgcggt tgccaagcgg tgaagtccca gagcaggagc aggcgcagga gcaggtgcag   14100
gcgcaggagc agcagcctgt gggagtcttt gcggctggcc ttgatgtcag acctgctgac   14160
ggcatggcag cgcatgcagc cgccgccgcc gcctctccgg ccaagcaggc cgtgcccgcg   14220
ttagaggggc cgccggggac tcggcctggc ctgcagcagc ccttcagctc accgacacac   14280
cagcagcagg ggtccgcatg ggcggcgcag aagcctgtta ttcaattcac accgccgccg   14340
atgccgccaa tgccttcggc gctgctgcag cagctgtcac aggggcaagg gcagagctac   14400
gctgttgccg cccaggcggg cgccggcggc caggcagtta gtccctacag caaccagtcg   14460
cacgcgcagg ccgctcacac gatggggtac aatcaagtct atggcggtct gggtggcata   14520
ggcgcagacc tgcctccggg cctgtcgcaa cacctggtt acggcgcggc tgcagctggc   14580 tcaacgccg gtatgctgc gtccgggttc gcgccgccca actttacggc gcaggctgga   14640
ttcccgttcc aacagcagca gcagttccag caacagcagc agcagcagca acagtatcaa   14700
tacttgccgc acatgcagca acagcagcag caacagcagc agcaacagta tcagccgtac   14760
ttgcagcagc agtaccagcc gccgtcgcct ggcatgaacg cttccatggt gtctccaggc   14820
ggcatgcctg gcttcatgcc gcagcagtac ggcatcggct acttcccaag cggagctgca   14880
ggtggaggag cggcggcagg gatgcaagga gtggctgcag ctgcagccat gggcgcggcg   14940
gcgcagttcg gtgctatggg cggcgcaggg ggctttccgg caggggagcc gggcacggac   15000
gccatcctgc aaggcgcact gatggaggac gatgacgagg acgacgacga gtggcagcag   15060
agccggcggc atggccgata tgacggcggg ggccggggcg ggggccgggg cgggcgggc   15120 cggggtcaca gcgcagggcc gcatgggagt ccctacgggc cgccaggccg tggacctgga   15180
ggcggtggag gccgcggtgg ccgcggcgcc ggtggatatg gcggtggcta tggcggtggg   15240
cgcggcagca acgtgtatga ggcgctgcgg ggtgccaatg ccacaccttc cagggccgcg   15300
cagcggatgg gcttgagcta atgttatttg agccaagccc gcatgactcc atgagcccat   15360
atgtgacgtg agcagatggc ggcagcaggt ggctatacgt tttagacaca tgcagtttgc   15420
tttcggagtg cggcgtgatg cgcagccggg aaaggagggt ggcggaagga ggaccgtgtc   15480
gctcattgct cttacagaca agaagcccct ggtgctggcc gacatgcctc atgtatgtga   15540
gcactgacac gtggtaggta gtgacagtgc gggataggt gcgatgggac aggataaggg   15600
gcaggctggg gtagcaccgt tgtgtgcagc gtgttcccag accccgacat tcaattcaag   15660
ttgctgtacc gtattgagac atcgctgact ggctggcagg ctgggagtgt gctgatgcgc   15720
aatcctcacg atccgggcgc ccggcgaggc gaggcgatag caccacacac acacacacac   15780
acacacacac acacacacac acacacacac acacacacac acacacaaac atgcacacac   15840
agtggaggct ggcatggtgg tcgcaactgg cacggtctgt agcagctgcc gagtcatagg   15900
```

```
gcaggcgcac ggcgtctggg ctcacgaaga gttgaggcca gaccccgccc gggggcagaa    15960
ggcatgcgag tcgttagagc gaggcgagac agcctggcac acaaccacgg acagacaatg    16020
cccagacagc ctggcacaca gccacggaca gacaatgccc actccagggg ctggggtttc    16080
tgacggcggc acgtgtggca cgcaatgtaa ataccaggc ga                       16122
```

<210> SEQ ID NO 82
<211> LENGTH: 15198
<212> TYPE: DNA
<213> ORGANISM: Chlamydomonas reinhardtii

<400> SEQUENCE: 82

```
atgagtgcta gatataagac ggtattatgt gtaaactggg agggagggag ctgcaagtat      60
ggagacgctt gccagtttgc gcacggagcg cacgagctac gatctcgggg cgaacaggtt     120
gcgactggct tggtggtcgc gccagtaagg accacaccaa agcttgcagg tcaacctgct     180
cagtcgctgc agaaaaggca gctctgcaaa tggcaccaag tgggcgcctg cagctttggc     240
gcccgctgca agttcgcgca cagcgagcat gagctgtgcg ccccaggcgg agcctacggt     300
ggcagcaaca gtcatgggtc ggcagtctcc cagaacggcg gtggagcctt ccgacatca      360 ccgcagcccg aggccgcgtc ttctcccacg tcccagaccc cgcctccccc gcctcctccg     420
cttcccctgc cgcgcctgag cccgtggaa gttcataaga tttacaagga ggcactggtg      480
gcggcgcggt cgggtgatgc ggtcaaggtg gggagcaagg ctggcgagct gctagcccgc     540 gggcggcgc cgcactacgg cctgtcgcgc aaccaggtgg ccgacctgat cgccgccgcc     600
accgccgagt accccagcct gccctgcctg aaggccctgc tgccgctggc ccagcccttc     660
ggcgactgga ccctcctgca ccggcagtac cccacggcct cccaccaaca ggccaccggc     720
caggccgtgt actgcgggct actgcaccag gccgctctga tgctgctgga gtggcacaag     780
gcgggcctcg cgcaggcagc caccaccggg ctggaggtgc tgcgagccat ctgtgccgcg     840
cggcccgccg ccgtcgtgga catgaaggcg ccgggcatcc tgtccacgcc gctggagacg     900
gtgctgctag ccggccagga gccgcgcggc ttcgtggctc ggctgctgcg cgaggtgtca     960
cccatcacct ggctgcacac ggcgccgggg cacgcggcgc acctgcgcgc ggtggaggtg    1020
tgcgaggcgc tggcggacga cgagggctgc ctggtggcgc gcaacctggg cttcagccag    1080
gcctacttcc tcacctgcgc ctcggtgctg cagggcatct atgaccgcaa gcggcccgcg    1140
tccgcctcct acgaggcggt gccggagccg gtgccgccgc cggcgtccgg ctacatccag    1200
ctgccggccc tggagatccc cggcatctcg cggaccttca ccggcgtacg gacaggggcg    1260
ccgccgccgc caccaccacc gcatgcagca gcaagcagcg cttccgggca tgtcaaggtg    1320
cacagccagc cggccacggc gccggcggct ggcagcactg cctccagcag ctcagtggca    1380
aagcagccac acacgcagca gctccagttg ccgtcgggcg cacgcagcgg cgccgcctcc    1440
tccgcttcct cggtgcagaa gggccctgtg cagccgcgg tcaagacgac agtcgccagc     1500
gccgctgtgg ccgcggctat cggtggcgct gttgccgccg ggagcgcgg cgcgcgccag    1560 cggcagcagc cgcagcaaga cgacgacgat gatgaagagg ggccgccgc gctgctggat     1620 gacaactcct cggatggcga cggcgacagc tcgggctccg aagacttgct ggggctgctg    1680
ctgcagcaaa agcagccacc caactccaag gctgctttga acagcaaac ggcaggcaag     1740 cagagcaacg gcgcagcggc ggccagcagc ggcttcgcgc gcggcttcct ggcgggggc     1800 ggagccagca cggcgcctgc agcgggcgcg gggggcaagg ccgctgggcc tgctccccaa    1860
```

```
cccgcagccg caagcaagcc ccaaggccag cagcagaatg cgatgcagca acaggggcag    1920
caggcacgac aatcgcagca gcagcagcag cagcagcagc agcagcagca gcagcaggca    1980
caggccaagc cagccagcgg cggccttgca cgcggcttcc tggctggcgg cgcaacaggg    2040
tcttccggca cagctcaggc cgctgccagt gcggcaggca aagcacccgc agccagcgct    2100
acaggtgcaa gtgctggtgc gcaggcgctc gccgccaaga gagcggcggg ctccgccggc    2160
gcggctgccg ccaaaacggt agtagcggcc cccgcggcgg caacgacccc ggccaaaccg    2220
gccaccgcgc agcccgccaa agcagttgca gcagcagcgg cagcagccgc cgccaagccg    2280
ttagcgccgc cgccgcagcc ggccggcgcg caagtgctga gggcactgct ggcggagctg    2340
acggcggcgg tggacgcgaa cgccgcgggc aaggtggcag acgtcgtgaa gcggctcaac    2400
aaggagaccg cggcgtgcac gcctccgcta cctgtggaaa aagcaatcca ggctccatgc    2460
tttgcggcca cccatagcgc gaagcagaag gtcggagacc tgacgccgct gacgatcaag    2520
gatgacccgc tttgggctgc ggagaacgcg gcgcgggccg cggcggagtc tgccccgcag    2580
gcggggctgc tggcggaact gcttgccgcg ctgcgcaagt gcacctggag ggcggtgctg    2640
ggccacatgt cgctctccat gctgcaggag ctacgcataa taaacatccc ctgcggcatt    2700
ccatggtggc cggagatcct gcgtgacgcc tctgtgccgg ccgaccagcc gtcacccagc    2760
ctgtttgaga tgctgctgga aagggcggc ccgtcgcca cgacttggc ggcgggcctg    2820
gtggagaagc acagctacgt gctgctgtac gccaacaaga gcccggtgtg cctggccctg    2880
acccgcaagc tgccgctgaa cgacaccgac tacatcttcc gcatgagcct cgcctaccgc    2940
tccaaggaga agggcggcgc cgccagggag accctcacgg cggagctgca gctgcccgat    3000
ccggccgcgc cgcagggctg gcgccgccgc caagtgagcg ccaccgcctt cggctggtgg    3060
gcgctgctgc cgcactgcag caatgacgcc cgggtgctgt cgacgctgcg ggccaaggtg    3120
gaccccaagg tggagctgcc cgccttcgag ggcctgccgc cgctgcacgt gctggtgcag    3180
tacgggcggg ggccgtggga tggggtggca acggtggcca cggaccggcg gctcagcgcg    3240
ctgctgttca cggatgaggg cgtgttaatc tcccggctgc tggagcaagt ggcgggcggc    3300
atcacaccgc tgtacagggc ggtgcgcgtg ggcgacatcc cggcagtgac gtggctgcgg    3360
cagcggggcg cgagcccgct ggtcagctgc acggaggagg gcgcgggcgg atacagcgat    3420
acgccgctac acctggcggt gacgcgcaag agcgccgagg ccgtggaggc aatcattaag    3480
cactccgcgc ccgacatcct caagaagctg acaccacat acgacagcga cggcgccaca    3540
cccctcatgc tcgcggcgga gctgggctac acccgcatcg tggacctgct gctggcggca    3600
ggtgccgacc cctccctgct gcacgacctg ccaaacaagg gcgcgagcaa gtcaaagaaa    3660
ggcggcgcgg ccggctctac ggacgcgccg cggggcacac accagtcggt cctgtcacgg    3720
acgctgcagc tgcaggaggc ggaggaggag cggcggaaga agcagggcag caacggtcag    3780
gcgcagggcg acgccaagaa gcccaacccg catgacgctg tgctggaggc gatcatcagc    3840
agttggaagc ccctgtggag tggtgcgcg ctgcagcgcg agctagggcc ggacgggtgc    3900
gcacgtgtgc gggcctggct gctgcagcac gcggacacga cgctgtggcc agtgatcaag    3960
gagatgggtg cggcggcgt gtcgccaggc gtgctgacag ccagcctcgt ggcgctgctg    4020
ctggaggtgt gccgcacggc aggtggcgcc gactggcgcg tgccaggcac caccgacccc    4080
ttcaagcccg cgggcgaagg cggcagcggc agcagcacgt ggacggggcc gaagggcaca    4140
cacccgcctc ggtcgcagct gtcggtgtgg tcactggttc cggagtcagc cgctgcccag    4200
gatcacgcca aggccatagc cgcaaaggag ggcagcggca gtttggcgcc ggcgtggctg    4260
```

```
acgctgcccc tgctgcgcga gatgctgcag cgcgggctgg cttcgccgca tgagcgcctg    4320
ccgtcgtacg gcatcatgtc tgagctctcc aagggcagca ccctgctcca caaggcctgt    4380
ttcatcggcg acttggacat ggcgcttctg cttctggagg cggggggcgga ctggagcagg    4440 aaggacgaca acggcaacac ggtgctgcac tacgtcgcca tgggcagcgc cggttacggc    4500
gagagccgcg tgctggcgct gtggcgcctc ttcatgtggg gccgtgcgga ggggattgcg    4560
gcgggcggcg gcaagggctc ggcagctgcg gcgtcggcgc tgccgccgct gctgattgat    4620
ccggagcgcc tggcgctggc gaccgcaacc aacaccaaga agcgcatgcc agaagacctg    4680
gcagccgcca agatcaagcc ggcgttgaag acagagatac aggccctcaa gcagcgcgtg    4740
aacgccaagc tgaagaacca ggaggccgca gccaaggccg gcggaaaggc cacaggcaac    4800
tccagcggca aagcagacag caaggcgggc gccgccgtgg ctgagcagcc ggccgctgac    4860
gcgggcacgg ccgccgcggc tgctgccccg gaggccccgg gtgcggctgc ggccccggct    4920
gtggccgtgc tgagcccggc ggagcagctg aaggcgctgc tggcggacga cgaggccctg    4980
gcctccgctc cgctggcgca actggtgggc gtgccggagg agtcggcgct gcagctagcc    5040
acgcggctgg ccaaggccct gcccggtacg ctgcttcgcg gcaagcgggc agcaggggct    5100
caaggagccg gcgcggcgga ggatggtggc ggcggcgacg gcggcgatga cggcctgtcg    5160
cggctccggg cggtggtgga ggagctgcgg gaggaggacg acgaacagga gaacggggac    5220
gacggcgccg agtacagcga ggacgacgcg ccgccgcccg gtgaggagct gttggaggac    5280
gaggatgcca acgcggccgc catgcggggga gtggccggtg acgccgcggc tgcctcagcg    5340
gccgccgcct ccgccagcag cagcggcagc gcggccgcga acgcggcgc ggcccaggcg    5400 gtggcggctg cgaccgactt cgacaaccac ccgctgcgca acctggcctg gccgctgctc    5460
atcaccaagg aggccatcgc gggctggggc acgctgaacg accagtggag gaagctggtg    5520
atggcccggc tgcgcgtcat cgggcagggg ctgtggccgc gctgccgcgg cgccaagcgc    5580
atcaccagcg acgacccact gctcatgccg caggagctgt ggcggctcaa gctcacaaag    5640
ggcggccgca tcctgttcga ggtggcggtg gacgaccacg acagcaaggg caccttctgc    5700
gagattatca gagtctggtg catcacgctg aaccacaagg agtacgaggt gatgattcag    5760
cgcgtgcagc gctccttcac caactcactg cgcatgcggc tgcgcaagaa gctgcagccg    5820
ctggagcagg aggggccggc agcggccgcg accgcgccg gcacaaagaa ggcggccggc    5880
gccaaggcgg cggcagccgg cgtcgtgggct gcgggcggcg accgcacccg gactcgcctg    5940
ccgcggtttt acaaggaggc ggggctggtg gacggcagcg cgctggggga tgcgggcggc    6000 agcaagggc aggagcaggg ccaggtgatg gtgctgcggg agcactaccc gcccgcaagc    6060
tgggccgacg acacgtacac cacgctcaag ttctacacgg tggacgggct gctggtgaag    6120
gcggtcatgt cggggctggc ggaggcgcag gtggacttca tgttcaagct gagcccgcag    6180
gagcgcgacc tcatcaccat ggtgcccagc ccgccctcct ccatcatcct gctgggccgc    6240
agcggcaccg gcaagaccac atgcgccgtg ttccgcctgt ggaccgcctg gctggcgccc    6300
tacctcagcc gcgcgcacga gacgccgcac ccgtgttcg tcaccgcgtc ggccacgctg    6360
cgggagcagg tggcccgcgc cttccgcaag ctgcagcgcg ccgcactgcg cgaccacgag    6420
tgggagcgcg cctccgcggc cttcaacacc acctatcaca ccttcaagga cgtgccgccc    6480
gaggccttcc cgctcttcct gtccagccgc acctacctgc gcatgctgga cggcaccacc    6540
gagcgcccct tcttcccgcg cgccgccaac ggctccatca ttcaggtggc gggcgacggc    6600
```

-continued

```
gaggaagcgg accccgacgg cgcggcgctg gtggtggccc tgaacgagga cctgagtgac    6660
gaggaggacg aggaggacgg cgccgccgcg gaccaggagc ggcagcgcgg cgggccggac    6720
gaggatggcg gcggccagga gggcggcgcg gcgctgtttg aggaggaggt ggcggcggcg    6780
gacgcggcgc ggcgggagga ggcggcgcgc gcgcggctgc tgatggacat ggagggagcg    6840
gaggcgggcg gcgcggcgga cggctacggg ctgggcgtgg cgggtcgcgc gcggctgaac    6900
cgcgaggtga cgtaccagca cttcgtcagt gccatgtggc ccaagatcac aaccccgag    6960 cagcgcaacc aggtggcgcc cgggcgcgtg taccaggaga ttgtgagcta catcaagggc    7020
agcgcagaag ccatctccag tcccgacggc cacctcagcc gcgagcagta catgcgcctg    7080
ggccgcaagc gcgccgccaa cttcagcgcc gacatgcgcg gcgacgtggt gtggcccatc    7140
ttcgagaagt acgagcggct gaagcgacag gagtggcgct acgacatgtt ggacctggtg    7200
ggccacatct accgcgagat gaccaccacg cccggggggct acgccggcac gcccgtgcac    7260
gcgctgtatc gtgacgaggt ccaggacttc acccagggcg agctgctgct ggacatggtg    7320
gtggccgccg accccaacag cctcttctac tgcggcgaca cggcgcagac cattgcgcga    7380
ggcatcgggt ccgctttgc tgacacgcgc acgctgttcc acgaggagaa cacgcggcgc    7440
caggaggcgg cggcgcggcg gctggcggcg gaggcggcgg acgaggagtc ggtgggcaag    7500
gcgctggcgc ggcgcggcca cggaatgacc atcgccacgc ctcccgtcct ccagctgacc    7560
atgaactacc ggacgcacca gggcgtgctg gacgtggcgg cggtggtggt ggaggcgctg    7620
aggcgctact tcccactgca gattgacaag ctggagcgcg agagcgcgca gttcccgggc    7680
cctcacccgc tgctgctcgg cagcatctcc gccgacgacc tcacctacct gctcagtggc    7740
tccgacaaga agacgtcgca ggtggagttc ggcgcgcacc aggtgatcct ggtccgcagc    7800 atggcggcg tggaccagct gccggaggag atccgggaca gcaacgccat catcatgacc    7860
gtgccgcagg ccaaggggct ggagttcgac gatgtgttcc tggtggactt ctttgcggac    7920
agccaggcca ccgccgagtg gcgcgtgctg tgctcctacc tggccgagct gcaggagcgg    7980
ggcggcaagg ggctggacgg cttccagtac ggcctgcagc aggtcgcccc gacggacccg    8040
ggcgcggtgc ggcctctgga gttgaacgag gcacgcacg tggtgctggc cgaggagctc    8100
aagcacctgt acaccgccat cacgcgcgcc aagaacaacg tggtcatctt cgaccgcaac    8160
gccgccaagc gcgcgcccct ctaccacctg ctgcagagcc tgggcatggc gcgcaccgtg    8220
cacaagtcgc tgctggagga cggcgcggac gccgccaagt tcgggctgac gcagaaggcc    8280
accagcagcc ggcacgagtg ggccaagcgc gcgcgcaacc tcatgggcaa ccgcaactac    8340
gccatggcgc gcaaggcctt cctgcaggcg gaggaccagg tgcgcgccga ggtggcggac    8400
gcactgctca gcgccagcg cgccggccag gagtccatgc cggacgtcga caagcggcgg    8460
ctgctggcgg cggcggcgct gcagctgctg gcggccaccg cccgctgcgg cgagtcgccg    8520
gaccctgtgg agccggagga gctgcggcgc tgggtgcgcg aggccagcaa gttcctggag    8580
ggttgcggca agagcattga ggctgcgcag ctcaagttca agctgggcac gcagcgcgcc    8640
gtggcagcgg cgctgcgcct gctggtggac gccaaggagt acgccgccgc tgccgagtgc    8700
tgcgtgcaca tggcggcggc cgagctggcg gcggcgcgcg cccgcgccgc ggaggaggac    8760
gcggcggcgg cgggcagcat gcagcggctg ctgatgacgg aggcggagct ggcggcgcag    8820
cgggaggcgc aggcgcacca ggcggcggtg ccgtggctgg ccaaagcagt ggagcagttc    8880
cagttcgcgg caacagcac ggccgtgctg gcgctgctcg cgccgcctgg cttcggcggc    8940
agcaagggta gcgccacagg cgcgcatgct ccgcttgcag cagcagccgg cattgactcg    9000
```

-continued

```
gaggacgatg atgatgcggc ggaggatgcg gcggaggatg cggcggagga cgtggaggag      9060
gatgagcagc agcagcgcga gctagaggcg caggagcgga cggggccgct ggcactgttt      9120
gcgccgctgg cgccgcggct gcacgccatg ctggcgaggc gctggcaggg ctacggccag      9180
gcgctgaggc cggccgccat cgcgctgcac tcgcgcggct cgctgcgcg ggcgggcgcc       9240 gtggcgcggc tggtgcccat gccgcaggag cgggacacat tgctggagac gctcggctac      9300
tggcgggcgc gggcgcgggc ccgcagcgcg gtggacccgc tgggcgcggc gcaggtgctg      9360
ctggagcacg gcgacacgcg gcgggcggtg cgcctggtgc tgcgctgcct ggagccgctg      9420
cccgcctcct cggggggcat ggaggcgcc gaggccgggg gcgcgggcgg cggcggcgac       9480
cggctgaccc gggcggcgcg gcagcagcag ctgtatgagc tgcagctgcg gcaggagcat      9540
gagcggcgtc agaagcaggt gctggaggcc aacgcgctgg ctgtgctgca ccggctcgtc      9600
gcggcgcaga ccaaggcagc ggaggcgacg cagctgcggc gagcgctgga ggcttggatg      9660
gcgcggcagg cgaagtcgga ggagggcggc aaggaaggtg aggagggcgc cggtctcacc      9720
aagcgcatgc tgcccatccg cggccacgtg ctgctgctgg aggcgcgctt gctgctggag      9780
ccatgggccg cagccgctgc cggggggcgcc aaaggcgctg caggtgacag caaggagcag    9840
caggcggcgg cagcggcggt ggccaccaac gcggcattgc gcgatgccgc atggcttgag     9900
gcccggccgc tgctcttgac ggcggttgag tgcttcctgc gctgtgacca gtggccgggc     9960
ttcatggagg cggctgagct gctgctgcgg gccgccccg acgcggcagt cgcaagccac      10020
acggccgcag ggcagctggc agacttcgag caggcgctgc tgcaggctat gcagcgaggc     10080
gcagagcgcg ccggtgacag cgccacagtg gcggccgcgg cttcgtctcg cacggccgca     10140
gccaagcagg ccctggcccg gagcctcgtg gtgccgagg cggcgctcaa gctgatgcgg      10200
accacgcaga ccgcgtgtga tgcgctcagc gtggggctag gcagcagtgc gggtagcaac     10260
gtctctctcc gcccaggcgg tggactggtg ggccgcgccg gtggcggcgg cgaaaggtcg     10320
cgcgccggcg ccgcctcttc attgagcaag ccgcagcagg aggcgctgtc ggcgctggag     10380
gggctgctgc tgctgccggg cctgtcgcgg ccgactgagg cgaagctgtc ggcgcgcaac     10440
gccagccaca gctggtgggc ggcgctgggg cagcagaaca cggatgcggt gcggcgcgcg    10500
gctgggccca aggcagcagc cggctccgga caggatggca aggagaagga aaagacgtct     10560
gggcagtcga gctgggcggc ggtggctgcc aaggggcgcg ccgcaacggc gatggtgtgg     10620
gatccggagg tgcccgcgct cgcacccacc tcgcacctgc tgctgcgttg ccaccagacc     10680
gccatggccc tgggcgaagg tggagccatg gcggcagccg tggaggcggc gggtgctggt     10740
gccagtcaga tgccgctgcc gcgtgccgcc gtcgcggcgg tcgcggctcg gagcctgact     10800
atccgggctg cctgcctggc acacctggcg gcacgcggcg ccctggctgc ctacttgcac     10860
cctgcgccgc cgcctcagcc cgccctgccc gcgggcgccg gcggcaaggc tgcggaggag     10920
ggcacggagg gtgatgccgg caagcaggag cagccggcgg aggccgcggc gccgctcagc     10980
tgtgaggtgg tcctggaccg gctgcggccg ctggtgtgcg ctgcccgggc ggtgcacctg     11040
gccaagatga tggtcggcag cgttgggcag gccttctcaa tggccgcggc ggcgagcctc     11100
cgcaagtgcc tagatgcgca gctgcgctac ttggcggctg ctctggtcgc ggcctcgctg     11160
ccgcctgcgg ctgcgcccga gctgctcgca gagctgctgc agccgcggcc gcagccgcag     11220
cgcaggcctg gcggcggcgg cgggccgcct cggcgggtca tgggcgatct gctagagttg     11280
ctggcgcgtg acggcttccc gcaccgcgag ctggcggact gggcggagca cctgctggtc     11340
```

```
aggtgcatgc cgctggaact gcgcatgccg ctggcgcctg ccgtgtcgta cctggcgtgc   11400
cgcacgatga tgctggtggc acccgacagc gaggaccgcg cctccaagct gtggttgatc   11460
aaggacagca gtgcgaaggc gaccggagac gtgcccccgg agcggctggt gcatgacgac   11520
aagaagacgg ggccggcgga ggcgctgctg gtgtccgcct ccgcgccat ggacagctcc    11580 ccgctccgcg ccgtggggga cctgctctac tacctggcgt ggtgcgcccg gagagacggg   11640
ctggcggcgg tgacgcccac tgacgctgcg cggaaggcg cgcaggcgcc ggctggtgca    11700
gctgccggcg gcagcaagcc cggaagcggt gcagcggcag cagccgggcc cgtgggcctg   11760
tcgctgccgc ttgaggccta cgccgagctg gtggaggtga cggtggggca gctgctgctg   11820
gcggcctgcg acaacgcgct gctgcccggc aacgtggcgg gcaccctctc ggggctgccg   11880
cgcgtcagtg accctcaggc gggcctgaac ggcgtggcgg acacctgggc gcagagctg    11940 ggcttccggg gccggccgt gggcgaagga gcaggcggcg gcggtggcag cggctggggc    12000
tggggccgag gccgtggccc gtcgcccaag gaggtggcag aggctaaggc gcgggcggtg   12060
acggcgcgca aggaggtggc gggtcagctg cgtctggccg cgcggatgac gttgttgctg   12120
gcgtcccaca ttgaccagcg cctgcaggac acggctgcgc ccgctgcggg cggcgcaggc   12180
ggcgactcgg ctgcgtcccc tccggagctg gagttgttgc agcaagaggt gctgccgctg   12240
ctggacgccc cggggcggcg cgaggcgcac gagctgctga gcagcccgg cggcccaggg    12300 gcgcagcctc gccgggcgca gggcaagagt cgcggcggtg gagcggaggc cggcgtgggc   12360
tcgggtgcgt ccgttgcacc gccgtccgca ggagccagcg ggctgcgctt gcgggcgatt   12420
gcgcagcgcg tcctgctggc ggcaggcgca gcctacgtct cgctggagct gcaagagagt   12480
gtggtgaagc cgcagcggca gcagcagaag gcggcggcgg agcggcagca gaagctggcg   12540
ggcggcggcc ctgtgccgga gccgccgccg ctgcgcgggg gctggccggc cgaggcctcc   12600
gcgggctttc gggacgcatg cacgctgctg caggcgcgtg tggcgccggc ctgcttccag   12660
ccggccaccg gcgcgaccga cctggcctcg gtggcgcagg ctgcgacgc gctggcacgg    12720 ctgtcgcagc gggtgtgcta ccccagctcg cgcctgagca cgggcatgcg gctggtgggc   12780
ccggacgcca accgcgagta cgagggcctc agcggcgcgc ggccgcccaa gggccccctg   12840
gcgctgctgt tccaggcggc gcaggccaag atgcagctgc ccaaggcggc ggcggacgcg   12900
gggataggag gccgcgtcaa ggccgccagc gacgcggtgg cgcgtgtggc cgcccgcgac   12960
ttccaggcca cggaggacga gcgcgtgcgg cagcgccacg cggcggcggt gatccaaaag   13020
cggtggcgcg cctggaggca gcggcgcatc gaggcggcgg aggcaatgcg gcggcgccag   13080
ctgcaggcca acgcgctgga gaccctgcgc cgctccatac gcttccgggt ctgggtgcgt   13140
gcgcgccttg caaacgcgcg caaggccctg gacgcgcggc acttcgggga gcgcttcacc   13200
gcggggtgcg ccgccgcggt ccagttcggc gagcaggcgc tgcacatggc ggacatcgag   13260
gcggtgctga aggcgcggtt tgtccagttg gaccggtgcc cggtgtgctc tggcgagacg   13320
ctgcgcaaac agacgaggga gctgaagcag cagatggcgc agcgggctgc gggcaagctc   13380
aagggcgcag cagcggagtt ccgaccgcac aagaacacgg ttgatcacct ggaggccgcc   13440
aactccttca caaccttccg ggacgtctac aacggcgacc tgccgacgcg gctgggcggc   13500
agcgccgcgc acatggacca gctgcgtgcc agcctagacc gcttggagca gctcggcgtc   13560
agcgacgctt cgctgatcaa gggccgactc gtgccggagg cggacctggc tctgcgcggc   13620
gtggagcagg cccgtgctgc gctggaggcc agtctgcgc agctggtgga ggagcgcgtc    13680
tgggacgtgg gtgtcctcgc atcgaggatg tttccgcagt acacctcgct tgacgcggcc   13740
```

```
gtgcagcggg ttgacatgat gcgggtccac gtggagggac tggccgcagc tgcgcgccgc   13800
acggcgctgc tgcccctga cgagcagctg cagccattc agcccaagca gcagcccag     13860 ccccagctgc agcagccaca ggagcaggac cagcaccagg agcaggagca ggagcaggcg   13920
ctgcggttgc caagcggtga agtcccagag caggagcagg cgcaggagca ggtgcaggcg   13980
caggagcagc agcctgtggg agtctttgcg gctggccttg atgtcagacc tgctgacggc   14040
atggcagcga tgcagccgc cgccgccgcc tctccggcca agcaggccgt gcccgcgtta   14100
gaggggccgc cggggactcg gcctggcctg cagcagccct tcagctcacc gacacaccag   14160
cagcaggggt ccgcatgggc ggcgcagaag cctgttattc aattcacacc gccgccgatg   14220
ccgccaatgc cttcggcgct gctgcagcag ctgtcacagg gcaagggca gagctacgct   14280 gttgccgccc aggcgggcgc cggcggccag gcagttagtc cctacagcaa ccagtcgcac   14340
gcgcaggccg ctcacacgat ggggtacaat caagtctatg gcggtctggg tggcataggc   14400
gcagacctgc ctccgggcct gtcgcaaaca cctggttacg gcgcggctgc agctggctca   14460
acggccgggt atgctgcgtc cgggttcgcg ccgcccaact ttacggcgca ggctggattc   14520
ccgttccaac agcagcagca gttccagcaa cagcagcagc agcagcaaca gtatcaatac   14580
ttgccgcaca tgcagcaaca gcagcagcaa cagcagcagc aacagtatca gccgtacttg   14640
cagcagcagt accagccgcc gtcgcctggc atgaacgctt ccatggtgtc tccaggcggc   14700
atgcctggct tcatgccgca gcagtacggc atcggctact tcccaagcgg agctgcaggt   14760
ggaggagcgg cggcagggat gcaaggagtg gctgcagctg cagccatggg cgcggcggcg   14820
cagttcggtg ctatgggcgg cgcaggggc tttccggcag gggagccggg cacggacgcc   14880
atcctgcaag gcgcactgat ggaggacgat gacgaggacg acgacgagtg gcagcagagc   14940
cggcggcatg gccgatatga cggcggggc cgggcgggg gccggggcgg gcggggccgg   15000
ggtcacagcg cagggccgca tgggagtccc tacgggccgc caggccgtgg acctggaggc   15060
ggtggaggcc gcggtggccg cggcgccgt ggatatggcg gtggctatgg cggtgggcgc   15120
ggcagcaacg tgtatgaggc gctgcggggt gccaatgcca caccttccag ggccgcgcag   15180
cggatgggct tgagctaa                                                  15198
```

<210> SEQ ID NO 83
<211> LENGTH: 5065
<212> TYPE: PRT
<213> ORGANISM: Chlamydomonas reinhardtii

<400> SEQUENCE: 83

Met Ser Ala Arg Tyr Lys Thr Val Leu Cys Val Asn Trp Glu Gly Gly
1               5                   10                  15

Ser Cys Lys Tyr Gly Asp Ala Cys Gln Phe Ala His Gly Ala His Glu
                20                  25                  30

Leu Arg Ser Arg Gly Glu Gln Val Ala Thr Gly Leu Val Val Ala Pro
            35                  40                  45

Val Arg Thr Thr Pro Lys Leu Ala Gly Gln Pro Ala Gln Ser Leu Gln
        50                  55                  60

Lys Arg Gln Leu Cys Lys Trp His Gln Val Gly Ala Cys Ser Phe Gly
65                  70                  75                  80

Ala Arg Cys Lys Phe Ala His Ser Glu His Glu Leu Cys Ala Pro Gly
                85                  90                  95

Gly Ala Tyr Gly Gly Ser Asn Ser His Gly Ser Ala Val Ser Gln Asn
            100                 105                 110

```
Gly Gly Gly Ala Phe Pro Thr Ser Pro Gln Pro Glu Ala Ser Ser
            115                 120                 125

Pro Thr Ser Gln Thr Pro Pro Pro Pro Pro Leu Pro Leu Pro
    130                 135                 140

Arg Leu Ser Pro Val Glu Val His Lys Ile Tyr Lys Glu Ala Leu Val
145                 150                 155                 160

Ala Ala Arg Ser Gly Asp Ala Val Lys Val Gly Ser Lys Ala Gly Glu
                165                 170                 175

Leu Leu Ala Arg Gly Pro Ala Pro His Tyr Gly Leu Ser Arg Asn Gln
            180                 185                 190

Val Ala Asp Leu Ile Ala Ala Thr Ala Glu Tyr Pro Ser Leu Pro
    195                 200                 205

Cys Leu Lys Ala Leu Leu Pro Leu Ala Gln Pro Phe Gly Asp Trp Thr
    210                 215                 220

Leu Leu His Arg Gln Tyr Pro Thr Ala Ser His Gln Gln Ala Thr Gly
225                 230                 235                 240

Gln Ala Val Tyr Cys Gly Leu Leu His Gln Ala Ala Leu Met Leu Leu
                245                 250                 255

Glu Trp His Lys Ala Gly Leu Ala Gln Ala Ala Thr Thr Gly Leu Glu
            260                 265                 270

Val Leu Arg Ala Ile Cys Ala Ala Arg Pro Ala Ala Val Val Asp Met
    275                 280                 285

Lys Ala Pro Gly Ile Leu Ser Thr Pro Leu Glu Thr Val Leu Leu Ala
    290                 295                 300

Gly Gln Glu Pro Arg Gly Phe Val Ala Arg Leu Leu Arg Glu Val Ser
305                 310                 315                 320

Pro Ile Thr Trp Leu His Thr Ala Pro Gly His Ala Ala His Leu Arg
                325                 330                 335

Ala Val Glu Val Cys Glu Ala Leu Ala Asp Asp Glu Gly Cys Leu Val
            340                 345                 350

Ala Arg Asn Leu Gly Phe Ser Gln Ala Tyr Phe Leu Thr Cys Ala Ser
        355                 360                 365

Val Leu Gln Gly Ile Tyr Asp Arg Lys Arg Pro Ala Ser Ala Ser Tyr
    370                 375                 380

Glu Ala Val Pro Glu Pro Val Pro Pro Ala Ser Gly Tyr Ile Gln
385                 390                 395                 400

Leu Pro Ala Leu Glu Ile Pro Gly Ile Ser Arg Thr Phe Thr Gly Val
                405                 410                 415

Arg Thr Gly Ala Pro Pro Pro Pro Pro His Ala Ala Ala Ser
            420                 425                 430

Ser Ala Ser Gly His Val Lys Val His Ser Gln Pro Ala Thr Ala Pro
        435                 440                 445

Ala Ala Gly Ser Thr Ala Ser Ser Ser Val Ala Lys Gln Pro His
    450                 455                 460

Thr Gln Gln Leu Gln Leu Pro Ser Gly Ala Arg Ser Gly Ala Ala Ser
465                 470                 475                 480

Ser Ala Ser Ser Val Gln Lys Gly Pro Val Ala Ala Val Lys Thr
                485                 490                 495

Thr Val Ala Ser Ala Ala Val Ala Ala Ala Ile Gly Gly Ala Val Ala
            500                 505                 510

Ala Gly Gln Arg Gly Ala Arg Gln Arg Gln Pro Gln Gln Asp Asp
        515                 520                 525
```

```
Asp Asp Asp Glu Glu Gly Pro Pro Ala Leu Leu Asp Asp Asn Ser Ser
    530                 535                 540

Asp Gly Asp Gly Asp Ser Ser Gly Ser Glu Asp Leu Leu Gly Leu Leu
545                 550                 555                 560

Leu Gln Gln Lys Gln Pro Pro Asn Ser Lys Ala Ala Leu Lys Gln Gln
                565                 570                 575

Thr Ala Gly Lys Gln Ser Asn Gly Ala Ala Ala Ser Ser Gly Phe
                580                 585                 590

Ala Arg Gly Phe Leu Gly Gly Gly Ala Ser Thr Gly Ala Ala Ala
        595                 600                 605

Gly Ala Gly Gly Lys Ala Ala Gly Pro Ala Pro Gln Pro Ala Ala
        610                 615                 620

Ser Lys Pro Gln Gly Gln Gln Asn Ala Met Gln Gln Gln Gly Gln
625                 630                 635                 640

Gln Ala Arg Gln Ser Gln Gln Gln Gln Gln Gln Gln Gln Gln Gln
                645                 650                 655

Gln Gln Gln Ala Gln Ala Lys Pro Ala Ser Gly Gly Leu Ala Arg Gly
                660                 665                 670

Phe Leu Ala Gly Gly Ala Thr Gly Ser Ser Gly Thr Ala Gln Ala Ala
        675                 680                 685

Ala Ser Ala Ala Gly Lys Ala Pro Ala Ala Ser Ala Thr Gly Ala Ser
690                 695                 700

Ala Gly Ala Gln Ala Leu Ala Ala Lys Arg Ala Ala Gly Ser Ala Gly
705                 710                 715                 720

Ala Ala Ala Ala Lys Thr Val Val Ala Ala Pro Ala Ala Ala Thr Thr
                725                 730                 735

Pro Ala Lys Pro Ala Thr Ala Gln Pro Ala Lys Ala Val Ala Ala Ala
                740                 745                 750

Ala Ala Ala Ala Ala Lys Pro Leu Ala Pro Pro Gln Pro Ala
        755                 760                 765

Gly Ala Gln Val Leu Arg Ala Leu Leu Ala Glu Leu Thr Ala Ala Val
        770                 775                 780

Asp Ala Asn Ala Ala Gly Lys Val Ala Asp Val Val Lys Arg Leu Asn
785                 790                 795                 800

Lys Glu Thr Ala Ala Cys Thr Pro Pro Leu Pro Val Glu Lys Ala Ile
                805                 810                 815

Gln Ala Pro Cys Phe Ala Ala Thr His Ser Ala Lys Gln Lys Val Gly
                820                 825                 830

Asp Leu Thr Pro Leu Thr Ile Lys Asp Asp Pro Leu Trp Ala Ala Glu
                835                 840                 845

Asn Ala Ala Arg Ala Ala Ala Glu Ser Ala Pro Gln Ala Gly Leu Leu
850                 855                 860

Ala Glu Leu Leu Ala Ala Leu Arg Lys Cys Thr Trp Arg Ala Val Leu
865                 870                 875                 880

Gly His Met Ser Leu Ser Met Leu Gln Glu Leu Arg Ile Ile Asn Ile
                885                 890                 895

Pro Cys Gly Ile Pro Trp Trp Pro Glu Ile Leu Arg Asp Ala Ser Val
        900                 905                 910

Pro Ala Asp Gln Pro Ser Pro Ser Leu Phe Glu Met Leu Leu Glu Lys
                915                 920                 925

Gly Gly Ala Val Ala Ser Asp Leu Ala Ala Gly Leu Val Glu Lys His
        930                 935                 940

Ser Tyr Val Leu Leu Tyr Ala Asn Lys Ser Pro Val Cys Leu Ala Leu
```

```
                945               950               955               960
          Thr Arg Lys Leu Pro Leu Asn Asp Thr Asp Tyr Ile Phe Arg Met Ser
                      965               970               975
          Leu Ala Tyr Arg Ser Lys Glu Lys Gly Gly Ala Ala Arg Glu Thr Leu
                      980               985               990
          Thr Ala Glu Leu Gln Leu Pro Asp Pro Ala Ala Pro Gln Gly Trp Arg
                      995               1000              1005
          Arg Arg Gln Val Ser Ala Thr Ala Phe Gly Trp Trp Ala Leu Leu
                      1010              1015              1020
          Pro His Cys Ser Asn Asp Ala Arg Val Leu Ser Thr Leu Arg Ala
                      1025              1030              1035
          Lys Val Asp Pro Lys Val Glu Leu Pro Ala Phe Glu Gly Leu Pro
                      1040              1045              1050
          Pro Leu His Val Leu Val Gln Tyr Gly Arg Arg Pro Trp Asp Gly
                      1055              1060              1065
          Val Ala Thr Val Ala Thr Asp Arg Arg Leu Ser Ala Leu Leu Phe
                      1070              1075              1080
          Thr Asp Glu Gly Val Leu Ile Ser Arg Leu Leu Glu Gln Val Ala
                      1085              1090              1095
          Gly Gly Ile Thr Pro Leu Tyr Arg Ala Val Arg Val Gly Asp Ile
                      1100              1105              1110
          Pro Ala Val Thr Trp Leu Arg Gln Arg Gly Ala Ser Pro Leu Val
                      1115              1120              1125
          Ser Cys Thr Glu Glu Gly Ala Gly Gly Tyr Ser Asp Thr Pro Leu
                      1130              1135              1140
          His Leu Ala Val Thr Arg Lys Ser Ala Glu Ala Val Glu Ala Ile
                      1145              1150              1155
          Ile Lys His Ser Ala Pro Asp Ile Leu Lys Lys Leu Asp Thr Thr
                      1160              1165              1170
          Tyr Asp Ser Asp Gly Ala Thr Pro Leu Met Leu Ala Ala Glu Leu
                      1175              1180              1185
          Gly Tyr Thr Arg Ile Val Asp Leu Leu Leu Ala Ala Gly Ala Asp
                      1190              1195              1200
          Pro Ser Leu Leu His Asp Leu Pro Asn Lys Gly Ala Ser Lys Ser
                      1205              1210              1215
          Lys Lys Gly Gly Ala Ala Gly Ser Thr Asp Ala Pro Arg Gly Thr
                      1220              1225              1230
          His Gln Ser Val Leu Ser Arg Thr Leu Gln Leu Gln Glu Ala Glu
                      1235              1240              1245
          Glu Glu Arg Arg Lys Lys Gln Gly Ser Asn Gly Gln Ala Gln Gly
                      1250              1255              1260
          Asp Ala Lys Lys Pro Asn Pro His Asp Ala Val Leu Glu Ala Ile
                      1265              1270              1275
          Ile Ser Ser Trp Lys Pro Leu Trp Ser Gly Ala Ala Leu Gln Arg
                      1280              1285              1290
          Glu Leu Gly Pro Asp Gly Cys Ala Arg Val Arg Ala Trp Leu Leu
                      1295              1300              1305
          Gln His Ala Asp Thr Thr Leu Trp Pro Val Ile Lys Glu Met Gly
                      1310              1315              1320
          Ala Gly Gly Val Ser Pro Gly Val Leu Thr Ala Ser Leu Val Ala
                      1325              1330              1335
          Leu Leu Leu Glu Val Cys Arg Thr Ala Gly Gly Ala Asp Trp Arg
                      1340              1345              1350
```

-continued

```
Val Pro Gly Thr Thr Asp Pro Phe Lys Pro Ala Gly Glu Gly Gly
    1355                1360                1365

Ser Gly Ser Ser Thr Trp Thr Gly Pro Lys Gly Thr His Pro Pro
    1370                1375                1380

Arg Ser Gln Leu Ser Val Trp Ser Leu Val Pro Glu Ser Ala Ala
    1385                1390                1395

Ala Gln Asp His Ala Lys Ala Ile Ala Ala Lys Glu Gly Ser Gly
    1400                1405                1410

Ser Leu Ala Pro Ala Trp Leu Thr Leu Pro Leu Leu Arg Glu Met
    1415                1420                1425

Leu Gln Arg Gly Leu Ala Ser Pro His Glu Arg Leu Pro Ser Tyr
    1430                1435                1440

Gly Ile Met Ser Glu Leu Ser Lys Gly Ser Thr Leu Leu His Lys
    1445                1450                1455

Ala Cys Phe Ile Gly Asp Leu Asp Met Ala Leu Leu Leu Leu Glu
    1460                1465                1470

Ala Gly Ala Asp Trp Ser Arg Lys Asp Asp Asn Gly Asn Thr Val
    1475                1480                1485

Leu His Tyr Val Ala Met Gly Ser Ala Gly Tyr Gly Glu Ser Arg
    1490                1495                1500

Val Leu Ala Leu Trp Arg Leu Phe Met Trp Gly Arg Ala Glu Gly
    1505                1510                1515

Ile Ala Ala Gly Gly Gly Lys Gly Ser Ala Ala Ala Ser Ala
    1520                1525                1530

Leu Pro Pro Leu Leu Ile Asp Pro Glu Arg Leu Ala Leu Ala Thr
    1535                1540                1545

Ala Thr Asn Thr Lys Lys Arg Met Pro Glu Asp Leu Ala Ala Ala
    1550                1555                1560

Lys Ile Lys Pro Ala Leu Lys Thr Glu Ile Gln Ala Leu Lys Gln
    1565                1570                1575

Arg Val Asn Ala Lys Leu Lys Asn Gln Glu Ala Ala Ala Lys Ala
    1580                1585                1590

Gly Gly Lys Ala Thr Gly Asn Ser Ser Gly Lys Ala Asp Ser Lys
    1595                1600                1605

Ala Gly Ala Ala Val Ala Glu Gln Pro Ala Ala Asp Ala Gly Thr
    1610                1615                1620

Ala Ala Ala Ala Ala Ala Pro Glu Ala Pro Gly Ala Ala Ala Ala
    1625                1630                1635

Pro Ala Val Ala Val Leu Ser Pro Ala Glu Gln Leu Lys Ala Leu
    1640                1645                1650

Leu Ala Asp Asp Glu Ala Leu Ala Ser Ala Pro Leu Ala Gln Leu
    1655                1660                1665

Val Gly Val Pro Glu Glu Ser Ala Leu Gln Leu Ala Thr Arg Leu
    1670                1675                1680

Ala Lys Ala Leu Pro Gly Thr Leu Leu Arg Gly Lys Arg Ala Ala
    1685                1690                1695

Gly Ala Gln Gly Ala Gly Gly Gly Glu Asp Gly Gly Gly Asp
    1700                1705                1710

Gly Gly Asp Asp Gly Leu Ser Arg Leu Arg Ala Val Val Glu Glu
    1715                1720                1725

Leu Arg Glu Glu Asp Asp Glu Gln Glu Asn Gly Asp Asp Gly Ala
    1730                1735                1740
```

-continued

| | | | | | | | | | | | |
|---|---|---|---|---|---|---|---|---|---|---|---|
|Glu|Tyr|Ser|Glu|Asp|Asp|Ala|Pro|Pro|Pro|Gly|Glu|Leu|Leu|
|1745| | | |1750| | | |1755| | | |

Glu Tyr Ser Glu Asp Asp Ala Pro Pro Pro Gly Glu Leu Leu
1745                1750                1755

Glu Asp Glu Asp Ala Asn Ala Ala Ala Met Arg Gly Val Ala Gly
1760                1765                1770

Asp Ala Ala Ala Ala Ser Ala Ala Ala Ser Ala Ser Ser Ser
1775                1780                1785

Gly Ser Ala Ala Ala Asn Gly Gly Ala Ala Gln Ala Val Ala Ala
1790                1795                1800

Ala Thr Asp Phe Asp Asn His Pro Leu Arg Asn Leu Ala Trp Pro
1805                1810                1815

Leu Leu Ile Thr Lys Glu Ala Ile Ala Gly Trp Gly Thr Leu Asn
1820                1825                1830

Asp Gln Trp Arg Lys Leu Val Met Ala Arg Leu Arg Val Ile Gly
1835                1840                1845

Gln Gly Leu Trp Pro Arg Cys Arg Gly Ala Lys Arg Ile Thr Ser
1850                1855                1860

Asp Asp Pro Leu Leu Met Pro Gln Glu Leu Trp Arg Leu Lys Leu
1865                1870                1875

Thr Lys Gly Gly Arg Ile Leu Phe Glu Val Ala Val Asp Asp His
1880                1885                1890

Asp Ser Lys Gly Thr Phe Cys Glu Ile Ile Arg Val Trp Cys Ile
1895                1900                1905

Thr Leu Asn His Lys Glu Tyr Glu Val Met Ile Gln Arg Val Gln
1910                1915                1920

Arg Ser Phe Thr Asn Ser Leu Arg Met Arg Leu Arg Lys Lys Leu
1925                1930                1935

Gln Pro Leu Glu Gln Glu Gly Pro Ala Ala Ala Thr Ala Ala
1940                1945                1950

Gly Thr Lys Lys Ala Ala Gly Ala Lys Ala Ala Ala Ala Gly Val
1955                1960                1965

Val Ala Ala Gly Gly Asp Arg Thr Arg Thr Arg Leu Pro Arg Phe
1970                1975                1980

Tyr Lys Glu Ala Gly Leu Val Asp Gly Ser Gly Ala Gly Asp Ala
1985                1990                1995

Gly Gly Ser Lys Gly Gln Glu Gln Gly Gln Val Met Val Leu Arg
2000                2005                2010

Glu His Tyr Pro Pro Ala Ser Trp Ala Asp Asp Thr Tyr Thr Thr
2015                2020                2025

Leu Lys Phe Tyr Thr Val Asp Gly Leu Leu Val Lys Ala Val Met
2030                2035                2040

Ser Gly Leu Ala Glu Ala Gln Val Asp Phe Met Phe Lys Leu Ser
2045                2050                2055

Pro Gln Glu Arg Asp Leu Ile Thr Met Val Pro Ser Pro Pro Ser
2060                2065                2070

Ser Ile Ile Leu Leu Gly Arg Ser Gly Thr Gly Lys Thr Thr Cys
2075                2080                2085

Ala Val Phe Arg Leu Trp Thr Ala Trp Leu Ala Pro Tyr Leu Ser
2090                2095                2100

Arg Ala His Glu Thr Pro His Thr Val Phe Val Thr Ala Ser Ala
2105                2110                2115

Thr Leu Arg Glu Gln Val Ala Arg Ala Phe Arg Lys Leu Gln Arg
2120                2125                2130

Ala Ala Leu Arg Asp His Glu Trp Glu Arg Ala Ser Ala Ala Phe

```
                2135                2140                2145
Asn Thr Thr Tyr His Thr Phe Lys Asp Val Pro Pro Glu Ala Phe
    2150                2155                2160

Pro Leu Phe Leu Ser Ser Arg Thr Tyr Leu Arg Met Leu Asp Gly
    2165                2170                2175

Thr Thr Glu Arg Pro Phe Phe Pro Arg Ala Ala Asn Gly Ser Ile
    2180                2185                2190

Ile Gln Val Ala Gly Asp Gly Glu Glu Ala Asp Pro Asp Gly Ala
    2195                2200                2205

Ala Leu Val Val Ala Leu Asn Glu Asp Leu Ser Asp Glu Glu Asp
    2210                2215                2220

Glu Glu Asp Gly Ala Ala Ala Asp Gln Glu Arg Gln Arg Gly Gly
    2225                2230                2235

Pro Asp Glu Asp Gly Gly Gly Gln Glu Gly Gly Ala Ala Leu Phe
    2240                2245                2250

Glu Glu Glu Val Ala Ala Ala Asp Ala Ala Arg Arg Glu Glu Ala
    2255                2260                2265

Ala Arg Ala Arg Leu Leu Met Asp Met Glu Gly Ala Glu Ala Gly
    2270                2275                2280

Gly Ala Ala Asp Gly Tyr Gly Leu Gly Val Ala Gly Arg Ala Arg
    2285                2290                2295

Leu Asn Arg Glu Val Thr Tyr Gln His Phe Val Ser Ala Met Trp
    2300                2305                2310

Pro Lys Ile Thr Thr Pro Glu Gln Arg Asn Gln Val Ala Pro Gly
    2315                2320                2325

Arg Val Tyr Gln Glu Ile Val Ser Tyr Ile Lys Gly Ser Ala Glu
    2330                2335                2340

Ala Ile Ser Ser Pro Asp Gly His Leu Ser Arg Glu Gln Tyr Met
    2345                2350                2355

Ala Leu Gly Arg Lys Arg Ala Ala Asn Phe Ser Ala Asp Met Arg
    2360                2365                2370

Gly Asp Val Val Trp Pro Ile Phe Glu Lys Tyr Glu Arg Leu Lys
    2375                2380                2385

Arg Gln Glu Trp Arg Tyr Asp Met Leu Asp Leu Val Gly His Ile
    2390                2395                2400

Tyr Arg Glu Met Thr Thr Thr Pro Gly Gly Tyr Ala Gly Thr Pro
    2405                2410                2415

Val His Ala Leu Tyr Arg Asp Glu Val Gln Asp Phe Thr Gln Gly
    2420                2425                2430

Glu Leu Leu Leu Asp Met Val Val Ala Ala Asp Pro Asn Ser Leu
    2435                2440                2445

Phe Tyr Cys Gly Asp Thr Ala Gln Thr Ile Ala Arg Gly Ile Gly
    2450                2455                2460

Phe Arg Phe Ala Asp Thr Arg Thr Leu Phe His Glu Glu Asn Thr
    2465                2470                2475

Arg Arg Gln Glu Ala Ala Ala Arg Arg Leu Ala Ala Glu Ala Ala
    2480                2485                2490

Asp Glu Glu Ser Val Gly Lys Ala Leu Ala Arg Arg Gly His Gly
    2495                2500                2505

Met Thr Ile Ala Thr Pro Pro Val Leu Gln Leu Thr Met Asn Tyr
    2510                2515                2520

Arg Thr His Gln Gly Val Leu Asp Val Ala Ala Val Val Val Glu
    2525                2530                2535
```

```
Ala Leu Arg Arg Tyr Phe Pro Leu Gln Ile Asp Lys Leu Glu Arg
    2540                2545                2550

Glu Ser Ala Gln Phe Pro Gly Pro His Pro Leu Leu Leu Gly Ser
    2555                2560                2565

Ile Ser Ala Asp Asp Leu Thr Tyr Leu Leu Ser Gly Ser Asp Lys
    2570                2575                2580

Lys Thr Ser Gln Val Glu Phe Gly Ala His Gln Val Ile Leu Val
    2585                2590                2595

Arg Ser Met Ala Ala Val Asp Gln Leu Pro Glu Glu Ile Arg Asp
    2600                2605                2610

Ser Asn Ala Ile Ile Met Thr Val Pro Gln Ala Lys Gly Leu Glu
    2615                2620                2625

Phe Asp Asp Val Phe Leu Val Asp Phe Phe Ala Asp Ser Gln Ala
    2630                2635                2640

Thr Ala Glu Trp Arg Val Leu Cys Ser Tyr Leu Ala Glu Leu Gln
    2645                2650                2655

Glu Arg Gly Gly Lys Gly Leu Asp Gly Phe Gln Tyr Gly Leu Gln
    2660                2665                2670

Gln Val Ala Pro Thr Asp Pro Gly Ala Val Arg Pro Leu Glu Leu
    2675                2680                2685

Asn Glu Gly Thr His Val Val Leu Ala Glu Glu Leu Lys His Leu
    2690                2695                2700

Tyr Thr Ala Ile Thr Arg Ala Lys Asn Asn Val Val Ile Phe Asp
    2705                2710                2715

Arg Asn Ala Ala Lys Arg Ala Pro Phe Tyr His Leu Leu Gln Ser
    2720                2725                2730

Leu Gly Met Ala Arg Thr Val His Lys Ser Leu Leu Glu Asp Gly
    2735                2740                2745

Ala Asp Ala Ala Lys Phe Gly Leu Thr Gln Lys Ala Thr Ser Ser
    2750                2755                2760

Arg His Glu Trp Ala Lys Arg Ala Arg Asn Leu Met Gly Asn Arg
    2765                2770                2775

Asn Tyr Ala Met Ala Arg Lys Ala Phe Leu Gln Ala Glu Asp Gln
    2780                2785                2790

Val Arg Ala Glu Val Ala Asp Ala Leu Leu Lys Arg Gln Arg Ala
    2795                2800                2805

Gly Gln Glu Ser Met Pro Asp Val Asp Lys Arg Leu Leu Ala
    2810                2815                2820

Ala Ala Ala Leu Gln Leu Leu Ala Ala Thr Ala Arg Cys Gly Glu
    2825                2830                2835

Ser Pro Asp Pro Val Glu Pro Glu Glu Leu Arg Arg Trp Val Arg
    2840                2845                2850

Glu Ala Ser Lys Phe Leu Glu Gly Cys Gly Lys Ser Ile Glu Ala
    2855                2860                2865

Ala Gln Leu Lys Phe Lys Leu Gly Thr Gln Arg Ala Val Ala Ala
    2870                2875                2880

Ala Leu Arg Leu Leu Val Asp Ala Lys Glu Tyr Ala Ala Ala Ala
    2885                2890                2895

Glu Cys Cys Val His Met Ala Ala Glu Leu Ala Ala Ala Arg
    2900                2905                2910

Ala Arg Ala Ala Glu Glu Asp Ala Ala Ala Ala Gly Ser Met Gln
    2915                2920                2925
```

-continued

Arg Leu Leu Met Thr Glu Ala Glu Leu Ala Ala Gln Arg Glu Ala
2930                    2935                    2940

Gln Ala His Gln Ala Ala Val Pro Trp Leu Ala Lys Ala Val Glu
2945                    2950                    2955

Gln Phe Gln Phe Ala Gly Asn Ser Thr Ala Val Leu Ala Leu Leu
2960                    2965                    2970

Ala Pro Pro Gly Phe Gly Gly Ser Lys Gly Ser Ala Thr Gly Ala
2975                    2980                    2985

His Ala Pro Leu Ala Ala Ala Gly Ile Asp Ser Glu Asp Asp
2990                    2995                    3000

Asp Asp Ala Ala Glu Asp Ala Ala Glu Asp Ala Ala Glu Asp Val
3005                    3010                    3015

Glu Glu Asp Glu Gln Gln Gln Arg Glu Leu Glu Ala Gln Glu Arg
3020                    3025                    3030

Thr Gly Pro Leu Ala Leu Phe Ala Pro Leu Ala Pro Arg Leu His
3035                    3040                    3045

Ala Met Leu Ala Arg Arg Trp Gln Gly Tyr Gly Gln Ala Leu Arg
3050                    3055                    3060

Ala Ala Ala Ile Ala Leu His Ser Arg Gly Ser Leu Arg Arg Ala
3065                    3070                    3075

Gly Ala Val Ala Arg Leu Val Pro Met Pro Gln Glu Arg Asp Thr
3080                    3085                    3090

Leu Leu Glu Thr Leu Gly Tyr Trp Arg Ala Arg Ala Arg Ala Arg
3095                    3100                    3105

Ser Ala Val Asp Pro Leu Gly Ala Ala Gln Val Leu Leu Glu His
3110                    3115                    3120

Gly Asp Thr Arg Arg Ala Val Arg Leu Val Leu Arg Cys Leu Glu
3125                    3130                    3135

Pro Leu Pro Ala Ser Ser Gly Gly Met Glu Ala Ala Glu Ala Gly
3140                    3145                    3150

Gly Ala Gly Gly Gly Gly Asp Arg Leu Thr Arg Ala Ala Arg Gln
3155                    3160                    3165

Gln Gln Leu Tyr Glu Leu Gln Leu Arg Gln Glu His Glu Arg Arg
3170                    3175                    3180

Gln Lys Gln Val Leu Glu Ala Asn Ala Leu Ala Val Leu His Arg
3185                    3190                    3195

Leu Val Ala Ala Gln Thr Lys Ala Ala Glu Ala Thr Gln Leu Arg
3200                    3205                    3210

Arg Ala Leu Glu Ala Trp Met Ala Arg Gln Ala Lys Ser Glu Glu
3215                    3220                    3225

Gly Gly Lys Glu Gly Glu Glu Gly Ala Gly Leu Thr Lys Arg Met
3230                    3235                    3240

Leu Pro Ile Arg Gly His Val Leu Leu Glu Ala Arg Leu Leu
3245                    3250                    3255

Leu Glu Pro Trp Ala Ala Ala Ala Ala Gly Gly Ala Lys Gly Ala
3260                    3265                    3270

Ala Gly Asp Ser Lys Glu Gln Gln Ala Ala Ala Ala Val Ala
3275                    3280                    3285

Thr Asn Ala Ala Leu Arg Asp Ala Ala Trp Leu Glu Ala Arg Pro
3290                    3295                    3300

Leu Leu Leu Thr Ala Val Glu Cys Phe Leu Arg Cys Asp Gln Trp
3305                    3310                    3315

Pro Gly Phe Met Glu Ala Ala Glu Leu Leu Leu Arg Ala Ala Pro

```
                    3320                3325                3330

Asp Ala Ala Val Ala Ser His Thr Ala Ala Gly Gln Leu Ala Asp
        3335                3340                3345

Phe Glu Gln Ala Leu Leu Gln Ala Met Gln Arg Gly Ala Glu Arg
        3350                3355                3360

Ala Gly Asp Ser Ala Thr Val Ala Ala Ala Ser Ser Arg Thr
        3365                3370                3375

Ala Ala Ala Lys Gln Ala Leu Ala Arg Ser Leu Val Val Pro Glu
        3380                3385                3390

Ala Ala Leu Lys Leu Met Arg Thr Thr Gln Thr Ala Cys Asp Ala
        3395                3400                3405

Leu Ser Val Gly Leu Gly Ser Ser Ala Gly Ser Asn Val Ser Leu
        3410                3415                3420

Arg Pro Gly Gly Gly Leu Val Gly Arg Ala Gly Gly Gly Glu
        3425                3430                3435

Arg Ser Arg Ala Gly Ala Ala Ser Ser Leu Ser Lys Pro Gln Gln
        3440                3445                3450

Glu Ala Leu Ser Ala Leu Glu Gly Leu Leu Leu Pro Gly Leu
        3455                3460                3465

Ser Arg Pro Thr Glu Ala Lys Leu Ser Ala Arg Asn Ala Ser His
        3470                3475                3480

Ser Trp Trp Ala Ala Leu Gly Gln Gln Asn Thr Asp Ala Val Arg
        3485                3490                3495

Arg Ala Ala Gly Pro Lys Ala Ala Gly Ser Gly Gln Asp Gly
        3500                3505                3510

Lys Glu Lys Glu Lys Thr Ser Gly Gln Ser Ser Trp Ala Ala Val
        3515                3520                3525

Ala Ala Lys Gly Ala Ala Ala Thr Ala Met Val Trp Asp Pro Glu
        3530                3535                3540

Val Pro Ala Leu Ala Pro Thr Ser His Leu Leu Leu Arg Cys His
        3545                3550                3555

Gln Thr Ala Met Ala Leu Gly Glu Gly Gly Ala Met Ala Ala Ala
        3560                3565                3570

Val Glu Ala Ala Gly Ala Gly Ala Ser Gln Met Pro Leu Pro Arg
        3575                3580                3585

Ala Ala Val Ala Ala Val Ala Ala Arg Ser Leu Thr Ile Arg Ala
        3590                3595                3600

Ala Cys Leu Ala His Leu Ala Ala Arg Gly Ala Leu Ala Ala Tyr
        3605                3610                3615

Leu His Pro Ala Pro Pro Pro Gln Pro Ala Leu Pro Ala Gly Ala
        3620                3625                3630

Gly Gly Lys Ala Ala Glu Glu Gly Thr Glu Gly Asp Ala Gly Lys
        3635                3640                3645

Gln Glu Gln Pro Ala Glu Ala Ala Ala Pro Leu Ser Cys Glu Val
        3650                3655                3660

Val Leu Asp Arg Leu Arg Pro Leu Val Cys Ala Ala Arg Ala Val
        3665                3670                3675

His Leu Ala Lys Met Met Val Gly Ser Val Gly Gln Ala Phe Ser
        3680                3685                3690

Met Ala Ala Ala Ala Ser Leu Arg Lys Cys Leu Asp Ala Gln Leu
        3695                3700                3705

Arg Tyr Leu Ala Ala Ala Leu Val Ala Ala Ser Leu Pro Pro Ala
        3710                3715                3720
```

-continued

```
Ala Ala Pro Glu Leu Leu Ala Glu Leu Leu Gln Pro Arg Pro Gln
    3725                3730                3735

Pro Gln Arg Arg Pro Gly Gly Gly Gly Pro Pro Arg Arg Val
    3740                3745                3750

Met Gly Asp Leu Leu Glu Leu Leu Ala Arg Asp Gly Phe Pro His
    3755                3760                3765

Arg Glu Leu Ala Asp Trp Ala Glu His Leu Leu Val Arg Cys Met
    3770                3775                3780

Pro Leu Glu Leu Arg Met Pro Leu Ala Pro Ala Val Ser Tyr Leu
    3785                3790                3795

Ala Cys Arg Thr Met Met Leu Val Ala Pro Asp Ser Glu Asp Arg
    3800                3805                3810

Ala Ser Lys Leu Trp Leu Ile Lys Asp Ser Ser Ala Lys Ala Thr
    3815                3820                3825

Gly Asp Val Pro Pro Glu Arg Leu Val His Asp Asp Lys Lys Thr
    3830                3835                3840

Gly Pro Ala Glu Ala Leu Leu Val Ser Ala Phe Arg Ala Met Asp
    3845                3850                3855

Ser Ser Pro Leu Arg Ala Val Gly Asp Leu Leu Tyr Tyr Leu Ala
    3860                3865                3870

Trp Cys Ala Arg Arg Asp Gly Leu Ala Ala Val Thr Pro Thr Asp
    3875                3880                3885

Ala Ala Ala Glu Gly Ala Gln Ala Pro Ala Gly Ala Ala Ala Gly
    3890                3895                3900

Gly Ser Lys Pro Gly Ser Gly Ala Ala Ala Ala Gly Pro Val
    3905                3910                3915

Gly Leu Ser Leu Pro Leu Glu Ala Tyr Ala Glu Leu Val Glu Val
    3920                3925                3930

Thr Val Gly Gln Leu Leu Leu Ala Ala Cys Asp Asn Ala Leu Leu
    3935                3940                3945

Pro Gly Asn Val Ala Gly Thr Leu Ser Gly Leu Pro Arg Val Ser
    3950                3955                3960

Asp Pro Gln Ala Gly Leu Asn Gly Val Ala Asp Thr Trp Ala Arg
    3965                3970                3975

Glu Leu Gly Phe Arg Gly Pro Ala Val Gly Glu Gly Ala Gly Gly
    3980                3985                3990

Gly Gly Gly Ser Gly Trp Gly Trp Gly Arg Gly Arg Gly Pro Ser
    3995                4000                4005

Pro Lys Glu Val Ala Glu Ala Lys Ala Arg Ala Val Thr Ala Arg
    4010                4015                4020

Lys Glu Val Ala Gly Gln Leu Arg Leu Ala Ala Arg Met Thr Leu
    4025                4030                4035

Leu Leu Ala Ser His Ile Asp Gln Arg Leu Gln Asp Thr Ala Ala
    4040                4045                4050

Pro Ala Ala Gly Gly Ala Gly Gly Asp Ser Ala Ala Ser Pro Pro
    4055                4060                4065

Glu Leu Glu Leu Leu Gln Gln Glu Val Leu Pro Leu Leu Asp Ala
    4070                4075                4080

Pro Gly Arg Arg Glu Ala His Glu Leu Leu Arg Gln Pro Gly Gly
    4085                4090                4095

Pro Gly Ala Gln Pro Arg Arg Ala Gln Gly Lys Ser Arg Gly Gly
    4100                4105                4110
```

```
Gly Ala Glu Ala Gly Val Gly Ser Gly Ala Ser Val Ala Pro Pro
4115                4120                4125

Ser Ala Gly Ala Ser Gly Leu Arg Leu Arg Ala Ile Ala Gln Arg
4130                4135                4140

Val Leu Leu Ala Ala Gly Ala Ala Tyr Val Ser Leu Glu Leu Gln
4145                4150                4155

Glu Ser Val Val Lys Pro Gln Arg Gln Gln Lys Ala Ala Ala
4160                4165                4170

Glu Arg Gln Gln Lys Leu Ala Gly Gly Gly Pro Val Pro Glu Pro
4175                4180                4185

Pro Pro Leu Arg Gly Gly Trp Pro Ala Glu Ala Ser Ala Gly Phe
4190                4195                4200

Arg Asp Ala Cys Thr Leu Leu Gln Ala Arg Val Ala Pro Ala Cys
4205                4210                4215

Phe Gln Pro Ala Thr Gly Ala Thr Asp Leu Ala Ser Val Ala Gln
4220                4225                4230

Ala Ala Asp Ala Leu Ala Arg Leu Ser Gln Arg Val Cys Tyr Pro
4235                4240                4245

Ser Ser Arg Leu Ser Thr Gly Met Arg Leu Val Gly Pro Asp Ala
4250                4255                4260

Asn Arg Glu Tyr Glu Gly Leu Ser Gly Ala Arg Pro Pro Lys Gly
4265                4270                4275

Pro Leu Ala Leu Leu Phe Gln Ala Ala Gln Ala Lys Met Gln Leu
4280                4285                4290

Pro Lys Ala Ala Ala Asp Ala Gly Ile Gly Gly Arg Val Lys Ala
4295                4300                4305

Ala Ser Asp Ala Val Ala Arg Val Ala Ala Arg Asp Phe Gln Ala
4310                4315                4320

Thr Glu Asp Glu Arg Val Arg Gln Arg His Ala Ala Ala Val Ile
4325                4330                4335

Gln Lys Arg Trp Arg Ala Trp Arg Gln Arg Arg Ile Glu Ala Ala
4340                4345                4350

Glu Ala Met Arg Arg Arg Gln Leu Gln Ala Asn Ala Leu Glu Thr
4355                4360                4365

Leu Arg Arg Ser Ile Arg Phe Arg Val Trp Val Arg Ala Arg Leu
4370                4375                4380

Ala Asn Ala Arg Lys Ala Leu Asp Ala Arg His Phe Gly Glu Arg
4385                4390                4395

Phe Thr Ala Gly Cys Ala Ala Ala Val Gln Phe Gly Glu Gln Ala
4400                4405                4410

Leu His Met Ala Asp Ile Glu Ala Val Leu Lys Ala Arg Phe Val
4415                4420                4425

Gln Leu Asp Arg Cys Pro Val Cys Ser Gly Glu Thr Leu Arg Lys
4430                4435                4440

Gln Thr Glu Glu Leu Lys Gln Gln Met Ala Gln Arg Ala Ala Gly
4445                4450                4455

Lys Leu Lys Gly Ala Ala Ala Glu Phe Arg Pro His Lys Asn Thr
4460                4465                4470

Val Asp His Leu Glu Ala Ala Asn Ser Phe Thr Thr Phe Arg Asp
4475                4480                4485

Val Tyr Asn Gly Asp Leu Pro Thr Arg Leu Gly Gly Ser Ala Ala
4490                4495                4500
```

-continued

```
His Met Asp Gln Leu Arg Ala Ser Leu Asp Arg Leu Glu Gln Leu
    4505                4510                4515

Gly Val Ser Asp Ala Ser Leu Ile Lys Gly Arg Leu Val Ala Glu
4520                4525                4530

Ala Asp Leu Ala Leu Arg Gly Val Glu Gln Ala Arg Ala Ala Leu
    4535                4540                4545

Glu Ala Ser Leu Arg Gln Leu Val Glu Glu Arg Val Trp Asp Val
4550                4555                4560

Gly Val Leu Ala Ser Arg Met Phe Pro Gln Tyr Thr Ser Leu Asp
    4565                4570                4575

Ala Ala Val Gln Arg Val Asp Met Met Arg Val His Val Glu Gly
    4580                4585                4590

Leu Ala Ala Ala Arg Arg Thr Ala Leu Leu Pro Pro Asp Glu
    4595            4600                4605

Gln Leu Ala Ala Ile Gln Pro Lys Gln Pro Gln Pro Gln Leu
    4610            4615                4620

Gln Gln Pro Gln Glu Gln Asp Gln His Gln Glu Gln Glu Glu
    4625            4630                4635

Gln Ala Leu Arg Leu Pro Ser Gly Glu Val Pro Gln Glu Gln
    4640            4645                4650

Ala Gln Glu Gln Val Gln Ala Gln Glu Gln Gln Pro Val Gly Val
    4655                4660                4665

Phe Ala Ala Gly Leu Asp Val Arg Pro Ala Asp Gly Met Ala Ala
    4670                4675                4680

His Ala Ala Ala Ala Ala Ser Pro Ala Lys Gln Ala Val Pro
    4685                4690                4695

Ala Leu Glu Gly Pro Pro Gly Thr Arg Pro Gly Leu Gln Gln Pro
    4700                4705                4710

Phe Ser Ser Pro Thr His Gln Gln Gly Ser Ala Trp Ala Ala
    4715                4720                4725

Gln Lys Pro Val Ile Gln Phe Thr Pro Pro Met Pro Pro Met
    4730                4735                4740

Pro Ser Ala Leu Leu Gln Gln Leu Ser Gln Gly Gln Gly Gln Ser
    4745                4750                4755

Tyr Ala Val Ala Ala Gln Gly Ala Gly Gly Gln Ala Val Ser
    4760                4765                4770

Pro Tyr Ser Asn Gln Ser His Ala Gln Ala Ala His Thr Met Gly
    4775                4780                4785

Tyr Asn Gln Val Tyr Gly Gly Leu Gly Gly Ile Gly Ala Asp Leu
    4790                4795                4800

Pro Pro Gly Leu Ser Gln Thr Pro Gly Tyr Gly Ala Ala Ala Ala
    4805                4810                4815

Gly Ser Thr Ala Gly Tyr Ala Ala Ser Gly Phe Ala Pro Pro Asn
    4820                4825                4830

Phe Thr Ala Gln Ala Gly Phe Pro Phe Gln Gln Gln Gln Gln Phe
    4835                4840                4845

Gln Gln Gln Gln Gln Gln Gln Gln Tyr Gln Tyr Leu Pro His
    4850                4855                4860

Met Gln Gln Gln Gln Gln Gln Gln Gln Gln Tyr Gln Pro
    4865                4870                4875

Tyr Leu Gln Gln Gln Tyr Gln Pro Pro Ser Pro Gly Met Asn Ala
    4880                4885                4890
```

```
Ser Met Val Ser Pro Gly Gly Met Pro Gly Phe Met  Pro Gln Gln
    4895             4900             4905

Tyr Gly Ile Gly Tyr Phe Pro Ser Gly Ala Ala Gly  Gly Gly Ala
4910             4915             4920

Ala Ala Gly Met Gln Gly Val Ala Ala Ala Ala Ala  Met Gly Ala
    4925             4930             4935

Ala Ala Gln Phe Gly Ala Met Gly Gly Ala Gly Phe  Pro Ala
    4940             4945             4950

Gly Glu Pro Gly Thr Asp Ala Ile Leu Gln Gly Ala  Leu Met Glu
    4955             4960             4965

Asp Asp Asp Glu Asp Asp Asp Glu Trp Gln Gln Ser  Arg Arg His
    4970             4975             4980

Gly Arg Tyr Asp Gly Gly Gly Arg Gly Gly Gly Arg  Gly Gly Arg
    4985             4990             4995

Gly Arg Gly His Ser Ala Gly Pro His Gly Ser Pro  Tyr Gly Pro
    5000             5005             5010

Pro Gly Arg Gly Pro Gly Gly Gly Gly Arg Gly  Gly Arg Gly
    5015             5020             5025

Ala Gly Gly Tyr Gly Gly Gly Tyr Gly Gly Gly Arg  Gly Ser Asn
    5030             5035             5040

Val Tyr Glu Ala Leu Arg Gly Ala Asn Ala Thr Pro  Ser Arg Ala
    5045             5050             5055

Ala Gln Arg Met Gly Leu Ser
    5060             5065

<210> SEQ ID NO 84
<211> LENGTH: 2827
<212> TYPE: DNA
<213> ORGANISM: Chlamydomonas reinhardtii

<400> SEQUENCE: 84
ttatatggcc ctatagtttg caccttgaaa gagcccggaa caacataact tcgcccgggc       60
cattgctccg ctcgcgaacg accacgcttg gagcgagctg ctgccgacga ggacaggcgc      120
gctgaacacg agccttgtgt acacgtcccg tgctcccggc ttggggcttg cggcggcgc       180
caagggcgga caccgggctc cggtcacgca cgcgacccgg tgggacacag cacggcacgg      240
ccaccccgtg cgccgtcggg ggcgggccgg acatcgccgt ggtcgccaaa catgtctgaa      300
aggtcccagg tcctgtgcaa gtaccacatc tccggtgcct gccggttcgg ctcggactgc      360
gccttctcgc acaacctgtc cgacctgccc agcaggtct gcaagttcta cctagccggg      420
aactgcgcct acgcgaccg ctgccgctac gaccaccgcc ggccggactg gtccaaagcc      480
gggcagctac ggcagcagca gcagcagcac gtacagcccg cacagccgca cgctagctcc      540
gcggggggctg ccgggcccag ctcccgagct ctgcgcgggg acccatatgt ggcggtgtgg      600
gatgcgcggg agcccaccga cccttcgcgc ctccccccag cccttgcggc agcggcagcg      660
gcagcctccc cctcggggcc agcccctca gggcctggcg ccgcgccttc agcgactgcg      720
agcaggggcc cggcctgggg cttagccgcc ggcgccaagg cgcccgtcgc aacaggagcg      780
gcagcaggcc gtgcagcggg tggtggcgg ggcgctgagc cggcggacga gtgggagcac      840
gtcgccgagg ccgttgcggc ggcggaggcg gcggaagcgg cagctgcggc tgggcggcgc      900
ggactggtgc tgattgatga cgatgtgggt ctggagcagg aggcgcggcg gctggagcag      960
gagcgagggc agcggcagc ggaggggca ggcgcgagc cgtcagtggt gtcaggagcc     1020
gcagcggcgg cggcgggc ggcgggcgcc gccggctcac ttccctggtc cccggacttg     1080
```

-continued

```
gatccctggg accagcgggg cggggcgggt ggggaacgcg aggcaggcgg ggaggaaggg      1140
tactacgacc cgtactacga cgagtatggg gagtacggcg aaggcgagga gggggcatgag     1200 ggggaggagc aggcgggcta tgaggccggc ggcgaggagg ggcaggaggg cccggcgggt      1260
caaggcgcgg gctggtggag tggcgccggt gctggtgctg gtgcaggggg tgaagcggtg      1320
gaccccgcgg acctggagct gtgtccggcg tttgcgctgc acggccggtg tgcggagggc      1380
gaggactgcc ccctcataca cggcctggag tgcgagacgt gccacaagtg gcggatacac      1440
ccctacaacg aggcggcggc ggcggagcac gcggcggagt gccggctgcg gcatgcgcgg      1500
ctggaggcgc ggctgcgcag tgcagacgtg gagtgcggca tctgcctgga gcacgtgatg      1560
cacaagccca gtgtgtcgga ccggcgcttc ggactgatgg actgcgacca cgccttctgc      1620
ctggcctgca tccgctcctg gcgagagcgc aacacagacg ccagcctggc cacggacacg      1680
gctgtgcgca cctgccccat ttgccgcacg tgcacgcact tcgtgacgcc ctccctggtg      1740
tggccggcca cggccgagga gaaggaggcc atcgtgggcg cctacaaggc caaactgggc      1800
accatcgact gccggcactt cgcatttggc gacggcacat gccccttctc cacctcctgc      1860
ttctaccgcc atgcctaccg cgatggccga ctagaggtgc cggtactgcg gcgcgccggc      1920
aacgcggacg gcgaggtgcg ggtggtggcg ccgctgcggc tgtccgcctt cctggacaca      1980
ccgcaggcgc agcggctgct gggcggccgc aggcggtgaa caggggtgca gcgggcggca      2040
gggtaagggg caggtgacga ggggtgaaca gggcggcagg cgggtaaggg atgctggatg      2100
gcagggtggc agagtggcag agatttacag gtattgtcag gcaggcagtt tgtgagtgta      2160
ggcgactaag caactaggca gcactaggca tagacgtgta ggaatgcatg ggtgttcccc      2220
gaggaccggg ccacgcccac agccacgccc acagccacta gagccgtgga ggagggccgt      2280
gcccgcgcac tcccgctggc aagctggtgg gccgtagcag atactaccaa ggtgttttga      2340
tggctaacgt tcattgagag atgtagcagg cgggtttggc gggaacatgg atccggccaa      2400
ccgcttaaaa ttgtgcactt gtgcaccagg gaattgtggc ccaggacgt atctattcaa       2460 tacttacgag ccgtgacact ccaaacttca caaaatgtcg ggcattgaca agtgtcttgg      2520
cccgggacgg ggaatcggca aaggcggcaa gcggcaccgc aaggttctgc gcgaaagcat      2580
caacacagct ctgacgcaag gctccattcg ccgcctggct cgccgtggcg gcgtgaagcg      2640
gctcagtggg cttgtctaca acgagattcg ctcggtcctc cgaggattcc tggaggcctt      2700
ggtcagggac acgatcacgt acacggagca cgcgcgtcgc caacatgtca agttaatgga      2760
tgtcatgtac gctcttaagc gtcaaggccg gactttgtat gggttcggcg tcttttaatt      2820
gcgccaa                                                                2827
```

<210> SEQ ID NO 85
<211> LENGTH: 1728
<212> TYPE: DNA
<213> ORGANISM: Chlamydomonas reinhardtii

<400> SEQUENCE: 85

```
atgtctgaaa ggtcccaggt cctgtgcaag taccacatct ccggtgcctg ccggttcggc        60
tcggactgcg ccttctcgca caacctgtcc gacctgccca gccaggtctg caagttctac       120
ctagccggga actgcgccta cggcgaccgc tgccgctacg accaccgccg gccggactgg       180
tccaaagccg ggcagctacg gcagcagcag cagcagcacg tacagcccgc acagccgcac       240
gctagctccg cggggctgc cgggcccagc tcccagcctc tgcgcgggga cccatatgtg        300
gcggtgtggg atgcgcggga gcccaccgac ccttcgcgcc tccccccagc ccttgcggca       360
```

-continued

| | |
|---|---|
| gcggcagcgg cagcctcccc ctcggggcca gcccccctcag ggcctggcgc cgcgccttca | 420 |
| gcgactgcga gcaggggccc ggcctggggc ttagccgccg cgccaaggc gcccgtcgca | 480 |
| acaggagcgg cagcaggccg tgcagcgggt ggtggcggcg gcgctgagcc ggcggacgag | 540 |
| tgggagcacg tcgccgaggc cgttgcggcg gcggaggcgg cggaagcggc agctgcggct | 600 |
| gggcggcgcg gactggtgct gattgatgac gatgtgggtc tggagcagga ggcgcggcgg | 660 |
| ctggagcagg agcgagggca gcgggcagcg gaggggcag gcgcgaggcc gtcagtggtg | 720 |
| tcaggagccg cagcggcggc ggcggggcg gcgggcgccg ccggctcact tccctggtcc | 780 |
| ccggacttgg atccctggga ccagcggggc ggggcgggtg gggaacgcga ggcaggcggg | 840 |
| gaggaagggt actacgaccc gtactacgac gagtatgggg agtacggcga aggcgaggag | 900 |
| gggcatgagg gggaggagca ggcgggctat gaggccggcg cgaggaggg gcaggagggc | 960 |
| ccggcgggtc aaggcgcggg ctggtggagt ggcgccggtg ctggtgctgg tgcaggggt | 1020 |
| gaagcggtgg accccgcgga cctggagctg tgtccggcgt ttgcgctgca cggccggtgt | 1080 |
| gcggagggcg aggactgccc cctcatacac ggcctggagt gcgagacgtg ccacaagtgg | 1140 |
| cggatacacc cctacaacga ggcggcggcg gcggagcacg cggcggagtg ccggctgcgg | 1200 |
| catgcgcggc tggaggcgcg gctgcgcagt gcagacgtgg agtgcggcat ctgcctggag | 1260 |
| cacgtgatgc acaagcccag tgtgtcggac cggcgcttcg gactgatgga ctgcgaccac | 1320 |
| gccttctgcc tggcctgcat ccgctcctgg cgagagcgca acacagacgc cagcctggcc | 1380 |
| acggacacgg ctgtgcgcac ctgccccatt tgccgcacgt gcacgcactt cgtgacgccc | 1440 |
| tccctggtgt ggccgccac ggccgaggag aaggaggcca tcgtgggcgc ctacaaggcc | 1500 |
| aaactgggca ccatcgactg ccggcacttc gcatttggcg acggcacatg ccccttctcc | 1560 |
| acctcctgct tctaccgcca tgcctaccgc gatggccgac tagaggtgcc ggtactgcgg | 1620 |
| cgcgccggca acgcggacgg cgaggtgcgg gtggtggcgc cgctgcggct gtccgccttc | 1680 |
| ctggacacac cgcaggcgca gcggctgctg ggcggccgca ggcggtga | 1728 |

<210> SEQ ID NO 86
<211> LENGTH: 575
<212> TYPE: PRT
<213> ORGANISM: Chlamydomonas reinhardtii

<400> SEQUENCE: 86

Met Ser Glu Arg Ser Gln Val Leu Cys Lys Tyr His Ile Ser Gly Ala
1               5                   10                  15

Cys Arg Phe Gly Ser Asp Cys Ala Phe Ser His Asn Leu Ser Asp Leu
            20                  25                  30

Pro Ser Gln Val Cys Lys Phe Tyr Leu Ala Gly Asn Cys Ala Tyr Gly
        35                  40                  45

Asp Arg Cys Arg Tyr Asp His Arg Arg Pro Asp Trp Ser Lys Ala Gly
    50                  55                  60

Gln Leu Arg Gln Gln Gln Gln His Val Gln Pro Ala Gln Pro His
65                  70                  75                  80

Ala Ser Ser Ala Gly Ala Ala Gly Pro Ser Ser Arg Ala Leu Arg Gly
                85                  90                  95

Asp Pro Tyr Val Ala Val Trp Asp Ala Arg Glu Pro Thr Asp Pro Ser
            100                 105                 110

Arg Leu Pro Pro Ala Leu Ala Ala Ala Ala Ala Ala Ser Pro Ser
        115                 120                 125

-continued

```
Gly Pro Ala Pro Ser Gly Pro Gly Ala Ala Pro Ser Ala Thr Ala Ser
130                 135                 140

Arg Gly Pro Ala Trp Gly Leu Ala Ala Gly Ala Lys Ala Pro Val Ala
145                 150                 155                 160

Thr Gly Ala Ala Ala Gly Arg Ala Ala Gly Gly Gly Gly Gly Ala Glu
                165                 170                 175

Pro Ala Asp Glu Trp Glu His Val Ala Glu Val Ala Ala Ala Glu
                180                 185                 190

Ala Ala Glu Ala Ala Ala Ala Gly Arg Arg Gly Leu Val Leu Ile
            195                 200                 205

Asp Asp Asp Val Gly Leu Glu Gln Glu Ala Arg Leu Glu Gln Glu
210                 215                 220

Arg Gly Gln Arg Ala Ala Glu Gly Ala Gly Ala Arg Pro Ser Val Val
225                 230                 235                 240

Ser Gly Ala Ala Ala Ala Ala Gly Ala Ala Gly Ala Ala Gly Ser
                245                 250                 255

Leu Pro Trp Ser Pro Asp Leu Asp Pro Trp Asp Gln Arg Gly Gly Ala
                260                 265                 270

Gly Gly Glu Arg Glu Ala Gly Gly Glu Glu Gly Tyr Tyr Asp Pro Tyr
                275                 280                 285

Tyr Asp Glu Tyr Gly Glu Tyr Gly Glu Gly Glu Gly His Glu Gly
                290                 295                 300

Glu Glu Gln Ala Gly Tyr Glu Ala Gly Gly Glu Glu Gln Glu Gly
305                 310                 315                 320

Pro Ala Gly Gln Gly Ala Gly Trp Trp Ser Gly Ala Gly Ala Gly Ala
                325                 330                 335

Gly Ala Gly Gly Glu Ala Val Asp Pro Ala Asp Leu Glu Leu Cys Pro
                340                 345                 350

Ala Phe Ala Leu His Gly Arg Cys Ala Glu Gly Glu Asp Cys Pro Leu
                355                 360                 365

Ile His Gly Leu Glu Cys Glu Thr Cys His Lys Trp Arg Ile His Pro
370                 375                 380

Tyr Asn Glu Ala Ala Ala Ala Glu His Ala Ala Glu Cys Arg Leu Arg
385                 390                 395                 400

His Ala Arg Leu Glu Ala Arg Leu Arg Ser Ala Asp Val Glu Cys Gly
                405                 410                 415

Ile Cys Leu Glu His Val Met His Lys Pro Ser Val Ser Asp Arg Arg
                420                 425                 430

Phe Gly Leu Met Asp Cys Asp His Ala Phe Cys Leu Ala Cys Ile Arg
                435                 440                 445

Ser Trp Arg Glu Arg Asn Thr Asp Ala Ser Leu Ala Thr Asp Thr Ala
                450                 455                 460

Val Arg Thr Cys Pro Ile Cys Arg Thr Cys Thr His Phe Val Thr Pro
465                 470                 475                 480

Ser Leu Val Trp Pro Ala Thr Ala Glu Glu Lys Glu Ala Ile Val Gly
                485                 490                 495

Ala Tyr Lys Ala Lys Leu Gly Thr Ile Asp Cys Arg His Phe Ala Phe
                500                 505                 510

Gly Asp Gly Thr Cys Pro Phe Ser Thr Ser Cys Phe Tyr Arg His Ala
                515                 520                 525

Tyr Arg Asp Gly Arg Leu Glu Val Pro Val Leu Arg Arg Ala Gly Asn
530                 535                 540
```

```
Ala Asp Gly Glu Val Arg Val Val Ala Pro Leu Arg Leu Ser Ala Phe
545                 550                 555                 560

Leu Asp Thr Pro Gln Ala Gln Arg Leu Leu Gly Gly Arg Arg Arg
                565                 570                 575
```

<210> SEQ ID NO 87
<211> LENGTH: 16
<212> TYPE: PRT
<213> ORGANISM: Artificial Sequence
<220> FEATURE:
<223> OTHER INFORMATION: antibody

<400> SEQUENCE: 87

```
Gln Gln Gln Gly Leu Ala Leu Gly Gly Tyr Gly Leu Thr Gln Gln Pro
1               5                   10                  15
```

<210> SEQ ID NO 88
<211> LENGTH: 16
<212> TYPE: PRT
<213> ORGANISM: Artificial Sequence
<220> FEATURE:
<223> OTHER INFORMATION: Antibody

<400> SEQUENCE: 88

```
Leu Gln His Gln Pro Gln Leu Leu Gln Pro Gln Gly Ser Leu Pro Ala
1               5                   10                  15
```

<210> SEQ ID NO 89
<211> LENGTH: 31
<212> TYPE: DNA
<213> ORGANISM: Artificial Sequence
<220> FEATURE:
<223> OTHER INFORMATION: Primer

<400> SEQUENCE: 89
ggaattccat atgctgtcgc agcatcaaga c                                31

<210> SEQ ID NO 90
<211> LENGTH: 30
<212> TYPE: DNA
<213> ORGANISM: Artificial Sequence
<220> FEATURE:
<223> OTHER INFORMATION: Primer

<400> SEQUENCE: 90
acaggatcct caatgggctt cagaggaacc                                  30

<210> SEQ ID NO 91
<211> LENGTH: 60
<212> TYPE: DNA
<213> ORGANISM: Artificial Sequence
<220> FEATURE:
<223> OTHER INFORMATION: Primer

<400> SEQUENCE: 91
tggagagcaa cccgggcccc ctcgaggaca aagctgaacg cgctgctggt ggccctaacg   60

<210> SEQ ID NO 92
<211> LENGTH: 59
<212> TYPE: DNA
<213> ORGANISM: Artificial Sequence
<220> FEATURE:
<223> OTHER INFORMATION: Primer

<400> SEQUENCE: 92
gagtgggtcg acgtcggaga ggtaccctat ggctccactc gctgccgctt tgcgcgatc    59

```
<210> SEQ ID NO 93
<211> LENGTH: 24
<212> TYPE: DNA
<213> ORGANISM: Artificial Sequence
<220> FEATURE:
<223> OTHER INFORMATION: Primer

<400> SEQUENCE: 93
gacaaagctg aacgcgctgc tggt                                            24

<210> SEQ ID NO 94
<211> LENGTH: 25
<212> TYPE: DNA
<213> ORGANISM: Artificial Sequence
<220> FEATURE:
<223> OTHER INFORMATION: Primer

<400> SEQUENCE: 94
ctatggctcc actcgctgcc gcttt                                           25

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
atgggcagta cttcatgc                                                   18

<210> SEQ ID NO 96
<211> LENGTH: 16
<212> TYPE: DNA
<213> ORGANISM: Artificial Sequence
<220> FEATURE:
<223> OTHER INFORMATION: Primer

<400> SEQUENCE: 96
tgacgaagcg gttgtg                                                     16

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
gccacaccga gtgggtgtcg tgcg                                            24

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
ccttgccgcc cgaggcgcac agcg                                            24

<210> SEQ ID NO 99
<211> LENGTH: 752
<212> TYPE: PRT
<213> ORGANISM: Chlamydomonas reinhardtii
```

```
<400> SEQUENCE: 99

Met Asp Lys Ala Glu Arg Ala Ala Gly Gly Pro Asn Ala Ala Ser Glu
1               5                   10                  15

Asp Asp Trp Leu Leu Glu Phe Trp Pro Glu Pro Ala Ala Asp Phe Pro
            20                  25                  30

Ala Pro Val Ala Pro Met Leu Ser Gln His Gln Asp Ala Ala Gln Leu
            35                  40                  45

Pro Glu Ala Met Pro Gln Gln Gln Gly Leu Ala Leu Gly Gly Tyr Gly
        50                  55                  60

Leu Thr Gln Gln Pro Ser Asp Phe Met Gln Thr Gly Met Pro Gly Phe
65                  70                  75                  80

Asp Ala Phe Ser Ser Gly Lys Ala Ala Thr Leu Gly Leu Pro Leu Leu
                85                  90                  95

Ala Asp Pro Gln Arg Ala Ser Thr Asp Gly Ala Ser Ala Leu Met Asn
            100                 105                 110

Ala Ala Gln Gln Ser Ser Glu Tyr Met Leu Ala Pro Gly Met Gly Gly
            115                 120                 125

Met Pro His Leu Leu Ala Pro Ser Val Gly Thr Ala Leu Pro Gly Thr
    130                 135                 140

Gly His Thr Gly Phe Ala Asp Leu Ser Met Gly Met Ala Gly Gly
145                 150                 155                 160

Ile Pro Gly Leu Gly Gly Pro Ile Met His Gly Gln Tyr Phe Met
                165                 170                 175

Gln Pro Gln Arg Ala Ala Thr Gly Pro Ala Lys Ser Arg Leu Arg Trp
            180                 185                 190

Thr Pro Glu Leu His Asn Arg Phe Val Asn Ala Val Asn Ser Leu Gly
            195                 200                 205

Gly Pro Asp Lys Ala Thr Pro Lys Gly Ile Leu Lys Leu Met Gly Val
        210                 215                 220

Asp Gly Leu Thr Ile Tyr His Ile Lys Ser His Leu Gln Lys Tyr Arg
225                 230                 235                 240

Leu Asn Ile Arg Leu Pro Gly Glu Ser Gly Leu Ala Gly Asp Ser Ala
                245                 250                 255

Asp Gly Ser Asp Gly Glu Arg Ser Asp Gly Glu Gly Val Arg Arg
            260                 265                 270

Ala Thr Ser Leu Glu Arg Ala Asp Thr Met Ser Gly Met Ala Gly Gly
        275                 280                 285

Ala Ala Ala Ala Leu Gly Arg Ala Gly Gly Thr Pro Gly Gly Ala Leu
    290                 295                 300

Ile Ser Pro Gly Leu Ala Gly Gly Thr Ser Ser Thr Gly Gly Met Ala
305                 310                 315                 320

Ala Gly Gly Gly Gly Gly Gly Leu Val Thr Glu Pro Ser Ile Ser
                325                 330                 335

Arg Gly Thr Val Leu Asn Ala Gly Ala Val Ala Thr Ala Ala Pro
            340                 345                 350

Ala Ala Ala Ala Pro Ala Gly Gly Ser Ala Ala Val Lys Arg Pro Ala
            355                 360                 365

Gly Thr Ser Leu Ser Ser Gly Ser Thr Ala Ser Ala Thr Arg Arg Asn
    370                 375                 380

Leu Glu Glu Ala Leu Leu Phe Gln Met Glu Leu Gln Lys Lys Leu His
385                 390                 395                 400

Glu Gln Leu Glu Thr Gln Arg Gln Leu Gln Leu Ser Leu Glu Ala His
            405                 410                 415
```

Gly Arg Tyr Ile Ala Ser Leu Met Glu Gln Glu Gly Leu Thr Ser Arg
                420                 425                 430

Leu Pro Glu Leu Ser Gly Gly Ala Pro Ala Ala Ala Pro Val Ala Ala
435                 440                 445

Gly Gly Ala Ala Gly Gly Met Ile Ala Pro Pro Pro Gln Gln Gln
    450                 455                 460

Leu Gln His Gln Pro Gln Leu Leu Gln Pro Gln Gly Ser Leu Pro Ala
465                 470                 475                 480

Gly Gly Ser Ser Glu Ala His Ala Ala Gly Ala Gly Thr Met Val
                485                 490                 495

Val His Gln Gln Gln Gln Gln His Val His His His Gln Gln Gln
        500                 505                 510

Gln Val Gln Met Gln Gln His Ala Arg His Cys Asp Thr Cys Gly Ala
        515                 520                 525

Gly Gly Ala Gly Gly Ala Pro Ser Gly Gly Ser Ser Met Gln Gln Leu
    530                 535                 540

Gln Ala Ala Glu Gln Gln Arg Thr Glu Leu Val Val Ala Gly Arg Leu
545                 550                 555                 560

Gly Ser Met Pro Ala Pro Ala Ser Ser Ser Pro Leu Ala Gly Gln Ala
                565                 570                 575

His Gln Gln Gln Pro Leu Ala Gly Gly Ala Ala His Leu Val His Val
        580                 585                 590

His Ser His Thr Pro Gly Gly Gln Pro His Val Gln His Gln Asp Ala
        595                 600                 605

Phe Ala Gly Ala Ala Thr Ala Ala Ala His Ala Ser Pro Gly Leu Pro
610                 615                 620

Gln Ser His Ser His Leu Leu Pro Ala Asp Leu Ser Ser Asn Ala Gly
625                 630                 635                 640

Pro Asp Thr Ser Ala Gly Gln Ile Lys Pro Glu Pro Asp Met Ser Gln
                645                 650                 655

Gln Gln Gln Gln Glu Gln Gln Glu Ala Glu Gln Leu Ala Gln Gly
        660                 665                 670

Leu Leu Asn Asp Ser Ser Ala Gly Ala Gly Ala Val Ser Gly Ser Asp
675                 680                 685

Gly Gly Gly Leu Gly Asp Phe Asp Phe Gly Asp Phe Gly Asp Leu Asp
    690                 695                 700

Gly Gly Ala Gln Gly Gly Leu Leu Gly Pro Gly Asp Leu Ile Gly Ile
705                 710                 715                 720

Ala Glu Leu Glu Ala Ala Ala Ala His Glu Gln Gln Gln Glu Gln Glu
                725                 730                 735

His Asp Pro Leu Asp Ala Asp Arg Ala Lys Arg Gln Arg Val Glu Pro
        740                 745                 750

<210> SEQ ID NO 100
<211> LENGTH: 6
<212> TYPE: DNA
<213> ORGANISM: Chlamydomonas reinhardtii

<400> SEQUENCE: 100 ccctaa                                                                        6

<210> SEQ ID NO 101
<211> LENGTH: 8
<212> TYPE: DNA
<213> ORGANISM: Chlamydomonas reinhardtii -continued

<400> SEQUENCE: 101 rtaccgta                                                                     8

<210> SEQ ID NO 102
<211> LENGTH: 8
<212> TYPE: DNA
<213> ORGANISM: Chlamydomonas reinhardtii

<400> SEQUENCE: 102 rtacvgta                                                                     8

<210> SEQ ID NO 103
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: ACETYLATION
<220> FEATURE:
<221> NAME/KEY: MOD_RES
<222> LOCATION: (17)..(17)
<223> OTHER INFORMATION: METHYLATION
<220> FEATURE:
<221> NAME/KEY: MOD_RES
<222> LOCATION: (18)..(18)
<223> OTHER INFORMATION: ACETYLATION
<220> FEATURE:
<221> NAME/KEY: MOD_RES
<222> LOCATION: (23)..(23)
<223> OTHER INFORMATION: ACETYLATION
<220> FEATURE:
<221> NAME/KEY: MOD_RES
<222> LOCATION: (26)..(27)
<223> OTHER INFORMATION: METHYLATION
<220> FEATURE:
<221> NAME/KEY: MOD_RES
<222> LOCATION: (28)..(28)
<223> OTHER INFORMATION: PHOSPHORYLATION
<220> FEATURE:
<221> NAME/KEY: MOD_RES
<222> LOCATION: (36)..(36)
<223> OTHER INFORMATION: METHYLATION

```
<400> SEQUENCE: 103

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
                20                  25                  30

Gly Gly Val Lys Lys Pro His
            35

<210> SEQ ID NO 104
<211> LENGTH: 18
<212> TYPE: DNA
<213> ORGANISM: Artificial Sequence
<220> FEATURE:
<223> OTHER INFORMATION: Synthetic construct

<400> SEQUENCE: 104
gtacggtagg catacaat                                             18
```